(12) United States Patent
Schalk et al.

(10) Patent No.: US 11,214,775 B2
(45) Date of Patent: Jan. 4, 2022

(54) METHOD FOR BIOCATALYTIC PRODUCTION OF TERPENE COMPOUNDS

(71) Applicant: FIRMENICH SA, Satigny (CH)

(72) Inventors: Michel Schalk, Satigny (CH); Letizia Rocci, Satigny (CH); Daniel Solis Escalante, Satigny (CH)

( * ) Notice: Subject to any disclaimer, the term of this patent is extended or adjusted under 35 U.S.C. 154(b) by 0 days.

(21) Appl. No.: 15/734,887

(22) PCT Filed: Jul. 10, 2019

(86) PCT No.: PCT/EP2019/068609
§ 371 (c)(1),
(2) Date: Dec. 3, 2020

(87) PCT Pub. No.: WO2020/011883
PCT Pub. Date: Jan. 16, 2020

(65) Prior Publication Data
US 2021/0222138 A1    Jul. 22, 2021

(30) Foreign Application Priority Data

Jul. 10, 2018 (EP) .................................. 18182783

(51) Int. Cl.
| | | |
|---|---|---|
| *C12N 9/16* | (2006.01) | |
| *C12N 9/04* | (2006.01) | |
| *C12P 7/04* | (2006.01) | |
| *C12P 7/18* | (2006.01) | |
| *C12P 17/04* | (2006.01) | |

(52) U.S. Cl.
CPC ............. *C12N 9/16* (2013.01); *C12N 9/0006* (2013.01); *C12P 7/04* (2013.01); *C12P 7/18* (2013.01); *C12P 17/04* (2013.01); *C12Y 101/01001* (2013.01); *C12Y 301/07003* (2013.01)

(58) Field of Classification Search
CPC ............ C12N 9/16; C12N 9/0006; C12P 7/18
See application file for complete search history.

(56) References Cited

FOREIGN PATENT DOCUMENTS

| CN | 107119001 A | 9/2017 |
| KR | 102017141384 A | 12/2017 |

OTHER PUBLICATIONS

Wang et al, "Farnesol production in *Escherichia coli* through the construction of a farnesol biosynthesis pathway—application of PgpB and YbjG phosphatases", Biotechnology Journal, vol. 11. 2016, pp. 1291-1297, XP002787099.
Mitsuhashi et al, Identification of chimeric alpha-beta-gamma diterpene synthases possessing both type II terpene cyclase and prenyltransferase activities, Chembiochem, vol. 18, 2017, pp. 2104-2109, XP002787120.
Song et al, "Engineering *Saccharomyces cerevisiae* for geranylgeraniol overproduction by combinatorial design", Scientific Reports, vol. 7, 2017, pp. 1-11, XP002787121.
Chen et al, "A(−)-kolavenyl diphosphate synthase catalyzes the first step of salvinorin A biosynthesis in Saliva divinorum", Jornal of Experimental Botany, vol. 68. 2017, pp. 1109-1122, XP002787100.
Misra et al, "Involvement of an ent-copalyl diphosphate synthase in tissue-specific accumulation of specialized diterpenes in Andrographis paniculata", Plant Science, vol. 240, 2015, pp. 50-64, XP002787101.
Hara et al, "Development of bio-based fine chemical production through synthetic bioengineering", Microbial Cell Factories, vol. 13, 2014, pp. 1-18, XP0021209952.
Database UniParc [Online] 2016, N.N.: "Aspergillus wentii DTO 134E9", XP002787102, Database accession No. UPI00090D881F.
Yu et al, 11 Regulatory mechanisms and novel therapeutic targeting strategies for protein tyrosine phosphatases, Chemical Reviews, vol. 118, Jul. 25, 2017 (Jul. 25, 2017), pp. 1069-1091, XP002794796.
Zada et al, "Metabolic engineering of *Escherichia coli* for production of mixed isoprenoid alcohols and their derivatives", Biotechnology for Biofuels, vol. 11, Jul. 24, 2018 (Jul. 24, 2018), pp. 1-12, XP055604904.
International Search Report and Written Opinion for corresponding PCT/EP2019/068609 dated Oct. 18, 2019, 17 pages.

*Primary Examiner* — Tekchand Saidha
(74) *Attorney, Agent, or Firm* — Armstrong Teasdale LLP

(57) ABSTRACT

Provided herein are biocatalytic methods of producing terpene compounds by applying a novel type of phosphatase enzyme. The method allows the fully biochemical synthesis of terpene compounds, like for example copalol and labdendiol, and derivatives thereof, which serve as valuable intermediates for the production of perfumery ingredients, such as, for example, ambrox. Also provided are novel fully biochemical multistep processes for the production of such compounds as well as novel phosphatase enzymes and mutants and variants derived therefrom.

17 Claims, 23 Drawing Sheets

Specification includes a Sequence Listing.

(13R) and (13S)-(8,13-epoxy-labdan-15-al

METHOD FOR BIOCATALYTIC PRODUCTION OF TERPENE COMPOUNDS

CROSS-REFERENCE TO RELATED APPLICATIONS

This application is a U.S. National Phase Application of International Patent Application No. PCT/EP2019/068609, filed Jul. 10, 2019, which claims the benefit of priority to European Patent Application No. 18182783.3, filed Jul. 10, 2018, the entire contents of each of which are hereby incorporated by reference herein.

TECHNICAL FIELD

Provided herein are biocatalytic methods of producing terpene compounds by applying a novel type of phosphatase enzyme. The method allows the fully biochemical synthesis of terpene compounds, like for example copalol and labdendiol, and derivatives thereof, which serve as valuable intermediates for the production of perfumery ingredients, such as, for example, ambrox or gamma-ambrol. Also provided are novel fully biochemical multistep processes for the production of such compounds as well as novel phosphatase enzymes and mutants and variants derived therefrom.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified.

Biosynthetic production of terpenes involves enzymes called terpene synthases. These enzymes convert an acyclic terpene precursor in one or more terpene products. In particular, diterpene synthases produce diterpenes by cyclization of the precursor geranylgeranyl diphosphate (GGPP). The cyclization of GGPP often requires two enzyme polypeptides, a type I and a type II diterpene synthase working in combination in two successive enzymatic reactions. The type II diterpene synthases catalyze a cyclization/rearrangement of GGPP initiated by the protonation of the terminal double bond of GGPP leading to a cyclic diterpene diphosphate intermediate. This intermediate is then further converted by a type I diterpene synthase catalyzing an ionization initiated cyclization.

Diterpene synthases are present in plants and other organisms and use substrates such as GGPP but they have different product profiles. Genes and cDNAs encoding diterpene synthases have been cloned and the corresponding recombinant enzymes characterized.

Enzymes that catalyze a specific or preferential cleavage or removal of diphosphate groups from terpene diphosphate intermediates, in particular from cyclic terpene diphosphate intermediates, like the diterpenes copalyl diphosphate (CPP) or labdendiol diphosphate (LPP) have so far not been described. In order to perform said cleavage a chemical cleavage of the phosphoester linkage would be required.

The problem to be solved by the present invention is to provide polypeptides which show the enzymatic activity of a phosphatase that is applicable in the enzymatic cleavage of terpenyl diphosphate linkages, and which allows for the biocatalytic production of terpene alcohols.

SUMMARY

The above-mentioned problem could surprisingly be solved by providing a new class of enzymes which show terpenyl-diphosphate phosphatase activity which are selected from a subgroup of diphosphate removing enzymes of the large protein tyrosine phosphatase family. The applicability of such enzymes of the protein tyrosine phosphatase family as phosphatases which utilize terpenyl diphosphates as substrates, in particular such complex bicyclic compounds like CPP and LPP has not been described in the prior art.

This approach allows the provision of more cost-effective methods of producing terpene intermediates such as copalol and labdendiol, which are building blocks for the preparation of highly valuable perfumery ingredients, such as Ambrox.

In some embodiments of the invention also the biocatalytic production of non-cyclic terpene alcohols, like farnesol or geranylgeraniol, from the corresponding diphosphate precursors is provided.

Said biocatalytic step may be coupled to several other preceding or successive enzymatic steps and allow the provision of a biocatalytic multistep process for the fully enzymatic synthesis of valuable complex terpene molecules from their respective precursors.

ABBREVIATIONS USED

Figure 1:
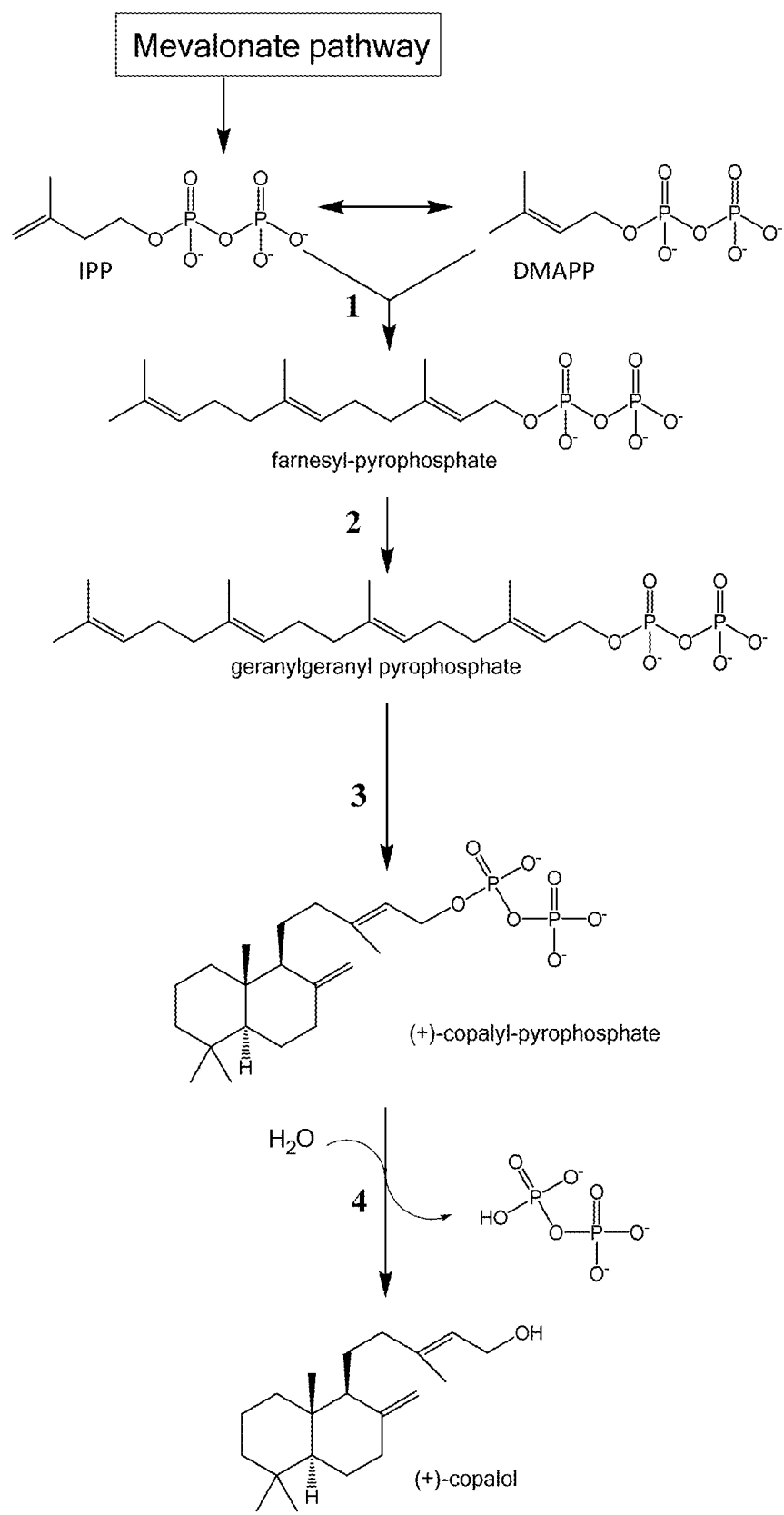
FIG. 1. Biosynthetic pathway of copalol. 1, farnesyl-pyrophosphate synthase. 2, geranylgeranyl-pyrophosphate synthase. 3, copalyl-pyrophosphate synthase. 4, Phosphatase.

ADH alcohol dehydrogenase
bp base pair
kb kilo base
CPP copalyl diphosphate
CPS copalyl diphosphate synthase
DNA deoxyribonucleic acid
cDNA complementary DNA
DMAPP dimethylallyl diphosphate
DTT dithiothreitol
FPP farnesyl diphosphate
GPP geranyldiphosphate
GGPP geranylgeranyl diphosphate
GGPS geranylgeranyl diphosphate synthase
GC gas chromatograph
IPP isopentenyl diphosphate
LPP labdendiol diphosphate
LPS labdendiol diphosphate synthase
MS mass spectrometer/mass spectrometry
MVA mevalonic acid
PP diphosphate, pyrophosphate
PCR polymerase chain reaction
RNA ribonucleic acid
mRNA messenger ribonucleic acid
miRNA micro RNA
siRNA small interfering RNA
rRNA ribosomal RNA
tRNA transfer RNA
TPP terpenyl diphosphate Definitions "Diphosphate" and "pyrophosphate" as used herein are synonyms.

"Terpenyl" designates noncyclic and cyclic chemical hydrocarbyl residues which are derived from the C5 building block isoprene and in particular contain one or more such building blocks.

"Bicyclic terpene" or bicyclic terpenyl" or "bicyclic diterpene" or bicyclic diterpenyl" relates to a terpene compound or terpenyl residue which comprises in its structure two carbocyclic rings, preferably two carbocyclic condensed rings.

A "hydrocarbyl" residue is a chemical group which essentially is composed of carbon and hydrogen atoms and may be a cyclic (for example mono- or polycyclic) or non-cyclic, linear or branched, saturated or unsaturated moiety. It comprises more than one, like 2, 3, 4 or 5, but in particular 5 or more carbon atoms, such as 5 to 30, 5 to 25, 5 to 20, 5 to 15 or 5 to 10 carbon atoms. Said hydrocarbyl group may be non-substituted or may carry at least one, like 1 to 5, preferably 0, 1 or 2 substituents. The substituent contains one hetero atom, like O or N. Preferably the substituents are independently selected from —OH, C═O, or —COOH. Most preferably said substituent is —OH.

A "mono- or polycyclic hydrocarbyl residue" comprise 1, 2 or 3 condensed (anellated) or non-condensed, optionally substituted, saturated or unsaturated hydrocarbon ring groups (or "carbocyclic" groups). Each cycle may comprise independently of each other 3 to 8, in particular 5 to 7, more particularly 6 ring carbon atoms. As examples of monocyclic residues there may be mentioned "cycloalkyl" groups which are carbocyclic radicals having 3 to 7 ring carbon atoms, such as cyclopropyl, cyclobutyl, cyclopentyl, cyclohexyl, cycloheptyl, and cyclooctyl; and the corresponding "cycloalkenyl" groups. Cycloalkenyl" (or "mono- or polyunsaturated cycloalkyl") represents, in particular, monocyclic, mono- or polyunsaturated carbocyclic groups having 5 to 8, preferably up to 6, carbon ring members, for example monounsaturated cyclopentenyl, cyclohexenyl, cycloheptenyl and cyclooctenyl radicals.

As examples of polycyclic residues there may be mentioned groups, wherein 1, 2 or 3 of such cycloalkyl and/or cycloalkenyl are linked together, as for example anellated, in order to form a polycyclic cycloalkyl or cycloalkenyl ring. As non-limiting example the bicyclic decalinyl residue composed of two anellated 6-membered carbon rings may be mentioned.

The number of substituents in such mono- or polycyclic hydrocarbyl residues may vary from 1 to 10, in particular 1 to 5 substituents. Suitable substituents of such cyclic residues are selected from lower alkyl, lower alkenyl, alkylidene, alkenylidene, or residues containing one hetero atom, like O or N, as for example —OH or —COOH. In particular, the substituents are independently selected from —OH, —COOH, methyl and methylidene.

The term "lower alkyl" or "short chain alkyl" represents saturated, straight-chain or branched hydrocarbon radicals having 1 to 4, 1 to 5, 1 to 6, or 1 to 7, in particular 1 to 4 carbon atoms. As examples there may be mentioned: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; and also n-heptyl, and the singly or multiply branched analogs thereof.

"Short chain alkenyl" or "lower alkenyl" represents mono- or polyunsaturated, especially monounsaturated, straight-chain or branched hydrocarbon radicals having 2 to 4, 2 to 6, or 2 to 7 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

An "alkylidene" group represents a straight chain or branched hydrocarbon substituent linked via a double bond to the body of the molecule. It comprises 1 to 6 carbon atoms. As examples of such "$C_1$-$C_6$-alkylidenes" there may be mentioned methylidene (═CH$_2$) ethylidene, (═CH—CH$_2$), n-propylidene, n-butylidene, n-pentlyiden, n-hexylidene and the constitutional isomers thereof, as for example iso-propylidene.

An "alkenylidene" represents the mono-unsaturated analogue of the above mentioned alkylidenes with more than 2 carbon atoms and may be called "$C_3$-$C_6$-alkenylidenes". n-propenylidene, n-butenylidene, n-pentenylidene, and n-hexenylidene may be mentioned as examples.

Unsaturated cyclic groups may contain 1 or more, as for example 1, 2 or 3 C═C bonds and are aromatic, or in particular nonaromatic.

Particular examples of cyclic residues are groups of the formula Cyc-A-, wherein A represents a straight chain or branched $C_1$-$C_4$-alkylene bridge, in particular methylene, and Cyc represents a mono- or polycyclic, in particular bicyclic, saturated or unsaturated hydrocarbyl residue, in particular a bicyclic annulated hydrocarbyl residue, comprising 5-7, in particular 6 ring atoms per cycle, optionally substituted with 1-10, 1-5 substituents which are independently selected from $C_1$-$C_4$-alkyl, $C_1$-$C_4$-alkylidene, $C_2$-$C_4$-alkenyl, oxo, hydroxy, or amino, in particular $C_1$-$C_4$-alkyl, like methyl, and $C_1$-$C_4$-alkylidene, like methylidene. Cyc-A represents in particular groups of the formulae IIIa, IIIb or IIIc

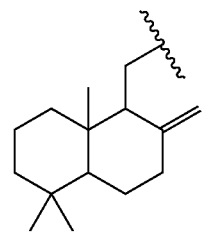

(IIIa)

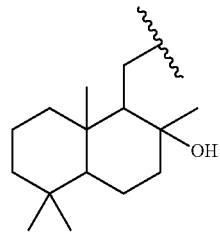

(IIIb)

-continued

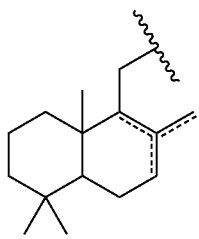

(IIIc)

Typical examples compounds containing such residues are those of formula (1) below, in particular copalol and labdendiol and their stereoisomers.

Non-limiting examples of $C_1$-$C_4$-alkyl are methyl, ethyl, n-propyl, 1-methylethyl, n-butyl, 1-methylpropyl, 2-methylpropyl, 1,1-dimethylethyl Non-limiting examples of $C_1$-$C_4$-alkylidene are methylidene (=$CH_2$), ethylidene, (=CH—$CH_3$), n-propylidene, n-butylidene, and the constitutional isomers thereof.

Non-limiting examples of $C_2$-$C_4$-alkenyl are ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, Non-limiting examples of $C_1$-$C_4$-alkylene are —$CH_2$—, —$(CH_2)_2$—, —$(CH_2)_3$—, —$(CH_2)_4$—, —$(CH_2)_2$—CH($CH_3$)—, —$CH_2$—CH($CH_3$)—$CH_2$—, A "precursor" molecule of a target compound as described herein is converted to said target compound, preferably through the enzymatic action of a suitable polypeptide performing at least one structural change on said precursor molecule. For example a "diphosphate precursor" (as for example a "terpenyl diphosphate precursor") is converted to said target compound (as for example a terpene alcohol) via enzymatic removal of the diphosphate moiety, for example by removal of mono- or diphosphate groups by a phosphatase enzyme. For example a "non-cyclic precursor" (like a non-cyclic terpenyl precursor") may be converted to the cyclic target molecule (like a cyclic terpene compound) through the action of a cyclase or synthase enzyme, irrespective of the particular enzymatic mechanism of such enzyme, in one or more steps.

A "terpene synthase" designates a polypeptide which converts a terpene precursor molecule to the respective terpene target molecule, like in particular a processed target terpene alcohol. Non-limiting examples of such terpene precursor molecules are for example non-cyclic compounds, selected from farnesyl pyrophosphate (FPP), geranylgeranyl-pyrophosphate (GGPP), or a mixture of isopentenyl pyrophosphate (IPP) and dimethyl allyl pyrophosphate (DMAPP). In case the obtained terpene contains a diphosphate moiety the synthase is designated "terpenyl diphosphate synthase"

The terms "terpenyl diphosphate synthase" or "polypeptide having terpenyl diphosphate synthase activity" or "terpenyl diphosphate synthase protein" or "having the ability to produce terpenyl diphosphate" relate to a polypeptide capable of catalyzing the synthesis of a terpenyl diphosphate, in the form of any of its stereoisomers or a mixture thereof, starting from an acyclic terpene pyrophosphate, particularly GPP, FPP or GGPP or to IPP together with DMAPP. The terpeny diphosphate may be the only product or may be part of a mixture of terpenyl phosphates. Said mixture may comprise terpenyl monophosphate and/or a terpene alcohol. The above definition also applies to the group of "bicyclic diterpenyl diphosphate synthases", which produce a bicyclic terpenyl diphosphate, like CPP or LPP.

As example of such "terpenyl diphosphate synthase" or "diterpenyl diphosphate synthase" enzymes there may be mentioned copalyl diphosphate synthase (CPS). Copalyldiphosphate may be the only product or may be part of a mixture of copalyl phosphates. Said mixture may comprise copalyl-monophosphate and/or other terpenyl diphosphate.

As example of such "terpenyl diphosphate synthase" or "diterpenyl diphosphate synthase" enzymes there may be mentioned and labdendiol diphosphate synthase (LPS). Labdendiol diphosphate may be the only product or may be part of a mixture of labdendiol phosphates. Said mixture may comprise labdendiol monophosphate and/or terpenyl diphosphate.

"Terpenyl diphosphate synthase activity" or "diterpenyl diphosphate synthase" (like CPS or LPS activity) is determined under "standard conditions" as described herein below: They can be determined using recombinant terpenyl diphosphate synthase expressing host cells, disrupted terpenyl diphosphate synthase expressing cells, fractions of these or enriched or purified terpenyl diphosphate synthase enzyme, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here in particular GGPP, either added at an initial concentration in the range of 1 to 100 μM mg/ml, preferably 5 to 50 μM, in particular 30 to 40 μM, or endogenously produced by the host cell. The conversion reaction to form a terpenyl diphosphate is conducted from 10 min to 5 h, preferably about 1 to 2 h. If no endogenous phosphatase is present, one or more exogenous phosphatases, for example an alkaline phosphatase, are added to the reaction mixture to convert the terpenyl diphosphate as formed by the synthase to the respective terpene alcohol. The terpene alcohol may then be determined in conventional matter, for example after extraction with an organic solvent, like ethyl acetate.

The term "protein tyrosine phosphatase" represents a group of enzymes that are generally known to remove phosphate groups from phosphorylated tyrosine residues on proteins. A particular subgroup of said family as described herein are enzymes useful to dephosphorylate phosphorylated terpene molecules.

The polypeptides of the invention having terpenyl diphosphate phosphatase activity are identified as member of the Protein tyrosine phosphatase family in particular of the Y_phosphatase3 family having the Pfam ID number PF13350. Polypeptides can be scanned for matches against the Pfam protein family signature databases, in particular in the Pfam 32.0 database release (September 2018), using for example the following web sites:
http://pfam.xfam.org/search#tabview=tab0,
https://www.ebi.ac.uk/Tools/hmmer/search/hmmscan or
https://www.ebi.ac.uk/Tools/pfa/pfamscan/.

The term "Pfam" refers to a large collection of protein domains and protein families maintained by the Pfam Consortium and available at several sponsored world wide web sites, including: pfam.sanger.ac.uk/ (Welcome Trust, Sanger Institute); pfam.sbc.su.se/ (Stockholm Bioinformatics Center) and pfam.janelia.org/ (Janelia Farm, Howard Hughes Medical Institute). The latest release of Pfam is Pfam 32.0 (September 2018), based on the UniProt Reference Proteomes (El-Gebali S. et al, 2019, Nucleic Acids Res. 47, Database issue D427-D432). Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment. (Unless otherwise specified, matches of a queried protein to a Pfam domain or family are Pfam-A matches) All identified sequences belonging to the family are then used to automatically generate a full alignment for the family (Sonnhammer (1998) Nucleic Acids Research 26, 320-322; Bateman (2000) Nucleic Acids Research 26, 263-266; Bateman (2004) Nucleic Acids Research 32, Database Issue, D138-D141; Finn (2006) Nucleic Acids Research Database Issue 34, D247-251; Finn (2010) Nucleic Acids Research Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain. Expectation values (e-values) can also be used as a criterion for inclusion of a queried protein in a Pfam or for determining whether a queried protein has a particular Pfam domain, where low e-values, much less than 1.0, for example less than 0.1, or less.

The "E-value" (expectation value) is the number of hits that would be expected to have a score equal to or better than this value, by chance alone. This means that a good E-value which gives a confident prediction is much less than 1. E-values around 1 is what is expected by chance. Thus, the lower the E-value, the more specific the search for domains will be. Only positive numbers are allowed. (definition by Pfam)) The terms "terpenyl diphosphate phosphatase" or "polypeptide having terpenyl diphosphate phosphatase activity" or "terpenyl diphosphate phosphatase protein" or "having the ability to produce terpene alcohol" relate to a polypeptide capable of catalyzing the removal (irrespective of a particular enzymatic mechanism) of a diphosphate moiety or monophosphate moieties, to form a dephosphorylated compound, in particular the corresponding alcohol compound of said terpenyl moiety. The terpene alcohol may be present in the product in any of its stereoisomers or as a mixture thereof. The terpene alcohol may be the only product or may be part of a mixture with other terpene compounds, as for example dephosphorylated analogs of the respective (for example non-cyclic) terpenyl diphosphate precursor of said terpenyl diphosphate. The above definition also applies to the group of "bicyclic terpenyl diphosphate phosphatase", which produce a bicyclic terpene alcohol, like copalol or labdendiol. Each of the above mentioned phosphatases exemplifies a "diphosphate removing enzyme".

As example of such "terpenyl diphosphate phosphatase" enzymes there may be mentioned copalyl diphosphate phosphatase (CPP phosphatase). Copalol may be the only product or may be part of a mixture with dephosphorylated precursors, like for example farnesol and/or geranylgeraniol; and/or side products resulting from enzymatic side activities in the reaction mixture, like esters or aldehydes of such alcohols or other cyclic or non-cyclic diterpenes.

As another example of such "terpenyl diphosphate phosphatase" enzymes there may be mentioned and labdendiol diphosphate phosphatase (LPP phosphatase). Labdendiol may be the only product or may be part of a mixture with dephosphorylated precursors, like for example farnesol and/or geranylgeraniol; and/or side products resulting from enzymatic side activities in the reaction mixture, like esters or aldehydes of such alcohols or other cyclic or non-cyclic diterpenes.

"Terpenyl diphosphate phosphatase activity" (like CPP or LPP phosphatase activity) is determined under "standard conditions" as described herein below: They can be determined using recombinant terpenyl diphosphate phosphatase expressing host cells, disrupted terpenyl diphosphate phosphatase expressing cells, fractions of these, or enriched or purified terpenyl diphosphate phosphatase enzyme, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here for example CPP or LPP, either added at an initial concentration in the range of 1 to 100 µM mg/ml, preferably 5 to 50 µM, in particular 30 to 40 µM, or endogenously produced by the host cell. The conversion reaction to form a terpenyl diphosphate is conducted from 10 min to 5 h, preferably about 1 to 2 h. The terpene alcohol may then be determined in conventional matter, for example after extraction with an organic solvent, like ethyl acetate.

Particular examples of suitable standard conditions may be taken from the Experimental Part below.

An "alcohol dehydrogenase" (ADH) in the context of the present invention refers to a polypeptide having the ability to oxidize an alcohol to the corresponding aldehyde in the presence of $NAD^+$ or $NADP^+$ as cofactor. Such enzymes are members of the E.C. families 1.1.1.1 ($NAD^+$ dependent) or 1.1.1.2 ($NADP^+$ dependent). More particularly, an ADH of the invention has the ability to oxidize copalol to copalal and/or labdendiol to the respective aldehyde.

"Copalol" as used herein designates (E)-5-[(1S,4aS,8aS)-5,5,8a-trimethyl-2-methylidene-3,4,4a,6,7,8-hexahydro-1H-naphthalen-1-yl]-3-methylpent-2-en-1-ol; CAS Registry Number 10395-43-4.

"Copalal" as used herein designates (2E)-3-methyl-5-[(1S,4aS,8aS)-5,5,8a-trimethyl-2-methylenedecahydro-1-naphthalenyl]-2-pentenal.

"Labdendiol" as used herein designates (1R,2R,4aS,8aS)-1-[(E)-5-hydroxy-3-methylpent-3-enyl]-2,5,5,8a-tetramethyl-3,4,4a,6,7,8-hexahydro-1H-naphthalen-2-ol; CAS Registry Number 10267-31-9.

"Manool as used herein designates 5-[(1S,4aS,8aS)-5,5,8a-trimethyl-2-methylidene-3,4,4a,6,7,8-hexahydro-1H-naphthalen-1-yl]-3-methylpent-1-en-3-ol (+)-Manoolxy as used herein designates 4-[(1S,4aS,8aS)-5,5,8a-trimethyl-2-methylenedecahydro-1-naphthalenyl]-2-butanone, "Z-11" as used herein designates (3S,5aR,7aS,11aS,11bR)-3,8,8,11a-tetramethyldodecahydro-3,5a-epoxynaphtho[2,1-c]oxepin.

"gamma-ambrol" as used herein designates 2-[(1S,4aS,8aS)-5,5,8a-trimethyl-2-methylenedecahydro-1-naphthalenyl]ethanol. and Ambrox® as used herein designates 3aR,5aS,9aS,9bR)-3a,6,6,9a-tetramethyldodecahydronaphtho[2,1-b]furan.

"Sclareolide" as used herein designates 3a,6,6,9a-tetramethyldecahydronaphtho[2,1-b]furan-2(1H)-one "DOL" as used herein designates (1R,2R,4aS,8aS)-1-(2-hydroxyethyl)-2,5,5,8a-tetramethyl-3,4,4a,6,7,8-hexahydro-1H-naphthalen-2-ol . . . CAS number 38419-75-9

"Farnesol" as used herein designates (2E,6E)-3,7,11-trimethyldodeca-2,6,10-trien-1-ol "Geranylgeraniol" as used herein designates (2E,6E,10E)-3,7,11,15-Tetramethylhexadeca-2,6,10,14-tetraen-1-ol.

More generically the following meanings apply:
For Z11-like compounds: 8,13:13,20-diepoxy-15,16-dinorlabdane (or diepoxy-dinorlabdane) of the general formula:

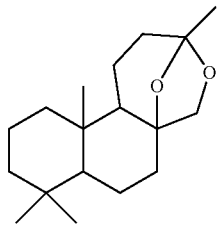

For Ambrox®-like compounds: 8,12-epoxy-13,14,15,16-tetranorlabdane (or epoxy-tetranorlabdane) of the general formula

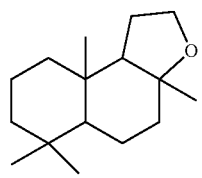

The terms "biological function," "function", "biological activity" or "activity" of a terpeyl synthase refer to the ability of a terpenyl diphosphate synthase as described herein to catalyze the formation of at least one terpenyl diphosphate from the corresponding precursor terpene.

The terms "biological function," "function", "biological activity" or "activity" of a terpenyl diphosphate phosphatase refer to the ability of the terpenyl diphosphate phosphatase as described herein to catalyze the removal of a diphosphate group from said terpenyl compound to form the corresponding terpene alcohol.

The "mevalonate pathway" also known as the "isoprenoid pathway" or "HMG-CoA reductase pathway" is an essential metabolic pathway present in eukaryotes, archaea, and some bacteria. The mevalonate pathway begins with acetyl-CoA and produces two five-carbon building blocks called isopentenyl pyrophosphate (IPP) and dimethyl allyl pyrophosphate (DMAPP). Key enzymes are acetoacetyl-CoA thiolase (atoB), HMG-CoA synthase (mvaS), HMG-CoA reductase (mvaA), mevalonate kinase (MvaK1), phosphomevalonate kinase (MvaK2), a mevalonate diphosphate decarboxylase (MvaD), and an isopentenyl diphosphate isomerase (idi). Combining the mevalonate pathway with enzyme activity to generate the terpene precursors GPP, FPP or GGPP, like in particular FPP synthase (ERG20), allows the recombinant cellular production of terpenes.

As used herein, the term "host cell" or "transformed cell" refers to a cell (or organism) altered to harbor at least one nucleic acid molecule, for instance, a recombinant gene encoding a desired protein or nucleic acid sequence which upon transcription yields at least one functional polypeptide of the present invention, i.p. a terpenyl diphosphate synthase protein or terpenyl diphosphate phosphatase enzyme as defined herein above. The host cell is particularly a bacterial cell, a fungal cell or a plant cell or plants. The host cell may contain a recombinant gene or several genes, as for example organized as an operon, which has been integrated into the nuclear or organelle genomes of the host cell. Alternatively, the host may contain the recombinant gene extra-chromosomally.

The term "organism" refers to any non-human multicellular or unicellular organism such as a plant, or a microorganism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing FPP" when it produces FPP naturally or when it does not produce FPP naturally but is transformed to produce FPP with a nucleic acid as described herein. Organisms or cells transformed to produce a higher amount of FPP than the naturally occurring organism or cell are also encompassed by the "organisms or cells capable of producing FPP".

A particular organism or cell is meant to be "capable of producing GGPP" when it produces GGPP naturally or when it does not produce GGPP naturally but is transformed to produce GGPP with a nucleic acid as described herein. Organisms or cells transformed to produce a higher amount of GGPP than the naturally occurring organism or cell are also encompassed by the "organisms or cells capable of producing GGPP".

A particular organism or cell is meant to be "capable of producing terpenyl diphosphate" when it produces a terpenyl diphosphate as defined herein naturally or when it does not produce said diphosphate naturally but is transformed to produce said diphosphate with a nucleic acid as described herein. Organisms or cells transformed to produce a higher amount of terpenyl diphosphate than the naturally occurring organism or cell are also encompassed by the "organisms or cells capable of producing a terpenyl diphosphate".

A particular organism or cell is meant to be "capable of producing terpene alcohol" when it produces a terpene alcohol as defined herein naturally or when it does not produce said alcohol naturally but is transformed to produce said alcohol with a nucleic acid as described herein. Organisms or cells transformed to produce a higher amount of a terpene alcohol than the naturally occurring organism or cell are also encompassed by the "organisms or cells capable of producing a terpene alcohol".

For the descriptions herein and the appended claims, the use of "or" means "and/or" unless stated otherwise. Similarly, "comprise", "comprises", "comprising", "include", "includes", and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

The terms "purified", "substantially purified", and "isolated" as used herein refer to the state of being free of other, dissimilar compounds with which a compound of the invention is normally associated in its natural state, so that the "purified", "substantially purified", and "isolated" subject comprises at least 0.5%, 1%, 5%, 10%, or 20%, or at least 50% or 75% of the mass, by weight, of a given sample. In one embodiment, these terms refer to the compound of the invention comprising at least 95, 96, 97, 98, 99 or 100%, of the mass, by weight, of a given sample. As used herein, the terms "purified," "substantially purified," and "isolated" when referring to a nucleic acid or protein, or nucleic acids or proteins, also refers to a state of purification or concentration different than that which occurs naturally, for example in an prokaryotic or eukaryotic environment, like, for example in a bacterial or fungal cell, or in the mammalian organism, especially human body. Any degree of purification or concentration greater than that which occurs naturally, including (1) the purification from other associated structures or compounds or (2) the association with structures or compounds to which it is not normally associated in said prokaryotic or eukaryotic environment, are within the meaning of "isolated". The nucleic acid or protein or classes of nucleic acids or proteins, described herein, may be isolated, or otherwise associated with structures or compounds to which they are not normally associated in nature, according to a variety of methods and processes known to those of skill in the art.

The term "about" indicates a potential variation of ±25% of the stated value, in particular ±15%, ±10%, more particularly ±5%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99,9%, more particularly 85 to 98,5%, like 95 to 99%.

A "main product" in the context of the present invention designates a single compound or a group of at least 2 compounds, like 2, 3, 4, 5 or more, particularly 2 or 3 compounds, which single compound or group of compounds is "predominantly" prepared by a reaction as described herein, and is contained in said reaction in a predominant proportion based on the total amount of the constituents of the product formed by said reaction. Said proportion may be a molar proportion, a weight proportion or, preferably based on chromatographic analytics, an area proportion calculated from the corresponding chromatogram of the reaction products.

A "side product" in the context of the present invention designates a single compound or a group of at least 2 compounds, like 2, 3, 4, 5 or more, particularly 2 or 3 compounds, which single compound or group of compounds is not "predominantly" prepared by a reaction as described herein.

Because of the reversibility of enzymatic reactions, the present invention relates, unless otherwise stated, to the enzymatic or biocatalytic reactions described herein in both directions of reaction.

"Functional mutants" of herein described polypeptides include the "functional equivalents" of such polypeptides as defined below.

The term "stereoisomers" includes conformational isomers and in particular configuration isomers.

Included in general are, according to the invention, all "stereoisomeric forms" of the compounds described herein, such as "constitutional isomers" and "stereoisomers".

"Stereoisomeric forms" encompass in particular, "stereoisomers" and mixtures thereof, e.g. configuration isomers (optical isomers), such as enantiomers, or geometric isomers (diastereomers), such as E- and Z-isomers, and combinations thereof. If one or more asymmetric centers are present in one molecule, the invention encompasses all combinations of different conformations of these asymmetry centers, e.g. enantiomeric pairs "Stereoselectivity" describes the ability to produce a particular stereoisomer of a compound in a stereoisomerically pure form or to specifically convert a particular stereoisomer in an enzyme catalyzed method as described herein out of a plurality of stereoisomers. More specifically, this means that a product of the invention is enriched with respect to a specific stereoisomer, or an educt may be depleted with respect to a particular stereoisomer. This may be quantified via the purity % ee-parameter calculated according to the formula:

$$\% \; ee = [X_A - X_B]/[X_A + X_B] * 100,$$

wherein $X_A$ and $X_B$ represent the molar ratio (Molenbruch) of the stereoisomers A and B.

The terms "selectively converting" or "increasing the selectivity" in general means that a particular stereoisomeric form, as for example the E-form, of an unsaturated hydrocarbon, is converted in a higher proportion or amount (compared on a molar basis) than the corresponding other stereoisomeric form, as for example Z-form, either during the entire course of said reaction (i.e. between initiation and termination of the reaction), at a certain point of time of said reaction, or during an "interval" of said reaction. In particular, said selectivity may be observed during an "interval" corresponding 1 to 99%, 2 to 95%, 3 to 90%, 5 to 85%, 10 to 80%, 15 to 75%, 20 to 70%, 25 to 65%, 30 to 60%, or 40 to 50% conversion of the initial amount of the substrate. Said higher proportion or amount may, for example, be expressed in terms of:

a higher maximum yield of an isomer observed during the entire course of the reaction or said interval thereof;

a higher relative amount of an isomer at a defined % degree of conversion value of the substrate; and/or an identical relative amount of an isomer at a higher % degree of conversion value;

each of which preferably being observed relative to a reference method, said reference method being performed under otherwise identical conditions with known chemical or biochemical means.

Generally also comprised in accordance with the invention are all "isomeric forms" of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

"Yield" and/or the "conversion rate" of a reaction according to the invention is determined over a defined period of, for example, 4, 6, 8, 10, 12, 16, 20, 24, 36 or 48 hours, in which the reaction takes place. In particular, the reaction is carried out under precisely defined conditions, for example at "standard conditions" as herein defined.

The different yield parameters ("Yield" or $Y_{P/S}$; "Specific Productivity Yield"; or Space-Time-Yield (STY)) are well known in the art and are determined as described in the literature.

"Yield" and "$Y_{P/S}$" (each expressed in mass of product produced/mass of material consumed) are herein used as synonyms.

The specific productivity-yield describes the amount of a product that is produced per h and L fermentation broth per g of biomass. The amount of wet cell weight stated as WCW describes the quantity of biologically active microorganism in a biochemical reaction. The value is given as g product per g WCW per h (i.e. g/gWCW$^{-1}$h$^{-1}$). Alternatively, the quantity of biomass can also be expressed as the amount of dry cell weight stated as DCW. Furthermore, the biomass concentration can be more easily determined by measuring the optical density at 600 nm ($OD_{600}$) and by using an experimentally determined correlation factor for estimating the corresponding wet cell or dry cell weight, respectively.

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean a liquid, particularly aqueous or aqueous/organic solution which is based on a fermentative process and has not been worked up or has been worked up, for example, as described herein.

An "enzymatically catalyzed" or "biocatalytic" method means that said method is performed under the catalytic action of an enzyme, including enzyme mutants, as herein defined. Thus the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein.

If the present disclosure refers to features, parameters and ranges thereof of different degree of preference (including general, not explicitly preferred features, parameters and ranges thereof) then, unless otherwise stated, any combination of two or more of such features, parameters and ranges thereof, irrespective of their respective degree of preference, is encompassed by the disclosure of the present description.

DETAILED DESCRIPTION a. Particular Embodiments of the Invention

The present invention relates to the following particular embodiments:
1. A first main embodiment relates to a biocatalytic method of producing a terpene alcohol compound, of the general formula 1

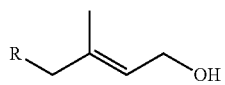

(1)

wherein
R represents H or, more particularly, a cyclic or non-cyclic, linear or branched, saturated or unsaturated, optionally substituted hydrocarbyl residue, preferably having a total carbon number dividable by 5, in particular 5, 10, 15 or 20, more particularly 10 or 15
comprising the steps of
(1) contacting the corresponding terpenyl diphosphate precursor of said terpene compound of formula (1) with a polypeptide having terpenyl-diphosphate phosphatase activity, as for example having mono-, sesqui- or diterpenyl-diphosphate phosphatase activity, to form said terpene alcohol; and
(2) optionally isolating the terpene alcohol of step (1),
wherein said polypeptide having terpenyl-diphosphate phosphatase activity is selected from a diphosphate removing enzyme member of the protein tyrosine phosphatase family.

Polypeptide of this embodiment with "terpenyl diphosphate phosphatase activity" are identified as member of the Protein tyrosine phosphatase family in particular of the Y_phosphatase3 family having the Pfam ID number PF13350.

Figure 16A:
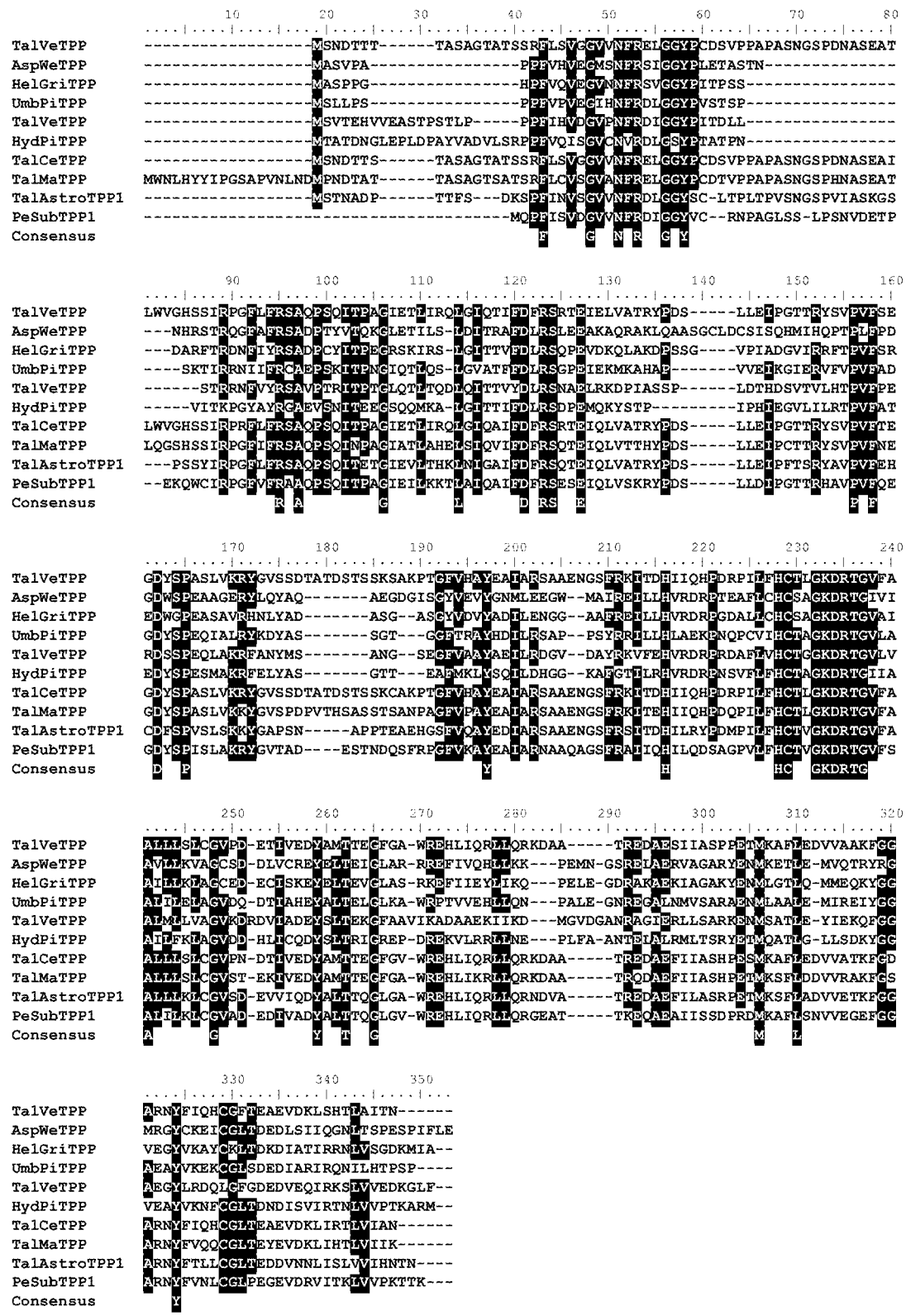
FIG. 16A. Alignment of the amino acid sequences of the terpenyl-diphosphate phosphatase and deduced consensus sequence. Conserved residues are in white letters on black background.
Figure 16B:
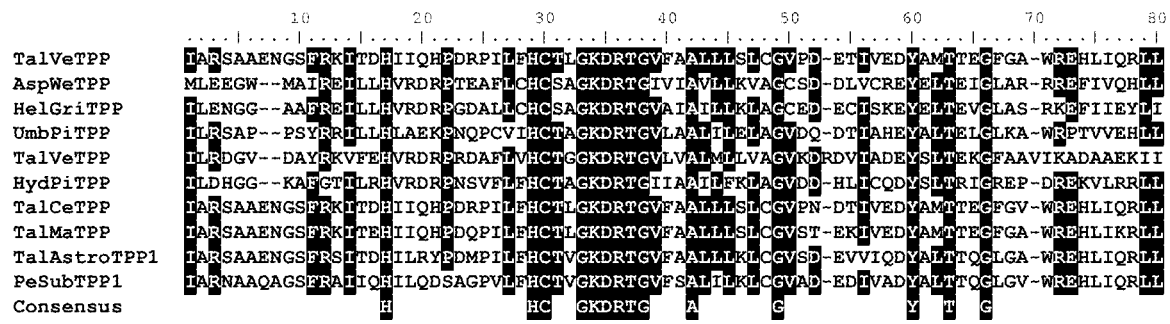
FIG. 16B. Alignment of the amino acid sequences of the conserved motif region of the terpenyl-diphosphate phosphatase and deduced consensus sequence. Conserved residues are in white letters on black background.

2. A second main embodiment of the invention relates to a biocatalytic method of producing a bicyclic diterpene alcohol compound,
comprising the steps of
a) contacting the corresponding bicyclic diterpenyl diphosphate precursor of said bicyclic diterpene compound with a polypeptide having terpenyl-diphosphate phosphatase activity, as for example having diterpenyl-diphosphate phosphatase activity or, more particularly, bicyclic diterpenyl-diphosphate phosphatase activity, to form said bicyclic diterpene alcohol; and
b) optionally isolating the bicyclic diterpene alcohol of step (1).
Polypeptide of this embodiment with "terpenyl diphosphate phosphatase activity" are identified as member of the Protein tyrosine phosphatase family in particular of the Y_phosphatase3 family having the Pfam ID number PF13350.
3. The method of embodiment 2, wherein said polypeptide having terpenyl-diphosphate phosphatase activity is selected from a diphosphate removing enzyme member of the protein tyrosine phosphatase family.
4. The method of embodiment 1 or 3, wherein said polypeptide having terpenyl-diphosphate phosphatase activity is selected form a class of diphosphate removing enzymes characterized by an amino acid sequence having the following active site signature motif:

HCxxGxxR (SEQ ID NO: 57)

wherein
each x independently of each other represents any natural amino acid residue.
5. The method of embodiment 4, wherein said active site signature motif is:

HC(T/S)xGKDRTG (SEQ ID NO: 58)

wherein
x represents any natural amino acid residue, and is, for example selected from the residues L, A, G and V.
In another embodiment said polypeptide having terpenyl-diphosphate phosphatase activity comprises an amino acid consensus sequence motif as depicted in FIG. 16b.
6. The method of anyone of the preceding embodiments, wherein said polypeptide having terpenyl-diphosphate phosphatase activity is selected from the group consisting of the polypeptides:
a) TalVeTPP comprising an amino acid sequence according to SEQ ID NO: 2,
b) AspWeTPP comprising an amino acid sequence according to SEQ ID NO: 6,
c) HelGriTPP comprising an amino acid sequence according to SEQ ID NO: 10,
d) UmbPiTPP1, comprising an amino acid sequence according to SEQ ID NO: 13,
e) TalVeTPP2, comprising an amino acid sequence according to SEQ ID NO: 16, f) HydPiTPP1, comprising an amino acid sequence according to SEQ ID NO: 19,
g) TalCeTPP1, comprising an amino acid sequence according to SEQ ID NO: 22,
h) TalMaTPP1, comprising an amino acid sequence according to SEQ ID NO: 25,
i) TalAstroTPP1 comprising an amino acid sequence according to SEQ ID NO: 28, and
j) PeSubTPP1 comprising an amino acid sequence according to SEQ ID NO: 31, and
k) a polypeptide having terpenyl-diphosphate phosphatase activity and comprising an amino acid sequence showing a degree of sequence identity of at least 60%, 65%, 70%, 75%, 80%, 85%, 90%, 95%, 96%, 97%, 98%, or 99% to at least one of said amino acid sequence according to a) to j).

7. The method of anyone of the embodiments 1 and 4 to 6, wherein a terpene alcohol compound of the general formula 1 is prepared, wherein R represents H or, more particularly, a non-cyclic, linear or branched, saturated or unsaturated, hydrocarbyl residue, preferably having a total carbon number dividable by 5, as for example 5, 10, 15 or 20.

8. The method of embodiment 7 wherein the terpene alcohol of formula 1 is selected from farnesol and geranylgeraniol.

9. The method of anyone of the embodiments 2 to 6, wherein step (1) also comprises contacting a non-cyclic terpenyl diphosphate precursor with a polypeptide having bicyclic diterpenyl diphosphate synthase activity to form said bicyclic diterpenyl diphosphate precursor.

10. The method of embodiment 9, wherein said bicyclic diterpenyl diphosphate synthase is selected from
a) SmCPS2 comprising an amino acid sequence according to SEQ ID NO: 34,
b) TaTps1-del59 comprising an amino acid sequence according to SEQ ID NO: 40,
c) SsLPS comprising an amino acid sequence according to SEQ ID NO: 38, and
d) a polypeptide having bicyclic diterpenyl diphosphate synthase activity and comprising an amino acid sequence showing a degree of sequence identity of at least 60%, 65%, 70%, 75%, 80%, 85%, 90%, 95%, 96%, 97%, 98%, or 99% to at least one of said amino acid sequences according to a), b) and c).

11. The method of anyone of the embodiments 2 to 6, 9 and 10, wherein said biocatalytically produced bicyclic diterpene alcohol is selected from copalol, in particular (+)-copalol and labdendiol each either in essentially pure stereoisomeric form or in the form of a mixture of at least two stereoisomers.

12. The method of anyone of the preceding embodiments further comprising as step (3) the processing of the terpene alcohol of step (1) or of step (2) to an alcohol derivative using chemical or biocatalytic synthesis or a combination of both.

13. The method of embodiment 12, wherein the derivative is a hydrocarbon, alcohol, diol, triol, acetal, ketal, aldehyde, acid, ether, amide, ketone, lactone, epoxide, acetate, glycoside and/or an ester.

14. The method of embodiment 12 or 13, wherein said terpene alcohol is biocatalytically oxidized.

15. The method of embodiment 14, wherein said terpene alcohol is converted by contacting with an alcohol dehydrogenase (ADH).

16. The method of embodiment 15, wherein said ADH is selected from a) CymB comprising an amino acid sequence according to SEQ ID NO:42;
b) AspWeADH1 comprising an amino acid sequence according to SEQ ID NO: 44;
c) PsAeroADH1 comprising an amino acid sequence according to SEQ ID NO: 46;
d) AzTolADH1 comprising an amino acid sequence according to SEQ ID NO: 48;
e) AroAroADH1 comprising an amino acid sequence according to SEQ ID NO: 50;
f) ThTerpADH1 comprising an amino acid sequence according to SEQ ID NO: 52;
g) CdGeoA comprising an amino acid sequence according to SEQ ID NO: 54;
h) VoADH1 comprising an amino acid sequence according to SEQ ID NO: 56; and
i) a polypeptide having ADH activity and comprising an amino acid sequence showing a degree of sequence identity of at least 60%, 65%, 70%, 75%, 80%, 85%, 90%, 95%, 96%, 97%, 98%, or 99% to at least one of said amino acid sequence according to a) to h).

17. The method of anyone of the embodiments 2 to 6 and 9 to 11 for the biocatalytic production of copalol, comprising the steps of
(1) contacting copalyl diphosphate with a polypeptide having copalyl diphosphate (CPP) phosphatase activity to form copalol either in essentially pure stereoisomeric form, in particular (+)-copalol, or in the form of a mixture of at least two stereoisomers; and
(2) optionally isolating copalol of step (1).

18. The method of embodiment 17, wherein said polypeptide having copalyl diphosphate phosphatase activity is selected from the group consisting of the polypeptides:
a) TalVeTPP, comprising an amino acid sequence according to SEQ ID NO: 2,
b) AspWeTPP, comprising an amino acid sequence according to SEQ ID NO: 6,
c) HelGriTPP, comprising an amino acid sequence according to SEQ ID NO: 10,
d) UmbPiTPP1, comprising an amino acid sequence according to SEQ ID NO: 13,
e) TalVeTPP2, comprising an amino acid sequence according to SEQ ID NO: 16,
f) HydPiTPP1, comprising an amino acid sequence according to SEQ ID NO: 19,
g) TalCeTPP1, comprising an amino acid sequence according to SEQ ID NO: 22,
h) TalMaTPP1, comprising an amino acid sequence according to SEQ ID NO: 25,
i) TalAstroTPP1, comprising an amino acid sequence according to SEQ ID NO: 28, and
j) PeSubTPP1, comprising an amino acid sequence according to SEQ ID NO: 31, and
k) a polypeptide having copalyl diphosphate phosphatase activity and comprising an amino acid sequence showing a degree of sequence identity of at least 60%, 65%, 70%, 75%, 80%, 85%, 90%, 95%, 96%, 97%, 98%, or 99% to at least one of said amino acid sequence according to a) to j).

19. The method of anyone of the embodiments 17 and 18, wherein step (1) also comprises the biocatalytic conversion of a terpene pyrophosphate, as for example geranylgeranyl-pyrophosphate (GGPP), or a mixture of isopentenyl pyrophosphate (IPP) and dimethyl allyl pyrophosphate (DMAPP), to copalyl diphosphate (CPP) through the catalytic action of a copalyl pyrophosphate synthase (CPS).

20. The method of embodiment 19, wherein said CPS is selected from
   a) SmCPS2 comprising an amino acid sequence according to SEQ ID NO: 34,
   b) TaTps1-del59 comprising an amino acid sequence according to SEQ ID NO: 40, and
   c) a polypeptide having copalyl pyrophosphate synthase activity and comprising an amino acid sequence showing a degree of sequence identity of at least 60%, 65%, 70%, 75%, 80%, 85%, 90%, 95%, 96%, 97%, 98%, or 99% to at least one of said amino acid sequences according to a) and b).
21. The method of anyone of the embodiments 17 to 20 further comprising as step (3) the processing of the copalol of step (1) or of step (2) to a copalol derivative using chemical or biocatalytic synthesis or a combination of both.
22. The method of embodiment 21, wherein the derivative is a hydrocarbon, alcohol, diol, triol, acetal, ketal, aldehyde, acid, ether, amide, ketone, lactone, epoxide, acetate, glycoside and/or an ester.
23. The method of embodiment 21 or 22, wherein copalol is biocatalytically oxidized.
24. The method of embodiment 23, wherein copalol is oxidized by contacting with an alcohol dehydrogenase (ADH).
25. The method of embodiment 24, wherein said ADH is selected from
   a) CymB comprising an amino acid sequence according to SEQ ID NO:42;
   b) AspWeADH1 comprising an amino acid sequence according to SEQ ID NO: 44;
   c) PsAeroADH1 comprising an amino acid sequence according to SEQ ID NO: 46;
   d) AzTolADH1 comprising an amino acid sequence according to SEQ ID NO: 48;
   e) AroAroADH1 comprising an amino acid sequence according to SEQ ID NO: 50;
   f) ThTerpADH1 comprising an amino acid sequence according to SEQ ID NO: 52;
   g) CdGeoA comprising an amino acid sequence according to SEQ ID NO: 54;
   h) VoADH1 comprising an amino acid sequence according to SEQ ID NO: 56; and
   i) a polypeptide having ADH activity comprising an amino acid sequence showing a degree of sequence identity of at least 60%, 65%, 70%, 75%, 80%, 85%, 90%, 95%, 96%, 97%, 98%, or 99% to at least one of said amino acid sequence according to a) to h).
26. The method of embodiment 1 for the biocatalytic production of labdendiol, comprising the steps of
   (1) contacting labdendiol diphosphate (also designated as labda-13-en-8-ol diphosphate or 8α-hydroxycopalyl diphosphate) with a polypeptide having labdendiol diphosphate (LPP) phosphatase activity to form labdendiol either in essentially pure stereoisomeric form or in the form of a mixture of at least two stereoisomers; and
   (2) optionally isolating labdendiol of step (1).
27. The method of embodiment 26 wherein said polypeptide having LPP phosphatase activity is selected from the group consisting of the polypeptides:
   a) TalVeTPP, comprising an amino acid sequence according to SEQ ID NO: 2,
   b) AspWeTPP, comprising an amino acid sequence according to SEQ ID NO: 6,
   c) HelGriTPP, comprising an amino acid sequence according to SEQ ID NO: 10,
   d) UmbPiTPP1, comprising an amino acid sequence according to SEQ ID NO: 13,
   e) TalVeTPP2, comprising an amino acid sequence according to SEQ ID NO: 16,
   f) HydPiTPP1, comprising an amino acid sequence according to SEQ ID NO: 19,
   g) TalCeTPP1, comprising an amino acid sequence according to SEQ ID NO: 22,
   h) TalMaTPP1, comprising an amino acid sequence according to SEQ ID NO: 25,
   i) TalAstroTPP1, comprising an amino acid sequence according to SEQ ID NO: 28, and
   j) PeSubTPP1, comprising an amino acid sequence according to SEQ ID NO: 31, and
   k) a polypeptide having LPP phosphatase activity and comprising an amino acid sequence showing a degree of sequence identity of at least 60%, 65%, 70%, 75%, 80%, 85%, 90%, 95%, 96%, 97%, 98%, or 99% to at least one of said amino acid sequence according to a) to j).
28. The method of anyone of the embodiments 26 and 27, wherein step (1) also comprises the biocatalytic conversion of a terpene pyrophosphate, as for example geranylgeranyl-pyrophosphate (GGPP), or a mixture of isopentenyl pyrophosphate (IPP) and dimethyl allyl pyrophosphate (DMAPP), to labdendiol diphosphate (LPP) through the catalytic action of a labdendiol pyrophosphate synthase (LPS).
29. The method of embodiment 28, wherein said LPS is selected from
   a) SsLPS comprising an amino acid sequence according to SEQ ID NO: 38, and
   b) a polypeptide having labdendiol pyrophosphate synthase activity and comprising an amino acid sequence showing a degree of sequence identity of at least 60%, 65%, 70%, 75%, 80%, 85%, 90%, 95%, 96%, 97%, 98%, or 99% to at least one of said amino acid sequence according to a).
30. The method of anyone of the embodiments 26 to 29 further comprising as step (3) the processing of the labdendiol of step (1) or of step (2) to a labdendiol derivative using chemical or biocatalytic synthesis or a combination of both.
31. The method of embodiment 30, wherein the derivative is a hydrocarbon, alcohol, diol, triol, acetal, ketal, aldehyde, acid, ether, amide, ketone, lactone, epoxide, acetate, glycoside and/or an ester.
32. The method of embodiment 30 or 31, wherein labdendiol is biocatalytically oxidized.
33. The method of embodiment 32, wherein labdendiol is oxidized by contacting with an alcohol dehydrogenase (ADH).
34. The method of embodiment 33, wherein said ADH is selected from
   a) CymB comprising an amino acid sequence according to SEQ ID NO:42;
   b) AspWeADH1 comprising an amino acid sequence according to SEQ ID NO: 44;
   c) PsAeroADH1 comprising an amino acid sequence according to SEQ ID NO: 46;
   d) AzTolADH1 comprising an amino acid sequence according to SEQ ID NO: 48;
   e) AroAroADH1 comprising an amino acid sequence according to SEQ ID NO: 50;

f) ThTerpADH1 comprising an amino acid sequence according to SEQ ID NO: 52;
g) CdGeoA comprising an amino acid sequence according to SEQ ID NO: 54;
h) VoADH1 comprising an amino acid sequence according to SEQ ID NO: 56;
i) SCH23-ADH1 comprising an amino acid sequence according to SEQ ID NO: 68
j) SCH24-ADH1a comprising an amino acid sequence according to SEQ ID NO: 70; and
k) a polypeptide having ADH activity comprising an amino acid sequence showing a degree of sequence identity of at least 60%, 65%, 70%, 75%, 80%, 85%, 90%, 95%, 96%, 97%, 98%, or 99% to at least one of said amino acid sequence according to a) to j).

35. The method of anyone of the embodiments 19 and 28, wherein said method also comprises the biocatalytic formation of GGPP from farnesyl pyrophosphate (FPP) through the catalytic action of a geranylgeranyl pyrophosphate synthase (GGPS).

36. The method of embodiment 35, wherein said GGPS is selected from
a) a polypeptide comprising an amino acid sequence according to SEQ ID NO: 36, and
b) a polypeptide having geranylgeranyl pyrophosphate synthase activity and comprising an amino acid sequence showing a degree of sequence identity of at least 60%, 65%, 70%, 75%, 80%, 85%, 90%, 95%, 96%, 97%, 98%, or 99% to at least one of said amino acid sequence according to a).

37. The method of anyone of the preceding embodiments performed in vitro or in vivo.

38. The method of anyone of the preceding embodiments performed in vivo, which comprises prior to step (1) introducing into a non-human host organism or cell and optionally stably integrated into the respective genome; one or more nucleic acid molecules encoding one or more polypeptides having the enzyme activities required for performing the respective biocatalytic conversion step or steps.

39. The method of embodiment 38, wherein said nucleic acids as introduced into said non-human host organism or cell are encoding
a) at least one polypeptide having terpenyl-diphosphate phosphatase activity, in particular bicyclic diterpenyl-diphosphate phosphatase activity; and optionally
b) at least one polypeptide having terpenyl-diphosphate synthase activity, in particular bicyclic diterpenyl-diphosphate synthase activity, and/or
c) at least one polypeptide having ADH activity; and/or
d) at least one polypeptide having acyclic terpenyl-diphosphate synthase activity, in particular acyclic diterpenyl-diphosphate synthase activity.

40. The method of embodiment 39, wherein said nucleic acids as introduced into said non-human host organism or cell are encoding
a) at least one polypeptide having bicyclic diterpenyl-diphosphate phosphatase activity which is selected from the polypeptides as defined in embodiment 6; or encoded by a nucleotide sequence selected from SEQ ID NO: 1, 3, 4, 5, 7, 8, 9, 11, 12, 14, 15, 17, 18, 20, 21, 23, 24, 26, 27, 29, 30 and 32; or a nucleotide sequence having at least 60%, 65%, 70%, 75%, 80%, 85%, 90%, 95%, 96%, 97%, 98%, or 99% sequence identity to anyone of said sequences; and optionally at least one of the following
b) at least one polypeptide having bicyclic diterpenyl-diphosphate synthase activity which is selected from the polypeptides as defined in embodiment 10; or encoded by a nucleotide sequence selected from SEQ ID NO: 33, 37 and 39; or a nucleotide sequence having at least 60%, 65%, 70%, 75%, 80%, 85%, 90%, 95%, 96%, 97%, 98%, or 99% sequence identity to anyone of said sequences;
c) at least one polypeptide having ADH activity which is selected from the polypeptides as defined in embodiment 16; or encoded by a nucleotide sequence selected from SEQ ID NO: 41, 43, 45, 47, 49, 51, 53, and 55; or a nucleotide sequence having at least 60%, 65%, 70%, 75%, 80%, 85%, 90%, 95%, 96%, 97%, 98%, or 99% sequence identity to anyone of said sequences;
d) at least one polypeptide having acyclic diterpenyl-diphosphate synthase activity as defined in embodiment 36; or encoded by a nucleotide sequence selected from SEQ ID NO:35 or a nucleotide sequence having at least 60%, 65%, 70%, 75%, 80%, 85%, 90%, 95%, 96%, 97%, 98%, or 99% sequence identity to said sequence.

41. The method of anyone of the embodiments 38 to 40, performed by applying a non-human host organism or cell endogenously producing FPP and/or GGPP; or a mixture of IPP and DMAPP; or a non-human host organism which is genetically modified to produce increased amounts of FPP and/or of GGPP and/or of a mixture of IPP and DMAPP.

Some of these host cells or organisms do not produce FPP or GGPP or a mixture of IPP and DMAPP naturally or do not produce FPP or GGPP or a mixture of IPP and DMAPP endogenously in an amount considered too low and which therefore should be increased. To be suitable to carry out the method of an embodiment as described herein, organisms or cells that do not produce an acyclic terpene pyrophosphate precursor, e.g. FPP or GGPP or a mixture of IPP and DMAPP, naturally or produce said compounds in sub-optimal quantity, are genetically modified to produce said precursor. They can be, for example, so transformed either before the modification with the nucleic acid described according to any of the above embodiments or simultaneously. Methods to transform organisms so that they produce an acyclic terpene pyrophosphate precursor, e.g. FPP or GGPP or a mixture of IPP and DMAPP, are already known in the art. For example, introducing enzyme activities of the mevalonate pathway, the isopreoid pathway or the MEP pathway, in particular the mevalonate pathway, is a suitable strategy to make the organism produce FPP or GGPP or a mixture of IPP and DMAPP.

42. The method of anyone of the embodiments 38 to 41, wherein said non-human host organism or cell is an eukaryote or a prokaryote, in particular a plant, a bacterium or a fungus, in particular a yeast.

43. The method of embodiment 42, wherein said bacterium is of the genus *Escherichia*, in particular *E. coli* and said yeast is of the genus *Saccharomyces*, in particular *S. cerevisiae*.

44. The method of embodiment 42, wherein said cell is a plant cell.

45. A non-human host organism or cell as defined to any one of embodiments 38 to 44.

46. A recombinant nucleic acid construct comprising at least one nucleic acid molecule as defined in anyone of the embodiments 38 to 44.

47. An expression vector comprising at least one nucleic acid construct of embodiment 46.
48. The expression vector of embodiment 47, wherein the vector is a prokaryotic vector, viral vector, a eukaryotic vector, or one or more plasmids.
49. A recombinant non-human host organism or cell as defined in embodiment 45, transformed with at least one nucleic acid construct of embodiment 46 or at least one vector of embodiment 47 or 48.
50. A polypeptide having terpenyl-diphosphate phosphatase activity, in particular bicyclic diterpenyl-diphosphate phosphatase activity, which is selected from a diphosphate removing enzyme member of the protein tyrosine phosphatase family and mutants or variants thereof; wherein said polypeptide catalyses the conversion of a terpenyl diphosphate to the respective terpene alcohol, preferably with a selectivity of >50%, as for example >60, 70, 80, 90, 95 or 99%. In particular it catalyzes the conversion of at least one terpenyl diphosphate, selected from CPP and LPP to the respective terpene alcohol copalol and labdendiol, preferably with a selectivity of >50%, as for example >60, 70, 80, 90, 95 or 99%.

Polypeptides of this embodiment with "terpenyl diphosphate phosphatase activity" are identified as member of the Protein tyrosine phosphatase family in particular of the Y_phosphatase3 family having the Pfam ID number PF13350.

In particular, a polypeptide of the invention having "terpenyl diphosphate phosphatase activity" is identified as member of the Protein tyrosine phosphatase family in particular of the Y_phosphatase3 family having the Pfam ID number PF13350 if the bit score is greater than or equal to the gathering threshold for the Pfam domain. Expectation values (e-values) can also be used as a criterion for inclusion of a queried protein in a Pfam family or for determining whether a queried protein has a particular Pfam domain. Matches with said domain have an e-value of less than $1 \times 10^{-5}$ or less than $1 \times 10^{-10}$, or less than $1 \times 10^{-20}$, as for example in the range of $1 \times 10^{-40}$ to $7.40 \times 10^{-80}$ or in the range of $1 \times 10^{-45}$ to $1 \times 10^{-70}$, like $3.50 \times 10^{-50}$ to $7.40 \times 10^{-66}$. As the query sequence the sequence of a polypeptide having "terpenyl diphosphate phosphatase activity" is applied.

For example, the following websites may be applied for the search and calculating such e-value: https://pfam.xfam.org/search#tabview=tab0 or https://www.ebi.ac.uk/Tools/hmmer/.

In one preferred alternative such phosphatase enzyme also converts FPP and/or GGPP to the respective alcohol farnesol and geranylgeraniol.

In another preferred alternative such phosphatase enzyme does not convert FPP and/or GGPP to the respective alcohol farnesol and geranylgeraniol, while retaining the ability to convert at least one bicyclic diterpenyl diphosphate, selected from CPP and LPP to the respective terpene alcohol copalol and labdendiol.

In another preferred alternative such phosphatase enzyme produces at least one alcohol selected from copalol and labdendiol as main product. In that case such enzymes do convert FPP and/or GGPP to the respective alcohol farnesol and geranylgeraniol at a lower molar yield compared to their ability to convert at least one bicyclic diterpenyl diphosphate, selected from CPP and LPP, to the respective terpene alcohol copalol and labdendiol. The relative molar yield for at least one bicyclic diterpene alcohol selected from copalol and labdendiol may be higher by a factor of equal to or greater than 2, as for example a factor of 2 to 1.000 or 5 to 100, or 10 to 50, compared to the yield for at least one of the non-cyclic terpene alcohols farnesol and geranylgeraniol.

51. The polypeptide of embodiment 50, characterized by an amino acid sequence having the following active site signature motif:

HCxxGxxR  (SEQ ID NO: 57)

wherein
each x independently of each other represents any natural amino acid residue.

52. The polypeptide of embodiment 51, wherein said active site signature motif is:

HC(T/S)xGKDRTG  (SEQ ID NO: 58)

wherein
x represents any natural amino acid residue.

53. The polypeptide of anyone of the embodiments 50 to 52, wherein said polypeptide having bicyclic diterpenyl-diphosphate phosphatase activity is selected from the group consisting of the polypeptides:
a) TalVeTPP comprising an amino acid sequence according to SEQ ID NO: 2,
b) AspWeTPP comprising an amino acid sequence according to SEQ ID NO: 6,
c) HelGriTPP comprising an amino acid sequence according to SEQ ID NO: 10,
d) UmbPiTPP1, comprising an amino acid sequence according to SEQ ID NO: 13,
e) TalVeTPP2, comprising an amino acid sequence according to SEQ ID NO: 16,
f) HydPiTPP1, comprising an amino acid sequence according to SEQ ID NO: 19,
g) TalCeTPP1, comprising an amino acid sequence according to SEQ ID NO: 22,
h) TalMaTPP1, comprising an amino acid sequence according to SEQ ID NO: 25,
i) TalAstroTPP1 comprising an amino acid sequence according to SEQ ID NO: 28,
j) PeSubTPP1 comprising an amino acid sequence according to SEQ ID NO: 31, and
k) a polypeptide having diterpenyl-diphosphate phosphatase activity and comprising an amino acid sequence showing a degree of sequence identity of at least 60%, 65%, 70%, 75%, 80%, 85%, 90%, 95%, 96%, 97%, 98%, or 99% to at least one of said amino acid sequence according to a) to j)

Another particular embodiment refers to polypeptide variants of the novel polypeptides of the invention having bicyclic diterpenyl-diphosphate phosphatase activity as identified above by anyone of the particular amino acid sequences of SEQ ID NO: 2, 6, 10, 13, 16, 19, 22, 25, 28 and 31, and wherein the polypeptide variants are selected from an amino acid sequence having at least 70%, 75%, 80%, 85%, 90%, 95%, 96%, 97%, 98%, or 99% sequence identity to anyone of SEQ ID NO: 2, 6, 10, 13, 16, 19, 22, 25, 28 and 31 and contain at least one substitution modification relative to anyone of the non-modified SEQ ID NO: 2, 6, 10, 13, 16, 19, 22, 25, 28 and 31.

54. A nucleic acid molecule comprising
  a) a nucleic acid sequence encoding a polypeptide of anyone of the embodiments 50 to 53;
  b) the complementary nucleic acid sequence of a); or
  c) nucleic acid sequence hybridizing under stringent conditions to a nucleic acid sequence of a) or b).
55. An expression construct comprising at least one nucleic acid molecule of claim 54.
56. A vector comprising at least one nucleic acid molecule of claim 54.
57. The vector of claim 56, wherein the vector is a prokaryotic, viral or eukaryotic vector.
58. The vector of embodiment 56 or 57, where the vector is an expression vector.
59. The vector of anyone of the embodiments 56 to 58, which is a plasmid vector.
60. A recombinant host cell or a recombinant non-human host organism comprising
  a) at least one isolated nucleic acid molecule of embodiment 54, optionally stably integrated into the genome; or
  b) at least one expression construct of embodiment 55, optionally stably integrated into the genome; or
  c) at least one vector of any one of embodiments 56 to 59.
61. The host cell or host organism of embodiment 60, selected from a prokaryotic or eukaryotic microorganism, or a cell derived therefrom.
62. The host cell or host organism of embodiment 61, selected from bacterial, fungal and plant cells or plants.
63. The host cell or host organism of embodiment 62, wherein said fungal cells are yeast cells.
64. The host cell or host organism of embodiment 63, wherein said bacterial cells are selected from the genus *Escherichia*, in particular from the species *E. coli* and said yeast cells are selected from the genus *Saccharomyces* or *Pichia*, in particular from the species *Saccharomyces cerevisiae* or *Pichia pastoris*.
65. A method for producing at least one catalytically active polypeptide according to any one of embodiments 50 to 53 comprising:
  (1) culturing a non-human host organism or host cell of one of the embodiments claims 60 to 64 to express or over-express at least one polypeptide according to anyone of embodiments 50 to 53; and
  (2) optionally isolating the polypeptide from the non-human host cell or organism cultured in step (1).
66. The method of embodiment 65, further comprising, prior to step a), transforming a non-human host organism or cell with at least one nucleic acid according to embodiment 54, at least one construct of embodiment 55, or at least one vector of anyone of the embodiments 56 to 59 so that it expresses or over-expresses the polypeptide according to any one of embodiments 50 to 53.
67. A method for preparing a mutant polypeptide comprising terpene synthase activity, in particular terpenyl diphosphate synthase activity, which method comprises the steps of:
  (1) selecting a nucleic acid molecule according to embodiment 54;
  (2) modifying the selected nucleic acid molecule to obtain at least one mutant nucleic acid molecule;
  (3) transforming host cells or unicellular host organisms with the mutant nucleic acid sequence to express a polypeptide encoded by the mutant nucleic acid sequence;
  (4) screening the expression product for at least one mutant comprising terpene synthase activity, in particular terpenyl diphosphate synthase activity;
  (5) optionally, if the polypeptide has no desired mutant activity, repeat the process steps (1) to (4) until a polypeptide with a desired mutant activity is obtained; and
  (6) optionally, if a polypeptide having a desired mutant activity was identified in step (4), isolating the corresponding mutant nucleic acid obtained in step (3).
68. The method of embodiment 22, wherein the copalol derivative is selected from the group consisting of copalal, manool, (+)-manoolxy, Z-11, gamma-ambrol and ambrox and structurally related compounds which, in particular, differ therefrom in stereochemistry.
69. The method of embodiment 31, wherein the labdendiol derivative is selected from the group consisting of sclareolide, DOL and ambrox and structurally related compounds which, in particular, differ therefrom in stereochemistry.
70. A method of preparing ambrox or an ambrox-like compound as defined above, which method comprises
  a) providing a labdendiol or copalol compound by performing a biocatalytic process as defined in anyone of the embodiments 1 to 44, optionally isolating said labdendiol or copalol compound; and
  b) converting said labdendiol or copalol compound of step (1) using chemical synthesis and/or biochemical synthesis to ambrox or an ambrox-like compound.
71. The invention further relates to the use of a polypeptide as defined in anyone of the above embodiments for preparing odorants, flavours or fragrance ingredients, in particular Ambrox; as well as to the use of a terpene alcohol as prepared according to anyone of the above embodiments for preparing odorants, flavours or fragrance ingredients, in particular Ambrox.

b. Polypeptides Applicable According to the Invention

In this context the following definitions apply:

The generic terms "polypeptide" or "peptide", which may be used interchangeably, refer to a natural or synthetic linear chain or sequence of consecutive, peptidically linked amino acid residues, comprising about 10 to up to more than 1.000 residues. Short chain polypeptides with up to 30 residues are also designated as "oligopeptides".

The term "protein" refers to a macromolecular structure consisting of one or more polypeptides. The amino acid sequence of its polypeptide(s) represents the "primary structure" of the protein. The amino acid sequence also predetermines the "secondary structure" of the protein by the formation of special structural elements, such as alpha-helical and beta-sheet structures formed within a polypeptide chain. The arrangement of a plurality of such secondary structural elements defines the "tertiary structure" or spatial arrangement of the protein. If a protein comprises more than one polypeptide chains said chains are spatially arranged forming the "quaternary structure" of the protein. A correct spacial arrangement or "folding" of the protein is prerequisite of protein function. Denaturation or unfolding destroys protein function. If such destruction is reversible, protein function may be restored by refolding.

A typical protein function referred to herein is an "enzyme function", i.e. the protein acts as biocatalyst on a substrate, for example a chemical compound, and catalyzes the conversion of said substrate to a product. An enzyme may show a high or low degree of substrate and/or product specificity.

A "polypeptide" referred to herein as having a particular "activity" thus implicitly refers to a correctly folded protein showing the indicated activity, as for example a specific enzyme activity.

Thus, unless otherwise indicated the term "polypeptide" also encompasses the terms "protein" and "enzyme".

Similarly, the term "polypeptide fragment" encompasses the terms "protein fragment" and "enzyme fragment".

The term "isolated polypeptide" refers to an amino acid sequence that is removed from its natural environment by any method or combination of methods known in the art and includes recombinant, biochemical and synthetic methods.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The present invention also relates to "functional equivalents" (also designated as "analogs" or "functional mutations") of the polypeptides specifically described herein.

For example, "functional equivalents" refer to polypeptides which, in a test used for determining enzymatic terpenyl diphosphate synthase activity, or terpenyl diphosphate phosphatase activity display at least a 1 to 10%, or at least 20%, or at least 50%, or at least 75%, or at least 90% higher or lower activity, as that of the polypeptides specifically described herein.

"Functional equivalents", according to the invention, also cover particular mutants, which, in at least one sequence position of an amino acid sequences stated herein, have an amino acid that is different from that concretely stated one, but nevertheless possess one of the aforementioned biological activities, as for example enzyme activity. "Functional equivalents" thus comprise mutants obtainable by one or more, like 1 to 20, in particular 1 to 15 or 5 to 10 amino acid additions, substitutions, in particular conservative substitutions, deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist or substrate, however at a different rate, (i.e. expressed by a $EC_{50}$ or $IC_{50}$ value or any other parameter suitable in the present technical field) is observed. Examples of suitable (conservative) amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |

-continued

| Original residue | Examples of substitution |
|---|---|
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described herein, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise "fragments", like individual domains or sequence motifs, of the polypeptides according to the invention, or N- and or C-terminally truncated forms, which may or may not display the desired biological function. Preferably such "fragments" retain the desired biological function at least qualitatively.

"Functional equivalents" are, moreover, fusion proteins, which have one of the polypeptide sequences stated herein or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Functional equivalents or homologues of the polypeptides according to the invention can be produced by mutagenesis, e.g. by point mutation, lengthening or shortening of the protein or as described in more detail below.

Functional equivalents or homologs of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art.

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues.

An embodiment provided herein provides orthologs and paralogs of polypeptides disclosed herein as well as methods for identifying and isolating such orthologs and paralogs. A definition of the terms "ortholog" and "paralog" is given below and applies to amino acid and nucleic acid sequences.

c. Coding Nucleic Acid Sequences Applicable According to the Invention

In this context the following definitions apply:

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material.

The term "naturally-occurring" as used herein as applied to a nucleic acid refers to a nucleic acid that is found in a cell of an organism in nature and which has not been intentionally modified by a human in the laboratory.

A "fragment" of a polynucleotide or nucleic acid sequence refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

As used herein, the term "hybridization" or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein below. Appropriate hybridization conditions can also be selected by those skilled in the art with minimal experimentation as exemplified in Ausubel et al. (1995, Current Protocols in Molecular Biology, John Wiley & Sons, sections 2, 4, and 6). Additionally, stringency conditions are described in Sambrook et al. (1989, Molecular Cloning: A Laboratory Manual, 2nd ed., Cold Spring Harbor Press, chapters 7, 9, and 11).

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, N.Y., Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

"Polycistronic" refers to nucleic acid molecules, in particular mRNAs, that can encode more than one polypeptide separately within the same nucleic acid molecule A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

The term "primer" refers to a short nucleic acid sequence that is hybridized to a template nucleic acid sequence and is used for polymerization of a nucleic acid sequence complementary to the template.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The invention also relates to nucleic acid sequences that code for polypeptides as defined herein.

In particular, the invention also relates to nucleic acid sequences (single-stranded and double-stranded DNA and RNA sequences, e.g. cDNA, genomic DNA and mRNA), coding for one of the above polypeptides and their functional equivalents, which can be obtained for example using artificial nucleotide analogs.

The invention relates both to isolated nucleic acid molecules, which code for polypeptides according to the invention or biologically active segments thereof, and to nucleic acid fragments, which can be used for example as hybridization probes or primers for identifying or amplifying coding nucleic acids according to the invention.

The present invention also relates to nucleic acids with a certain degree of "identity" to the sequences specifically disclosed herein. "Identity" between two nucleic acids means identity of the nucleotides, in each case over the entire length of the nucleic acid.

The "identity" between two nucleotide sequences (the same applies to peptide or amino acid sequences) is a function of the number of nucleotide residues (or amino acid residues) or that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web.

Particularly, the BLAST program (Tatiana et al, *FEMS Microbiol Lett.*, 1999, 174:247-250, 1999) set to the default parameters, available from the National Center for Biotechnology Information (NCBI) website at ncbi.nlm.nih.gov/BLAST/bl2seq/wblast2.cgi, can be used to obtain an optimal alignment of protein or nucleic acid sequences and to calculate the percentage of sequence identity.

In another example the identity may be calculated by means of the Vector NTI Suite 7.1 program of the company Informax (USA) employing the Clustal Method (Higgins D G, Sharp P M. ((1989))) with the following settings:

| Multiple alignment parameters: | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: http://www.ebi.ac.uk/Tools/clustalw/index.html# and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |

| | |
|---|---|
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (as defined herein elsewhere) on at least about 12, preferably at least about 25, for example about 40, 50 or 75 successive nucleotides of a sense strand of a nucleic acid sequence according to the invention or of a corresponding antisense strand.

"Homologous" sequences include orthologous or paralogous sequences. Methods of identifying orthologs or paralogs including phylogenetic methods, sequence similarity and hybridization methods are known in the art and are described herein.

"Paralogs" result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

"Orthologs", or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, organism such as plants or microorganisms producing terpene synthase proteins.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

An "isolated" nucleic acid molecule is separated from other nucleic acid molecules that are present in the natural source of the nucleic acid and can moreover be substantially free from other cellular material or culture medium, if it is being produced by recombinant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)).

In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These "standard conditions" vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58°

C. in an aqueous buffer solution with a concentration between 0.1 to 5×SSC (1×SSC=0.15 M NaCl, 15 mM sodium citrate, pH 7.2) or additionally in the presence of 50 formamide, for example 42° C. in 5×SSC, 50% formamide. Advantageously, the hybridization conditions for DNA: DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, Current Protocols in Molecular Biology, John Wiley & Sons, sections 2, 4, and 6). Additionally, stringency conditions are described in Sambrook et al. (1989, Molecular Cloning: A Laboratory Manual, 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×106 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×106 cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

A detection kit for nucleic acid sequences encoding a polypeptide of the invention may include primers and/or probes specific for nucleic acid sequences encoding the polypeptide, and an associated protocol to use the primers and/or probes to detect nucleic acid sequences encoding the polypeptide in a sample. Such detection kits may be used to determine whether a plant, organism, microorganism or cell has been modified, i.e., transformed with a sequence encoding the polypeptide.

To test a function of variant DNA sequences according to an embodiment herein, the sequence of interest is operably linked to a selectable or screenable marker gene and expression of said reporter gene is tested in transient expression assays, for example, with microorganisms or with protoplasts or in stably transformed plants.

The invention also relates to derivatives of the concretely disclosed or derivable nucleic acid sequences.

Thus, further nucleic acid sequences according to the invention can be derived from the sequences specifically disclosed herein and can differ from it by one or more, like 1 to 20, in particular 1 to 15 or 5 to 10 additions, substitutions, insertions or deletions of one or several (like for example 1 to 10) nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism.

According to a particular embodiment of the invention variant nucleic acids may be prepared in order to adapt its nucleotide sequence to a specific expression system. For example, bacterial expression systems are known to more efficiently express polypeptides if amino acids are encoded by particular codons. Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the polypeptides described herein may be optimized for increased expression in the host cell. For example, nucleic acids of an embodiment herein may be synthesized using codons particular to a host for improved expression.

The invention also encompasses naturally occurring variants, e.g. splicing variants or allelic variants, of the sequences described therein.

Allelic variants may have at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

The invention also relates to sequences that can be obtained by conservative nucleotide substitutions (i.e. as a result thereof the amino acid in question is replaced by an amino acid of the same charge, size, polarity and/or solubility).

The invention also relates to the molecules derived from the concretely disclosed nucleic acids by sequence polymorphisms. Such genetic polymorphisms may exist in cells from different populations or within a population due to natural allelic variation. Allelic variants may also include functional equivalents. These natural variations usually produce a variance of 1 to 5% in the nucleotide sequence of a gene. Said polymorphisms may lead to changes in the amino acid sequence of the polypeptides disclosed herein. Allelic variants may also include functional equivalents.

Furthermore, derivatives are also to be understood to be homologs of the nucleic acid sequences according to the invention, for example animal, plant, fungal or bacterial homologs, shortened sequences, single-stranded DNA or RNA of the coding and noncoding DNA sequence. For example, homologs have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

d. Generation of Functional Polypeptide Mutants

Moreover, a person skilled in the art is familiar with methods for generating functional mutants, that is to say nucleotide sequences which code for a polypeptide with at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to anyone of amino acid related SEQ ID NOs as disclosed herein and/or encoded by a nucleic acid molecule comprising a nucleotide sequence having at least 70% sequence identity to anyone of the nucleotide related SEQ ID NOs as disclosed herein.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the polypeptide encoded by them have been known to the skilled worker for a long time, such as, for example site-specific mutagenesis, where individual or several nucleotides of a gene are replaced in a directed fashion (Trower M K (Ed.) 1996; In vitro mutagenesis protocols. Humana Press, New Jersey), saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Barik S (1995) Mol Biotechnol 3:1), error-prone polymerase chain reaction, where nucleotide sequences are mutated by error-prone DNA polymerases (Eckert K A, Kunkel T A (1990) Nucleic Acids Res 18:3739);

the SeSaM method (sequence saturation method), in which preferred exchanges are prevented by the polymerase. Schenk et al., Biospektrum, Vol. 3, 2006, 277-279 the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction in which, by repeated strand separation and reassociation, full-length mosaic genes are ultimately generated (Stemmer W P C (1994) Nature 370:389; Stemmer W P C (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

e. Constructs for Expressing Polypeptides of the Invention

In this context the following definitions apply:

"Expression of a gene" encompasses "heterologous expression" and "over-expression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one "regulatory sequence", which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

An "expression system" as used herein encompasses any combination of nucleic acid molecules required for the expression of one, or the co-expression of two or more polypeptides either in vivo of a given expression host, or in vitro. The respective coding sequences may either be located on a single nucleic acid molecule or vector, as for example a vector containing multiple cloning sites, or on a polycistronic nucleic acid, or may be distributed over two or more physically distinct vectors. As a particular example there may be mentioned an operon comprising a promotor sequence, one or more operator sequences and one or more structural genes each encoding an enzyme as described herein As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid. "Promoter" in particular refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

In this context, a "functional" or "operative" linkage is understood as meaning for example the sequential arrangement of one of the nucleic acids with a regulatory sequence. For example the sequence with promoter activity and of a nucleic acid sequence to be transcribed and optionally further regulatory elements, for example nucleic acid sequences which ensure the transcription of nucleic acids, and for example a terminator, are linked in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, Calif. (1990).

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of the product or products of interest as herein defined in the cell or organism. Particularly, the nucleotide sequence encodes a polypeptide having an enzyme activity as herein defined.

The nucleotide sequence as described herein above may be part of an "expression cassette". The terms "expression cassette" and "expression construct" are used synonymously. The (preferably recombinant) expression construct contains a nucleotide sequence which encodes a polypeptide according to the invention and which is under genetic control of regulatory nucleic acid sequences.

In a process applied according to the invention, the expression cassette may be part of an "expression vector", in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

Nucleic acid constructs according to the invention comprise in particular a sequence coding for a polypeptide for example derived from the amino acid related SEQ ID NOs as described therein or the reverse complement thereof, or derivatives and homologs thereof and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lacI$^q$, T7, T5, T3, gal, trc, ara, rhaP (rhaP$_{BAD}$)SP6, lambda-P$_R$ or in the lambda-P$_L$ promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, phasmids, cosmids and linear or circular DNA or artificial chromosomes. These vectors are capable of replicating autonomously in the host organism or else chromosomally. These vectors are a further development of the invention. Binary or cpo-integration vectors are also applicable.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^+$, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

An alternative embodiment of an embodiment herein provides a method to "alter gene expression" in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, provided herein is also an isolated, recombinant or synthetic polynucleotide encoding a polypeptide or variant polypeptide provided herein.

In one embodiment, several polypeptide encoding nucleic acid sequences are co-expressed in a single host, particularly under control of different promoters. In another embodiment, several polypeptide encoding nucleic acid sequences can be present on a single transformation vector or be co-transformed at the same time using separate vectors and selecting transformants comprising both chimeric genes. Similarly, one or polypeptide encoding genes may be expressed in a single plant, cell, microorganism or organism together with other chimeric genes.

f. Hosts to be Applied for the Present Invention

Depending on the context, the term "host" can mean the wild-type host or a genetically altered, recombinant host or both.

In principle, all prokaryotic or eukaryotic organisms may be considered as host or recombinant host organisms for the nucleic acids or the nucleic acid constructs according to the invention.

Using the vectors according to the invention, recombinant hosts can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example co-precipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, N.Y., 1989.

Advantageously, microorganisms such as bacteria, fungi or yeasts are used as host organisms. Advantageously, gram-positive or gram-negative bacteria are used, preferably bacteria of the families Enterobacteriaceae, Pseudomonadaceae, Rhizobiaceae, Streptomycetaceae, Streptococcaceae or Nocardiaceae, especially preferably bacteria of the genera *Escherichia, Pseudomonas, Streptomyces, Lactococcus, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria. Advantageously also yeasts of families like *Saccharomyces* or *Pichia* are suitable hosts.

Alternatively, entire plants or plant cells may serve as natural or recombinant host. As non-limiting examples the following plants or cells derived therefrom may be mentioned the genera *Nicotiana*, in particular *Nicotiana benthamiana* and *Nicotiana tabacum* (tobacco); as well as *Arabidopsis*, in particular *Arabidopsis thaliana*.

Depending on the host organism, the organisms used in the method according to the invention are grown or cultured in a manner known by a person skilled in the art. Culture can be batchwise, semi-batchwise or continuous. Nutrients can be present at the beginning of fermentation or can be supplied later, semicontinuously or continuously. This is also described in more detail below.

g. Recombinant Production of Polypeptides According to the Invention

The invention further relates to methods for recombinant production of polypeptides according to the invention or functional, biologically active fragments thereof, wherein a polypeptide-producing microorganism is cultured, optionally the expression of the polypeptides is induced by applying at least one inducer inducing gene expression and the expressed polypeptides are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1.

Einführung in die Bioverfahrenstechnik [Bioprocess technology 1. Introduction to bioprocess technology] (Gustav Fischer Verlag, Stuttgart, 1991)) or in the textbook by Storhas (Bioreaktoren and periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D.C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, New York or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

h. Polypeptide Immobilization

The enzymes or polypeptides according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

i. Reaction Conditions for Biocatalytic Production Methods of the Invention

The reaction of the present invention may be performed under in vivo or in vitro conditions.

The at least one polypeptide/enzyme which is present during a method of the invention or an individual step of a multistep-method as defined herein above, can be present in living cells naturally or recombinantly producing the enzyme or enzymes, in harvested cells. i.e. under in vivo conditions, or, in dead cells, in permeabilized cells, in crude cell extracts, in purified extracts, or in essentially pure or completely pure form, i.e. under in vitro conditions. The at least one enzyme may be present in solution or as an enzyme immobilized on a carrier. One or several enzymes may simultaneously be present in soluble and/or immobilised form.

The methods according to the invention can be performed in common reactors, which are known to those skilled in the art, and in different ranges of scale, e.g. from a laboratory scale (few millilitres to dozens of litres of reaction volume) to an industrial scale (several litres to thousands of cubic meters of reaction volume). If the polypeptide is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one polypeptide/enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger and Crueger, Biotechnologie—Lehrbuch der angewandten Mikrobiologie, 2. Ed., R. Oldenbourg Verlag, München, Wien, 1984).

Cells containing the at least one enzyme can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween 20, deoxycholate, CHAPS (3-[(3-Cholamidopropyl)dimethylammonio]-1-propansulfonate), Nonidet® P40 (Ethylphenolpoly(ethyleneglycolether), and the like.

Instead of living cells biomass of non-living cells containing the required biocatalyst(s) may be applied of the biotransformation reactions of the invention as well.

If the at least one enzyme is immobilised, it is attached to an inert carrier as described above.

The conversion reaction can be carried out batch wise, semi-batch wise or continuously. Reactants (and optionally nutrients) can be supplied at the start of reaction or can be supplied subsequently, either semi-continuously or continuously.

The reaction of the invention, depending on the particular reaction type, may be performed in an aqueous, aqueous-organic or non-aqueous reaction medium.

An aqueous or aqueous-organic medium may contain a suitable buffer in order to adjust the pH to a value in the range of 5 to 11, like 6 to 10.

In an aqueous-organic medium an organic solvent miscible, partly miscible or immiscible with water may be applied. Non-limiting examples of suitable organic solvents are listed below. Further examples are mono- or polyhydric, aromatic or aliphatic alcohols, in particular polyhydric aliphatic alcohols like glycerol.

The non-aqueous medium may contain is substantially free of water, i.e. will contain less that about 1 wt.-% or 0.5 wt.-% of water.

Biocatalytic methods may also be performed in an organic non-aqueous medium. As suitable organic solvents there may be mentioned aliphatic hydrocarbons having for example 5 to 8 carbon atoms, like pentane, cyclopentane, hexane, cyclohexane, heptane, octane or cyclooctane; aromatic carbohydrates, like benzene, toluene, xylenes, chlorobenzene or dichlorobenzene, aliphatic acyclic and ethers, like diethylether, methyl-tert.-butylether, ethyl-tert.-butylether, dipropylether, diisopropylether, dibutylether; or mixtures thereof.

The concentration of the reactants/substrates may be adapted to the optimum reaction conditions, which may depend on the specific enzyme applied. For example, the initial substrate concentration may be in the 0,1 to 0,5 M, as for example 10 to 100 mM.

The reaction temperature may be adapted to the optimum reaction conditions, which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours. These parameters are non-limiting examples of suitable process conditions.

If the host is a transgenic plant, optimal growth conditions can be provided, such as optimal light, water and nutrient conditions, for example.

k. Product Isolation

The methodology of the present invention can further include a step of recovering an end or intermediate product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like High Performance Liquid Chromatography (HPLC), gas chromatography (GC), Spektroskopy (like IR, UV, NMR), Colouring methods, TLC, NIRS, enzymatic or microbial assays. (see for example: Patek et al. (1994) Appl. Environ. Microbiol. 60:133-140; Malakhova et al. (1996) Biotekhnologiya 11 27-32; und Schmidt et al. (1998) Bioprocess Engineer. 19:67-70. Ullmann's Encyclopedia of Industrial Chemistry (1996) Bd. A27, VCH: Weinheim, S. 89-90, S. 521-540, S. 540-547, S. 559-566, 575-581 und S. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.)

The cyclic terpene compound produced in any of the method described herein can be converted to derivatives such as, but not limited to hydrocarbons, esters, amides, glycosides, ethers, epoxides, aldehydes, ketons, alcohols, diols, acetals or ketals. The terpene compound derivatives can be obtained by a chemical method such as, but not limited to oxidation, reduction, alkylation, acylation and/or rearrangement. Alternatively, the terpene compound derivatives can be obtained using a biochemical method by contacting the terpene compound with an enzyme such as, but not limited to an oxidoreductase, a monooxygenase, a dioxygenase, a transferase. The biochemical conversion can be performed in-vitro using isolated enzymes, enzymes from lysed cells or in-vivo using whole cells.

l. Fermentative Production of Terpene Alcohols

The invention also relates to methods for the fermentative production of terpene alcohols.

A fermentation as used according to the present invention can, for example, be performed in stirred fermenters, bubble columns and loop reactors. A comprehensive overview of the possible method types including stirrer types and geometric designs can be found in "Chmiel: Bioprozesstechnik: Einführung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 1 hour to 160 hours.

The methodology of the present invention can further include a step of recovering said terpene alcohol.

The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The following examples are illustrative only and are not intended to limit the scope of the embodiments an embodiments described herein.

The numerous possible variations that will become immediately evident to a person skilled in the art after heaving considered the disclosure provided herein also fall within the scope of the invention.

Experimental Part

The invention will now be described in further detail by way of the following Examples.

Materials:

Unless otherwise stated, all chemical and biochemical materials and microorganisms or cells employed herein are commercially available products.

Unless otherwise specified, recombinant proteins are cloned and expressed by standard methods, such as, for example, as described by Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, N.Y., 1989.

General Methods:

Standard Assay for Determining Copalyl Diphosphate Phosphatase Activity

*E. coli* cells (DP1205 strain) are transformed with two plasmids,
- a plasmid carrying the genes encoding for enzymes necessary for the biosynthesis of copalyl diphosphate (CPP), for example the pACYC-CrtE-SmCPS2 plasmid
- a plasmid carrying a gene encoding for a protein with terpenyl-phosphate phosphatase activity, for example the pJ401-TalVeTPP or pJ401-AspWeTPP plasmid.

The cells are cultivated and the production of copalol is analyzed by GC-MS as described below.

Standard Assay for Determining 8-Hydroxy-Copalyl Diphosphate Phosphatase Activity

*E. coli* cells (DP1205 strain) are transformed with two plasmids,
- a plasmid carrying gene encoding for enzymes necessary for the biosynthesis of 8-hydroxy-copalyl diphosphate (LPP), for example the pACYC-CrtE-SsLPS plasmid
- a plasmid carrying a gene encoding for a protein with terpenyl-phosphate phosphatase activity, for example the pJ401-TalVeTPP or pJ401-AspWeTPP plasmid.

The cells are cultivated and the production of labdendiol is analyzed by GC-MS as described below.

Standard Assay for Determining Copalol Dehydrogenase Activity

E. coli cells (DP1205 strain) are transformed with two plasmids,
- a plasmid carrying the genes encoding for the enzymes necessary for the biosynthesis of Copalol, for example the pJ401-CPOL-2 plasmid,
- a plasmid carrying a gene encoding for an alcohol dehydrogenase for example using pJ423 as background plasmid.

The cells are cultivated and the production of copalal is analyzed by GC-MS as described below.

Standard Assay for Determining Labdendiol Dehydrogenase Activity

E. coli cells (DP1205 strain) are transformed with two plasmids,
- a plasmid carrying the genes encoding for the enzymes necessary for the biosynthesis of labdendiol, for example the pJ401-LOH-2 plasmid,
- a plasmid carrying a gene encoding for an alcohol dehydrogenase for example using pJ423 as background plasmid.

The cells are cultivated and the production of the products is analyzed by GC-MS as described below.

Gas Chromatography Mass Spectrometry (GC-MS)

The terpene content was analyzed by GC-MS using an Agilent 6890 Series GC system connected to an Agilent 5975 mass detector. The GC was equipped with 0.25 mm inner diameter by 30 m HP-5MS capillary column (Agilent). The carrier gas was helium at a constant flow of 1 mL/min. The inlet temperature was set at 250° C. The initial oven temperature was 100° C. for 1 min, followed by a gradient of 10° C./min to 300° C. The identification of the products was based on the comparison of the mass spectra and retention indices with authentic standards and proprietary mass spectra databases. The concentrations were estimated based on the internal standard.

Figure 15:
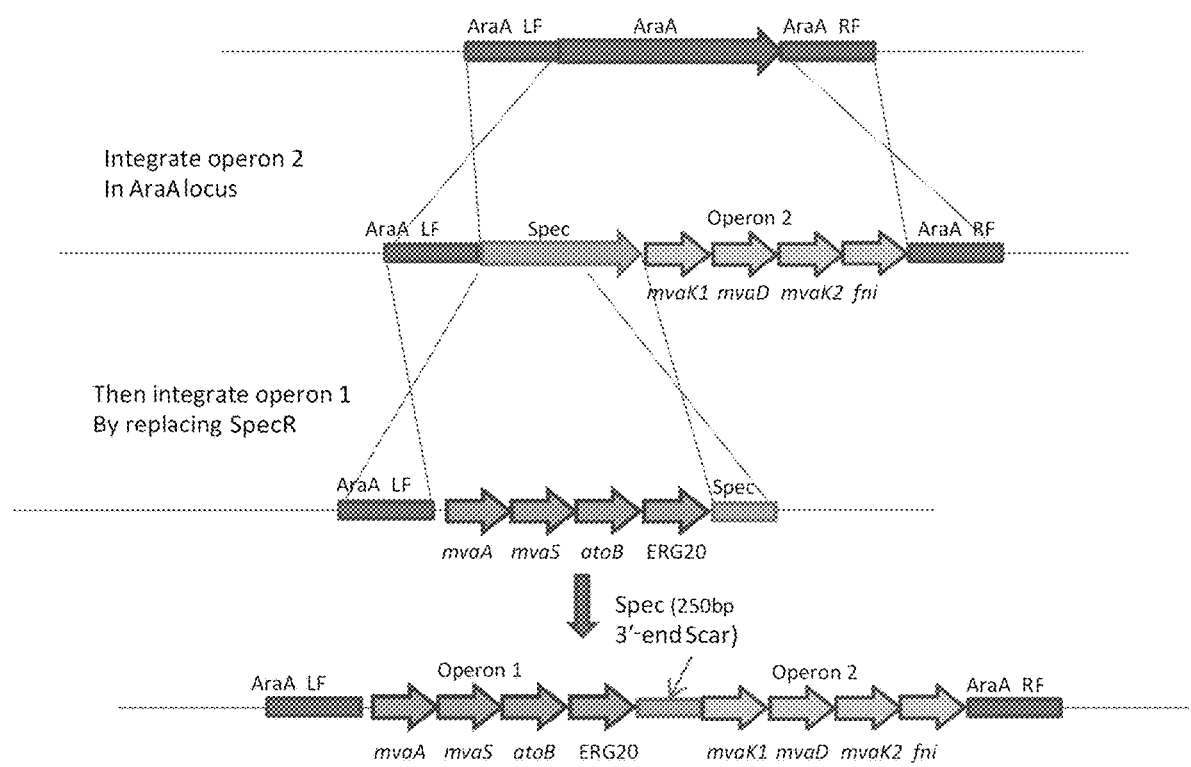
FIG. 15. Schematic representation of the chromosomal integration of the genes encoding for mevalonate pathway enzymes and organisation of the two synthetic gene operons. mvaK1, a gene encoding a mevalonate kinase from *S. pneumoniae*; mvaD, a gene encoding a phosphomevalonate decarboxylase from *S. pneumoniae*; mvaK2, a gene encoding a phosphomevalonate kinase from *S. pneumoniae*; fni a gene encoding an isopentenyl diphosphate isomerase from *S. pneumoniae*; mvaA, a gene encoding an HMG-CoA synthase from *S. aureus*; mvaS a gene encoding an HMG-CoA reductase from *S. aureus*; atoB a gene encoding an acetoacetyl-CoA thiolase from *E. coli*; ERG20, a gene encoding an FPP synthase from *S. cerevisiae*.

Preparation of a Recombinant Bacterial Strain with Chromosomal Integration of Genes Encoding Mevalonate Pathway Enzymes An E. coli strain was engineered to produce the terpene precursor farnesyl-pyrophosphate (FPP) by chromosomal integration of recombinant genes encoding mevalonate pathway enzymes. See also construction scheme and recombination events depicted in FIG. 15.

An upper pathway operon (operon 1 from acetyl-CoA to mevalonate) was designed consisting of the atoB gene from E. coli encoding an acetoacetyl-CoA thiolase, and the mvaA and mvaS genes from Staphylococcus aureus encoding a HMG-CoA synthase and a HMG-CoA reductase, respectively.

As a lower mevalonate pathway operon (operon 2 from mevalonate to farnesyl pyrophosphate), a natural operon from the Gram-negative bacteria, Streptococcus pneumoniae was selected, encoding a mevalonate kinase (mvaK1), a phosphomevalonate kinase (mvaK2), a phosphomevalonate decarboxylase (mvaD), and an isopentenyl diphosphate isomerase (fni).

A codon optimized Saccharomyces cerevisiae FPP synthase encoding gene (ERG20) was introduced at the 3'-end of the upper pathway operon to convert isopentenyl-diphosphate (IPP) and dimethylallyl-diphosphate (DMAPP) into FPP.

The above described operons were synthesized by DNA2.0 and integrated into the araA gene of the Escherichia coli strain BL21(DE3). The heterologous pathway was introduced in two separate recombination steps using CRISPR/Cas9 genome engineering system. The first operon (lower pathway; operon 2) to be integrated carries a spectinomycin (Spec) marker which was used to screen for Spec resistant candidate integrants. The second operon was designed to displace the Spec marker of the previously integrated operon and was accordingly screened for Spec candidate integrants following the second recombination event (see FIG. 15). Guide RNA expression vectors targeting the araA gene were designed and synthetized by DNA 2.0. PCR was used to verify operon integration by designing PCR primers to amplify across the araA gene integration target and across recombination junctions of integrants. One clone yielding correct PCR results was then fully sequenced and archived as strain DP1205.

Cultivation of Bacteria Cells and Analysis of Terpene Production

The E. coli cells were transformed with one or two expression plasmids carrying the terpene biosynthesis genes and the transformed cells were cultured with the appropriate antibiotics (kanamycin (50 µg/ml) and/or chloramphenicol (34 µg/ml) on LB-agarose plates. Single colonies were used to inoculate 5 mL liquid LB medium supplemented with the same antibiotics, 4 g/l glucose and 10% (v/v) dodecane. The next day 2 mL of TB medium supplemented with the same antibiotics and 10% (v/v) dodecane were inoculated with 0.2 mL of the overnight culture. The cultures were incubated at 37° C. until an optical density of 3 was reached. The expression of the recombinant proteins was the induced by addition of 1 mM IPTG and the cultures were incubated for 72 h at 20° C.

The cultures were then extracted with tert.-butyl methyl ether (MTBE) and the internal standard (α-longipinene (Aldrich)) was added to the organic phase. The terpene content of the organic phase was analyzed by GC-MS as described above.

Example 1: Identification and Characterization of Copalyl-Diphosphate Phosphatase Activity of TalVeTPP and AspVeTPP The TalVeTPP and AspWeTPP proteins are encoded by two predicted genes in the genome of Talaromyces verruculosus and Aspergillus wentii, respectively. The TalVeTPP encoding gene is located in the 150095 . . . 151030 region of the Talaromyces verruculosus genomic scaffold sequence having the NCBI accession No LHCL01000010.1. The encoded protein is reported as a putative protein with no functional characterization (NCBI accession No KUL89334.1). The AspWeTPP encoding gene is located in the 2482776 . . . 2483627 region of the Aspergillus wentii DTO 134E9 unplaced genomic scaffold ASPWEscaffold_5 (NCBI accession No KV878213.1). The encoded protein has the NCBI accession No OJJ34585.1 and is also reported as a putative protein with no functional characterization.

The TalVeTPP and AspWeTPP encoding genes are located in the genome next to genes potentially involved in biosynthesis of secondary metabolites such as genes encoding for oxidases, hydroxylases, dehydrogenases and particularly genes having strong homology with monofunctional copalyl-diphosphate synthases or bifunctional copalyl-diphosphate synthases reported in Mitsuhashi et al, Chembiochem. 2017 Nov. 2; 18(21):2104-2109. The functional analysis of the TalVeTPP and AspWeTPP amino acid sequences by search for the presence of protein family domains signatures (for example using the Interpro sequence analysis tool at www.ebi.ac.uk/interpro/ or the Pfam database search tool http://pfam.xfam.org/search#tabview=tab0 or https://www.ebi.ac.uk/Tools/pfa/pfamscan/) revealed that the two proteins are predicted to containing Protein tyrosine phosphatase signatures. Enzymes from the Tyrosine phosphatase family are described to remove phosphate groups from various phosphorylated molecules and particularly from protein. But enzymes from this protein family have never been shown to act on compounds such as copalyl-diphosphate. However, given the genome localization of the genes encoding for TalVeTPP and AspWeTP, we hypothesized that TalVeTPP and AspWeTPP could catalyse the cleavage of the diphosphate group of copalyl-diphosphate or other isoprenoid-diphosphate compounds (FIG. 1.)

The TalVeTPP and AspWeTPP encoding cDNA (SEQ ID NO: 3 and 7, respectively) were codon optimized (SEQ ID NO: 1 and 5, respectively) and cloned individually in the expression plasmid pJ401 (ATUM, Newark, Calif.) providing the plasmids pJ401-TalVeTPP and pJ401-AspWeTPP.

Another expression plasmid carrying a gene encoding a geranylgeranyl-pyrophosphate synthase (GGPS) and a gene encoding a copalyl-pyrophosphate synthase (CPS) was constructed. For the CPS gene, the cDNA encoding for a CPS from *Salvia miltiorrhiza* (NCBI accession No ABV57835.1) was codon optimized for optimal expression in *E. coli* cells. In addition first 58 codons were removed and an ATG start codon was added. The optimized cDNA encoding the truncated *Salvia miltiorrhiza* CPS (SmCPS2) (SEQ ID NO:33) was synthesized in-vitro and first cloned in the pJ208 plasmid flanked with the NdeI and KpnI restriction enzyme recognition sites (ATUM, Newark, Calif.). For the GGPS, the CrtE gene from *Pantoea agglomerans* (NCBI accession M38424.1) encoding for a GGPP synthase (NCBI accession number AAA24819.1) was used. The CrtE gene was synthesized with codon optimization (SEQ ID NO:35) and addition of the NcoI and BamHI restriction enzyme recognition sites at the 3' and 5' ends (ATUM, Newark, Calif.) and ligated between NcoI and BamHI site of the pACYC-Duet™-1 plasmid (Merck) to obtain the pACYC-CrtE plasmid. The modified SmCPS2 encoding cDNA was digested with NdeI and KpnI and ligated into the pACYC-CrtE plasmid thus providing the pACYC-CrtE-SmCPS2 construct.

Figure 2A:
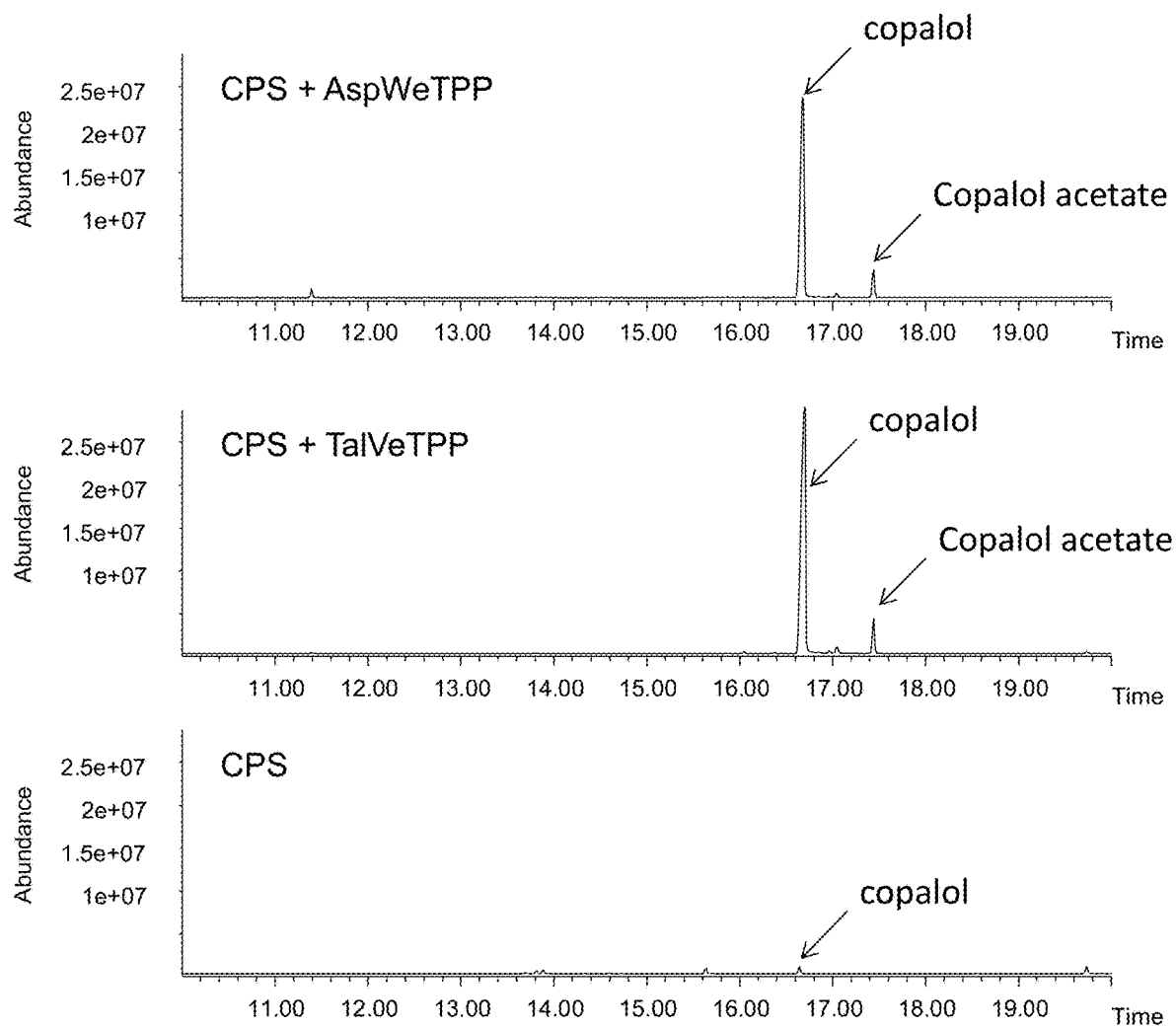
FIG. 2A. Chromatogram of a GC-MS analysis of copalol produced by E. coli cells. Upper chromatogram: E. coli cells producing the recombinant enzymes of a mevalonate pathway, a CPP synthase and AspWeTPP. Middle chromatogram: E. coli cells producing the recombinant enzymes of a mevalonate pathway, a CPP synthase and TalVeTPP. Lower chromatogram: Control with E. coli cells producing the recombinant enzymes of a mevalonate pathway and a CPP synthase.
Figure 2B:
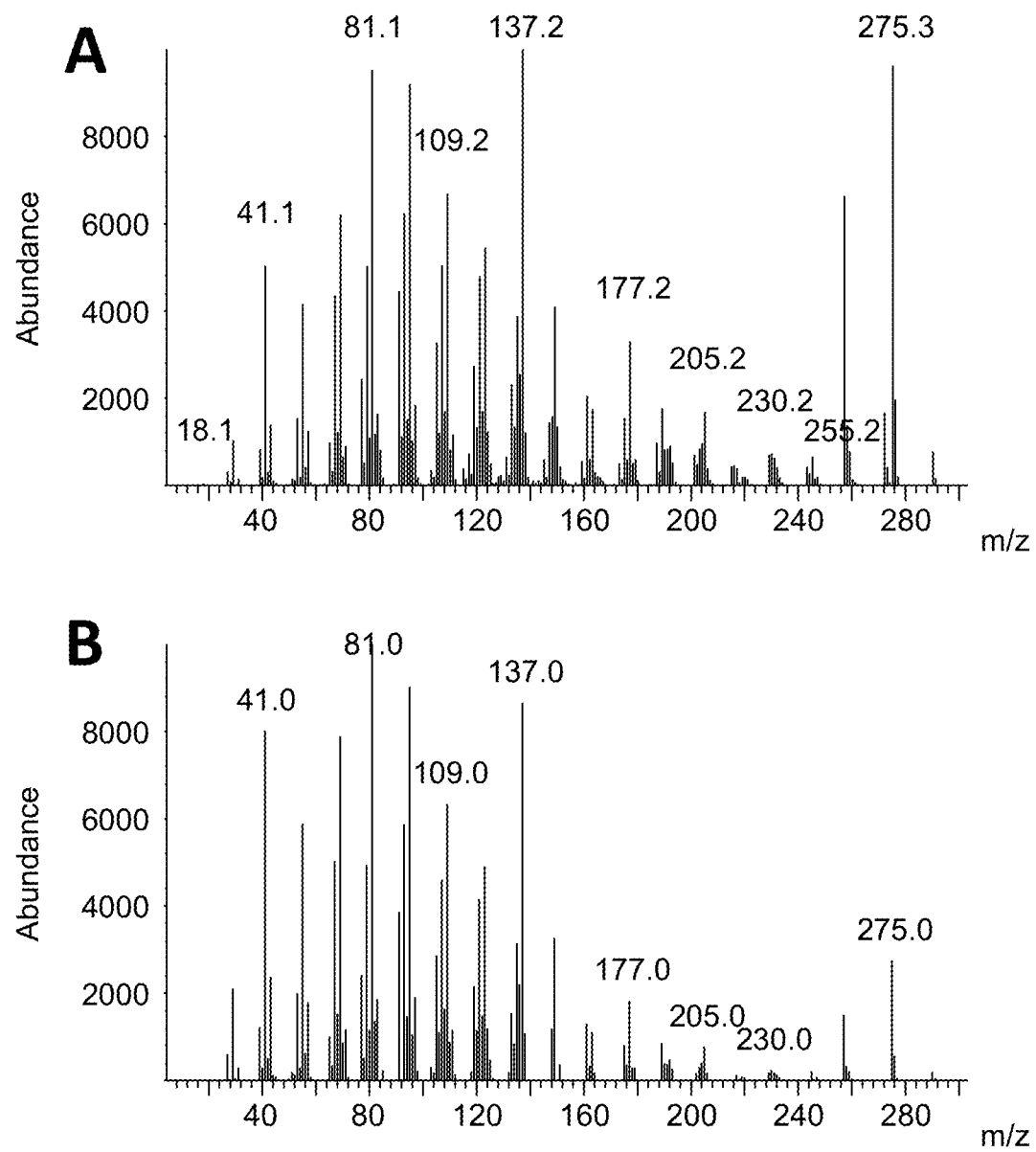
FIG. 2B. Mass spectrum of the copalol produced by E. coli cells (peak with retention time of 16.7 in FIG. 1A) (A) and mass spectrum of authentic copalol (B).
Figure 3:
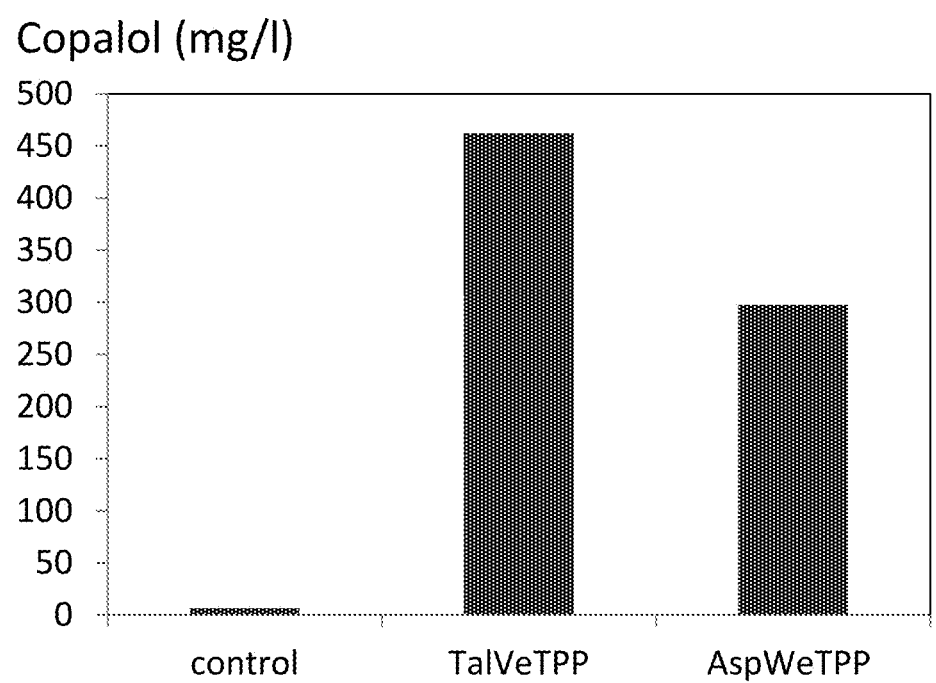
FIG. 3. Copalol production in engineered E. coli cells using TalVeTPP and AspWeTPP.

*E. coli* cells (DP1205 strain as prepared above) were transformed with two plasmids, the pACYC-CrtE-SmCPS2 plasmid and the pJ401-TalVeTPP or pJ401-AspWeTPP. The cells were cultivated and the production of terpene compounds was analyzed as described in the methods section. FIG. 2 shows typical GC-MS of copalol produced by recombinant *E. coli* cells. Cells expressing only the mevalonate pathway enzymes and a SmCPS2 produced small amounts of copalol (6.7 mg/l, FIG. 3) due to the hydrolysis of CPP by endogenous alkaline phosphatase enzymes. *E. coli* cells transformed to express in addition the TalVeTPP or AspWeTPP produce significantly higher amounts of copalol: 462 mg/l and 298 mg/l for TalVeTPP and AspWeTPP, respectively (FIGS. 2 and 3). This experiment shows that TalVeTPP and AspWeTPP can efficiently hydrolyse (+)-CPP to produce (+)-copalol. The Copalol is produced with high purity (>95%). The smaller amounts of copalyl acetate observed in the GC-MS analysis (FIG. 2) is due to cells endogenous acetyl transferase activity.

Example 2: Identification and Characterization Variants of TalVeTPP and AspVeTPP with Copalyl-Pyrophosphate Phosphatase Activity The TalVeTPP and AspVeTPP sequences were used to search for homologous sequences in public databases. Eight new sequences having the signatures of the Pfam Protein tyrosine phosphatase protein family PF13350 were selected: HelGriTPP1, an hypothetical protein *Helicocarpus griseus* (SEQ ID NO:10) (GenBank: PGG95910.1); UmbPiTPP1, a tyrosine phosphatase fro *Umbilicaria pustulata* (SEQ ID NO:13) (GenBank: SLM34787.1); TAlVeTPP2, a hypothetical protein from *Talaromyces verruculosus* (SEQ ID NO:16) (GenBank: KUL92314.1); HydPiTPP1, a hypothetical protein from *Hydnomerulius pinastri* (SEQ ID NO:19) (GenBank: KIJ69780.1); TalCeTPP1, a hypothetical protein fro *Talaromyces cellulolyticus* (SEQ ID NO:22) (GenBank: GAM42000.1); TalMaTPP1, a hypothetical protein from *Talaromyces marneffei* (SEQ ID NO:25) (NCBI XP 002152917.1); TalAstroTPP1, a hypothetical protein from *Talaromyces atroroseus* (SEQ ID NO:28) (NCBI XP_020117849.1); PeSubTPP1, PeSubTPP1, a hypothetical protein from *Penicillium subrubescens* (SEQ ID NO:31) (GenBank: OKP14340.1). The search for protein family signatures showed that the eight amino acid sequences are members of the Pfam Protein tyrosine phosphatase protein family PF13350.

The sequence comparison of the 10 amino acid sequences shows sequences identities ranging from 24% to 93% (Table 1).

TABLE 1

Pairwise sequence comparison of the selected putative terpene phosphatase. The percentage of sequence identity is listed for each pairwise comparison.

| | TalVeTPP | AspWeTPP | HelGriTPP1 | UmbPiTPP1 |
|---|---|---|---|---|
| TalVeTPP | — | 26.3 | 28.1 | 35.6 |
| AspWeTPP | 26.3 | — | 52.2 | 38.2 |
| HelGriTPP1 | 28.1 | 52.2 | — | 43.2 |
| UmbPiTPP1 | 35.6 | 38.2 | 43.2 | — |
| TalVeTPP2 | 28.9 | 36 | 41.3 | 38.6 |
| HydPiTPP1 | 28.6 | 34.8 | 40.2 | 39.5 |
| TalCeTPP1 | 93.5 | 26.3 | 27.5 | 34.7 |
| TalMaTPP1 | 76.8 | 23.8 | 25.4 | 31.6 |
| TalAstroTPP1 | 62.9 | 27.6 | 28.8 | 34.6 |
| PeSubTPP1 | 56.6 | 26.4 | 28.9 | 34.1 |

| | TalVeTPP2 | HydPiTPP1 | TalCeTPP1 | TalMaTPP1 |
|---|---|---|---|---|
| TalVeTPP | 28.9 | 28.6 | 93.5 | 76.8 |
| AspWeTPP | 36 | 34.8 | 26.3 | 23.8 |
| HelGriTPP1 | 41.3 | 40.2 | 27.5 | 25.4 |
| UmbPiTPP1 | 38.6 | 39.5 | 34.7 | 31.6 |
| TalVeTPP2 | — | 36.7 | 28 | 25.7 |
| HydPiTPP1 | 36.7 | — | 28 | 26.2 |
| TalCeTPP1 | 28 | 28 | — | 75.9 |
| TalMaTPP1 | 25.7 | 26.2 | 75.9 | — |
| TalAstroTPP1 | 29 | 30.5 | 63.2 | 59.2 |
| PeSubTPP1 | 29 | 30.1 | 57.3 | 51.8 |

| | TalAstroTPP1 | PeSubTPP1 |
|---|---|---|
| TalVeTPP | 62.9 | 56.6 |
| AspWeTPP | 27.6 | 26.4 |
| HelGriTPP1 | 28.8 | 28.9 |
| UmbPiTPP1 | 34.6 | 34.1 |
| TalVeTPP2 | 29 | 29 |
| HydPiTPP1 | 30.5 | 30.1 |
| TalCeTPP1 | 63.2 | 57.3 |
| TalMaTPP1 | 59.2 | 51.8 |
| TalAstroTPP1 | — | 55.5 |
| PeSubTPP1 | 55.5 | — |

The cDNA sequence encoding for HelGriTPP1 (SEQ ID NO:11), UmbPiTPP1 (SEQ ID NO:14), TalVeTPP2 (SEQ ID NO:17), HydPiTPP1 (SEQ ID NO:20), TalCeTPP1(SEQ ID NO:23), TalMaTPP1(SEQ ID NO:26), TalAstroTPP1 (SEQ ID NO:29) and PeSubTPP1 (SEQ ID NO:32) were codon optimized (for *E. coli* expression and cloned individually in the pJ401 expression plasmid (ATUM, Newark, Calif.).

Figure 4:
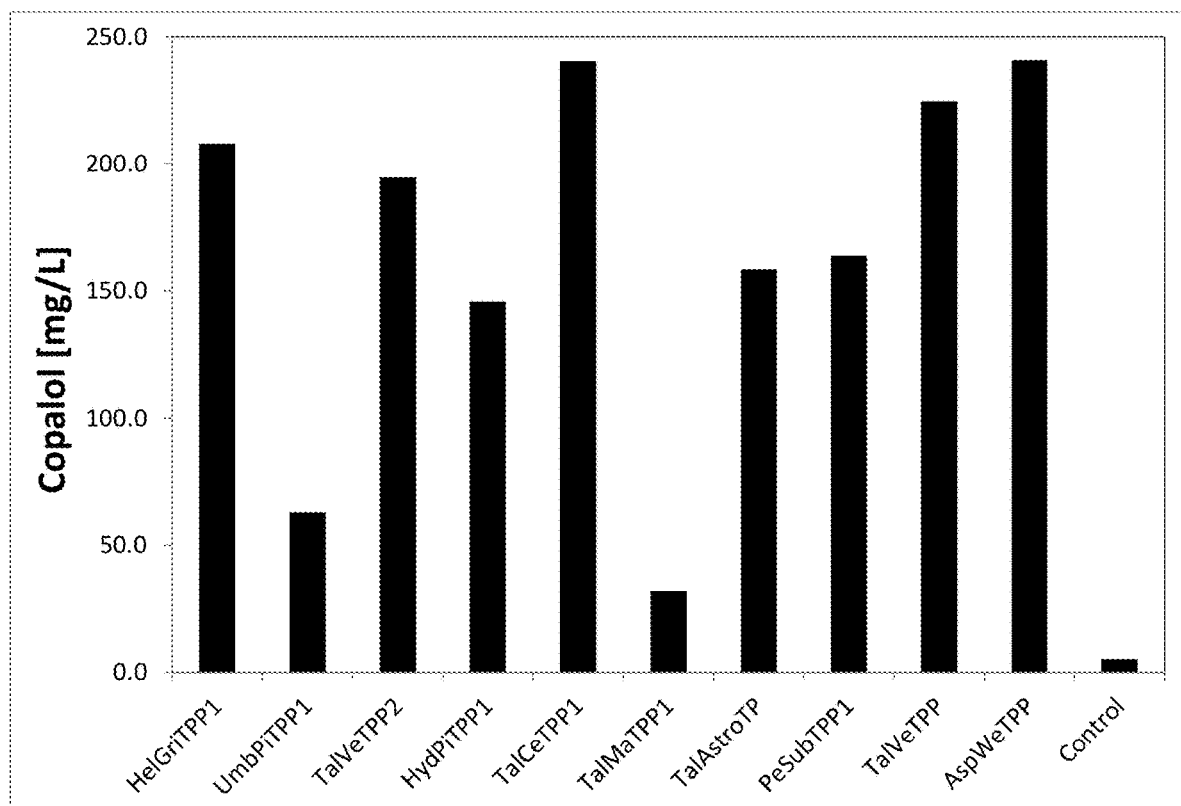
FIG. 4. Copalol production in engineered E. coli cells using TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1.

The DP1205 *E. coli* cells were transformed with the pACYC-CrtE-SmCPS2 plasmid and one of the pJ401 plasmid carrying a optimized cDNA encoding for HelGriTPP1 (SEQ ID NO:9), UmbPiTPP1 (SEQ ID NO:12), TalVeTPP2 (SEQ ID NO:15), HydPiTPP1 (SEQ ID NO:18), TalCeTPP1 (SEQ ID NO:21), TalMaTPP1(SEQ ID NO:24), TalAstroTPP1 (SEQ ID NO:27) and PeSubTPP1 (SEQ ID NO:30). The cells were cultivated and the production of copalol was analyzed in the conditions described the methods section. Cells transformed with the pACYC-CrtE-SaLPS plasmid and an empty pJ401 plasmid were used as a control strain. All strains expressing the recombinant TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1 proteins accumulated copalol in quantities ranging from 32 to 240 mg/l confirming enzymatic conversion of CPP to copalol with all these recombinant enzymes (FIG. 4).

This example shows that TalVeTPP, AspWeTPP, HelGriTPP1, UmbPiTPP1, TalVeTPP2, HydPiTPP1, TalCeTPP1, TalMaTPP1, TalAstroTPP1 and PeSubTPP1 can be used for the enzymatic conversion of CPP to copalol and can be used to produce copalol in engineered cells.

Example 3: Production of Labdendiol in *E. coli* Cells

Figure 5:
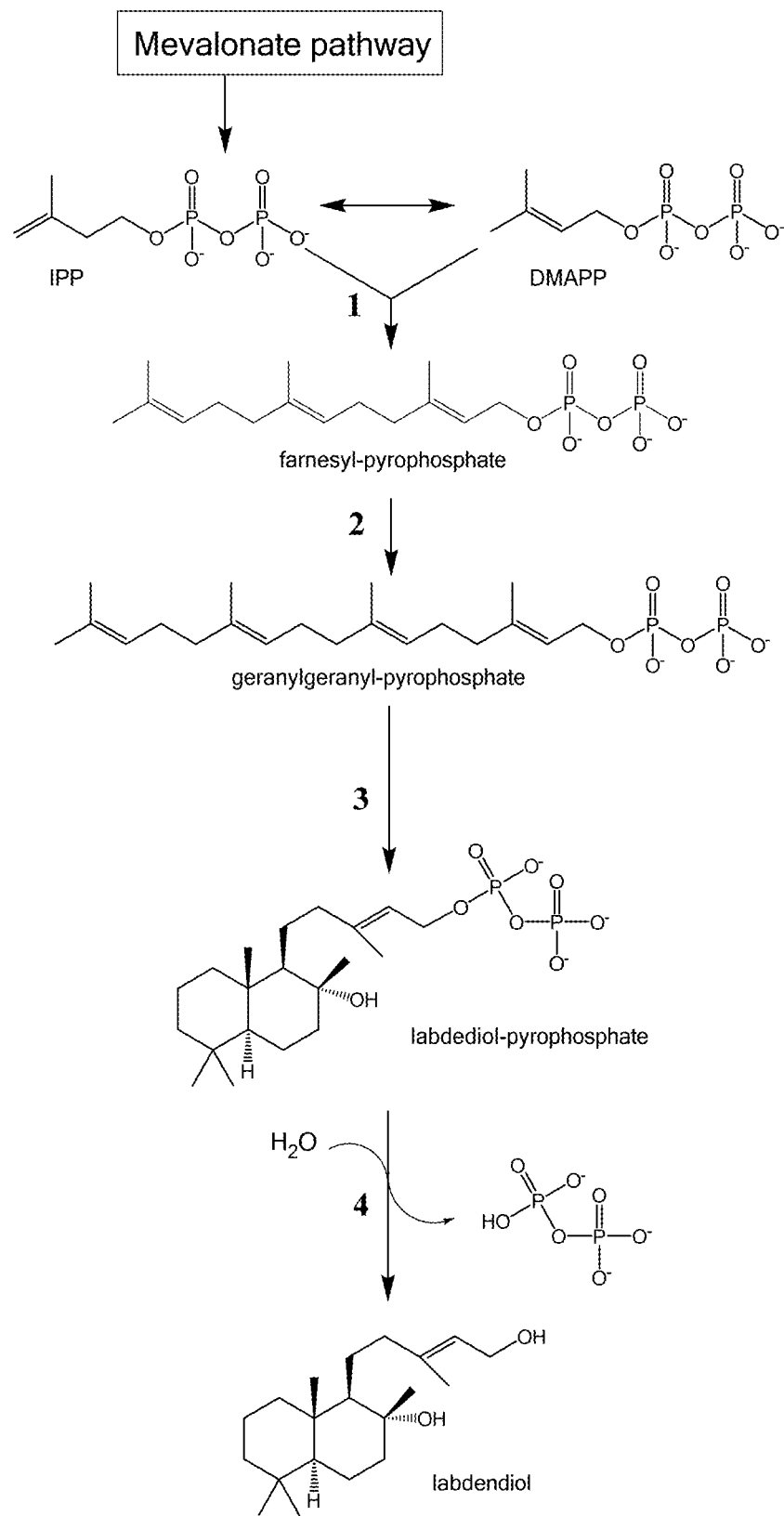
FIG. 5. Biosynthetic pathway of labdendiol. 1, farnesyl-pyrophosphate synthase. 2, geranylgeranyl-pyrophosphate synthase. 3, labdendiol-pyrophosphate synthase. 4, Phosphatase.

An expression plasmid carrying a gene encoding a geranylgeranyl-pyrophosphate synthase (GGPS) and a gene encoding a labdendiol-phyrophosphate synthase (LPS) was constructed. For the GGPS, the CrtE gene from *P. agglomerans* described in Example 1 was used. For the LPS gene, the cDNA encoding for SsLPS from *Salvia sclarea* (WO2009095366, GenBank: AET21246.1) was used. The SsLPS encoding cDNA sequence was optimized (SEQ ID NO:37) as described in WO2009095366 and cloned between the NdeI and KpnI sites in the pACYC-Crte plasmid providing the plasmid pACYC-CrtE-SaLPS carrying a GGP synthase gene and a LPP synthase gene. *E. coli* cells, such as the DP1205 strain, transformed with the pACYC-CrtE-SsLPS accumulate LPP as the diterpene precursor compound (FIG. 5).

Figure 6:
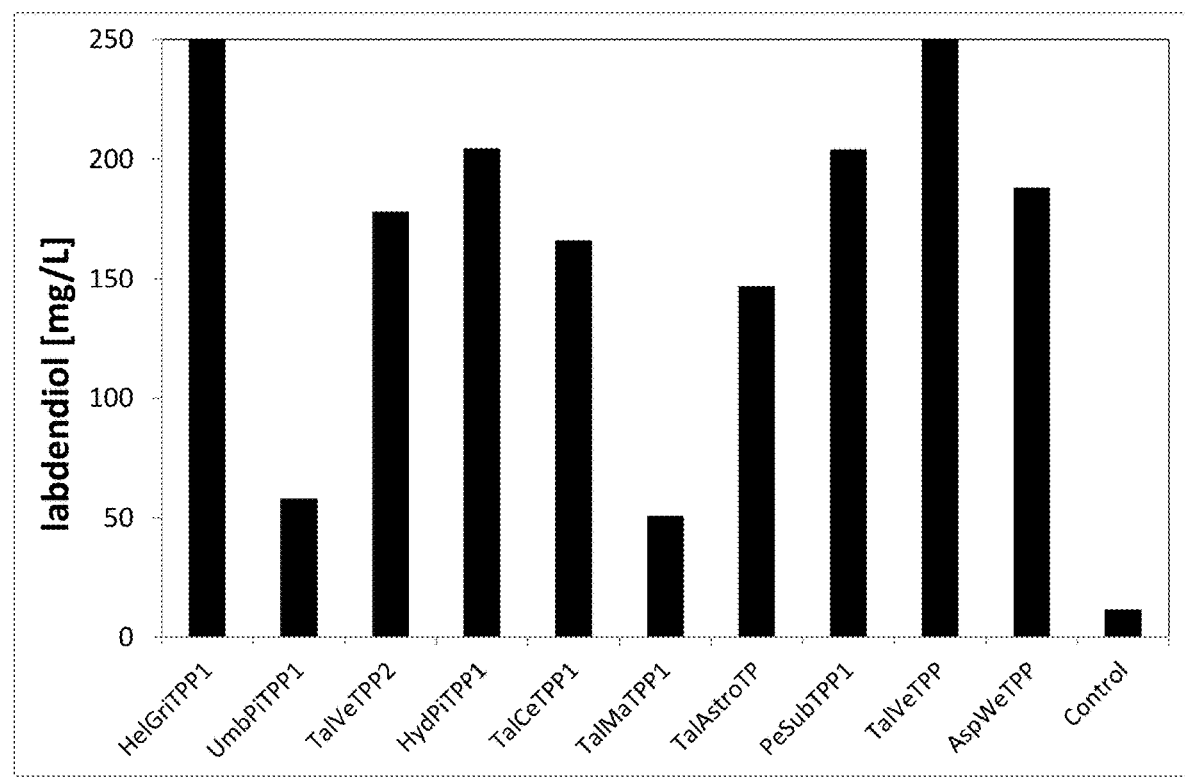
FIG. 6. Labdendiol production in engineered E. coli cells using TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1.
Figure 7A:
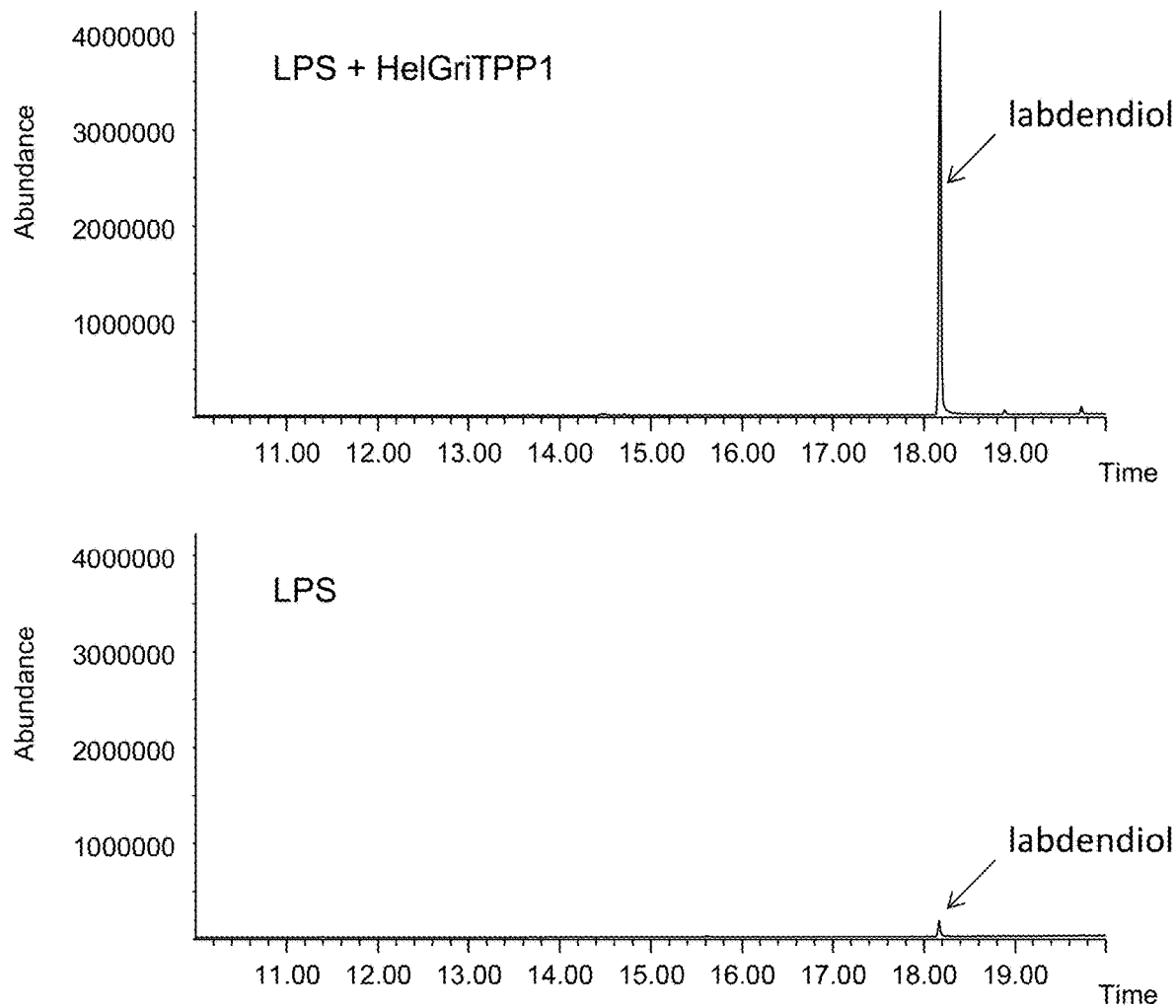
FIG. 7A. Chromatogram of a GC-MS analysis of labdendiol produced by E. coli cells. Upper chromatogram: E. coli cells producing the recombinant enzymes of a mevalonate pathway, a LPP synthase and HelGriTPP1. Lower chromatogram: Control with *E. coli* cells producing the recombinant enzymes of a mevalonate pathway and a LPP synthase.
Figure 7B:
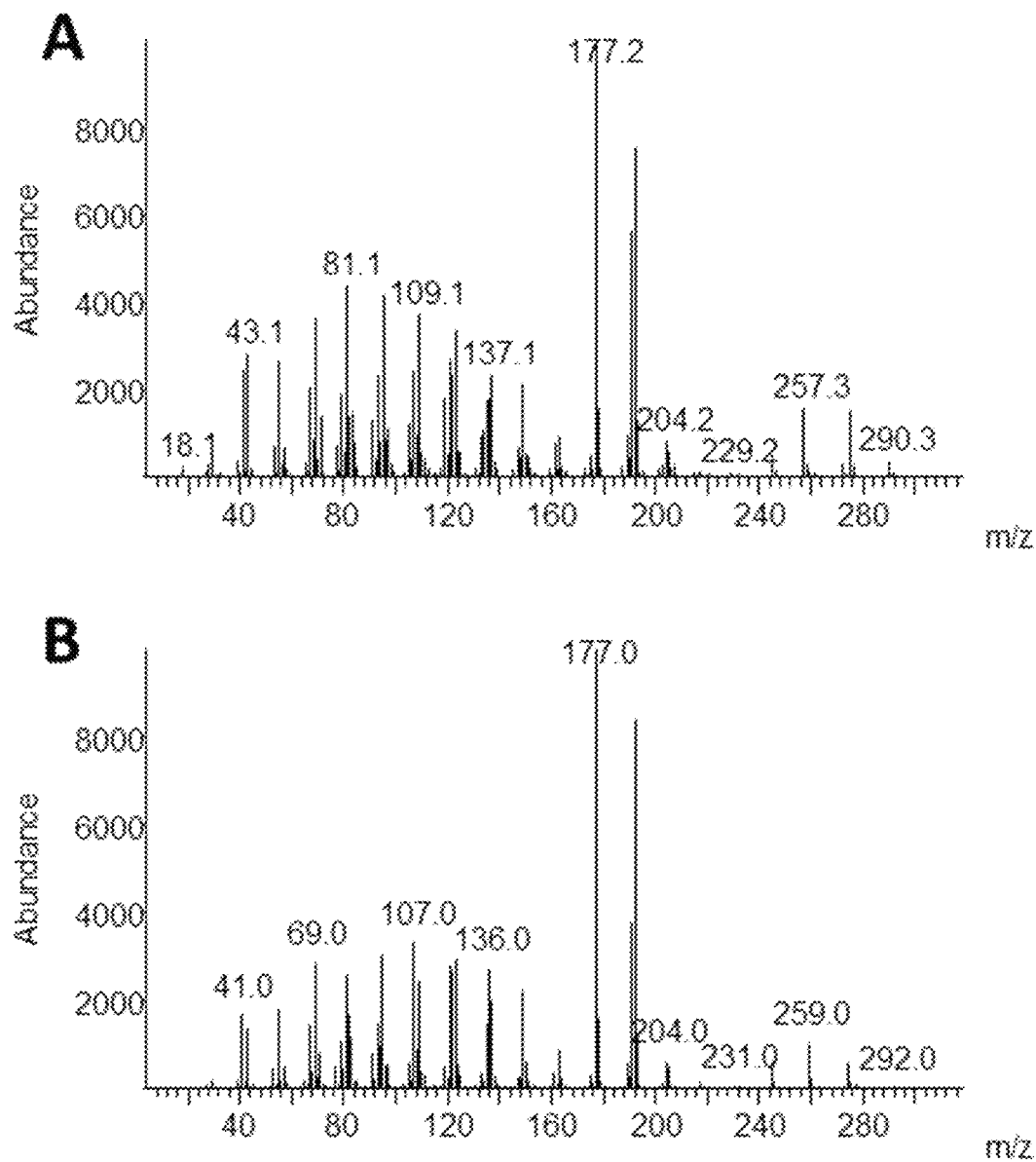
FIG. 7B. Mass spectrum of the labdendiol produced by *E. coli* cells (peak with retention time of 18.2 in FIG. 6A) (A) and mass spectrum of authentic copalol (B).

The DP1205 *E. coli* cells (as prepared above) were transformed with the pACYC-CrtE-SsLPS plasmid and one of the pJ401 plasmid carrying a optimized cDNA encoding for TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1 (see Examples 1 and 2, above). The cells were cultivated and the production of labdendiol was analyzed in the conditions described in the methods section. Compared to the control cells transformed with an empty pJ401 plasmid and the pACYC-CrtE-SsLPS, all cells transformed to produce either of the recombinant TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1 proteins produced significantly increased amounts of labdendiol (5 to 25 fold increase) (FIG. 6). The labdendiol concentrations in the cell cultures were between 50 and 272 g/l at the end of the cultivation period. FIG. 7 shows the GC-MS analysis of a typical *E. coli* producing labdendiol cell. The total ion chromatogram shows that the labdendiol produced in these conditions has a purity of at least 98%.

Example 4: Production of Farnesol and Geranylgeraniol in *E. coli* Cells

Figure 8:
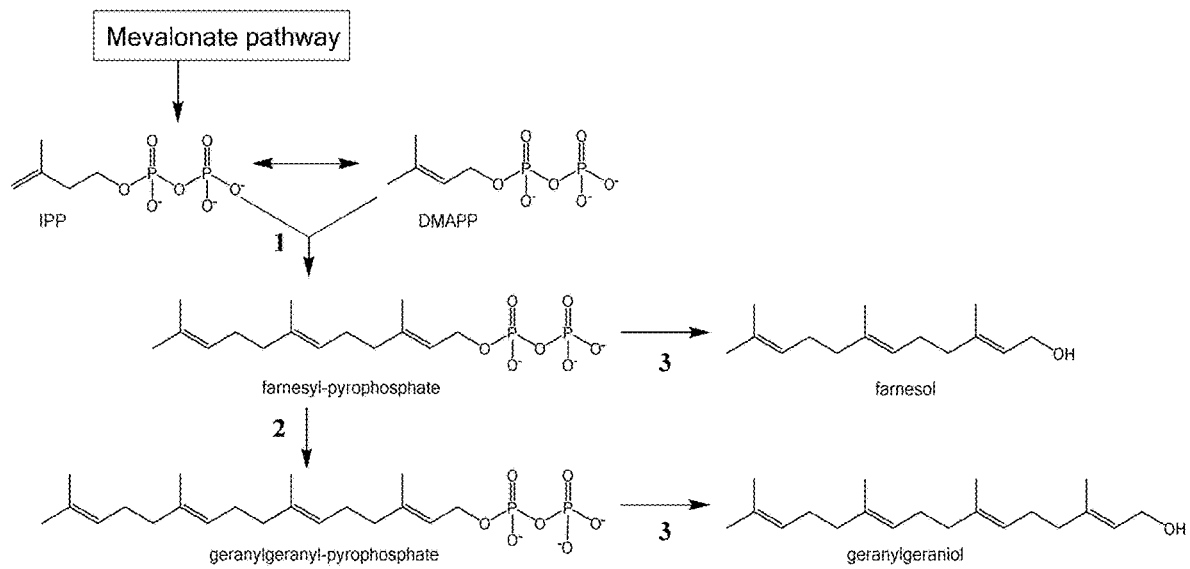
FIG. 8. Biosynthetic pathway of farnesol and geranylgeraniol. 1, farnesyl-pyrophosphate synthase. 2, geranylgeranyl-pyrophosphate synthase. 3, Phosphatase.

The recombinant proteins TalVeTPP, AspWeTPP, HelGriTPP1, UmbPiTPP1, TalVeTPP2, HydPiTPP1, TalCeTPP1, TalMaTPP1, TalAstroTPP1 and PeSubTPP1 were also evaluated for enzymatic activity on linear substrates such as farnesyl-pyrophosphate (FPP) and geranylgeranyl-pyrophosphate (GGPP). Assays were performed in conditions similar to examples 1 and 2 and in the methods section except for the pACYCDuet™-1 plasmid which was adapted to produce in-vivo FPP and GGPP. For the FPP accumulating *E. coli* cells an empty pACYCDuet™-1 plasmid was used. *E. coli* cells, such as the DP1205 strain, transformed with the empty plasmid pACYCDuet™-1 (Merck) will accumulate FPP as the terpene precursor compound (FIG. 8). For the GGPP accumulating *E. coli* cells the plasmid pACYC-CrtE (Example 1) was used. *E. coli* cells, such as the DP1205 strain, transformed with the pACYC-CrtE plasmid will accumulate the GGPP as the terpene precursor compound (FIG. 5 and FIG. 8).

Figure 9:
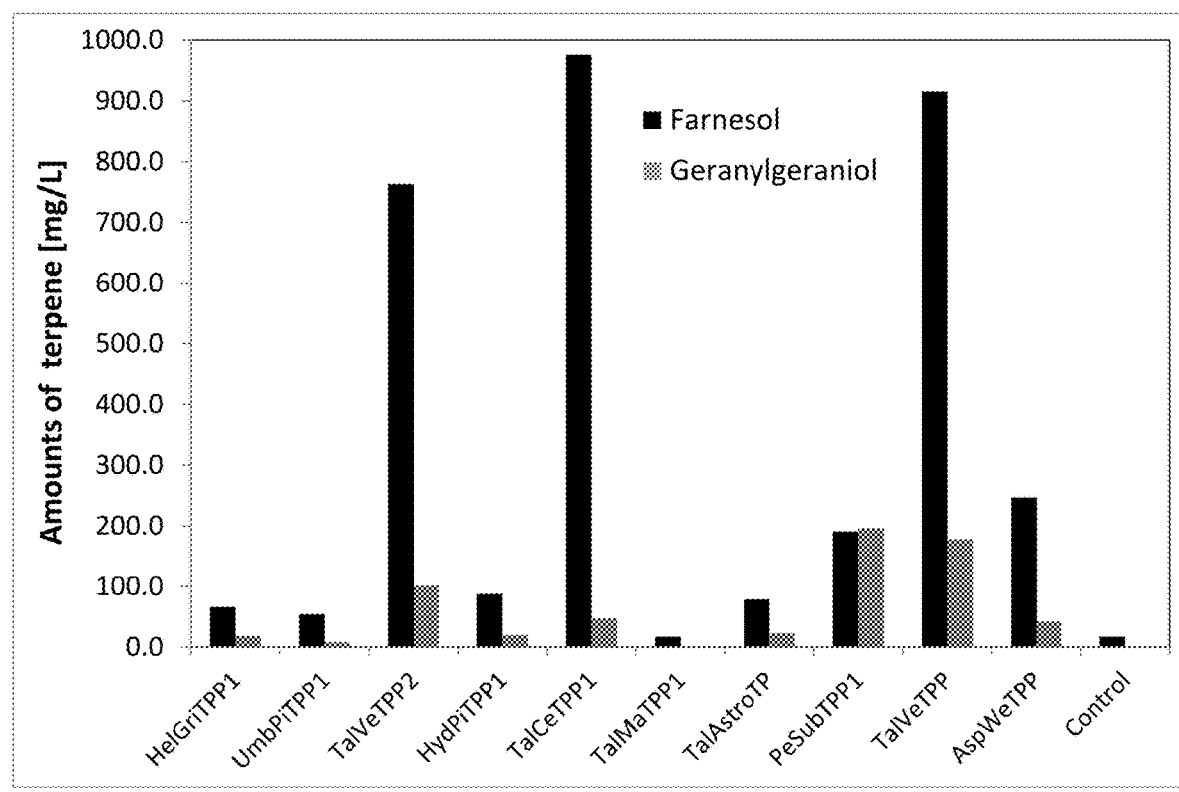
FIG. 9. Farnesol and geranylgeraniol production in engineered *E. coli* cells using TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1.

The DP1205 *E. coli* cells were transformed with the pACYC-CrtE or pACYCDuet™-1 plasmid and with one of the pJ401 plasmid carrying a optimized cDNA encoding for TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1 (see Examples 1 and 2). The cells were cultivated and the production of farnesol and geranygeraniol was analyzed in the conditions described in the methods section. Compared to the control cells transformed with an empty pJ401 some of the cells transformed to produce the recombinant TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1 proteins produced significantly increased amounts of farnesol and geranylgeraniol (FIG. 9). For example cell expressing TalVeTPP2, TalCeTPP1 and TalVeTPP produce high amounts (763 to 976 mg/ml) of farnesol. Similarly, cells expressing PeSubTPP1 and TalVeTPP produce high amounts (196 to 198 mg/ml) of geranylgeraniol. In contrast, HelGriTPP1, UmbPiTPP1, HydPiTPP1 or TalMaTPP1 show low FPP and GGPP phosphatase activity.

Example 5: Substrate Selectivity of the Phosphatases

Figure 10:
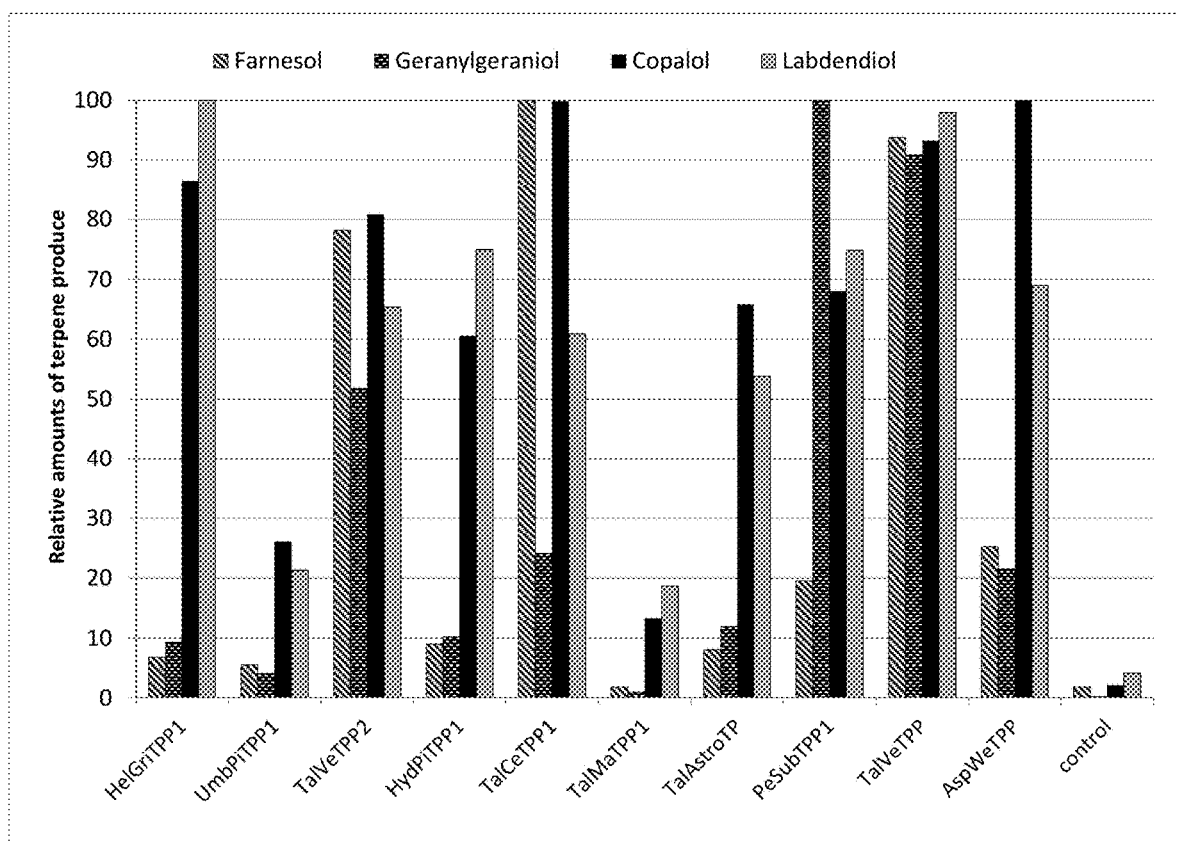
FIG. 10. Comparison of the production of farnesol, geranylgeraniol, copalol and labdediol in engineered *E. coli* cells using TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1. The values are relative to the maximum amount produced for each compounds set at 100.

The comparison of the enzymatic activities observed in the previous examples with the four different substrates reveals distinct substrate selectivity for TalVeTPP, AspWeTPP, HelGriTPP1, UmbPiTPP1, TalVeTPP2, HydPiTPP1, TalCeTPP1, TalMaTPP1, TalAstroTPP1 or PeSubTPP1 (FIG. 10). This approach thus allows selecting enzymes with phosphatase activity based on their substrate selectivity. For example, HelGriTPP1, HydPiTPP1 or AspWeTPP show relative higher activity for CPP and LPP and lower activity for FPP and GGP compared to other the other listed enzymes. These enzymes can thus be used to most effectively produce copalol or labdendiol with limited side activity on the pathway intermediates. UmbPiTPP1, TalMaTPP1 and TalAstroTPP1 also show limited side activity on FPP and GGPP, however, produce lower amounts of labdendiol and copalol.

Example 6: Production of Copalol and Labdendiol Using Operons Containing a GGPP Synthase, a Diterpene Synthase and a Phosphatase An operon was constructed containing 3 cDNAs encoding TalVeTPP; TaTps1-del59 and a GGPP synthase. TaTps1- del59 is an N-terminal truncated CPP synthase from *Triticum aestivum* (NCBI accession No BAH56559.1). The cDNA encoding for TaTps1-del59 was codon optimized (SEQ ID NO:39). For the GGPP synthase, the codon optimized version of the CrtE gene from *Pantoea agglomerans* (NCBI accession M38424.1) was used (SEQ ID NO: 35). The operon was cloned in the pJ401 expression plasmid (ATUM, Newark, Calif.) providing the construct pJ401-CPOL-2.

Another operon was constructed with an organization similar to CPOL-2 above, except for the gene encoding for TaTps1-del59 which was replaced by the optimized gene encoding for SaLPS(SEQ ID NO:37). This operon was cloned into plasmid pJ401(ATUM, Newark, Calif.) providing the construct pJ401-LOH-2

The DP1205 *E. coli* cells as prepared above were transformed with the plasmid pJ401-CPOL-2 or pJ401-LOH-2. The cells were cultivated as described and the production of diterpenes was analyzed as described in the methods section. In parallel, cells transformed with the empty PJ401 plasmid and with the pACYC-CrtE-SsLPS or pACYC-CrtE-SmCPS plasmid were used as controls.

Figure 11:
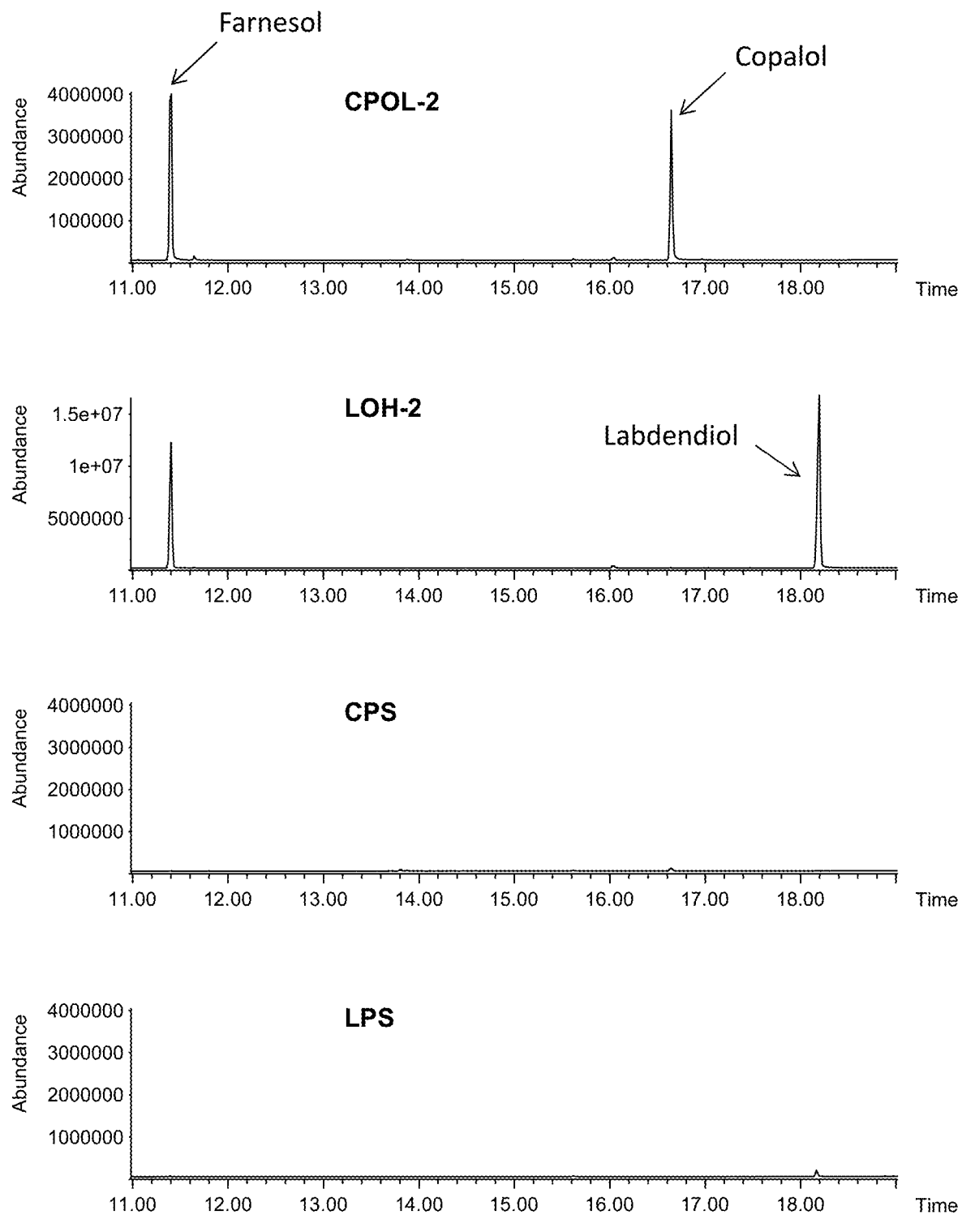
FIG. 11. Production of terpene compounds in engineered *E. coli* cells transformed with the plasmid CPOL-2 and LOH-2 and comparison with cells producing LPP and CPP without expressing a recombinant phosphatase.

Cells transformed with the plasmid CPOL-2 produced copalol and farnesol with an average concentration of 200 mg/l and 300 mg/l for copalol and farnesol, respectively. Cells transformed with the plasmid LOH-2 produced labdendiol and farnesol with an average concentration of 1260 mg/l and 830 mg/l for copalol and farnesol, respectively (FIG. 11). The significant amounts of farnesol produced using these two constructs is due to an incomplete conversion of the FPP pool to GGPP and the enzymatic activity of TalVeTPP on FPP in addition to CPP (see FIG. 10). Corresponding experiments with, for example, HelGriTPP1 (and others shown in FIG. 10 with higher specificity) will produce less farnesol.

Example 7: Enzymatic Oxidation of the Terpene Compounds Produced by the Recombinant Phosphatase to Produce the Corresponding Alpha,Beta-Unsaturated Aldehydes The following alcohol dehydrogenases (ADH) can be used for the oxidation of the terpene compounds produced by the phosphatases described in the previous examples:
CymB (SEQ ID NO: 42) (GenBank accession AEO27362.1) from the strain *Pseudomonas* sp. 19-rlim;
AspWeADH1 (SEQ ID NO: 44) (GenBank accession OJJ34588.1) encoded by the gene located in the 2487333 . . . 2488627 region of the *Aspergillus wentii* DTO 134E9 unplaced genomic scaffold ASPWEscaffold_5 (NCBI accession No KV878213.1);
PsAeroADH1 (SEQ ID NO: 46) (GenBank accession WP_079868259.1) from *Pseudomonas aeruginosa;*
AzTolADH1 (SEQ ID NO: 48) (GenBank accession WP_018990713.1) from *Azoarcus toluclasticus;*
AroAroADH1 (SEQ ID NO: 50) (GenBank accession KM105875.2) from *Aromatoleum aromaticum.*
ThTerpADH1 (SEQ ID NO: 52) (Genbank accession WP_021250577.1) from *Thauera terpenica.*
CdGeoA (SEQ ID NO: 54) (NCBI accession WP_043683915.1) from *Castellaniella defragrans.*
VoADH1 (SEQ ID NO: 56) (GenBan accession AVX32614.1) from *Valeriana officinalis.*
Codon optimized cDNAs encoding for each of the above ADHs were synthetized (see SEQ ID NO: 41, 43, 45, 47, 49, 51, 53 and 55, respectively) and cloned in the pJ423 expression plasmid (ATUM, Newark, Calif.).

Figure 12A:
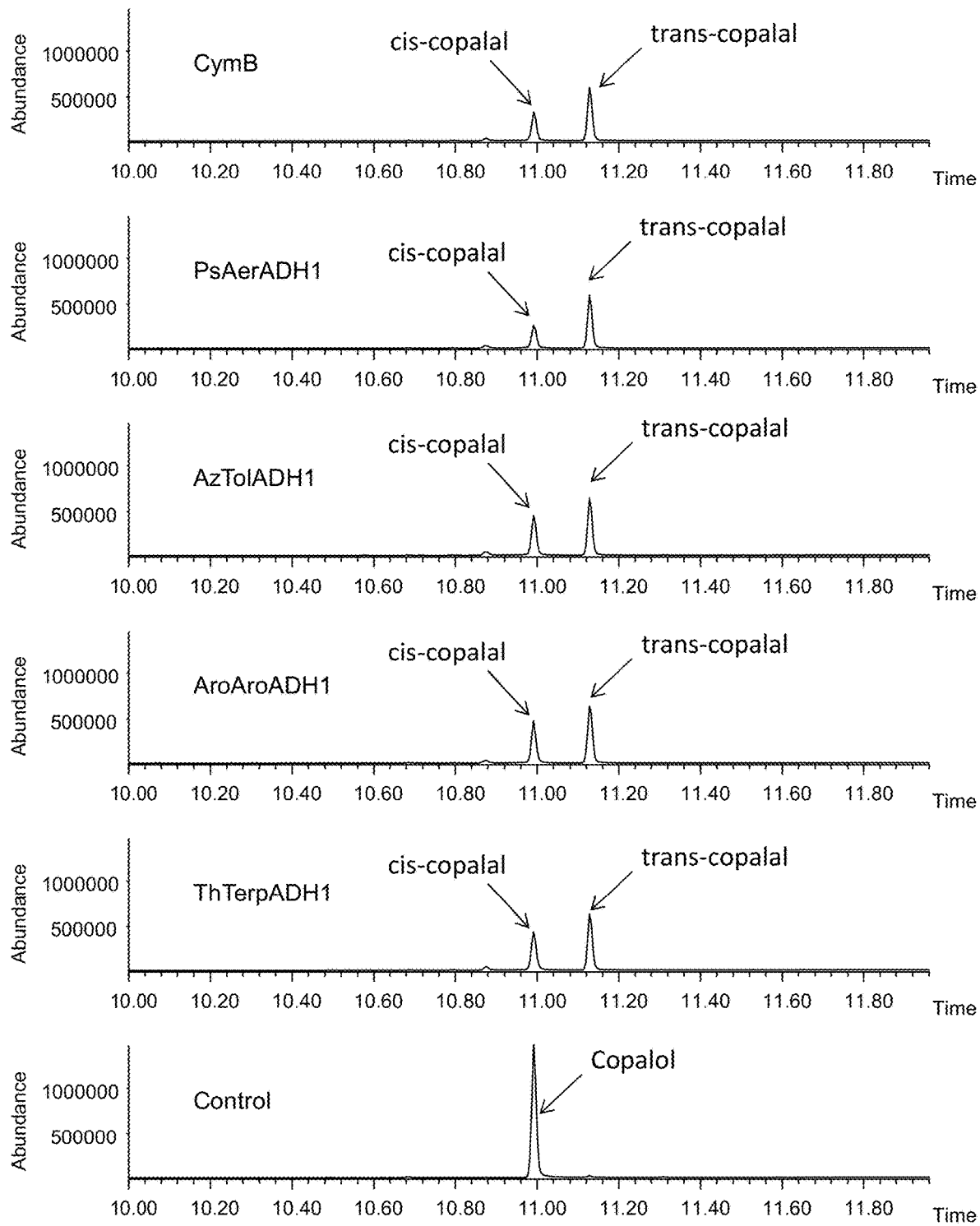
FIG. 12A. Production of copalal in engineered cells. The figure shows the chromatograms of the GC-MS analysis of copalal produced by *E. coli* cells. The cells were engineered to produce copalyl-diphosphate from the mevalonate pathway and to express a Protein tyrosine phosphatase and an ADH enzyme. The different ADHs expressed in the cells are indicated for each chromatogram.
Figure 12B:
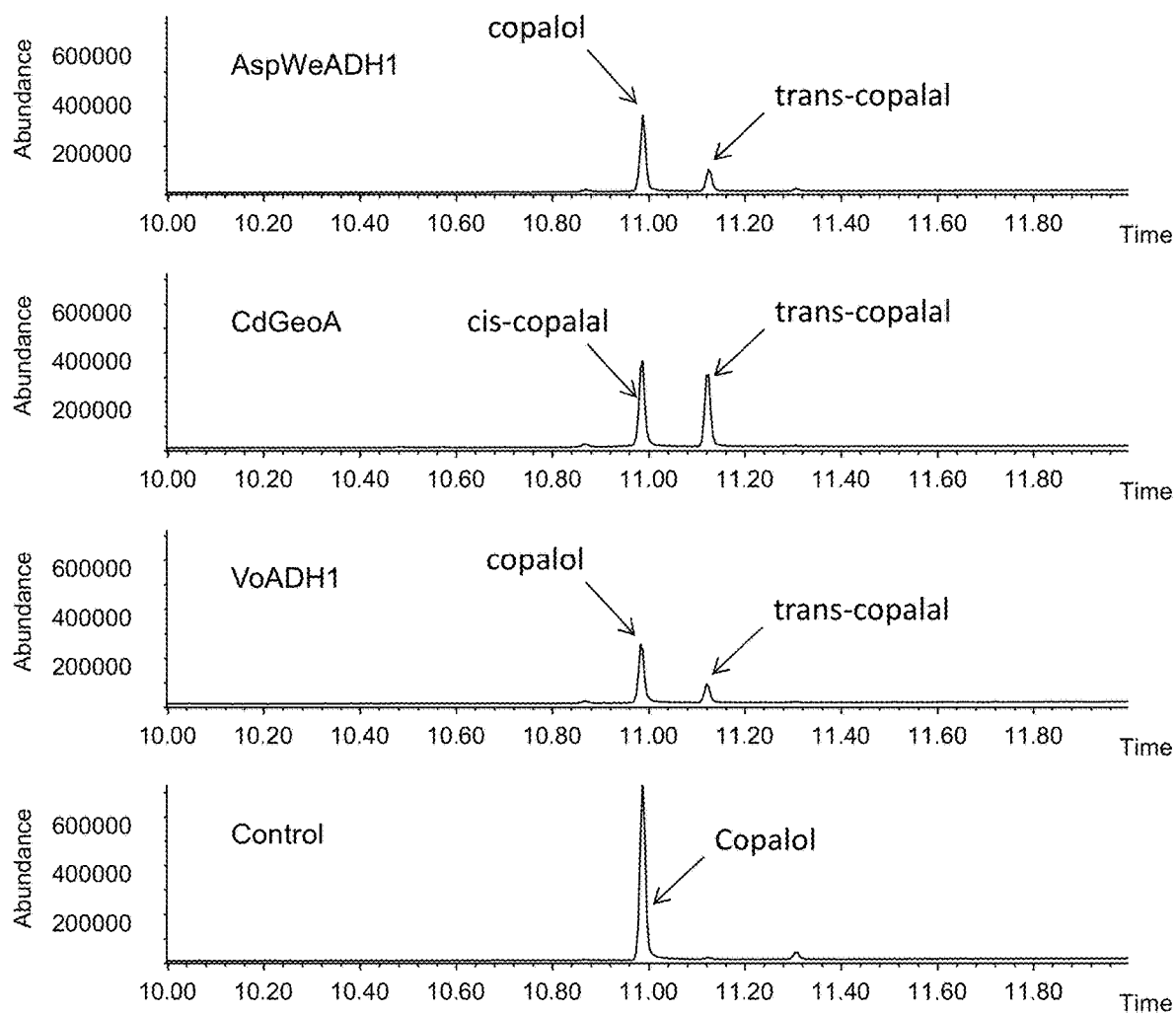
FIG. 12B. Production of copalal in engineered cells. The figure shows the chromatograms of the GC-MS analysis of copalal produced by *E. coli* cells. The cells were engineered to produce copalyl-diphosphate from the mevalonate pathway and to express a Protein tyrosine phosphatase and an ADH enzyme. The different ADHs expressed in the cells are indicated for each chromatogram.
Figure 13A:
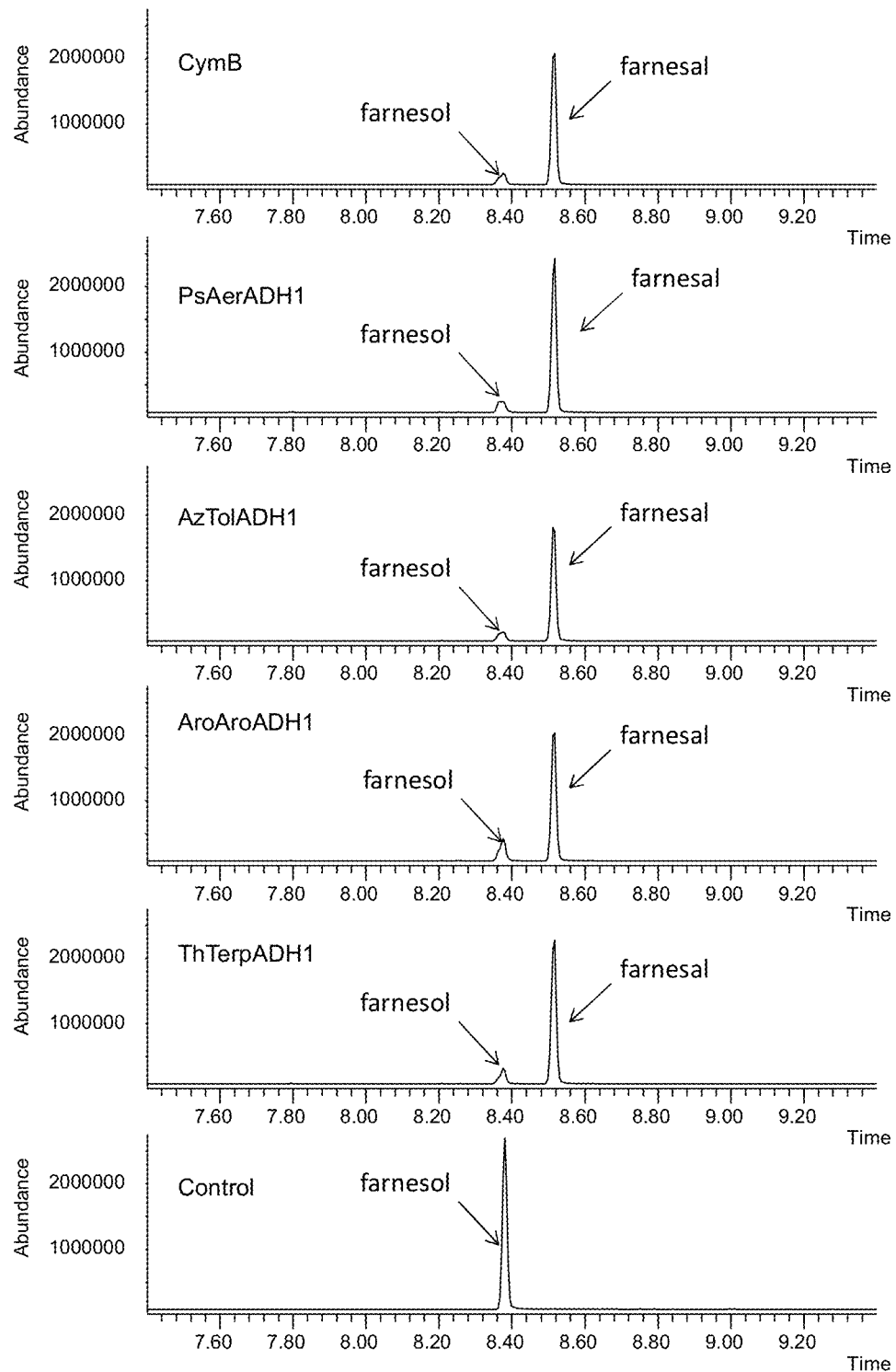
FIG. 13A. GCMS chromatogramme showing the formation of farnesal from farnesol in cells engineered to produce the recombinant enzymes of a mevalonate pathway, a CPP synthase, a Protein tyrosine phosphatase and an ADH.
Figure 13B:
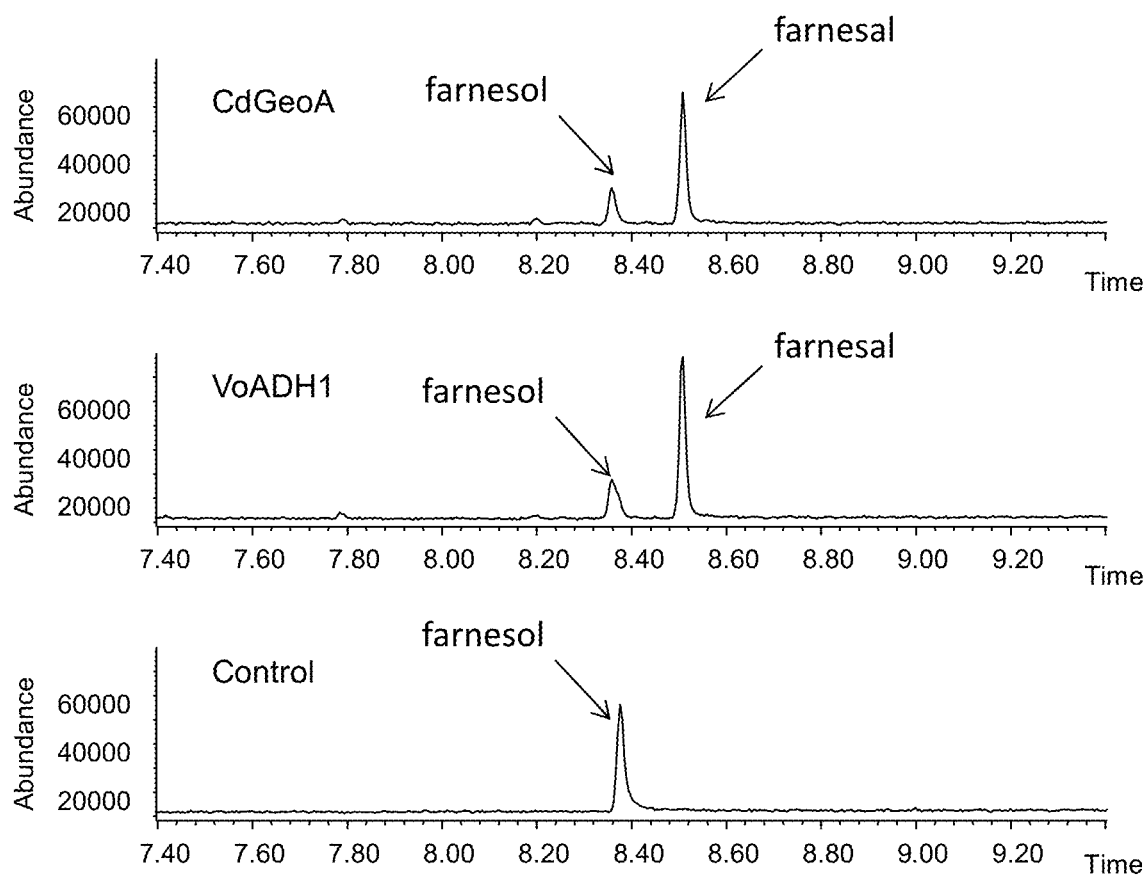
FIG. 13B. GCMS chromatogramme showing the formation of farnesal from farnesol in cells engineered to produce the recombinant enzymes of a mevalonate pathway, a CPP synthase, a Protein tyrosine phosphatase and an ADH.

The DP1205 *E. coli* cells as prepared above were transformed with the plasmid pJ401-CPOL-2 and one of these pJ423-ADH plasmids. The cells were cultivated as described and the production of diterpenes was analyzed as described in the methods section. In parallel, cells transformed with the pJ401-CPOL-2 plasmid and with the empty pJ423 plasmid was used as a control (FIG. 12). Formation of copalal was observed with all cells showing that the combination of enzymes of a copalol biosynthetic pathway including a protein tyrosine phosphatase and an ADH selected from the ADHs listed above can be used to efficiently produce copalal. Expect for AspWeADH1 and VoADH1, the conversion of copalol to copalal in the cells was at least 90%. A mixture of cis- and trans-isomers of copalal was observed due to non-enzymatic isomerisation of the trans-copalal produced by the ADHs. Using the same ADHs, conversion of farnesol to farnesal was also observed (FIG. 13).

Figure 14:
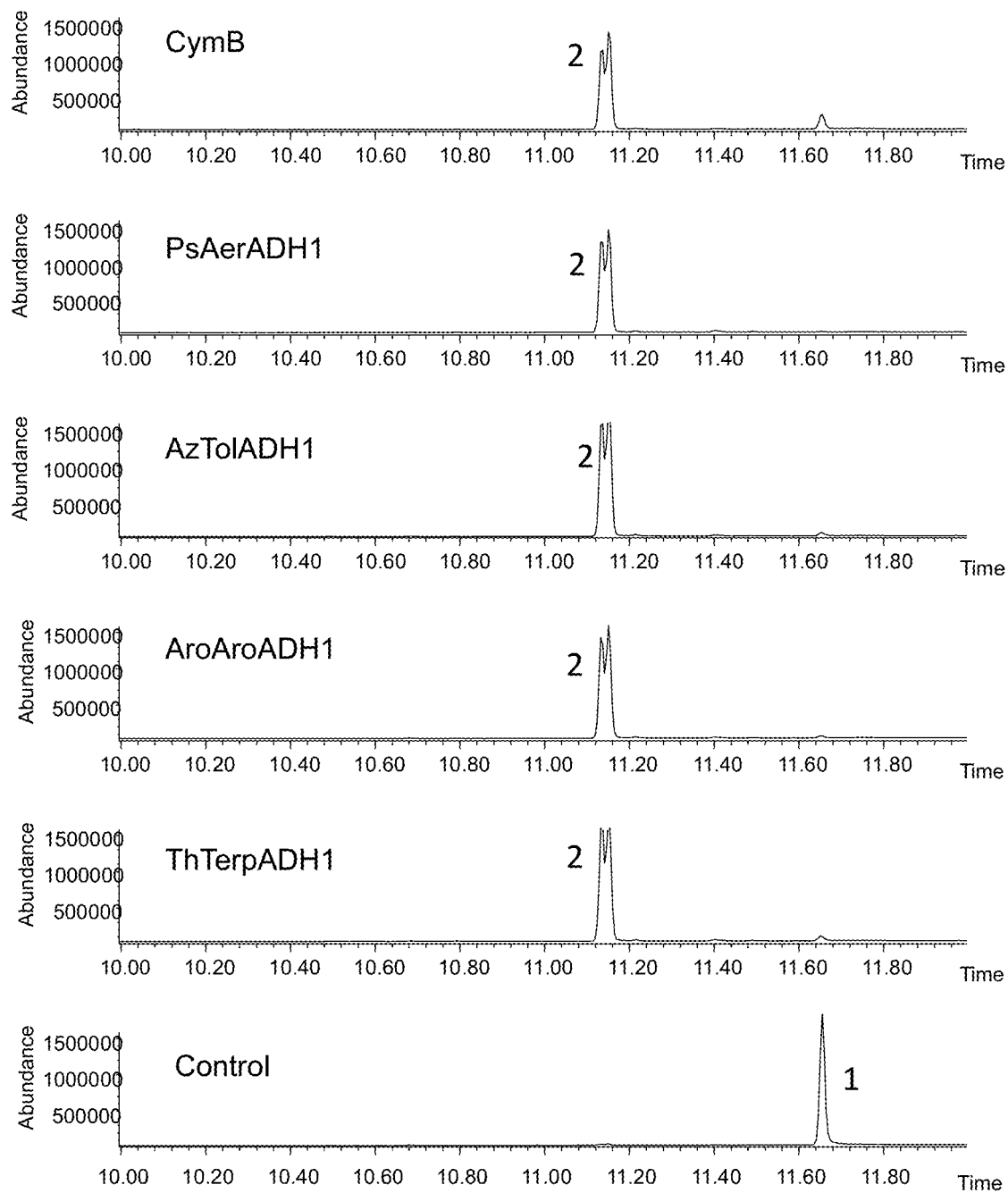
FIG. 14. GCMS analysis of the production of the labdendiol oxidized products in *E. coli* cells engineered to produce the recombinant enzymes of a mevalonate pathway, a LPP synthase, a Protein tyrosine phosphatase and an ADH. The different ADHs expressed in the cells are indicated for each chromatogram. The peak of labdendiol and its oxidized products are label 1 and 2, respectively.
Figure 17:
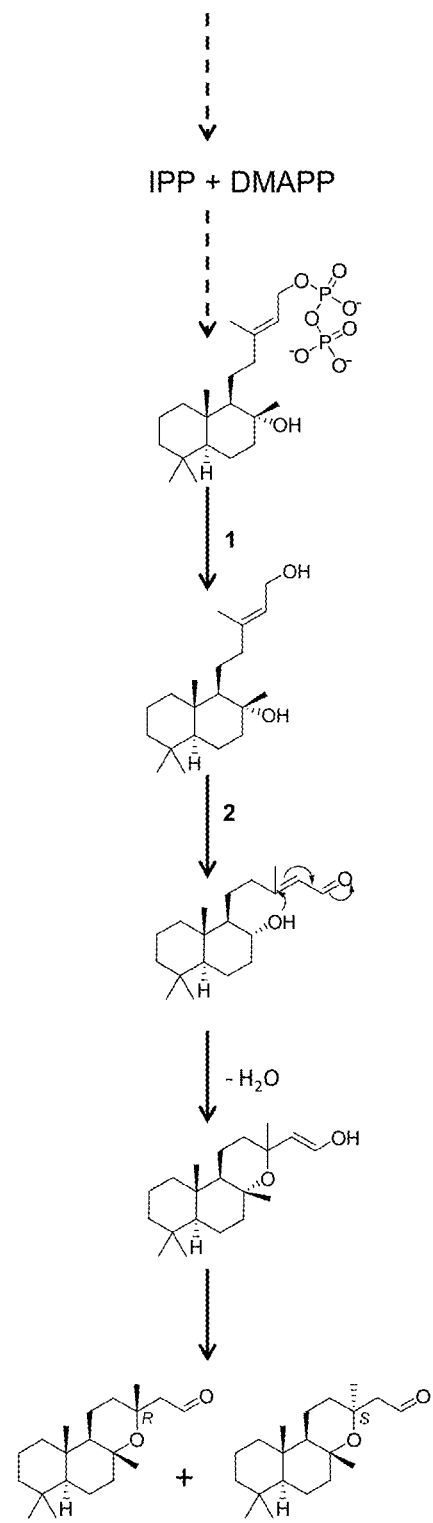
FIG. 17. Biosynthetic pathway of 18,13-epoxy-labdan-15-al. Dashed arrows represent multiple enzymatic steps. 1, Phosphatase; 2, alcohol dehydrogenase. The following steps are non-enzymatic rearrangement reactions.

With *E. coli* cells co-transformed with the pJ401-LOH-2 and one of the pJ423-ADH plasmids, formation of two oxidation products of labdendiol was observed (FIG. 14). NMR analysis confirmed the two compounds as being two isomers ((13R) and (13S)) of 8,13-epoxy-labdan-15-al as shown in the scheme of FIG. 17. These two compounds result from the instability of the alpha,beta-unsaturated aldehyde 8-hydroxy-labd-13-en-15-al produced by the oxidation of labdendiol. A postulated mechanism of dehydration and rearrangement of the aldehyde to said ismers is shown in the scheme below.

Example 8: Engineering of Recombinant Bacterial Cells for the Production of Copalol Using a Multifunctional CPP Synthase An operon was constructed containing two cDNAs encoding for:
AspWeTPP from *Aspergillus wentii* (SEQ ID NO: 6),
PvCPS, a protein having prenyl-transferase and copalyl-diphosphate synthase activities from *Talaromyces verruculosus* (SED ID NO: 59) (GenBank accession BBF88128.1). PvCPS catalyzes the production of copalyl PP from IPP and DMAPP.

The cDNAs encoding for AspWeTPP and PvCPS were codon optimized (SEQ ID NOs: 8 and 60). An operon was designed containing the two cDNAs and an RBS sequence (AAGGAGGTAAAAAA) (SEQ ID NO: 61) placed upstream of the each cDNAs. The operon was synthesized and cloned into the pJ401 expression plasmid (ATUM, Newark, Calif.) providing the plasmid pJ401-CPOL-4.

The DP1205 *E. coli* cells were transformed with the plasmid pJ401-CPOL-4. The transformed cells were cultivated as described and the production of diterpenes was analyzed as described in the methods section. In these conditions, cells transformed with the plasmid pJ401-CPOL-4 produced copalol as major product with a concentration significantly higher (up to 1 mg/1) than cells transformed with the plasmid pJ401-CPOL-2. This experiment shows that higher concentrations of copalol can be obtained using a multifunctional protein carrying prenyl transferase activity and CPP synthase activity compare to multiple mono-functional proteins.

Example 9: In Vivo Copalol and Copalal Production in Saccharomyces cerevisiae Cells Using a Copalyl-Pyrophosphate Phosphatase and Different Alcohol Dehydrogenases For the production of copalol and copalal, the genes (cDNA optimized for expression in yeast) encoding for the GGPP synthase CrtE (SEQ ID NO: 61) (from *Pantoea agglomerans*, NCBI accession M38424.1), the copalyl-pyrophosphate synthase SmCPS2 (SEQ ID NO: 63) (from *Salvia miltiorrhiza*, NCBI accession ABV57835.1), the copalyl-pyrophosphate phosphatase TalVeTPP (SEQ ID NO: 65) and different alcohol dehydrogenases were expressed in engineered *Saccharomyces cerevisiae* cells with increased level of endogenous farnesyl-diphosphate (FPP).

Four alcohol dehydrogenases were evaluated.
AzTolADH1 (SEQ ID NO: 48) (yeast optimized cDNA SEQ ID NO: 66)
PsAeroADH1 (SEQ ID NO: 46), (yeast optimized cDNA SEQ ID NO: 67)
SCH23-ADH1 from *Hyphozyma roseonigra* (SEQ ID NOs: 69) (yeast optimized cDNA SEQ ID NO: 68)
SCH24-ADH1a from *Cryptococcus albidus* (SEQ ID NOs: 71) (yeast optimized cDNA SEQ ID NO: 70)

To increase the level of endogenous farnesyl-diphosphate (FPP) pool in *S. cerevisiae* cells, an extra copy of all the yeast endogenous genes involved in the mevalonate pathway, from ERG10 coding for acetyl-CoA C-acetyltransferase to ERG20 coding for FPP synthetase, were integrated in the genome of the *S. cerevisiae* strain CEN.PK2-1C (Euroscarf, Frankfurt, Germany) under the control of galactose-inducible promoters, similarly as described in Paddon et al., Nature, 2013, 496:528-532. Briefly, three cassettes were integrated in the LEU2, TRP1 and URA3 loci respectively. A first cassette containing the genes ERG20 and a truncated HMG1 (tHMG1 as described in Donald et al., Proc Natl Acad Sci USA, 1997, 109:E111-8) under the control of the bidirectional promoter of GAL10/GAL1 and the genes ERG19 and ERG13 also under the control of GAL10/GAL1 promoter, the cassette was flanked by two 100 nucleotides regions corresponding to the up- and down-stream sections of LEU2. A second cassette where the genes IDI1 and tHMG1 were under the control of the GAL10/GAL1 promoter and the gene ERG13 under the control of the promoter region of GAL7, the cassette was flanked by two 100 nucleotides regions corresponding to the up- and down-stream sections of TRP1. A third cassette with the genes ERG10, ERG12, tHMG1 and ERG8, all under the control of GAL10/GAL1 promoters, the cassette was flanked by two 100 nucleotides regions corresponding to the up- and down-stream sections of URA3. All genes in the three cassettes included 200 nucleotides of their own terminator regions. Also, an extra copy of GAL4 under the control of a mutated version of its own promoter, as described in Griggs and Johnston, Proc Natl Acad Sci USA, 1991, 88:8597-8601, was integrated upstream the ERG9 promoter region. In addition, the expression of ERG9 was modified by promoter exchange. The GAL7, GAL10 and GAL1 genes were deleted using a cassette containing the HISS gene with its own promoter and terminator. The resulting strain was mated with the strain CEN.PK2-1D (Euroscarf, Frankfurt, Germany) obtaining a diploid strain termed YST045 which was induced for sporulation according to Solis-Escalante et al, FEMS Yeast Res, 2015, 15:2. Spore separation was achieved by resuspension of asci in in 200 µL 0.5M sorbitol with 2 µL zymolyase (1000 U mL-1, Zymo research, Irvine, Calif.) and incubated at 37° C. for 20 minutes. The mix then was plated on media containing 20 g/L peptone, 10 g/L yeast extract and 20 g/L agar, one germinated spore was isolated and termed YST075.

For expression of the different genes encoding alcohol dehydrogenases, genome integrations in the strain YST075 were performed. Each integration cassette was formed by four fragments.

1) A fragment containing 261 bp corresponding to the upstream section of the BUD9 gene and the sequence 5'-GCACTTGCTACACTGTCAGGATAGCTTCCGT-CACATGGTGGCGATCAC CGTACATCTGAG-3' (SEQ ID NO: 72), this fragment was obtained by PCR with genomic DNA from the strain YST075 as template;
2) a fragment containing the sequence 5'-GCACTTGC-TACACTGTCAGGATAGCTTCCGTCA-CATGGTGGCGATCAC CGTACATCTGAG-3' (SEQ ID NO: 72), the promoter region of the GAL1 gene, one of the genes encoding an alcohol dehydrogenase codon optimized for expression in *S. cerevisiae*, the terminator region of PGK1 gene and the sequence 5'-AGGTGCAGTTCGCGTGCAAT-TATAACGTCGTGGCAACTGTTATCAGTC GTACCGCGCCAT-3' (SEQ ID NO: 73), this fragment was obtained by DNA synthesis (ATUM, Menlo Park, Calif. 94025),
3) a fragment containing the sequence 5'-AGGTGCAGTTCGCGTGCAAT-TATAACGTCGTGGCAACTGTTATCAGTC GTACCGCGCCAT-3' (SEQ ID NO: 73), the TRP1 gene with its own promoter and terminator regions and the sequence 5'-TGGTCAGCAACAACGCCGAAGAAT-CACTCTCGTGTTGAGAATTGCACG CCTTGAC-CACGA-3' (SEQ ID NO: 74), this fragment was obtained by PCR with pESC-TRP1 (Agilent Technologies, California, USA) as template; and
4) a fragment containing the sequence 5'-TGGTCAGCAACAACGCCGAAGAAT-CACTCTCGTGTTGAGAATTGCACG CCTTGAC-CACGA-3' (SEQ ID NO: 74) and 344 bp corresponding to the BUD9 gene, this fragment was obtained by PCR with genomic DNA from the strain YST075 as template.

YST075 was transformed with the four fragments required for genome integration for each of the evaluated alcohol dehydrogenases. Yeast transformations were performed with the lithium acetate protocol as described in Gietz and Woods, Methods Enzymol., 2002, 350:87-96. Transformation mixtures were plated on SmTrp-media containing 6.7 g/L of Yeast Nitrogen Base without amino acids (BD Difco, New Jersey, USA), 1.92 g/L Dropout supplement without leucine (Sigma Aldrich, Missouri, USA), 20 g/L glucose and 20 g/L agar. Plates were incubated for 3-4 days at 30° C. Single colonies containing the correct integrations were isolated and termed YST149 (with SCH23-ADH1), YST150 (with SCH24-ADH1a), YST151 (with AzTolADH1) and YST152 (with PsAeroADH1).

For expression of CrtE, SmCPS2 and TalVeTPP in YST149, YST150, YST151 and YST152, a plasmid was constructed in vivo using yeast endogenous homologous recombination as previously described in Kuijpers et al., Microb Cell Fact., 2013, 12:47. The plasmid is composed of six DNA fragments which were used for *S. cerevisiae* co-transformation. The fragments were:
a) LEU2 yeast marker, constructed by PCR using the primers 5'AGGTGCAGTTCGCGTGCAAT-TATAACGTCGTGGCAACTGTTATCAGTC GTACCGCGCCATTCGACTACGTCGTAAGGCC-3' (SEQ ID NO: 75) and 5'TCGTGGT- CAAGGCGTGCAATTCTCAACACGAGAGTGAT-TCTTCGGCGT TGTTGCTGAC-CATCGACGGTCGAGGAGAACTT-3' (SEQ ID NO: 76) with the plasmid pESC-LEU (Agilent Technologies, California, USA) as template;

b) AmpR *E. coli* marker, constructed by PCR using the primers 5'-TGGTCAGCAACAACGCCGAAGAAT-CACTCTCGTGTTGAGAATTGCACG CCTTGAC-CACGACACGTTAAGGGATTTTGGTCATGAG-3' (SEQ ID NO: 77) and 5'-AACGCGTACCCTAAGTACGGCAC-CACAGTGACTATGCAGTCCGCACTTT GCCAATGCCAAAAATGTGCGCGGAACCCCTA-3' (SEQ ID NO: 78) with the plasmid pESC-URA as template;

c) Yeast origin of replication, obtained by PCR using the primers 5'-TTGGCATTGGCAAAGTGCGGACTG-CATAGTCACTGTGGTGCCGTACTTA GGGTACGCGTTCCT-GAACGAAGCATCTGTGCTTCA-3' (SEQ ID NO: 79) and 5'-CCGAGATGCCAAAGGATAGGTGC-TATGTTGATGACTACGACACAGAAC TGCGGGTGACATAATGATAGCATTGAAGGAT-GAGACT-3' (SEQ ID NO: 80) with pESC-URA as template;

d) *E. coli* replication origin, obtained by PCR using the primers 5'-ATGT-CACCCGCAGTTCTGTGTCGTAGTCATCAACAT-AGCACCTATCCTT TGGCATCTCGGT-GAGCAAAAGGCCAGCAAAAGG-3' (SEQ ID NO: 81) and 5'-CTCAGATGTACGGTGATCGCCAC-CATGTGACGGAAGCTATCCTGACAGT GTAGCAAGTGCTGAGCGTCA-GACCCCGTAGAA-3' (SEQ ID NO: 82) with the plasmid pESC-URA as template;

e) a fragment composed by the last 60 nucleotides of the fragment "d", 200 nucleotides downstream the stop codon of the yeast gene PGK1, the GGPP synthase coding sequence CrtE codon optimized for its expression in *S. cerevisiae* (SEQ ID NO: 62), the bidirectional yeast promoter of GAL10/GAL1, the coding sequence of TalVeTPP codon optimized for its expression in *S. cerevisiae* (SEQ ID NO: 65), 200 nucleotides downstream the stop codon of the yeast gene CYC1 and the sequence 5'-ATTCCTAGTGACGGCCTTGG-GAACTCGATACACGATGTTCAGTAGACCG CTCACACATGG-3'(SEQ ID NO: 83), this fragment was obtained by DNA synthesis (ATUM, Menlo Park, Calif. 94025) and f) a fragment composed by the last 60 nucleotides of fragment "e", 200 nucleotides downstream the stop codon of the yeast gene CYC1, the SmCPS2 synthase coding sequence codon optimized for its expression in *S. cerevisiae* (SEQ ID NO: 63), the bidirectional yeast promoter of GAL10/GAL1 and 60 nucleotides corresponding to the beginning of the fragment "a", this fragment was obtained by DNA synthesis (ATUM, Menlo Park, Calif. 94025).

All strains were transformed with the fragments required for in vivo plasmid assembly. Yeast transformations were performed with the lithium acetate protocol as described in Gietz and Woods, Methods Enzymol., 2002, 350:87-96. Transformation mixture was plated on SmLeu-media containing 6.7 g/L of Yeast Nitrogen Base without amino acids (BD Difco, New Jersey, USA), 1.6 g/L Dropout supplement without leucine (Sigma Aldrich, Missouri, USA), 20 g/L glucose and 20 g/L agar. Plate was incubated for 3-4 days at 30° C. Individual colonies were used to produce copalol and copalal in glass tubes containing 2 mL of media as described in Westfall et al., *Proc Natl Acad Sci USA*, 2012, 109:E111-118 and dodecane as organic overlay.

Figure 18:
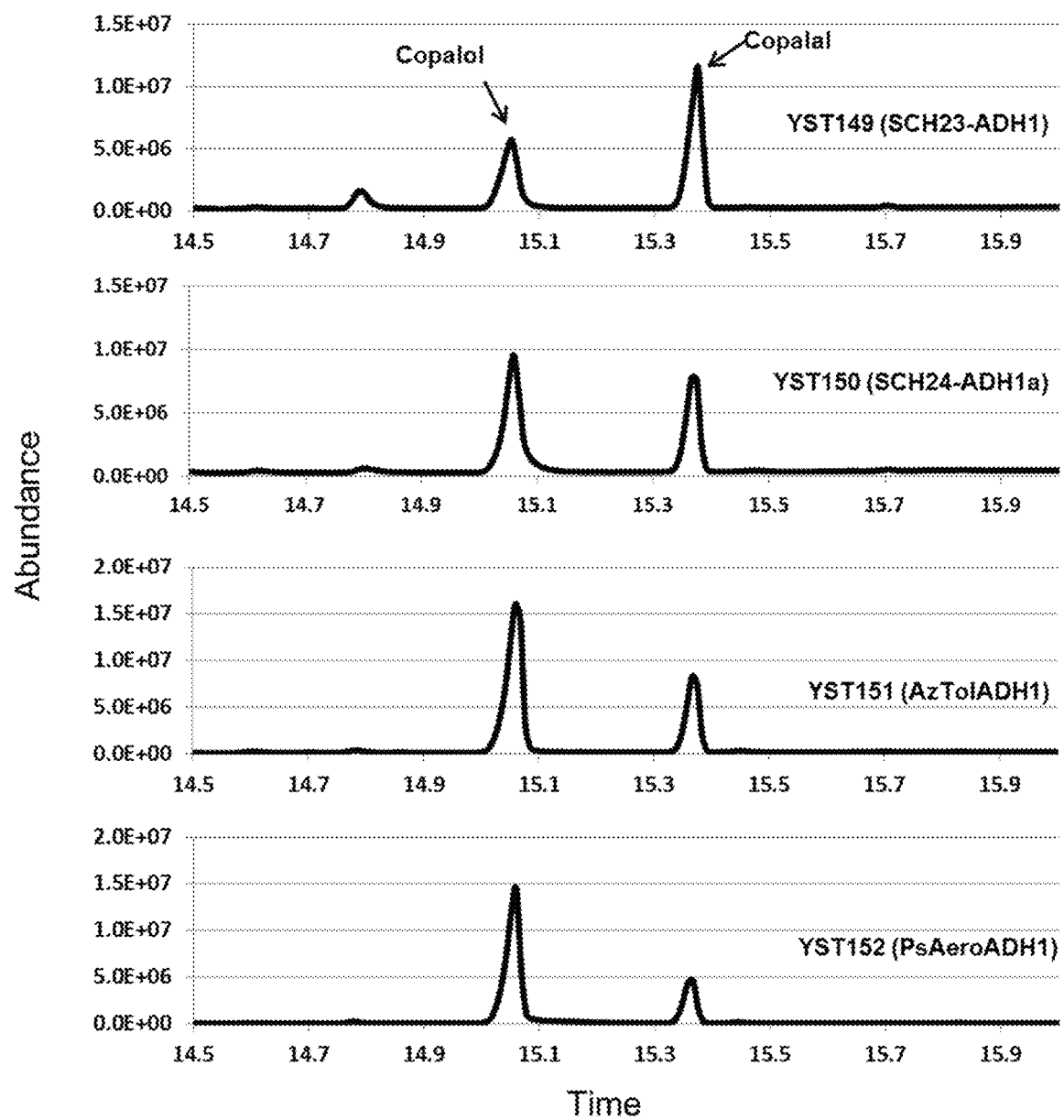
FIG. 18. GC-MS analysis of copalol and copalal produced using the modified *S. cerevisiae* strains expressing the GGPP synthase CrtE, the CPP synthase SmCPS2, the CPP phosphatase TalVeTPP and one of the following alcohol dehydrogenases: AzTolADH1, PsAeroADH1, SCH23-ADH1 or SCH24-ADH1.

Under these culture conditions, the highest average concentration of copalol was 153.51 mg/L produced by the strain YST152 containing the copalol biosynthesis plasmid. The highest average concentration of copalal was 98.47 mg/L produced by the strain YST149 with copalol biosynthesis plasmid. The average percentage of conversion of copalol to copalal in the strains YST149, YST150, YST151 and YST152 containing the copalol biosynthesis plasmid was 61.6%, 39.9%, 30.1% and 22.1% respectively. The production of copalol and copalal was identified and quantified using GC-MS analysis (FIG. 18) with an internal standard.

Sequences as Applied in the Present Invention:

| SEQ ID NO | Name | Source | Type |
|---|---|---|---|
| 1 | TalVeTPP optimized cDNA ORF only | Talaromyces verruculosus | NA |
| 2 | TalVeTPP amino acid sequence | " | |
| 3 | TalVeTPP wild type cDNA | " | NA |
| 4 | TalVeTPP optimized cDNA including non coding sequences | " | NA |
| 5 | AspWeTPP optimized cDNA | Aspergillus wentii | NA |
| 6 | AspWeTPP amino acid sequence | " | |
| 7 | AspWeTPP wild type cDNA | " | NA |
| 8 | AspWeTPP optimized cDNA including non coding ends | " | NA |
| 9 | HelGriTPP1 optimized cDNA | Helicocarpus griseus | NA |
| 10 | HelGriTPP1 amino acid sequence | " | |
| 11 | HelGriTPP1 wild type cDNA | " | NA |
| 12 | UmbPiTPP1 optimized cDNA | Umbilicaria pustulata | NA |

-continued

| 13 | UmbPiTPP1 amino acid sequence | " | |
| 14 | UmbPiTPP1 wild type cDNA | " | NA |
| 15 | TalVeTPP2 optimized cDNA | *Talaromyces verruculosus* | NA |
| 16 | TalVeTPP2 amino acid sequence | " | |
| 17 | TalVeTPP2 wild type cDNA | " | NA |
| 18 | HydPiTPP1 optimized cDNA | *Hydnomerulius pinastri* | NA |
| 19 | HydPiTPP1 amino acid sequence | " | |
| 20 | HydPiTPP1 wild type cDNA | " | NA |
| 21 | TalCeTPP1 optimized cDNA | *Talaromyces cellulolyticus* | NA |
| 22 | TalCeTPP1 amino acid sequence | " | |
| 23 | TalCeTPP1 wild type cDNA | " | NA |
| 24 | TalMaTPP1 optimized cDNA | *Talaromyces marneffei* | NA |
| 25 | TalMaTPP1 amino acid sequence | " | |
| 26 | TalMaTPP1 wild type cDNA | " | NA |
| 27 | TalAstroTPP1 optimized cDNA | *Talaromyces atroroseus* | NA |
| 28 | TalAstroTPP1 amino acid sequence | " | |
| 29 | TalAstroTPP1 wild type cDNA | " | NA |
| 30 | PeSubTPP1 optimized cDNA | *Penicillium subrubescens* | NA |
| 31 | PeSubTPP1 amino acid sequence | " | |
| 32 | PeSubTPP1 wild type cDNA | " | NA |
| 33 | SmCPS, codon optimized cDNA | *Salvia miltiorrhiza* | NA |
| 34 | SmCPS, amino acid sequence | " | |
| 35 | CrtE, GGPS Codon optimized cDNA | *Pantoea agglomerans* | NA |
| 36 | CrtE, GGPS amino acid sequence | " | |
| 37 | SsLPS Optimized cDNA encoding for | " | NA |
| 38 | SsLPS amino acid sequence | " | AA |
| 39 | TaTps1-del59Optimized cDNA | *Triticum aestivum* | NA |
| 40 | TaTps1-del59, truncated copalyl diphosphate synthase | " | AA |
| 41 | CymB, optimized cDNA | *Pseudomonas* sp. 19-rlim | NA |
| 42 | CymB, amino acid sequence | " | |
| 43 | AspWeADH1, optimized cDNA | *Aspergillus wentii* DTO 134E9 | NA |
| 44 | AspWeADH1, amino acid sequence | " | |
| 45 | PsAerADH1, opimized cDNA | *Pseudomonas aeruginosa;* | NA |
| 46 | PsAerADH1, amino acid sequence | " | |
| 47 | AzTolADH1, optimized cDNA | *Azoarcus toluclasticus* | NA |
| 48 | AzTolADH1, amino acid sequence | " | |
| 49 | AroAroADH1, optimized cDNA | *Aromatoleum aromaticum* | NA |
| 50 | AroAroADH1, amino acid sequence | " | |
| 51 | ThTerpADH1, optimized cDNA | *Thauera terpenica* | NA |

-continued

| 52 | ThTerpADH1, amino acid sequence | " | |
| 53 | CdGeoA optimized cDNA | *Castellaniella defragrans* | NA |
| 54 | CdGeoA, amino acid sequence | " | |
| 55 | VoADH1, optimized cDNA | *Valeriana officinalis* | NA |
| 56 | VoADH1, amino acid sequence | " | |
| 57 | active site signature motif | artificial | AA |
| 58 | active site signature motif | artificial | AA |
| 59 | PvCPS, optimized, cDNA | *Talaromyces ferruculosus* | NA |
| 60 | PvCPS, amino acid sequence | *Talaromyces ferruculosus* | AA |
| 61 | RBS Sequence | artificial | NA |
| 62 | CrtE, optimized cDNA (yeast) | *Pantoea agglomerans* | NA |
| 63 | SmCPS2, optimized cDNA (yeast) | *Salvia miltiorrhiza* | NA |
| 64 | SmCPS2, amino acid sequence | *Salvia miltiorrhiza* | AA |
| 65 | TalVeTPP, optimized cDNA (yeast) | *Talaromyces verruculosus* | NA |
| 66 | AzTolADH1, optimized cDNA (yeast) | *Azoarcus toluclasticus* | NA |
| 67 | PSAeroADH1, optimized cDNA (yeast) | *Pseudomonas aeruginosa* | NA |
| 68 | SCH23-ADH1, optimized cDNA (yeast) | *Hyphozyma roseonigra* | NA |
| 69 | SCH23-ADH1, amino acid sequence | *Hyphozyma roseonigra* | AA |
| 70 | SCH24-ADH1a, optimized cDNA (yeast) | *Cryptococcus albus* | NA |
| 71 | SCH24-ADH1a | *Cryptococcus albus* | AA |
| 72 | Sequence for homologuous recombination | artificial | NA |
| 73 | Sequence for homologuous recombination | artificial | NA |
| 74 | Sequence for homologuous recombination | artificial | NA |
| 75 | Primer for LEU2 yeast marker | artificial | NA |
| 76 | Primer for LEU2 yeast marker | artificial | NA |
| 77 | Primer for AmpR bacterial marker | artificial | NA |
| 78 | Primer for AmpR bacterial marker | artificial | NA |
| 79 | Primer for yeast origin of replication | artificial | NA |
| 80 | Primer for yeast origin of replication | artificial | NA |
| 81 | Primer for *E. coli* origin of replication | artificial | NA |
| 82 | Primer for *E. coli* origin of replication | artificial | NA |
| 83 | Sequence for homologous recombination | artificial | NA |

NA = Nucleic Acid
AA = Amino Acid

TalVeTPP optimized cDNA ORF only-SEQ ID NO: 1
ATGAGCAATGACACGACGACCACCGCGAGCGCCGGTACTGCAACTTCTAGCCGTTTTCTGAGCGTCGGCGGC
GTTGTGAATTTTCGCGAGCTGGGTGGCTATCCATGCGACAGCGTGCCGCCGGCTCCGGCAAGCAACGGTTCG
CCTGATAATGCGTCCGAGGCAACGCTGTGGGTTGGTCACTCCAGCATTCGTCCGGGTTTCCTGTTCCGCAGCG
CGCAGCCGAGCCAGATTACGCCGGCGGGTATCGAAACGCTGATCCGCCAACTGGGCATCCAGACCATTTTTG
ATTTCCGTAGCCGTACCGAGATCGAACTGGTGGCGACCCGTTACCCGGACTCTCTGTTGGAAATTCCGGGCAC
CACGCGCTATTCCGTCCCGGTTTTCTCCGAGGGTGACTATTCTCCGGCGAGCCTGGTGAAGCGCTATGGTGTT
AGCAGCGATACCGCCACGGACAGCACCTCTAGCAAGAGCGCGAAGCCGACCGGCTTCGTTCATGCATACGAA
GCCATTGCGCGCAGCGCCGCTGAGAACGGTAGCTTCCGTAAAATTACCGACCACATCATCCAGCATCCTGATC
GTCCAATTTTGTTCCACTGTACCCTGGGTAAAGACCGTACGGGTGTCTTTGCGGCGCTGTTGCTGAGCCTGTGT
GGTGTGCCGGACGAAACCATCGTCGAAGATTACGCGATGACCACCGAAGGCTTTGGTGCATGGCGTGAGCAC CTGATCCAACGTCTGCTGCAACGTAAAGACGCTGCAACCCGTGAAGATGCCGAGAGCATCATTGCGTCGCCGC
CGGAGACTATGAAAGCATTTCTGGAAGATGTTGTGGCAGCGAAATTTGGTGGCGCGCGTAACTACTTCATTCA
ACATTGCGGCTTCACTGAAGCTGAAGTCGATAAGCTGAGCCACACCCTGGCGATCACGAACTAA TalVeTPP amino acid sequence-SEQ ID NO: 2
MSNDTTTTASAGTATSSRFLSVGGVVNFRELGGYPCDSVPPAPASNGSPDNASEATLWVGHSSIRPGFLFRSAQPS
QITPAGIETLIRQLGIQTIFDFRSRTEIELVATRYPDSLLEIPGTTRYSVPVFSEGDYSPASLVKRYGVSSDTATDSTSSKS
AKPTGFVHAYEAIARSAAENGSFRKITDHIIQHPDRPILFHCTLGKDRTGVFAALLLSLCGVPDETIVEDYAMTTEGF
GAWREHLIQRLLQRKDAATREDAESIIASPPETMKAFLEDVVAAKFGGARNYFIQHCGFTEAEVDKLSHTLAITN TalVeTPP wild type cDNA-SEQ ID NO: 3
ATGTCTAATGACACCACTACCACGGCTTCTGCCGGAACAGCAACTTCTTCGCGGTTTCTTTCCGTGGGGGGAGT
TGTGAACTTCCGTGAACTGGGCGGTTACCCATGTGATTCTGTCCCTCCTGCTCCTGCCTCAAACGGCTCACCGG
ACAATGCATCTGAAGCGACCCTTTGGGTTGGCCACTCGTCCATTCGGCCTGGATTTCTGTTTCGATCGGCACAG
CCGTCTCAGATTACCCCGGCCGGTATTGAGACATTGATCCGCCAGCTTGGCATCCAGACAATTTTTGACTTTCG
TTCAAGGACGGAAATTGAGCTTGTTGCCACTCGCTATCCTGATTCGCTACTTGAGATACCTGGCACGACTCGCT
ATTCCGTGCCCGTCTTCTCGGAAGGCGACTATTCCCCAGCGTCATTAGTCAAGAGGTACGGAGTGTCCTCCGA
TACTGCAACCGATTCCTCCAAAAGTGCTAAGCCTACAGGATTCGTCCACGCATATGAGGCTATCGCAC
GCAGTGCAGCAGAAAACGGCAGTTTTCGTAAGATAACGGACCACATAATACAACATCCGGACCGGCCTATTCT
GTTTCACTGTACACTGGGGAAAGACCGAACCGGTGTGTTTGCAGCATTGTTATTGAGTCTTTGCGGGGTACCA
GACGAGACGATAGTTGAAGACTATGCTATGACTACCGAGGGGATTTGGAGCCTGGCGGGAACATCTAATTCAA
CGCTTGCTACAAAGGAAGGATGCAGCTACGCGCGAGGATGCAGAATCCATTATTGCCAGCCCCCCGGAGACT
ATGAAGGCTTTTCTAGAAGATGTGGTAGCAGCCAAGTTCGGGGGTGCTCGAAATTACTTTATCCAGCACTGTG
GATTTACGGAAGCTGAGGTTGATAAGTTAAGCCATACACTGGCCATTACGAATTGA TalVeTPP optimized cDNA including non coding sequences-SEQ ID NO: 4
GGTACCAAGGAGGTAAAAAATGAGCAATGACACGACGACCACCGCGAGCGCCGGTACTGCAACTTCTAGCCG
TTTTCTGAGCGTCGGCGGCGTTGTGAATTTTCGCGAGCTGGGTGGCTATCCATGCGACAGCGTGCCGCCGGCT
CCGGCAAGCAACGGTTCGCCTGATAATGCGTCCGAGGCAACGCTGTGGGTTGGTCACTCCAGCATTCGTCCG
GGTTTCCTGTTCCGCAGCGCGCAGCCGAGCCAGATTACGCCGGCGGGTATCGAAACGCTGATCCGCCAACTG
GGCATCCAGACCATTTTTGATTTCCGTAGCCGTACCGAGATCGAACTGGTGGCGACCCGTTACCCGGACTCTCT
GTTGGAAATTCCGGGCACCACGCGCTATTCCGTCCCGGTTTTCTCCGAGGGTGACTATTCTCCGGCGAGCCTG
GTGAAGCGCTATGGTGTTAGCAGCGATACCGCCACGGACAGCACCTCTAGCAAGAGCGCGAAGCCGACCGG
CTTCGTTCATGCATACGAAGCCATTGCGCGCAGCGCCGCTGAACAGGTAGCTTCCGTAAAATTACCGACCAC
ATCATCCAGCATCCTGATCGTCCAATTTTGTTCCACTGTACCCTGGGTAAAGACCGTACGGGTGTCTTTGCGGC
GCTGTTGCTGAGCCTGTGTGGTGTGCCGGACGAAACCATCGTCGAAGATTACGCGATGACCACCGAAGGCTT
TGGTGCATGGCGTGAGCACCTGATCCAACGTCTGCTGCAACGTAAAGACGCTGCAACCCGTGAAGATGCCGA
GAGCATCATTGCGTCGCCGCCGGAGACTATGAAAGCATTTCTGGAAGATGTTGTGGCAGCGAAATTTGGTGG
CGCGCGTAACTACTTCATTCAACATTGCGGCTTCACTGAAGCTGAAGTCGATAAGCTGAGCCACACCCTGGCG
ATCACGAACTAACTCGAG AspWeTPP optimized cDNA-SEQ ID NO: 5
ATGGCGTCTGTCCCTGCTCCACCGTTTGTTCATGTTGAAGGTATGTCTAATTTTCGTAGCATCGGTGGCTACCC
GCTGGAGACTGCCTCCACGAATAACCATCGCTCGACCCGTCAAGGCTTCGCGTTTCGTAGCGCGGACCCGACG
TATGTGACGCAGAAAGGCCTGGAAACCATTCTGTCCCTGGATATTACCCGCGCATTTGACTTGCGTAGCTTGG
AAGAAGCAAAGGCACAACGTGCGAAGTTGCAGGCCGCGAGCGGTTGTCTGGATTGCAGCATTAGCCAACAC
ATGATCCACCAACCGACCCCGCTGTTCCCGGATGGTGACTGGTCCCCGGAAGCGGGCGAGCGCTACTTG
CAGTACGCACAAGCTGAGGGTGATGGTATCAGCGGTTATGTCGAAGTTTATGGTAATATGCTGGAAGAGGGC
TGGATGGCGATCCGTGAGATTCTGCTGCACGTCCGTGACCGCCCGACCGAAGCATTCCTGTGCCACTGTTCCG
CCCGGTAAAGATCGTACGGGTATCGTGATTGCTGTTCTGCTCAAAGTCGCGGGTTGCAGCGACGACCTGGTGT
GTCGTGAGTACGAACTGACCGAGATTGGCCTGGCGCGCCGTAGAGAGTTCATCGTTCAGCATCTGCTGAAGA
AACCGGAAATGAACGGCAGCCGTGAGCTGGCGGAGCGCGTCGCAGGCGCCCGTTACGAGAACATGAAAGAA
ACCCTGGAAATGGTGCAGACCCGTTACCGCGGCATGCGCGGCTATTGCAAAGAAATCTGCGGTCTGACCGAC
GAAGATCTGAGCATTATCCAGGGTAACCTGACGAGCCCGGAGAGCCCGATTTTCTAA AspWeTPP amino acid sequence-SEQ ID NO: 6
MASVPAPPFVHVEGMSNFRSIGGYPLETASTNNHRSTRQGFAFRSADPTYVTQKGLETILSLDITRAFDLRSLEEAK
AQRAKLQAASGCLDCSISQHMIHQPTPLFPDGDWSPEAAGERYLQYAQAEGDGISGYVEVYGNMLEEGWMAIR
EILLHVRDRPTEAFLCHCSAGKDRTGIVIAVLLKVAGCSDDLVCREYELTEIGLARREFIVQHLLKKPEMNGSRELAE
RVAGARYENMKETLEMVQTRYRGMRGYCKEICGLTDEDLSIIQGNLTSPESPIF AspWeTPP wild type cDNA-SEQ ID NO: 7
ATGGCATCTGTACCAGCTCCCCCATTTGTCCACGTCGAAGGAATGAGCAATTTCCGATCGATAGGAGGATATC
CCCTTGAGACAGCATCGACAAACAATCACCGCTCCACGAGGCAAGGATTCGCATTTCGCAGTGCCGATCCAAC
CTACGTCACCCAGAAAGGCCTGGAAACCATCCTTTTCGCTCGACATCACTCGAGCCTTTGACCTCCGCTCACTGG
AAGAAGCAAAGGCACAGCGCGCAAAACTCCAGGCCGCCTCAGGATGTCTCGACTGCAGCATCAGCCAGCACA
TGATCCACCAGCCCACACCCCTATTTCCAGATGGGGACTGGAGTCCAGAGGCCGCAGGGGAGCGGTATCTGC
AGTACGCCCAGGCTGAGGGAGATGGGATATCGGGCTACGTGGAGGTTCAGAGAACATGCTGGAGGAAGGT
TGGATGGCGATTCGCGAGATTCTGCTTCATGTCCGGGACCGGCCTACAGAGGCGTTTCTATGCCATTGTAGTG
CAGGGAAAGATCGTACGGGGATTGTCATTGCGGTTTTGTTGAAGGTTGCAGGGTGCTCGGATGATCTTGTGT
GCAGAGAGTATGAGTTGACCGAGATCGGGTTGGCTCGACGGAGGGAGTTTATCGTGCAGCATCTGCTTAAGA
AGCCGGAAATGAATGGATCGAGGGAACTGGCCGAAAGAGTGGCGGGGGCCAGGTATGAGAATATGAAGGA
AACGCTGGAGATGGTGCAAACTAGATATAGAGGGATGAGGGGCTATTGCAAGGAGATTTGCGGCTTGACCG
ACGAAGATCTATCTATTATCCAGGGGAACTTGACTAGTCCGGAGAGTCCTATCTTCTAA AspWeTPP optimized cDNA including non coding ends-SEQ ID NO: 8
GGTACCAAGGAGGTAAAAAATGGCGTCTGTCCCTGCTCCACCGTTTGTTCATGTTGAAGGTATGTCTAATTTTC
GTAGCATCGGTGGCTACCCGCTGGAGACTGCCTCCACGAATAACCATCGCTCGACCCGTCAAGGCTTCGCGTT
TCGTAGCGCGGACCCGACGTATGTGACGCAGAAAGGCCTGGAAACCATTCTGTCCCTGGATATTACCCGCGCA

```
TTTGACTTGCGTAGCTTGGAAGAAGCAAAGGCACAACGTGCGAAGTTGCAGGCCGCGAGCGGTTGTCTGGAT
TGCAGCATTAGCCAACACATGATCCACCAACCGACCCCGCTGTTCCCGGATGGTGACTGGTCCCCGGAAGCGG
CGGGTGAGCGCTACTTGCAGTACGCACAAGCTGAGGGTGATGGTATCAGCGGTTATGTCGAAGTTTATGGTA
ATATGCTGGAAGAGGGCTGGATGGCGATCCGTGAGATTCTGCTGCACGTCCGTGACCGCCCGACCGAAGCAT
TCCTGTGCCACTGTTCCGCCGGTAAAGATCGTACGGGTATCGTGATTGCTGTTCTGCTCAAAGTCGCGGGTTG
CAGCGACGACCTGGTGTGTCGTGAGTACGAACTGACCGAGATTGGCCTGGCGCGCCGTAGAGAGTTCATCGT
TCAGCATCTGCTGAAGAAACCGGAAATGAACGGCAGCCGTGAGCTGGCGGAGCGCGTCGCAGGCGCCCGTT
ACGAGAACATGAAAGAAACCCTGGAAATGGTGCAGACCCGTTACCGCGGCATGCGCGGCTATTGCAAAGAAA
TCTGCGGTCTGACCGACGAAGATCTGAGCATTATCCAGGGTAACCTGACGAGCCCGGAGAGCCCGATTTCTA
ACTCGAG

HelGriTPP1 optimized cDNA-SEQ ID NO: 9
ATGGCATCCCCACCAGGTCATCCGTTCGTTCAAGTTGAAGGCGTTAATAATTTTCGCTCTGTGGGTGGCTATCC
GATTACGCCTAGCAGCGATGCGCGCTTCACGCGTGACAACTTTATCTACCGTAGCGCTGATCCGTGTTACATTA
CTCCGGAAGGCCGTAGCAAGATTCGCAGCCTGGGTATCACCACCGTGTTCGATCTGCGTAGCCAGCCGGAGG
TTGACAAGCAACTGGCGAAAGACCCGAGCAGCGGTGTGCCGATTGCGGATGGTGTCATTCGTCGCTTCACCC
CGGTTTTTAGCCGCGAGGATTGGGGTCCGGAAGCATCCGCGGTTCGTCACAACCTGTATGCAGACGCGTCCG
GTGCTAGCGGTTACGTCGATGTGTACGCGGATATCCTGGAAAACGGTGGCGCAGCGTTCCGTGAGATCCTGC
TGCACGTGCGTGACCGTCCGGGTGACGCTCTGTTGTGCCACTGCTCCGCAGGCAAAGACCGTACCGGCGTTG
CGATTGCGATCCTGCTCAAACTGGCCGGTTGCGAAGATGAGTGCATTTCGAAAGAGTATGAACTGACCGAGG
TCGGTCTGGCCAGCCGTAAAGAATTTATTATCGAGTACCTGATTAAGCAACCTGAGCTGGAAGGCGACCGTGC
GAAAGCCGAGAAAATTGCTGGCGCGAAATACGAAAACATGTTGGGTACGCTGCAGATGATGGAACAGAAAT
ATGGTGGCGTTGAGGGCTACGTGAAGGCCTACTGTAAGTTGACGGATAAAGACATCGCAACCATCCGTCGCA
ATCTGGTCAGCGGTGACAAGATGATTGCGTAA HelGriTPP1 amino acid sequence-SEQ ID NO: 10
MASPPGHPFVQVEGVNNFRSVGGYPITPSSDARFTRDNFIYRSADPCYITPEGRSKIRSLGITTVFDLRSQPEVDKQL
AKDPSSGVPIADGVIRRFTPVFSREDWGPEASAVRHNLYADASGASGYVDVYADILENGGAAFREILLHVRDRPGD
ALLCHCSAGKDRTGVAIAILLKLAGCEDECISKEYELTEVGLASRKEFIIEYLIKQPELEGDRAKAEKIAGAKYENMLGTL
QMMEQKYGGVEGYVKAYCKLTDKDIATIRRNLVSGDKMIA HelGriTPP1 wild type cDNA-SEQ ID NO: 11
ATGGCATCACCCCCAGGGCACCCTTTCGTGCAAGTTGAAGGCGTCAACAACTTCCGCTCTGTAGGAGGATATC
CCATCACCCCATCCTCCGACGCACGCTTCACACGAGATAACTTCATCTACCGCAGCGCCGACCCGTGTTACATC
ACGCCCGAAGGACGCTCCAAAATCCGCTCACTCGGAATCACGACTGTTTTTGATCTGCGCTCCCAGCCAGAGG
TTGACAAGCAGCTTGCCAAAGACCCTTCCTCAGGGGTTCAATCGCCGACGGCGTCATTAGACGTTTTACGCC
GGTATTTTCCCGAGAGGATTGGGGTCCGGAAGCTTCCGCCGTCCGCCATAATCTGTATGCTGATGCCTCTGGG
GCTTCTGGGTACGTCGATGTGTATGCCGACATTCTGGAGAATGGAGGGGCGGCATTCCGCGAGATCTTGTTG
CACGTAAGAGACCGGCCTGGTGATGCGCTGCTATGTCATTGTAGTGCCGGAAAAGATCGTACCGGCGTGGCG
ATAGCGATACTGCTCAAGCTTGCGGGGTGCGAGGATGAATGTATCTCAAAGGAGTACGAGCTGACCGAGGTT
GGTCTAGCCTCAAGAAAGGAGTTCATTATAGAGTACCTCATCAAGCAGCCGGAACTAGAGGGGATAGAGCA
AAAGCTGAAAAAATTGCGGGAGCCAAATATGAGAACATGTTAGGGACCTTGCAAATGATGGAACAGAAATAC
GGGGGTGTTGAGGGGTACGTGAAAGCGTATTGCAAGTTGACGGATAAAGATATTGCTACGATACGCAGGAA
TCTCGTCTCAGGTGACAAAATGATTGCCTAG UmbPiTPP1 optimized cDNA-SEQ ID NO: 12
ATGTCCCTGCTGCCTAGCCCACCGTTTGTTCCAGTTGAAGGTATTCACAATTTTCGCGATCTGGGCGGCTATCC
GGTTAGCACCAGCCCGAGCAAGACCATTCGTCGCAATATCATCTTTCGTTGTGCCGAACCGTCGAAAATCACC
CCGAACGGCATTCAAACGCTGCAGAGCCTGGGTGTGGCGACGTTCTTTGACCTCCGTAGCGGTCCGGAAATC
GAGAAAATGAAAGCGCATGCACCGGTCGTTGAGATCAAGGGTATTGAGCGTGTTTTCGTGCCGGTTGCTGCG
GATGGTGATTATAGCCCGGAACAAATTGCGCTGCGTTACAAAGACTATGCGTCCTGGCACTGGTGGCTTCA
CCCGTGCGTACCACGACATTCTGCGCTTCTGCCCCTCCGAGCTATCGTCGTATCCTGCTGCACCTGGCAGAGAAG
CCGAACCAGCCGTGCGTGATCCACTGTACCGCTGGCAAAGACCGCACGGGTGTTCTGGCAGCGCTGATTCTG
GAACTGGCGGGTGTCGATCAAGACACCATCGCGCATGAGTACGCCCTGACCGAGCTGGGCCTGAAGGCATG
GCGTCCGACGGTTGTCGAGCACTTACTGCAGAATCCGGCGCTGGAAGGCAATCGCGAGGGTGCATTGAATAT
GGTCAGCGCTCGTGCGGAGAACATGCTGGCCGCCTTGGAAATGATTCGCGAGATCTACGGTGGTGCTGAGGC
GTACGTGAAAGAAAAGTGCGGTCTGAGCGACGAAGATATTGCACGCATTCGCCAGAACATTTTGCATACGCC
GAGCCCGTAA UmbPiTPP1 amino acid sequence-SEQ ID NO: 13
MSLLPSPPFVPVEGIHNFRDLGGYPVSTSPSKTIRRNIIFRCAEPSKITPNGIQTLQSLGVATFFDLRSGPEIEKMKAHA
PVVEIKGIERVFVPVFADGDYSPEQIALRYKDYASSGTGGFTRAYHDILRSAPPSYRRILLHLAEKPNQPCVIHCTAGK
DRTGVLAALILELAGVDQDTIAHEYALTELGLKAWRPTVVEHLLQNPALEGNREGALNMVSARAENMLAALEMIR
EIYGGAEAYVKEKCGLSDEDIARIRQNILHTPSP UmbPiTPP1 wild type cDNA-SEQ ID NO: 14
ATGTCTCTGCTACCGTCACCTCCCTTCGTACCCGTTGAGGGTATCCACAACTTCCGGGACCTAGGCGGCTACCC
CGTCTCGACTTCCCCTTCCAAGACCATACGTCGCAACATCATCTTTCGTTGCGCCGAACCCTCGAAAATCACTCC
CAATGGCATCCAGACGCTCCAATCTTTGGGCGTCGCTACGTTCTTCGACCTCCGCTCCGGCCCGGAAATCGAG
AAGATGAAAGCACATGCACCTGTCGTCGAGATTAAGGGCATCGAGCGTGTGTTCGTTCCCGTCTTCGCCGACG
GGGATTACTCGCCCGAACAAATCGCTCTGCGATACAAAGACTACGCTTCCAGCGGAACGGGGGGTTTTACCA
GGGCGTACCATGATATCCTCCGAAGTGCCCCTCCGAGCTATCGGCGCATACTATTACATCTGGCGGAGAAGCC
CAACCAGCCATGCGTCATTCATTGCACGGCCGGGAAAGATAGGACGGGCGTATTGGCGGCGTTGATACTCGA
GTTGGCCGGGGTTGATCAGGATACAATTGCGCACGAGTACGCATTGACGGAACTGGGGTTGAAGGCCTGGC
GTCCCACTGTGGTGGAGCACCTCTTGCAGAATCCAGCGTTGGAGGGAAATCGGAAGGGGCATTGAACATG
GTCAGCGCGAGGGCAGAGAACATGCTGGCAGCCTTGGAGATGATCCGGGAGATCTATGGCGGCGCCGAAGC
ATATGTGAAGGAGAAGTGTGGCCTCAGCGACGAAGACATTGCGCGGATACGGCAGAATATTCTACACACGCC
ATCTCCGTGA
```

TalVeTPP2 optimized cDNA-SEQ ID NO: 15
ATGTCTGTCACCGAACATGTTGTCGAAGCTAGCACCCCGTCCACTCTGCCGCCACCGTTCATTCACGTGGACGG
TGTTCCGAACTTCCGTGACATTGGTGGCTATCCGATTACCGATCTGCTGAGCACCCGTCGCAATTTCGTTTATC
GCTCCGCAGTTCCTACCCGCATCACCCCAACGGGCCTGCAGACGCTGACCCAAGATCTGCAGATTACGACGGT
CTACGACTTACGTTCGAATGCTGAGCTGCGTAAAGATCCTATCGCCAGCAGCCCGTTGGACACCCACGACAGC
GTGACTGTCCTGCATACCCCGGTTTTCCCGGAGCGCGATTCTAGCCCGGAACAGCTGGCAAAGCGTTTTGCCA
ACTATATGAGCGCGAACGGTTCCGAGGGTTTCGTTGCGGCGTACGCAGAGATTCTGCGTGATGGTGTGGATG
CCTACCGCAAGGTTTTTGAACACGTGCGTGACCGTCCGCGTGATGCGTTTCTGGTGCACTGCACCGGTGGCAA
AGACCGTACGGGTGTGTTGGTTGCGCTGATGCTGTTGGTGGCAGGCGTCAAAGACCGTGACGTTATTGCCGA
TGAGTACAGCCTGACGGAAAAGGGTTTTGCGGCTGTCATCAAAGCCGATGCTGCGGAAAAGATCATCAAAGA
CATGGGTGTTGACGGTGCCAATCGTGCGGGCATCGAGCGTCTGTTGAGCGCACGCAAAGAAACATGAGCGC
GACCCTGGAGTACATTGAGAAGCAATTTGGTGGCGCAGAGGGCTATCTGCGCGACCAACTGGGTTTCGGCGA
CGAAGATGTGGAACAGATCCGTAAGAGCCTGGTCGTTGAGGATAAAGGCCTGTTCTAA TalVeTPP2 amino acid sequence-SEQ ID NO: 16
MSVTEHVVEASTPSTLPPPFIHVDGVPNFRDIGGYPITDLLSTRRNFVYRSAVPTRITPTGLQTLTQDLQITTVYDLRS
NAELRKDPIASSPLDTHDSVTVLHTPVFPERDSSPEQLAKRFANYMSANGSEGFVAAYAEILRDGVDAYRKVFEHVR
DRPRDAFLVHCTGGKDRTGVLVALMLLVAGVKDRDVIADEYSLTEKGFAAVIKADAAEKIIKDMGVDGANRAGIER
LLSARKENMSATLEYIEKQFGGAEGYLRDQLGFGDEDVEQIRKSLVVEDKGLF TalVeTPP2 wild type cDNA-SEQ ID NO: 17
ATGAGCGTCACAGAACATGTAGTCGAAGCCTCGACACCATCAACCCTTCCACCACCCTTCATCCATGTCGACGG
CGTCCCCAACTTCCGCGACATCGGCGGCTACCCCATCACAGACTTACTGTCAACACGACGAAACTTCGTGTATC
GCTCCGCAGTCCCAACACGCATCACTCCCACAGGTCTACAGACACTCACCCAAGACCTCCAAATCACAACAGTC
TACGACCTACGCTCCAACGCTGAACTGCGCAAGGATCCCATTGCCTCCAGCCCTCTAGACACCCATGACTCTGT
AACGGTGCTACACACCCCGTCTTTCCCGAACGGGACTCAAGTCCCGAACACTCGCAAAGAGGTTTGCGAAT
TACATGTCCGCCAACGGCTCGGAAGGGTTTAGCCGCCTACGCCGAGATTTTCGCTGATGGCGTTGATGCAT
ACCGCAAGGTGTTTGAGCATGTCCGTGATCGGCCCCGGGATGCGTTTTTGGTGCATTGTACTGGTGGGAAGG
ATAGAACGGGTGTCCTTGTAGCGCTCATGTTACTTGTTGCGGGTGTCAAGGATAGAGATGTGATTGCCGACGA
GTACTCGTTGACGGAGAAGGGGTTTGCTGCTGTTATTAAGGCGGATGCGGCGGAAAAGATTATAAAGGATAT
GGGAGTGGATGGGGCGAATAGGGCGGGCATTGAGAGATTGCTGTCGGCGAGGAAGGAGAATATGAGTGCT
ACGTTGGAGTATATCGAGAAACAGTTTGGTGGGCGGAGGGTTATTGAGGGATCAGTTAGGGTTTGGTGAT
GAGGATGTTGAGCAGATTAGGAAGAGTCTTGTCGTGGAGGATAAGGGTTTATTTTAG HydPiTPP1 optimized cDNA-SEQ ID NO: 18
ATGACTGCAACCGACAATGGCTTAGAACCGCTGGACCCTGCATACGTTGCTGATGTGTTGAGCCGTCCGCCGT
TTGTCCAGATCTCCGGCGTGTGTAACGTCAGAGATCTGGGCAGCTATCCGACCGCTACCCCGAATGTGATTAC
CAAGCCTGGTTATGCATACCGTGGTGCCGAAGTTTCCAATATCACCGAAGAGGGCAGCCAACAAATGAAAGC
ACTGGGTATTACCACGATCTTTGATCTGCGTTCTGACCCAGAGATGCAGAAGTACAGCACGCCGATTCCGCAT
ATCGAGGGTGTCCTGATTCTGCGTACCCCGGTGTTCGCCACCGAGGACTATAGCCCGGAGTCGATGGCGAAG
CGTTTTGAGCTGTACGCGTCTGGTACGACCGAAGCATTCATGAAGCTGTATAGCCAGATTCTGGACCACGGCG
GCAAAGCGTTCGGTACTATTGCGCGTCATGTTCGTGACCGCCCGAACAGCGTTTTCTGTTTCACTGCACGGCC
GGTAAAGATCGCACGGGCATTATTGCGGCCATCCTGTTCAAATTGGCGGGTGTGGATGATCACTTGATCTGTC
AGGACTACAGCCTGACGCGCATCGGTCGTGAGCCAGACCGTGAAAAGTTCTGCGCCGTCTGCTGAATGAAC
CGCTGTTCGCGGCGAATACCGAGCTTGCGCTGCGCATGTTGACGAGCCGCTACGAAACCATGCAAGCGACCC
TGGGTCTGTTGAGCGACAAATATGGCGGTGTGGAAGCATACGTCAAGAACTTCTGCGGTCTGACCGATAACG
ACATCAGCGTTATCCGTACCAACCTGGTTGTGCCGACGAAAGCGCGTATGTAA HydPiTPP1 amino acid sequence-SEQ ID NO: 19
MTATDNGLEPLDPAYVADVLSRPPFVQISGVCNVRDLGSYPTATPNVITKPGYAYRGAEVSNITEEGSQQMKALGI
TTIFDLRSDPEMQKYSTPIPHIEGVLILRTPVFATEDYSPESMAKRFELYASGTTEAFMKLYSQILDHGGKAFGTILRH
VRDRPNSVFLFHCTAGKDRTGIIAAILFKLAGVDDHLICQDYSLTRIGREPDREKVLRRLLNEPLFAANTELALRMLTS
RYETMQATLGLLSDKYGGVEAYVKNFCGLTDNDISVIRTNLVVPTKARM HydPiTPP1 wild type cDNA-SEQ ID NO: 20
ATGACCGCAACAGACAACGGACTAGAACCCTTAGACCCTGCATATGTCGCAGATGTGCTCTCAAGACCACCAT
TCGTACAAATATCTGGTGTTTGCAACGTCCGTGATCTAGGATCCTACCCTACCGCCACTCCCAATGTCATAACA
AAGCCGGGATATGCATACCGGGGCGCAGAGGTCTCTAACATTACCGAAGAAGGTAGCCAGCAAATGAAGGC
GCTAGGCATAACGACTATATTTGATCTTAGATCGGATCCAGAGATGCAGAAATACAGCACTCCAATACCCCAC
ATTGAAGGCGTACTGATATTGCGCACGCCTGTCTTCGCGACCGAGGATTATAGTCCGGAAAGTATGGCCAAG
AGATTTGAGCTATACGCAAGTGGTACTACTGAAGCATTTATGAAACTATACTCTCAAATACTAGACCATGGAG
GCAAAGCCTTCGGAACAATTCTCCGGCACGTTCGGGACAGGCCAAATTCTGTCTTTCTTTTCCATTGCACTGCG
GGGAAAGACCGGACCGGCATCATTGCTGCAATTCTGTTCAAGCTCGCCGGCGTAGACGACCATCTCATATGTC
AAGATTACTCCCTCACACGAATAGGTCGCGAGCCTGATCGTGAAAAGGTCCTCCGGCGACTCTTGAATGAACC
TCTATTTGCCGCCAACACGGAACTTGCACTACGAATGCTCACGTCTCGATATGAAACTATGCAAGCAACGTTG
GGGCTTCTTAGCGATAAGTATGGCGGGTGGAGGCGTATGTGAAGAATTTCTGTGGGCTCACGGATAATGAT
ATATCGGTCATACGAACAAATCTCGTTGTACCTACAAAGGCGCGGATGTAG TalCeTPP1 optimized cDNA-SEQ ID NO: 21
ATGAGCAACGACACGACCAGCACCGCATCCGCAGGCACCGCAACTTCTTCGCGCTTTCTGAGCGTCGGTGGCG
TGGTTAACTTCCGTGAGTTGGGTGGCTACCCGTGCGACAGCGTTCCTCCTGCACCAGCAAGCAATGGTAGCCC
GGACAATGCGAGCGAAGCGATTCTGTGGGTTGGTCACAGCAGCATTCGTCCGCGCTTCTTGTTTCGTAGCGCA
CAGCCGTCCCAGATCACCCCGGCCGGTATTGAAACGCTGATTCGCCAACTCGGTATTCAAGCGATCTTTGACTT
TCGTTCCCGTACCGAGATCCAACTGGTGGCAACCCGTCTACCCAGATAGCCTGCTGGAAATTCCGGGCACGACT
CGTTACTCTGTTCCGGTCTTTACCGAGGGCGACTACAGCCCGGCTTCTCTGGTTAAGCGTTATGGTGTCTCTAG
CGACACGGCAACGGATAGCACCAGCTCAAAGTGCGCGAAACCGACCGGCTTTGTGCATGCTTATGAAGCGAT
TGCTCGTTCTGCCGCGGAGAACGGTAGCTTCCGCAAGATCACCGACCACATTATCCAACATCCGGATCGCCCG
ATCCTGTTTCACTGCACGCTGGCAAAGACCGTACCGGTGTTTCGCAGCGCTGCTGCTGAGCTTGTGTGGTG
TCCCGAATGACACCATCGTGGAAGATTATGCGATGACGACCGAAGGCTTCGGTGTGTGGCGTGAGCACTTGA

```
TTCAGCGTCTGCTGCAGCGCAAAGATGCGGCTACGCGTGAAGATGCCGAGTTCATTATCGCGAGCCATCCGG
AGAGCATGAAAGCGTTCCTGGAAGATGTCGTTGCGACCAAATTCGGTGACGCCCGCAACTACTTTATCCAGCA
CTGTGGTCTGACCGAAGCCGAAGTGGATAAGCTGATCCGTACGCTGGTGATCGCGAATTAA
```

TalCeTPP1 amino acid sequence-SEQ ID NO: 22
```
MSNDTTSTASAGTATSSRFLSVGGVVNFRELGGYPCDSVPPAPASNGSPDNASEAILWVGHSSIRPRFLFRSAQPS
QITPAGIETLIRQLGIQAIFDFRSRTEIQLVATRYPDSLLEIPGTTRYSVPVFTEGDYSPASLVKRYGVSSDTATDSTSSK
CAKPTGFVHAYEAIARSAAENGSFRKITDHIIQHPDRPILFHCTLGKDRTGVFAALLLSLCGVPNDTIVEDYAMTTEG
FGVWREHLIQRLLQRKDAATREDAEFIIASHPESMKAFLEDVVATKFGDARNYFIQHCGLTEAEVDKLIRTLVIAN
```

TalCeTPP1 wild type cDNA-SEQ ID NO: 23
```
ATGTCTAATGACACCACTAGCACGGCTTCTGCCGGAACAGCAACTTCTTCGCGGTTTCTTTCTGTGGGCGGAGT
TGTGAATTTCCGTGAACTGGGCGGTTATCCATGTGATTCTGTCCCTCCTGCTCCTGCCTCAAACGGCTCACCGG
ACAACGCATCTGAAGCGATCCTTTGGGTTGGCCACTCGTCCATTCGGCCTAGGTTTCTCTTTCGATCGGCACAG
CCGTCTCAGATTACCCCGGCCGGTATTGAGACATTGATCCGCCAGCTTGGCATCCAGGCAATTTTTGACTTTCG
TTCACGGACGGAAATTCAGCTTGTCGCCACTCGCTATCCTGATTCGCTACTGAGATACCTGGTACGACTCGCT
ATTCCGTGCCCGTCTTCACGGAGGGCGACTATTCCCCGGCGTCATTAGTCAAGAGGTACGGAGTGTCCTCCGA
TACTGCAACTGATTCCTCCACTTCCAAATGTGCCAAGCCTACAGGATTCGTCCACGCATATGAGGCTATCGCAC
GCAGCGCAGCAGAAAACGGCAGTTTTCGTAAAATAACGGACCACATAATACAACATCCGGACCGGCCTATCCT
GTTTCACTGTACATTGGGAAAAGACCGAACCGGTGTATTTGCAGCATTGTTATTGAGTCTTTGCGGGGTACCA
AACGACACGATAGTTGAAGACTATGCTATGACTACCGAGGGATTTGGGGTCTGGCGAGAACATCTAATTCAA
CGCCTGTTACAAAGAAAGGATGCAGCTACGCGTGAGGATGCAGAATTCATTATTGCCAGCCACCCGGAGAGT
ATGAAGGCTTTTCTAGAAGATGTGGTAGCAACCAAGTTCGGGGATGCTCGAAATTACTTTATCCAGCACTGTG
GATTGACGGAAGCGGAGGTTGATAAGCTAATTCGGACACTGGTCATTGCGAATTGA
```

TalMaTPP1 optimized cDNA-SEQ ID NO: 24
```
ATGTGGAATTTGCACTATTATATTCCGGGCTCTGCACCAGTTAATTTGAACGACATGCCGAACGATACGGCGA
CGACGGCTTCCGCAGGCACTAGCGCCACGAGCCGCTTCCTCTGTGTCAGCGGTGTTGCGAACTTCCGTGAACT
GGGTGGCTATCCGTGCGACACCGTTCCTCCAGCACCGGCGAGCAATGGTAGCCCGCATAATGCATCCGAGGC
CACGCTGCAAGGTTCCCACTCTAGCATTCGTCCGGGCTTCATCTTCCGTAGCGCGCAACCGAGTCAGATCAATC
CGGCAGGCATCGCGACGCTGGCGCATGAACTGTCTATTCAAGTCATCTTCGACTTCCGTTCGCAGACCGAGAT
CCAGCTGGTCACCACCCACTACCCGGATAGCCTGTTGGAGATCCCGTGTACCACCCGTTACAGCGTGCCGGTG
TTTAACGAGGGTGACTATAGCCCGGCTTCGCTGGTCAAGAAATACGGTGTGAGCCCGGACCCAGTGACGCAT
TCCGCTAGCACGCACCAGCGCGAATCCTGCCGGCTTTGTGCCGGCAGCAATCGCTCGTAGCGCAGCCG
AAAACGGTAGCTTTCGCAAAATCACCGAGCACATTATTCAGCACCCGGATCAGCCGATTTTGTTTCATTGCACC
CTGGGTAAAGATCGCACGGGTGTGTTTGCGGCCCTGCTGCTGAGCCTGTGCGGTGTTTCCACCGAAAAGATC
GTGGAAGATTACGCGATGACCACCGAGGGTTTCGGTGCTTGGCGTGAGCACCTGATTAAGCGCCTGCTGCAG
CGTAAAGATGCGGCAACCCGCCAAGACGCTGAGTTCATCATTGCCAGCCACCCGGAAACCATGAAATCTTTTC
TGGACGACGTTGTTCGTGCGAAGTTTGGCTCCGCGCGTAACTATTTCGTGCAACAGTGCGGTCTGACTGAGTA
CGAAGTTGATAAGCTGATTCATACGCTGGTCATTATCAAGTAA
```

TalMaTPP1 amino acid sequence-SEQ ID NO: 25
```
MWNLHYYIPGSAPVNLNDMPNDTATTASAGTSATSRFLCVSGVANFRELGGYPCDTVPPAPASNGSPHNASEAT
LQGSHSSIRPGFIFRSAQPSQINPAGIATLAHELSIQVIFDFRSQTEIQLVTTHYPDSLLEIPCTTRYSVPVFNEGDYSPA
SLVKKYGVSPDPVTHSASSTSANPAGFVPAYEAIARSAAENGSFRKITEHIIQHPDQPILFHCTLGKDRTGVFAALLLS
LCGVSTEKIVEDYAMTTEGFGAWREHLIKRLLQRKDAATRQDAEFIIASHPETMKSFLDDVVRAKFGSARNYFVQQ
CGLTEYEVDKLIHTLVIIK
```

TalMaTPP1 wild type cDNA-SEQ ID NO: 26
```
ATGTGGAACCTACACTACTATATTCCTGGATCAGCACCAGTCAACTTGAACGACATGCCTAATGACACCGCTAC
CACGGCTTCTGCCGGAACATCAGCAACTTCACGGTTTCTTTGCGTGAGCGGAGTGGCGAATTTCCGTGAACTG
GGCGGTTACCCATGCGATACTGTCCCTCCTGCTCCTGCGTCAAACGGTTCACCGCACAATGCATCTGAAGCGA
CCCTCCAGGGTAGTCATTCGTCTATTCGGCCTGGATTATCTTTCGATCGGCTCAGCCGTCGCAGATTAACCCG
GCTGGTATTGCCACATTAGCACACGAGCTTAGCATCCAGGTGATTTTTGACTTTCGTTCGCAAACCGAAATTCA
GCTTGTCACTACTCATTATCCTGATTCGTACTTGAGATACCTTGCACGACTCGCATTCCGGTGCCTTCAA
TGAGGGCGACTATTCCCCAGCGTCGTTAGTCAAGAAGTACGGGGTATCCCCGATCCTGTAACACATTCCGCT
TCCTCCACGAGTGCCAATCCTGCAGGATTTGTCCCCGCGTATGAAGCCATCGCACGAAGCGCAGCAGAAAACG
GCAGTTTCCGTAAAATAACAGAGCACATAATACAGCATCCGGACCAGCCGATCCTGTTTCATTGTACTCTGGG
AAAGGACCGGACCGGAGTTTTGCAGCATTGTATTGAGCCGTTGGACACGGTGTTCGACTGAGAAGATAGTTGAA
GACTATGCTATGACTACCGAGGGTTTCGGAGCCTGGCGGAACATCTAATTAAACGCCTGCTGCAAAGGGAAA
GATGCAGCAACACGCCAGGATGCGGAATTCATTATCGCCAGCCACCCGGAGACTATGAAGTCTTTCCTAGACG
ATGTCGTGCGAGCTAAGTTCGGAAGTGCTCGAAATTACTTTGTCCAGCAGTGTGGATTGACAGAATATGAGGT
TGATAAGTTAATCCATACACTCGTGATTATAAAATGA
```

TalAstroTPP1 optimized cDNA-SEQ ID NO: 27
```
ATGTCCACCAATGCAGATCCGACCACGTTTTCCGATAAGTCCCCGTTCATCAATGTCAGCGGCGTGGTGAATTT
TCGTGACCTGGGCGGCTACAGCTGCTTGACCCCGTTGACGCCAGTCAGCAACGGCAGCCCGGTAATTGCGTC
GAAGGGTAGCCCTTCTAGCTATATCCGTCCAGGTTTCCTGTTTCGCCTCTGCTCAGCCGAGCCAGATTACCGAAA
CCGGTATCGAGGTCCTGACCCACAAGCTGAATATCGGTGCGATTTTTGACTTCCGTTCCCAAACCGAGATCCAA
CTGGTTGCGACGCGTTACCGGACAGCCTGCTGGAAATTCCGTTTACCTCTCGTTATGCAGTCCCGGTTTTCGA
GCATTGTGATTTCAGCCCGGTTAGCTTGAGCAAGAAATATGGTGCGCCGAGCAACGCACCGCCTACCGAAGC
GGAGCACGGTAGCTTTGTGCAGGCGTACGAAGATATTGCCCGTAGCGCAGCAGAAACGGCAGCTTCCGCA
GCATCACGGACCACATTTTTGCGCTACCCGGATGCCGATCGTGTTCCACTGGGTAAAGACCGGCACC
CGGCGTTTTTGCGGCGCTGCTGCTGAAACTGTGTGGTGTGAGCGACGAAGTTGTGATTCAGGACTATGCCCTG
ACTACGCAAGGTCTGGGTGCCTGGAGAGAGCATCTGATCCAACGCCTGCTGCAGCGTAATGACGTCGCGACG
CGTGAAGATGCAGAGTTTATCCTGGCTAGCCGTCCGGAGACTATGAAATCGTTCCTGGCCGATGTTGTGGAAA
CCAAGTTCGGTGGCGCTCGCAACTACTTCACGCTGCTGTGCGGTCTGACCGAAGATGATGTTAACAACCTGAT
TAGCCTGGTTGTCATTCATAACACGAATTAA
```

```
TalAstroTPP1 amino acid sequence-SEQ ID NO: 28
MSTNADPTTFSDKSPFINVSGVVNFRDLGGYSCLTPLTPVSNGSPVIASKGSPSSYIRPGFLFRSAQPSQITETGIEVLT
HKLNIGAIFDFRSQTEIQLVATRYPDSLLEIPFTSRYAVPVFEHCDFSPVSLSKKYGAPSNAPPTEAEHGSFVQAYEDIA
RSAAENGSFRSITDHILRYPDMPILFHCTVGKDRTGVFAALLLKLCGVSDEVVIQDYALTTQGLGAWREHLIQRLLQ
RNDVATREDAEFILASRPETMKSFLADVVETKFGGARNYFTLLCGLTEDDVNNLISLVVIHNTN TalAstroTPP1 wild type cDNA-SEQ ID NO: 29
ATGTCTACCAACGCTGACCCTACTACTTTTTCCGATAAATCACCGTTTATTAACGTAAGCGGCGTTGTCAATTTT
CGTGATCTGGGCGGTTACTCATGTCTCACTCCTCTCACCCCTGTCTCAAATGGTTCACCGGTGATAGCGTCAAA
GGGATCCCCCTCATCATACATTCGCCCCGGCTTCTTGTTCCGTTCAGCACAGCCTTCACAAATTACCGAGACTG
GTATCGAAGTTCTGACGCACAAGCTTAATATCGGAGCTATATTTGACTTTCGGTCACAGACAGAAATCCAGCTT
GTTGCGACTCGATATCCAGATTCCTGCTCGAAATACCATTTACTAGCCGATACGCTGTTCCAGTGTTCGAACA
TTGCGACTTTTCTCCGGTCTCGCTGTCTAAGAAGTATGGGGCTCCGTCAAACGCTCCTCCTACAGAAGCCGAGC
ACGGTAGCTTCGTCCAGGCTTATGAAGATATCGCCCGCAGTGCAGCGGAAAATGGAAGTTTTCGCAGCATAA
CAGATCATATTCTGCGATATCCCGACATGCCAATTCTTTTTCATTGTACGGTTGGCAAAGACAGAACTGGTGTG
TTTGCAGCATTGTTGTTGAAGCTGTGTGGAGTGTCTGATGAAGTAGTTATTCAAGACTACGCACTCACTACTCA
AGGCCTAGGTGCATGGCGCGAACACCTGATTCAGCGCCTGCTGCAAAGGAATGATGTTGCTACCCGTGAGGA
TGCCGAGTTCATACTCGCTAGCCGACCAGAGACTATGAAGTCATTCTTGGCAGATGTGGTGGAAACCAAATTT
GGAGGAGCTCGCAACTATTTTACTCTGCTGTGCGGATTGACCGAGGACGATGTCAATAACTTGATCTCCCTTGT
AGTTATTCATAATACAAATTAG PeSubTPP1 optimized cDNA-SEQ ID NO: 30
ATGCAACCTTTTATTAGCGTCGATGGTGTGGTGAATTTTCGTGATATTGGTGGTTATGTTTGCCGTAATCCGGC
CGGTTTTGTCGAGCCTGCCGAGCAACGTTGACGAAACCCCGGAAAAGCAATGGTGTATCCGCCCAGGCTTCGTT
TTCCGTGCAGCGCAACCGTCCCAAATTACGCCGGCTGGTATCGAGATTCTTAAGAAAACGCTGGCGATCCAAG
CGATTTTCGATTTTCGTAGCGAGTCCGAGATCCAACTGGTGAGCAAGCGTTACCCGGACAGCCTGCTGGACAT
CCCCGGGCACTACGCGTCATGCTGTTCCGGTGTTTCAGGAGGGTGATTACAGCCGATCTCGTTGGCCAAACGT
TACGGTGTGACCGCGGACGAGAGCACCAACGATCAGTCCTTCCGTCGGGTTTTGTCAAAGCGTATGAAGCC
ATCGCACGCAACGCAGCACAGGCTGGTAGCTTCCGCGCCATTATCCAGCATATCCTGCAGGACTCCGCTGGCC
CAGTTTTGTTTCCACTGCACCGTAGGCAAAGATCGCACGGGTGTTTTCTCTGACTGATTCTGAAGCTGTGCGGT
GTGGCCGACGAAGATATTGTGGCAGACTATGCGCTGACCACTCAGGGCCTGGGTGTCTGGCGTGAGCACCTG
ATCCAGCGCCTGTTGCAGCGTGGTGAAGCGACCACCAAAGAACAAGCGGAAGCGATCATCTCTAGCGACCCG
CGCGACATGAAAGCGTTCCTGAGCAACGTCGTTGAGGGCGAGTTTGGTGGCACGCAACTACTTCGTGAAT
CTGTGTGGCCTGCCTGAAGGCGAGGTTGACCGTGTCATTACCAAACTGGTCGTCCCGAAAACCACCAAGTAA PeSubTPP1 amino acid sequence-SEQ ID NO: 31
MQPFISVDGVVNFRDIGGYVCRNPAGLSSLPSNVDETPEKQWCIRPGFVFRAAQPSQITPAGIEILKKTLAIQAIFDF
RSESEIQLVSKRYPDSLLDIPGTTRHAVPVFQEGDYSPISLAKRYGVTADESTNDQSFRPGFVKAYEAIARNAAQAGS
FRAIIQHILQDSAGPVLFHCTVGKDRTGVFSALILKLCGVADEDIVADYALTTQGLGVWREHLIQRLLQRGEATTKEQ
AEAIISSDPRDMKAFLSNVVEGEFGGARNYFVNLCGLPEGEVDRVITKLVVPKTTK PeSubTPP1 wild type cDNA-SEQ ID NO: 32
ATGCAGCCATTCATCTCGGTGGATGGAGTCGTCAACTTCCGCGATATCGGAGGCTATGTATGCCGGAATCCCG
CTGGTTTATCCTCCTTGCCCTCGAATGTCGACGAAACCCCAGAGAAACAGTGGTGCATTCGGCCAGGATTCGT
CTTCCGCGCGGCACAGCCATCCCAAATCACCCCTGCAGGGATTGAGATCCTGAAAAAGACCCTTGCTATCCAA
GCCATCTTTGACTTTCGGTCAGAGAGTGAGATTCAGCTTGTGTCTAAGCGCTATCCAGACTCCCTCCTCGATAT
TCCCGGGACAACTCGCCATGCAGTACCGGTCTTCAAGAAGGTGATTACTCTCCCATCTCACTGGCAAAACGG
TATGGAGTCACCGCGGACGAATCCACGAATGATCAGTCCTTTAGACCGGGATTCGTCAAGGCCTACGAGGCC
ATTGCGCGCAACGCGGCTCAAGCGGGCAGCTTCCGTGCAATCATACAGCACATTCTGCAGGATTCGGCCGGC
CCGGTACTTTTCCACTGCACGGTGGGCAAGGACCGGACAGGGGTCTTTTCGGCTTTGATCCTCAAGCTGTGCG
GGGTGGCCGATGAGGACATTGTCGCTGATTATGCACTCACCACGCAAGGCTTAGGTGTGTGCGGGAGCATT
TGATTCAACGGCTCTTGCAGAGAGGGGAGGCCACAACCAAGGAACAAGCCGAAGCCATAATCAGCAGTGACC
CGAGAGACATGAAGGCGTTTTTGAGCAATGTAGTGGAAGGGAATTTGGAGGTGCTCGGAACTACTTCGTCA
ACCTCTGCGGACTACCGGAAGGCGAAGTCGATCGGGTTATCACCAAGCTTGTGGTACCAAAGACTACTAAATA
G Codon optimized cDNA sequence encoding for SmCPS-SEQ ID NO: 33
ATGGCAACTGTTGATGCACCACAAGTTCACGATCATGACGGCACCACTGTTCACCAAGGCCACGATGCAGTCA
AGAATATCGAGGACCCGATCGAGTACATTCGCACGCTGTTGCGCACCAAGGGCGACGGTCGTATTTCCGTGA
GCCCGTATGATACCGCATGGGTCGCGATGATCAAAGACGTTGAGGGCCGTGATGGTCCGCAGTTTCCGTCTA
GCTTGGAATGGATCGTGCAAAATCAGTTGGAAGATGGTTCGTGGGGTGACCAGAAACTGTTTTGTGTGTATG
ATCGCTTGGTTAATACGATCGCGTGTGTGGTTGCTTTGCGTTCTTGGAACGTGCACGCGCACAAAGTGAAGCG
TGGTGTGACCTATATTAAGGAAAACGTTGATAAGCTGATGGAGGGTAACGAGGAGCACATGACTTGCGGCTT
CGAAGTCGTTTTCCCGGCACTGCTGCAGAAAGCCAAAAGCCTGGGTATTGAGGATTTGCCTTACGATTCGCCG
GCGGTCAAGAAGTGTATCACGTCCGCGAACAAAAGCTGAAGCGCATCCCGTTGGAATTATGCACAAAATTC
CGACCAGCCTGCTGTTTAGCCTGGAAGGTCTGGAGAATCTCGACTGGGACAAACTGCTGAAACTCCAGAGCG
CTGACGGCTCTTTTCTGACGAGCCCGAGCAGCACGGCGTTCGCATTTATGCAGACGAAAGACGAAAAATGCTA
TCAATTTATTAAGAATACGATTGACACCTTCAATGGTGGCGCCGCATACCTATCCGGTGGATGTTTTGGTC
GTTTATGGGCGATTGATCGTCTGCAGAGACTGGGTATTAGCCGTTTCTTTGAGCCGGAAATTGCCGATTGCCT
GTCTCATATTCACAAATTTGGACCGACAAGGGTGTTTTCTCTGGTCGCGAGAGCGAATTTTGCGACATCGAC
GACACCAGCATGGGCATGCGCCTGATGCGCATGCACGGTTATGACGTCGATCCAAATGTCCTGCGCAATTTCA
AACAAAAGGACGGCAAGTTCAGCTGCTACGGCGGCCAGATGATCGAGTCTCCGAGCCCGATCTATAATCTGT
ATCGTGCGAGCCAGTTGCGCTTCCCGGGTGAAGAAATCCTGGAAGATGCCAAACGCTTTGCTTACGACTTCTT
GAAAGAGAAACTGGCGAACAACCAGATTCTGGACAAGTGGGTTATTTGAAACACTTGCCGGACGAGATCAA
ACTGGGCTTAGAAATGCCGTGGTTGGCAACCCTGCCGCGCGTGGAGGCGAAGTACTACATCCAGTACTACGC
GGGCAGCGGTGATGTTTGGATCGGCAAAACGTTGTACCGCATGCCTGAGATCTCGAACGACACCTATCACGA
CCTGGCTAAGACCGATTTTAAACGTTGTCAGGCCAAACACCAATTCGAGTGGCTGTACATGCAAGAGTGGTAT
GAAAGCTGCGGCATCGAAGAGTTTGGTATCAGCCGTAAAGACCTCCTGCTGAGCTATTTTCTGGCGACGGCG
AGCATCTTCGAGTTGGAGCGCACCAACGAACGTATTGCGTGGGCAAAATCTCAGATTATCGCAAAAATGATCA
```

```
CGAGCTTCTTTAACAAAGAAACCACGAGCGAGGAAGATAAGCGCGCCCTGCTGAATGAGCTGGGCAACATCA
ATGGTCTGAATGATACGAACGGTGCAGGCCGCGAGGGTGGTGCTGGTAGCATCGCGCTGGCGACCCTGACCC
AATTTCTGGAAGGTTTCGACCGTTATACCCGCCATCAACTCAAAAACGCCTGGAGCGTGTGGCTGACTCAGTT
ACAGCATGGCGAGGCAGATGATGCTGAGCTGCTGACCAATACGCTCAACATCTGCGCGGGCCATATCGCGTT
CCGTGAGGAAATTCTGGCCCATAACGAGTACAAGGCCTTGAGCAACCTGACCAGCAAAATCTGCCGCCAACT
GAGCTTTATTCAAAGCGAAAAGGAAATGGGCGTCGAGGGCGAGATTGCGGCAAAGAGCAGCATCAAGAATA
AAGAACTGGAAGAAGATATGCAGATGCTGGTCAAACTGGTCCTGGAAAAGTACGGTGGTATCGACCGTAACA
TCAAAAAAGCGTTTCTGGCTGTCGCGAAAACCTATTACTATCGTGCATATCATGCTGCGGACACCATCGACACC
CACATGTTTAAGGTTCTGTTTGAGCCGGTTGCATAA

SmCPS, a CPP synthase from Salvia miltiorrhiza, amino acid sequence. -SEQ ID NO: 34
MATVDAPQVHDHDGTTVHQGHDAVKNIEDPIEYIRTLLRTTGDGRISVSPYDTAWVAMIKDVEGRDGPQFPSSLE
WIVQNQLEDGSWGDQKLFCVYDRLVNTIACVVALRSWNVHAHKVKRGVTYIKENVDKLMEGNEEHMTCGFEVV
FPALLQKAKSLGIEDLPYDSPAVQEVYHVREQKLKRIPLEIMHKIPTSLLFSLEGLENLDWDKLLKLQSADGSFLTSPSS
TAFAFMQTKDEKCYQFIKNTIDTFNGGAPHTYPVDVFGRLWAIDRLQRLGISRFFEPEIADCLSHIHKFWTDKGVFS
GRESEFCDIDDTSMGMRLMRMHGYDVDPNVLRNFKQKDGKFSCYGGQMIESPSPIYNLYRASQLRFPGEEILEDA
KRFAYDFLKEKLANNQILDKWVISKHLPDEIKLGLEMPWLATLPRVEAKYYIQYYAGSGDVWIGKTLYRMPEISNDT
YHDLAKTDFKRCQAKHQFEWLYMQEWYESCGIEEFGISRKDLLLSYFLATASIFELERTNERIAWAKSQIIAKMITSFF
NKETTSEEDKRALLNELGNINGLNDTNGAGREGGAGSIALATLTQFLEGFDRYTRHQLKNAWSVWLTQLQHGEA
DDAELLTNTLNICAGHIAFREEILAHNEYKALSNLTSKICRQLSFIQSEKEMGVEGEIAAKSSIKNKELEEDMQMLVKL
VLEKYGGIDRNIKKAFLAVAKTYYYRAYHAADTIDTHMFKVLFEPVA Codon optimized cDNA encoding for a GGPP synthase from Pantoea agglomerans. -SEQ ID NO: 35
ATGGTTTCTGGTTCGAAAGCAGGAGTATCACCTCATAGGGAAATCGAAGTCATGAGACAGTCCATTGATGACC
ACTTAGCAGGATTGTTGCCAGAAACAGATTCCCAGGATATCGTTAGCCTTGCTATGAGAGAAGGTGTTATGGC
ACCTGGTAAACGTATCAGACCTTTGCTGATGTTACTTGCTGCAAGAGACCTGAGATATCAGGGTTCTATGCCTA
CACTACTGGATCTAGCTTGTGCTGTTGAACTGACACATACTGCTTCCTTGATGCTGGATGACATGCCTTGTATG
GACAATGCGGAACTTAGAAGAGGTCAACCAACAACCCACAAGAAATTCGGAGAATCTGTTGCCATTTTGGCTT
CTGTAGGTCTGTTGTCGAAAGCATTTGGCTTGATTGCTGCAACTGGTGATCTTCCAGGTGAAAGGAGAGCACA
AGCTGTAAACGAGCTATCTACTGCAGTTGGTGTTCAAGGTCTAGTCTTAGGACAGTTCAGAGATTTGAATGAC
GCAGCTTTGGACAGAACTCCTGATGCTATCCTGTCTACGAACCATCTGAAGACTGGCATCTTGTTCTCAGCTAT
GTTGCAAATCGTAGCCATTGCTTCTGCTTCTTCACCATCTACTAGGGAAACGTTACACGCATTCGCATTGGACTT
TGGTCAAGCCTTTCAACTGCTAGACGATTTGAGGGATGATCATCCAGAGACAGGTAAAGACCGTAACAAAGA
CGCTGGTAAAAGCACTCTAGTCAACAGATTGGGTGCTGATGCAGCTAGACAGAAACTGAGAGAGCACATTGA
CTCTGCTGACAAACACCTGACATTTGCATGTCCACAAGGAGGTGCTATAAGGCAGTTTATGCACCTATGGTTTG
GACACCATCTTGCTGATTGGTCTCCAGTGATGAAGATCGCCTAA GGPP synthase from Pantoea agglomerans, amino acid sequence-SEQ ID NO: 36
MVSGSKAGVSPHREIEVMRQSIDDHLAGLLPETDSQDIVSLAMREGVMAPGKRIRPLLMLLAARDLRYQGSMPTL
LDLACAVELTHTASLMLDDMPCMDNAELRRGQPTTHKKFGESVAILASVGLLSKAFGLIAATGDLPGERRAQAVN
ELSTAVGVQGLVLGQFRDLNDAALDRTPDAILSTNHLKTGILFSAMLQIVAIASASSPSTRETLHAFALDFGQAFQLL
DDLRDDHPETGKDRNKDAGKSTLVNRLGADAARQKLREHIDSADKHLTFACPQGGAIRQFMHLWFGHHLADWS
PVMKIA Optimized cDNA encoding for SsLPS-SEQ ID NO: 37
ATGGCATCCCAAGCGTCCGAGAAAGATATTAGCCTGGTTCAAACCCCGCATAAGGTCGAGGTCAACGAAAAG
ATCGAAGAGAGCATCGAGTACGTCCAAAATCTGCTGATGACGAGCGGTGACGGTCGTATCTCCGTGTCTCCGT
ACGATACCGCGGTCATCGCTCTGATTAAAGATCTGAAGGGTCGCGACGCACCGCAGTTCCCGAGCTGTCTGGA
GTGGATTGCGCACCACCAGTTAGCGGATGGTAGCTGGGGCGACAGTTTCTTTTGTATCTATGACCGCATTTTG
AATACCCTGGCGTGCGTCGTCGCACTGAAATCTTGGAATCTGCACAGCGACATTATTGAAAAGGCGTGACCT
ACATTAAGGAAAACGTCCATAAGCTGAAAGGCGCGAATGTTGAGCATAGAACCGCCGGTTTTGAGCTGGTTG
TTCCGACCTTCATGCAGATGGCGACTGACCTGGGTATTCAGGATCTGCCGTACGATCATCCTCTTATCAAAGAA
ATCGCTGATACGAAGCAACAGCGCCTGAAAGAAATTCCGAAAGATTTGGTTTATCAGATGCCGACCAATCTGC
TGTATAGCCTGGAAGGCCTGGGCGATTTAGAGTGGGAGCGTTTGCTGAAGCTGCAGTCTGGTAATGGTAGCT
TCCTGACGAGCCCAAGCAGCACGGCGCAGTTCTGATGCATACCAAGACGCGAAGTGTTTGAAATACATTG
AGAATGCGCTGAAGAACTGCGACGGTGGCGCTCCTCATACGTATCCGGTTGACATCTTTAGCCGCTTGTGGGC
GATCGACCGTTTGCAACGTCTGGGCATTAGCCGTTTCTTCCAACACGAGATCAAATACTTTCTGGACCACATCG
AGTCAGTCTGGGAAGAAACCGGCGTGTTTAGCGGTCGTTACACGAAGTTTAGCGACATCGATGACACGAGCA
TGGGTGTCCGCCTGCTGAAAATGCACGGTTACGACGTAGACCCAAACGTGTTGAAACACTTTAAGCAGCAAG
ACGGCAAATTCAGCTGCTACATCGGCCAGTCGAAGCGGCAAGTGTATAATCTGTACCGTGCCG
CCCAGCTGCGTTTCCCGGGTGAAGAAGTGCTTGAAGAAGCAACTAAATTCGCGTTTAACTTCCTGCAAGAGAT
GCTGGTGAAGGATCGCTTCAAGAGCGTTGGGTTATTAGCGATCACCTGTTTGACGAGATTAAGCTCGGTCTG
AAGATGCCGTGGTATGCTACCCTGCCGCGTGTTGAGGCCGCTTATTACCTGGATCACTATGCGGGTAGCGGTG
ATGTGTGGATTGGTAAGTCTTTTTACCGCATGCCGGAGATTAGCAATGACACCTACAAAGAATTGGCCATCCT
GGACTTTAACCGTTGTCAGACTCAGCATCAGCTGGAGTGGATTCACATGCAAGAGTGGTATGACCGCTGCTCT
CTGTCCGAGTTTGGTATTAGCAAGCGTGAGCTGCTGCGTAGCTACTTCCTGGCTGCCGCAACCATTTTCGAACC
GGAACGCACCCAAGAGCGTCTGCTCTGGGCAAAGACCCGCATCCTGAGCAAGATGATTACCAGCTTCGTCAA
CATCTCCGGTACGACCCTGAGCCTGGATTACAACTTCAACGGTTTGGATGAGATCATTTCCAGCGCGAATGAA
GATCAGGGTCTGGCGGGTACGCTGTTGGCCACGTTCCATCAACTGCTGGATGGTTTCGACATTTACACCCTGC
ACCAACTGAAACACGTCTGGTCGCAATGGTTTATGAAAGTTCAGCAAGGCGAGGGCTCCGGCGGCGAAGATG
CGGTCCTGCTGGCAAATACTCTGAATATCTGCGCGGGTCTGAATGAAGATGTCTGTGAACAACGAGTATAC
CGCGCTGAGCACGCTGACGAACAAGATCTGCAACCGTCTGGCCCAGATCCAGGACAACAAGATTCTGCAAGT
GGTGGACGGCAGCATCAAAGACAAAGAACTGGAACAGGATATGCAGGCATTGTTAAACTGGTGCTGCAGG
AAAACGGTGGCGCAGTGGACCGTAACATCCGTCACACGTTTCTGAGCGTTAGCAAGACCTTCTACTATGACGC
GTATCACGACGATGAAACCACCGATCTGCATATCTTTAAAGTCCTGTTCCGTCCGGTTGTTTAA
```

```
SsLPS amino acid sequence. -SEQ ID NO: 38
MASQASEKDISLVQTPHKVEVNEKIEESIEYVQNLLMTSGDGRISVSPYDTAVIALIKDLKGRDAPQFPSCLEWIAHH
QLADGSWGDEFFCIYDRILNTLACVVALKSWNLHSDIIEKGVTYIKENVHKLKGANVEHRTAGFELVVPTFMQMAT
DLGIQDLPYDHPLIKEIADTKQQRLKEIPKDLVYQMPTNLLYSLEGLGDLEWERLLKLQSGNGSFLTSPSSTAAVLMH
TKDEKCLKYIENALKNCDGGAPHTYPVDIFSRLWAIDRLQRLGISRFFQHEIKYFLDHIESVWEETGVFSGRYTKFSDI
DDTSMGVRLLKMHGYDVDPNVLKHFKQQDGKFSCYIGQSVESASPMYNLYRAAQLRFPGEEVLEEATKFAFNFLQ
EMLVKDRLQERWVISDHLFDEIKLGLKMPWYATLPRVEAAYYLDHYAGSGDVWIGKSFYRMPEISNDTYKELAILD
FNRCQTQHQLEWIHMQEWYDRCSLSEFGISKRELLRSYFLAAATIFEPERTQERLLWAKTRILSKMITSFVNISGTTL
SLDYNFNGLDEIISSANEDQGLAGTLLATFHQLLDGFDIYTLHQLKHVWSQWFMKVQQGEGSGGEDAVLLANTLN
ICAGLNEDVLSNNEYTALSTLTNKICNRLAQIQDNKILQVVDGSIKDKELEQDMQALVKLVLQENGGAVDRNIRHTF
LSVSKTFYYDAYHDDETTDLHIFKVLFRPVV Optimized cDNA encoding for TaTps1-del59-SEQ ID NO: 39
ATGTATCGCCAAAGAACTGATGAGCCAAGCGAAACCCGCCAGATGATCGATGATATTCGCACCGCTTTGGCTA
GCCTGGGTGACGATGAAACCAGCATGAGCGTGAGCGCATACGACACCGCCCTGGTTGCCCTGGTGAAGAACC
TGGACGGTGGCGATGGCCCGCAGTTCCCGAGCTGCATTGACTGGATTGTTCAGAACCAGCTGCCGGACGGTA
GCTGGGGCGACCCGGCTTTCTTTATGGTTCAGGACCGTATGATCAGCACCCTGGCCTGTGTGGCCGTGAA
ATCCTGGAATATCGATCGTGACAACTTGTGCGATCGTGGTGTCCTGTTTATCAAAGAAACATGTCGCGTCTG
GTTGAAGAAGAACAAGATTGGATGCCATGTGGCTTCGAGATTAACTTTCCTGCACTGTTGGAGAAAGCTAAA
GACCTGGACTTGGACATTCCGTACGATCATCCTGTGCTGGAAGAGATTTACGCGAAGCGTAATCTGAAACTGC
TGAAGATTCCGTTAGATGTCCTCCATGCGATCCCGACGACGCTGTTGTTTTCCGTTGAGGGTATGGTCGATCTG
CCGCTGGATTGGGAGAAACTGCTGCGTCTGCGTTGCCCGGACGGTTCTTTTCATTCTAGCCGGCGGCGACGG
CAGCGGCGCTGAGCCACACGGGTGACAAAGAGTGTCACGCCTTCCTGGACCGCCTGATTCAAAAGTTCGAGG
GTGGCGTCCCGTGCTCCCACAGCATGGACACCTTCGAGCAACTGTGGGTTGTTGACCGTTTGATGCGTCTGGG
TATCAGCCGTCATTTTACGAGCGAGATCCAGCAGTGCTTGGAGTTCATCTATCGTCGTTGGACCCAGAAAGGT
CTGGCGCACAATATGCACTGCCCGATCCCGGACATTGATGACACTGCGATGGGTTTTCGTCTTGTTGAGACAGC
ACGGTTACGACGTGACCCCGTCGGTTTTCAAGCATTTCGAGAAAGACGGCAAGTTCGTATGCTTCCCGATGGA
AACCAACCATGCGAGCGTGACGCCGATGCACAATACCTACCGTGCGAGCCAGTTCATGTTCCCGGGTGATGAC
GACGTGCTGGCCCGTGCCGGCCGCTACTGTCGCGCATTCTTGCAAGAGCGTCAGAGCTCTAACAAGTTGTACG
ATAAGTGGATTATCACGAAAGATCTGCCGGGTGAGGTTGGCTACAGTGGCGACTTTCCGTGGAAAAGCTCCCT
GCCGCGTATTGAAACTCGTATGTATCTGGATCAGTACGGTGGCAATAACGATGTCTGGATTGCAAAGGTCCTG
TATCGCATGAACCTGGTTAGCAATGACCTGTACCTGAAAATGGCGAAAGCCGACTTTACCGAGTATCAACGTC
TGTCTCGCATTGAGTGGAACGGCCTGCGCAAATGGTATTTTCGCAATCATCTGCAGCGTTACGGTGCGACCCC
GAAGTCCGCGCTGAAAGCGTATTTCCTGGCGTCGGCAAACATCTTTGAGCCTGGCCGCGAGCCGAGCGCCT
GGCATGGGCACGTATGGCCGTGCTGGCTGAAGCTGTAACGACTCATTTCCGTCACATTGGCGGCCCGTGCTAC
AGCACCGAGAATCTGGAAGAACTGATCGACCTTGTTAGCTTCGACGACGTGAGCGGCGGCTTGCGTGAGGCG
TGGAAGCAATGGCTGATGGCGTGGACCGCAAAAGAATCACACGGCAGCGTGGACGGTGACACGGCACTGCT
GTTTGTCCGCACGATTGAGATTTGCAGCGGCCGCATCGTTTCCAGCGAGCAGAAACTGAATCTGTGGGATTAC
AGCCAGTTAGAGCAATTGACCAGCAGCATCTGTCATAAACTGGCCACCATCGGTCTGAGCCAGAACGAAGCTA
GCATGGAAAATACCGAAGATCTGCACCAACAAGTCGATTTGGAAATGCAAGAACTGTCATGGCGTGTTCACCA
GGGTTGTCACGGTATTAATCGCGAAACCCGTCAAACCTTCCTGAATGTTGTTAAGTCTTTTTATTACTCCGCACA
CTGCAGCCCGGAAACCGTGGACAGCCATATTGCAAAAGTGATCTTTCAAGACGTTATCTGA TaTps1-del59, truncated copalyl diphosphate synthase from Triticum aestivum. -SEQ ID NO: 40
MYRQRTDEPSETRQMIDDIRTALASLGDDETSMSVSAYDTALVALVKNLDGGDGPQFPSCIDWIVQNQLPDGSW
GDPAFFMVQDRMISTLACVVAVKSWNIDRDNLCDRGVLFIKENMSRLVEEEQDWMPCGFEINFPALLEKAKDLD
LDIPYDHPVLEEIYAKRNLKLLKIPLDVLHAIPTTLLFSVEGMVDLPLDWEKLLRLRCPDGSFHSSPAATAAALSHTGD
KECHAFLDRLIQKFEGGVPCSHSMDTFEQLWVVDRLMRLGISRHFTSEIQQCLEFIYRRWTQKGLAHNMHCPIPDI
DDTAMGFRLLRQHGYDVTPSVFKHFEKDGKFVCFPMETNHASVTPMHNTYRASQFMFPGDDDVLARAGRYCRA
FLQERQSSNKLYDKWIITKDLPGEVGYTLNFPWKSSLPRIETRMYLDQYGGNNDVWIAKVLYRMNLVSNDLYLKM
AKADFTEYQRLSRIEWNGLRKWYFRNHLQRYGATPKSALKAYFLASANIFEPGRAAERLAWARMAVLAEAVTTHF
RHIGGPCYSTENLEELIDLVSFDDVSGGLREAWKQWLMAWTAKESHGSVDGDTALLFVRTIEICSGRIVSSEQKLNL
WDYSQLEQLTSSICHKLATIGLSQNEASMENTEDLHQQVDLEMQELSWRVHQGCHGINRETRQTFLNVVKSFYYS
AHCSPETVDSHIAKVIFQDVI CymB, optimized cDNA-SEQ ID NO: 41
ATGACTATCAATTCTATTCAACCGATTCAAGCAAAAGCCGCTGTGCTGCGTGCCGTAGGCTCCCCGTTTAACAT
TGAGCCGATTCGTATCAGCCCGCCGAAGGGTGATGAAGTTCTGGTCCGTATTGTGGGTGTGGGTGTCTGCCAT
ACCGACGTCGTTTGCCGTGACAGCTTCCCGGTTCCGCTGCCAATCATCCTTGGGTCACGAAGGCTCGGGTGTGA
TTGAAGCGATCGGTGATCAAGTTACGAGCCTGAAGCCAGGTGACCACGTCGTTCTGAGCTTCAATAGCTGCG
GCCACTGTTATAACTGCGGTCATGCGGAGCCGGCAAGCTGCCTGCAGATGTTACCGTTGAACTTTGGTGGCGC
GGAGCGTGCGGCGGACGGCACCATCCAAGACGACAAGGGTGAAGCCGTCCGCGGTATGTTCTTTGGCCAGTC
CAGCTTTGGCACGTACGCAATCGCACGTGCGGTGAATGCTGTCAAAGTTGACGATCTGCCGCTGCCTCTG
TTGGGCCCGCTGGGCTGTGGTATCCAGACCGGTGCGGGTGCAGCGATGAACAGCCTGTCTCTGCAGAGCGGT
CAGAGCTTCATCGTTTTCGGTGGCGGCGCGGTCGGTCTGAGCGCTGTTATGGCAGCTAAAGCGCTGGGCGTG
AGCCCGCTGATCGTTGTGGAGCCAACGAAAGCCGCCGCGCCCTGGCCCTGGAACTGGGTGCATCCCACGTG
TTTGATCCGTTCAACACCGAAGATCTGGTTGCCAGCATTCGCGAAGTCGTGCCTGCGGGTGCGAACCATGCAC
TGGACACGACCGGTCTGCCGAAAGTGATCGCGAGCGCGGATTGATTGTATTATGAGCGGTGGCAAACTGGGTT
TGCTGGGTATGGCGAGCCCGGAAGCGAATGTGCCGGCTACCCTGTTGGATTTGCTGAGCAAAAATGTCACGC
TGAAGCCGATCACCGAGGGCGATGCGAACCCACAAGAGTTCATCCCGCGTATGCTGGCACTCTACCGTGAGG
GTAAGTTCCCGTTTGAGAAACTGATCACGACCTTTCCGTTTGAGCACATTAATGAAGCAATGGAAGCCACTGA
GTCCGGTAAGGCCATTAAACCGGTTCTGACGCTGTAA CymB, amino acid sequence-SEQ ID NO: 42
MTINSIQPIQAKAAVLRAVGSPFNIEPIRISPPKGDEVLVRIVGVGVCHTDVVCRDSFPVPLPIILGHEGSGVIEAIGD
QVTSLKPGDHVVLSFNSCGHCYNCGHAEPASCLQMLPLNFGGAERAADGTIQDDKGEAVRGMFFGQSSFGTYAI
ARAVNAVKVDDDLPLPLLGPLGCGIQTGAGAAMNSLSLQSGQSFIVFGGGAVGLSAVMAAKALGVSPLIVVEPNE
SRRALALELGASHVFDPFNTEDLVASIREVVPAGANHALDTTGLPKVIASAIDCIMSGGKLGLLGMASPEANVPATL
LDLLSKNVTLKPITEGDANPQEFIPRMLALYREGKFPPFEKLITTFPFEHINEAMEATESGKAIKPVLTL
```

AspWeADH1, optimized cDNA-SEQ ID NO: 43
ATGGGTAGCATTACTGAAGATATCCCAACCATGCGCGCTGCTACTGTTGTTGAGTACAATAAGCCGCTTCAAA
TCCTGAATATCCCTATTCCGACCCCGTCCCAGGATCAGATTCTGGTCAAGGTCACCGCATGCAGCCTGTGCAAC
AGCGACCTGGCGGGCTGGCTGGGTGTTGTTGGTGCGGTTGCGCCGTATTGTCCGGGCCATGAACCGGTGGGT
GTAATTGAGAGCGTCGGTAGCGCCGTTCGCGGTTTCAAGAAAGGCGACCGTGCCGGTTTCATGCCGAGCTCC
TTTACGTGTAAAGACTGCAATGAATGTCAAACCGGTAATCATCGTTTTTGTAATAAGAAAACCAGCGTGGGTT
TCCAGGGTCCGTATGGCGGCTTCAGCCAATATGCCGTTGCTGACCCGTTGAGCACGGTTAAGATCCCGGACGC
GCTGTCTGATGAAGTCACGGCGCCGCTGTTGTGCGCGGGTGTGACGGCGTATGGCGCACTGCGCAAGGTCCC
GCCAGGCGTGCAGAGCGTGAACGTTATCGGTTGCGGTGGCGTTGGCCACCTGGTGATCCAATATGCGAAGGC
TCTGGGTTACTACGTCGTGGCTTTGACGTTAACGACAAGAAACTGGGCCTGGCAGCGCGTAGCGGTGCGGA
TGAAACCTTTTACAGCACCGATGCCACCCATGCGGACCAGGCATCTGCAACGATCGTCGCGACCGGCGCGGTT
GCAGCGTACAAAGCCGCATTCGCAGTCACCGCCAACCACGGTCGTATCATTGCGATCGGTGTCCCGAAGGGT
GAGATTCCGGTGTCGCTGCTGGACATGGTCAAACGTGATCTGAGCTTAGTGGCGACGAACCAAGGCTCCAAA
GAAGAATTGGAAGAGGCTCTGGAAATTGCAGTGCAACACCAGATCGCACCGGAGTACGAAATTCGCCAGCTG
GACCAGCTGAACGATGGCTTTCAAGAGATGATGAAAGGTGAGAGCCACGGTCGTCTGGTGTACCGTCTGTGG
TAA AspWeADH1, amino acid sequence-SEQ ID NO: 44
MGSITEDIPTMRAATVVEYNKPLQILNIPIPTPSQDQILVKVTACSLCNSDLAGWLGVVGAVAPYCPGHEPVGVIES
VGSAVRGFKKGDRAGFMPSSFTCKDCNECQTGNHRFCNKKTSVGFQGPYGGFSQYAVADPLSTVKIPDALSDEVT
APLLCAGVTAYGALRKVPPGVQSVNVIGCGGVGHLVIQYAKALGYYVRGFDVNDKKLGLAARSGADETFYSTDAT
HADQASATIVATGAVAAYKAAFAVTANHGRIIAIGVPKGEIPVSLLDMVKRDLSLVATNQGSKEELEEALEIAVQHQ
IAPEYEIRQLDQLNDGFQEMMKGESHGRLVYRLW PsAerADH1, opimized cDNA-SEQ ID NO: 45
ATGAACTCGATCCAACCTACTCAAGCAAAAGCAGCAGTCTTGCGCGCAGTCGGCGGCCCGTTCTCTATTGAGC
CGATCCGCATCAGCCCACCGAAGGGTGACGAAGTGCTGGTTCGTATCGTTGGTGTGGGTGTCTGCCACACCG
ACGTCGTCTGTCGTGATAGCTTTCCGGTGCCGTTGCCGATCATTCTGGGTCACGAGGGCTCCGGTGTGATTGA
AGCTGTGGGTGACCAAGTGACCGGTCTGAAACCGGGTGACCACGTTGTGCTGTCCTTCAATAGCTGCGGCCAT
TGCTACAACTGTGGTCATGACGAGCCTGCGTCTTGTCTGCAGATGCTGCCGTTGAATTTCGGTGGCGCGGAGC
GTGCGGCGGACGGCACCATCGAAGATGACCAGGGCGCAGCTGTTCGTGGCCTGTTCTTCGGCCAAAGCTCCT
TTGGTAGCTACGCGATTGCACGTGCGGTTAACACTGTCAAAGTTGATGACGATCTGCCGTTGGCGCTGCTGGG
TCCGCTGGGTTGCGGTATTCAGACCGGCGCGGGTGCAGCCATGAATAGCCTGGGTTTACAGGGTGGCCAGAG
CTTCATTGTGTTTGGCGGCGGCGCCGTCGGTCTGAGCGCGGTCATGGCCGCCAAGGCCCTGGGTGTTAGCCC
GCTGATTGTTGGAGCCGAACGAAGCTCGCCGTGCGCTGGCACTGGAATTGGGTGCGAGCCACGCGTTTGA
CCCCATTTAACACCGAAGATCTGGTCGCGAGCATTCGCGAAGTCGTTCCGGCTGGCGCAAACCACGCGCTGGAC
ACGACGGGTCTGCCGAAAGTTATTGCCAACGCGATCGATTGCATCATGAGCGGCGGCAAACTGGGTCTGCTC
GGTATGGCGAATCCGGAAGCGAATGTGCCGGCGACCCTGCTGGATCTGCTGAGCAAAAATGTGACGCTGAA
GCCGATCACCGAGGGTGACGCAAACCCACAAGAATTTATTCCGCGTATGCTGGCTCTGTATCGTGAGGGTAA
GTTTCCGTTCGATAAGCTGATCACCACGTTCCCGTTCGAGCATATCAACGAAGCAATGGAAGCTACCGAGAGC
GGTAAGGCCATTAAACCGGTTCTGACCCTGTAA PsAerADH1, amino acid sequence-SEQ ID NO: 46
MNSIQPTQAKAAVLRAVGGPFSIEPIRISPPKGDEVLVRIVGVGVCHTDVVCRDSFPVPLPIILGHEGSGVIEAVGDQ
VTGLKPGDHVVLSFNSCGHCYNCGHDEPASCLQMLPLNFGGAERAADGTIEDDQGAAVRGLFFGQSSFGSYAIAR
AVNTVKVDDDLPLALLGPLGCGIQTGAGAAMNSLGLQGGQSFIVFGGGAVGLSAVMAAKALGVSPLIVVEPNEA
RRALALELGASHAFDPFNTEDLVASIREVVPAGANHALDTTGLPKVIANAIDCIMSGGKLGLLGMANPEANVPATL
LDLLSKNVTLKPITEGDANPQEFIPRMLALYREGKFPFDKLITTFPFEHINEAMEATESGKAIKPVLTL AzTolADH1, optimized cDNA-SEQ ID NO: 47
ATGGGTTCTATTCAAGATTCTCTGTTCATCCGTGCACGCGCCGCTGTTCTGCGTACTGTCGGTGGCCCGCTGGA
AATTGAAAACGTCCGCATTAGCCCTCCGAAGGGTGACGAAGTGCTCGTGCGTATGGTTGGTGTTGGTGTGTG
CCATACCGACGTTGTGTGTCGCGATGGCTTCCCGGTTCCGCTGCCGATTGTGCTGGGTCACGAGGGCAGCGGT
ATTGTCGAGGCAGTGGGCGAGCGTGTGACCAAGGTTAAACCGGGTCAGCGTGTCGTTTTATCCTTCAATAGCT
GTGGTCATTGCGCGTCCTGCTGCGAGGACCACCCGGCCACCTGTCACCAGATGCTGCCACTGAACTTTGGTGC
GGCGCAGCGCGTGGATGGTGGCACCGTTATCGACGCGAGCGGCGAGGCAGTGCAGAGCCTGTTTTTTGGTC
AAAGCTCTTTCGGTACGTATGCATTGGCGCGTGAAGTCAATACCGTACCGGTGCCGGATGCAGTTCCGTTGGA
AATCCTGGGCCCGTTGGGTTGCGGCATCCAGACGGGTGCGGGTGCGGCTATCAACAGCCTGGCGCTGAAACC
TGGTCAATCGCTGGCAATCTTCGGTGGCGGCAGCGTCGGTCTGTCCGCCCTGCTGGGCGCGCTGGCCGTGGG
CGCGGGCCCGGTCGTTGTCATTGAGCCGAACGAACGTCGTCGTGCGTTGGCGCTGGACCTGGGTGCGAGCCA
TGCATTTGATCCGTTCAACACTGAAGATTTGGTTGCGAGCATCAAAGCCGCTACGGGTGGCGGCGTTACCCAC
AGCCTGGACAGCACGGGTCTGCCGCCGGTCATCGCGAATGCAATCAACTGTACCTTGCCGGGCGGCACGGTC
GGTCTGCTGGGCGTCCCGAGCCCAGAGGCTGCCGTTCCGGTGACGCTGCTGGATCTGCTGGTTAAATCAGTTA
CCCTGCGTCCGATTACCGAGGGTGACGCAATCCGCAAGAATTTATTCCGCGTATGGTCCAGCTGTACCGCGA
CGGTAAATTTCCGTTTGATAAGCTGATTACGACCTACCGCTTCGACGACATCAATCAAGCGTTCAAGGCAACC
GAAACCGGTGAAGCGATTAAGCCAGTGCTGGTGTTTTAA AzTolADH1, amino acid sequence-SEQ ID NO: 48
MGSIQDSLFIRARAAVLRTVGGPLEIENVRISPPKGDEVLVRMVGVGVCHTDVVCRDGFPVPLPIVLGHEGSGIVEA
VGERVTKVKPGQRVVLSFNSCGHCASCCEDHPATCHQMLPLNFGAAQRVDGGTVIDASGEAVQSLFFGQSSFGT
YALAREVNTVPVPDAVPLEILGPLGCGIQTGAGAAINSLALKPGQSLAIFGGGSVGLSALLGALAVGAPVVVIEPNE
RRRALALDLGASHAFDPFNTEDLVASIKAATGGGVTHSLDSTGLPPVIANAINCTLPGGTVGLLGVPSPEAAVPVTLL
DLLVKSVTLRPITEGDANPQEFIPRMVQLYRDGKFPFDKLITTYRFDDINQAFKATETGEAIKPVLVF AroAroADH1, optimized cDNA-SEQ ID NO: 49
ATGGGCTCAATTCAAGATTCTCTGTTCATCCCGGCTAGAGCGGCAGTGTTGCGTGCGGTCGGTGGCCCACTGG
AAATCGAAGATGTTCGTATCAGCCCGCCTAAGGGCGACGAAGTTCTGGTCCGTATGGTTGCGTGGGCGTTT
GCCACACCGACGTTGTGTGCCGCGATGGTTTCCCGGTCCCGCTGCCGATTGTCTTGGGTCACGAGGGTGCGG -continued

```
GTATCGTGGAAGCTGTGGGTGAGCGTGTGACCAAGGTCAAACCTGGCCAGCGTGTGGTGCTGAGCTTCAACA
GCTGCGGTCACTGCAGCTCCTGTGGTGAGGATCACCCGGCGACGTGTCATCAGATGCTGCCGCTGAATTTTGG
TGCAGCGCAACGTGTTGACGGTGGCTGTGTCACCGATGCGAGCGGTGAAGCTGTACATAGCCTGTTTTTCGGT
CAGAGCTCTTTTTGCACCTTTGCACTGGCGCGCGAAGTGAACACCGTTCCTGTCGGTGACGGCGTTCCGCTGG
AAATTCTGGGTCCGCTGGGTTGTGGTATTCAAACCGGTGCAGGCGCAGCGATCAACAGCCTGGCCATTAAACC
GGGTCAGAGCCTGGCGATTTTCGGTGGCGGCAGCGTTGGTCTGTCCGCCCTGCTGGGCGCACTGGCCGTGGG
CGCGGGTCCGGTTGTTGTGGTGGAGCCGAATGATCGTCGTCGTGCACTGGCCCTGGACCTGGGTGCGTCGCA
TGTGTTTGACCCGTTCAATACCGAAGATCTGGTTGCGAGCATTAAAGCCGCGACGGGTGGCGGCGTTACTCAC
AGCCTGGACAGCACTGGCTTGCCGCCGGTGATCGCAAAGGCCATTGATTGTACGTTGCCGGGTGGCACCGTC
GGTTTACTGGGTGTTCCGGCTCCGGACGCCGCAGTGCCGGTCACGCTGCTGGACTTGCTGGTGAAGTCCGTTA
CCCTGCGCCCGATCACCGAGGGTGACGCAAACCCGCAAGAATTTATTCCACGCATGGTTCAGCTCTACCGTGA
TGGTAAGTTCCCATTTGATAAACTGATCACCACGTATCGTTTTGAGAACATCAATGACGCGTTCAAAGCGACG
GAAACGGGTGAAGCGATCAAACCGGTCCTGGTTTTCTAA

AroAroADH1, amino acid sequence-SEQ ID NO: 50
MGSIQDSLFIPARAAVLRAVGGPLEIEDVRISPPKGDEVLVRMVGVGVCHTDVVCRDGFPVPLPIVLGHEGAGIVE
AVGERVTKVKPGQRVVLSFNSCGHCSSCGEDHPATCHQMLPLNFGAAQRVDGGCVTDASGEAVHSLFFGQSSFC
TFALAREVNTVPVGDGVPLEILGPLGCGIQTGAGAAINSLAIKPGQSLAIFGGGSVGLSALLGALAVGAGPVVVEP
NDRRRALALDLGASHVFDPFNTEDLVASIKAATGGGVTHSLDSTGLPPVIAKAIDCTLPGGTVGLLGVPAPDAAVPV
TLLDLLVKSVTLRPITEGDANPQEFIPRMVQLYRDGKFPFDKLITTYRFENINDAFKATETGEAIKPVLVF ThTerpADH1, optimized cDNA-SEQ ID NO: 51
ATGTGTAGCAATCATGATTTCACCGCAGCCCGTGCAGCAGTCTTACGTAAAGTTGGTGGCCCGTTGGAAATCG
AAGATGTCCGTATTTCTGCCCCGAAAGGCGACGAAGTCCTGGTGCGTATGGTTGGCGTGGGTGTGTGTCATA
CCGACCTCGTCTGCCGTGATGCGTTCCCGGTGCCGCTGCCTATTGTTCTGGGTCACGAGGGTGCAGGCATCGT
TGAAGCCGTGGGTGAGGGCGTGCGCTCCCTGGAGCCGGGTGACCGTGTTGTGCTGAGCTTCAATAGCTGCGG
CCGCTGTGGCAACTGCGGTAGCGGTCACCCGAGCAACTGCCTGCAAATGCTGCCGCTGAATTTTGGTGGCGC
GCAACGCGTTGACGGTGGCCGCATGTTGGACGCGGCGGGTAACGCTGTCCAGGGTCTGTTTTTTGGTCAATCT
AGCTTCGGCACGTATGCGATCGCGCGTGAGATTAACGCCGTGAAAGTCGCCGAAGATCTGCCGCTGGAAATC
CTGGGTCCGCTGGGTTGCGGTATTCAGACCGGTGCGGGTGCAGCGATTAACAGCCTGGGTATTGGTCCGGGT
CAGTCCTTGGCTGTGTTCGGTGGCGGCGGCGTGGGTCTTAGCGCGTTGCTGGGCGCTCGTGCTGTGGGTGCC
GCCCAAGTTGTTGTTGAGCCGAACGCCGCACGTCGCGCGCTGGCGCTGGAACTGGGTGCGAGCCATGCA
TTCGACCCGTTTGCGGGTGACGACCTGGTCGCGGCGATCCGCGCAGCGACGGGTGGCGGCGCAACCCACGC
GCTGGATACGACCGGCCTGCCGTCGGTGATTGGCAATGCAATCGATTGTACTTTGCCGGGTGGCACGGTTGG
TATGGTCGGCATGCCAGCGCCTGACGCTGCGGTCCCGGCGACCCTGCTGGATTTGCTGACTAAGAGCGTCAC
GCTGCGTCCGATCACCGAGGGTGACGCAGATCCGCAGGCCTTCATCCCACAGATGCTGCGCTTTTACCGTGAG
GGTAAGTTCCCGTTTGACCGTCTGATTACCCGTTACCGTTTTGATCAGATCAATGAAGCTCTGCACGCAACCGA
AAAGGGTGGCGCGATTAAACCGGTTCTGGTGTTCTAA ThTerpADH1, amino acid sequence-SEQ ID NO: 52
MCSNHDFTAARAAVLRKVGGPLEIEDVRISAPKGDEVLVRMVGVGVCHTDLVCRDAFPVPLPIVLGHEGAGIVEA
VGEGVRSLEPGDRVVLSFNSCGRCGNCGSGHPSNCLQMLPLNFGGAQRVDGGRMLDAAGNAVQGLFFGQSSF
GTYAIAREINAVKVAEDLPLEILGPLGCGIQTGAGAAINSLGIGPGQSLAVFGGGGVGLSALLGARAVGAAQVVVVE
PNAARRALALELGASHAFDPFAGDDLVAAIRAATGGGATHALDTTGLPSVIGNAIDCTLPGGTVGMVGMPAPDA
AVPATLLDLLTKSVTLRPITEGDADPQAFIPQMLRFYREGKFPFDRLITRYRFDQINEALHATEKGGAIKPVLVF CdGeoA optimized cDNA-SEQ ID NO: 53
ATGAACGATACGCAGGATTTTATTAGCGCCCAAGCCGCAGTGTTACGTCAGGTCGGTGGCCCGCTGGCCGTTG
AGCCTGTTCGTATCAGCATGCCGAAGGGTGACGAAGTCCTGATTCGTATCGCGGGTGTTGGTGTGTGCCACAC
CGACTTGGTGTGCCGTGATGGCTTCCCGGTGCCGCTGCCAATTGTGCTGGGTCACGAGGGTAGCGGTACTGT
CGAAGCCGTCGGTGAACAAGTCCGTACCCTGAAACCGGGCGATCGCGTCGTGCTGAGCTTTAACAGCTGCGG
TCATTGCGGTAACTGTCACGACGGTCACCCGAGCAATTGCCTGCAGATGCTGCCGCTGAACTTCGGTGGCGCG
CAACGCGTGGACGGTGGCCAAGTTTTGGACGGTGCGGGTCATCCGGTTCAGTCCATGTTTTTCGGCCAGTCCA
GCTTTGGCACCCACGCAGTAGCGCGCGAGATCAACGCAGTCAAGGTCGGCGATGATCTGCCACTGGAACTGC
TGGGTCCGTTGGGTTGTGGCATTCAAACCGGTGCGGGTGCAGCTATCAATTCTCTGGGCATTGGTCCGGGTCA
GTCTCTGGCTATCTTCGGCGGCGGCGGCGTGGGTCTGAGCGCACTGCTGGGCGCCCGTGCGGTGGGTGCCGA
CCGTGTTGTTGTCATTGAGCCGAATGCAGCGCGCCGTGCGCTGGCATTGAACTGGGTGCCAGCCACGCACT
GGACCCGCATGCCGAGGGCGACCTTGTTGCGGCGATTAAAGCTGCGACGGGTGGCGGCGCTACGCATAGCTT
GGATACGACCGGCCTGCCGCCAGTCATTGGCTCCGCGATCGCGTGTACTCTGCCGGGTGGCACCGTTGGTAT
GGTTGGTCTGCCGGCGCCGGACGCACCGGTCCCTGCGACGCTGTTGGATCTGCTGAGCAAATCGGTTACCCT
GCGTCCGATTACCGAGGGTGACGCTGACCCGCAACGCTTCATCCCGCGTATGCTGGATTTCCATCGTGCGGGC
AAGTTTCCGTTCGACCGCCTGATCACCCGTTACCGCTTTGATCAGATCAATGAAGCGCTGCACGCGACCGAGA
AAGGTGAAGCAATCAAACCGGTTCTGGTGTTTTAA CdGeoA, amino acid sequence-SEQ ID NO: 54
MNDTQDFISAQAAVLRQVGGPLAVEPVRISMPKGDEVLIRIAGVGVCHTDLVCRDGFPVPLPIVLGHEGSGTVEAV
GEQVRTLKPGDRVVLSFNSCGHCGNCHDGHPSNCLQMLPLNFGGAQRVDGGQVLDGAGHPVQSMFFGQSFG
THAVAREINAVKVGDDLPLELLGPLGCGIQTGAGAAINSLGIGPGQSLAIFGGGGVGLSALLGARAVGADRVVVIEP
NAARRALALELGASHALDPHAEGDLVAAIKAATGGGATHSLDTTGLPPVIGSAIACTLPGGTVGMVGLPAPDAPVP
ATLLDLLSKSVTLRPITEGDADPQRFIPRMLDFHRAGKFPFDRLITRYRFDQINEALHATEKGEAIKPVLVF VoADH1, optimized cDNA-SEQ ID NO: 55
ATGACTAAATCCAGCGGTGAAGTGATTTCTTGTAAGGCAGCAGTGATCTATAAGAGCGGTGAGCCTGCTAAA
GTTGAAGAAATTCGTGTTGATCCGCCTAAGAGCAGCGAAGTTCGTATTAAGATGCTGTACGCCTCCTTGTGTC
ACACGGACATTCTGTGTTGCAACGGCCTGCCGGTGCCGCTGTTTCCGCGCATTCCGGGTCACGAGGGCGTGG
GTGTTGTGGAGAGCGCGGGTGAAGATGTGAAAGATGTTAAAGAGGGCGACATCGTTATGCCACTGTACCTG
GGCGAGTGTGGTGAGTGCCTCAATTGCAGCAGCGGTAAGACGAATCTGTGCCACAAGTACCCACTGGACTTC
TCTGGTGTGCTGCCGAGCGACGGTACGAGCCGCATGTCAGTAGCAAAATCCGGTGAGAAATTTCCATCACT
TCAGCTGTAGCACCTGGTCCGAATATGTTGTCATCGAGAGCTCGTATGTCGTCAAAGTTGATAGCCGTCTGCC
```

```
GCTGCCGCATGCGTCCTTTCTGGCATGCGGCTTCACCACGGGTTACGGCGCGGCGTGGAAAGAGGCTGACAT
TCCGAAGGGCAGCACCGTCGCGGTGCTGGGCCTGGGTGCGGTCGGTCTGGGTGTGGTTGCTGGTGCGCGTTC
TCAGGGTGCGAGCCGCATTATTGGCGTGGACATCAACGACAAGAAAAAGCAAAAGCCGAGATCTTTGGTGT
TACTGAGTTTCTGAATCCGAAGCAACTGGGTAAAAGCGCGAGCGAAAGCATCAAAGACGTCACCGGCGGCCT
GGGCGTTGACTACTGTTTCGAGTGCACCGGTGTCCCGGCCCTGCCAAACGAAGCCGTGGATGCGAGCAAGAT
CGGCTTGGGTACGATCGTCATGATTGGTGCGGGTATGGAAACCAGCGGTGTTATTAACTATATCCCGCTGCTG
TGCGGCCGTAAACTGATCGGTAGCATTTACGGTGGCGTTCGCATCCGTAGCGACTTACCGCTGATCATTGAGA
AATGCATCAACAAAGAAATTCCGCTGAACGAACTGCAGACCCACGAAGTGAGCTTGGAAGGCATTAATGATG
CATTCGGCATGCTGAAGCAACCGGACTGCGTTAAGATCGTCATCAAGTTCGAGCAGAAATAA

VoADH1, amino acid sequence-SEQ ID NO: 56
MTKSSGEVISCKAAVIYKSGEPAKVEEIRVDPPKSSEVRIKMLYASLCHTDILCCNGLPVPLFPRIPGHEGVGVVESAG
EDVKDVKEGDIVMPLYLGECGECLNCSSGKTNLCHKYPLDFSGVLPSDGTSRMSVAKSGEKIFHHFSCSTWSEYVVI
ESSYVVKVDSRLPLPHASFLACGFTTGYGAAWKEADIPKGSTVAVLGLGAVGLGVVAGARSQGASRIIGVDINDKKK
AKAEIFGVTEFLNPKQLGKSASESIKDVTGGLGVDYCFECTGVPALLNEAVDASKIGLGTIVMIGAGMETSGVINYIP
LLCGRKLIGSIYGGVRIRSDLPLIIEKCINKEIPLNELQTHEVSLEGINDAFGMLKQPDCVKIVIKFEQK Active site signature motif-SEQ ID NO: 57
HCxxGxxR
wherein
each x independently of each other represents any natural amino acid residue.

Active site signature motif-SEQ ID NO: 58
HC(T/S)xGKDRTG
wherein
x represents any natural amino acid residue.

PvCPS, Multifunctional protein having prenyl-transferase and copalyl-diphosphate synthase,
codon optimized cDNA-SEQ ID NO: 59
ATGAGCCCTATGGATTTGCAAGAAAGCGCCGCAGCCCTGGTCCGTCAATTGGGTGAACGCGTTGAGGATCGC
CGCGGTTTTGGTTTCATGAGCCCGGCCATTTATGACACGGCCTGGGTTAGCATGATTAGCAAGACCATCGACG
ACCAAAAAACTTGGCTGTTTGCGGAGTGCTTCCAGTACATTCTGTCTCACCAACTGGAAGATGGTGGCTGGGC
GATGTACGCATCCGAAATCGATGCCATCTTGAATACTTCCGCGTCACTGCTGTCCCTGAAACGCCACCTGTCCA
ACCCTTACCAGATCACCAGCATCACTCAGGAAGATCTGAGCGCTCGGCCATCAACCGCGCTCAAAACGCCCTGCA
GAAATTGCTGAACGAGTGGAACGTTGACTCCACGCTGCACGTCGGTTTCGAGATTCTTGGTTCCGGCGCTGCTG
CGCTATCTGGAAGATGAAGGCATCGCGTTTGCGTTCTCGGGTCGTGAGCGTTTGTTAGAGATTGAGAAACAA
AAAACTGTCCAAGTTTAAAGCGCAGTATTTGTACTTACCGATTAAGGTCACCGCACTGCATAGCCTGGAAGCCTT
CATCGGCGGTTATTGAGTTCGACAAAGTCAGCCATCACAAAGTATCCGGTGCTTTCATGGCGTCGCCGTCTAGC
ACCGCAGCATACATGATGCATGCGACGCAATGGGATGACGAATGTGAGGATTACTTGCGTCACGTGATCGCG
CATGCGTCAGGTAAGGGTTCTGGCGGCGTGCCGAGCGCCTTTCCGAGCACCATCTTCGAGAGCGTTTGGCCG
CTGTCTACTCTGCTGAAAGTTGGCTATGATCTGAATAGCGCTCCGTTCATCGAGAAAATTCGTAGCTACTTGCA
CGATGCCTATATCGCAGAGAAAGGTATTCTCGGTTTTCACCCCGTTCGTTGGCGCTGCGACGCGGACGACACCGCT
ACCACGATTCTGGTGTTGAATCTGCTGAACCAACCGGTGAGCGTGGACGCGATGTTGAAAGAATTTGAAGAG
GAACATCACTTCAAGACCTACAGCCAAGAGCGTAATCCGAGCTTTTCCGCAAACTGTAATGTTCTGCTGGCGCT
GCTGTACAGCCAGGAACCGAGCCTGTACAGCGCGCAAATCGAAAAAGCGATCCGTTTTCTGTATAAGCAATTC
ACCGACTCTGAGATGGATGTGCGCGATAAATGGAACCTGTCCCCGTATTATAGCTGGATGCTGATGACCCAGG
CCATCACCCGTCTGACGACCCTGCAAAAGACCAGCAAGCTGCAGCTGCTGGATGACAGCATTAGCAAGG
GCCTGATTTCTCTGCTGTTCCGCATTGCATCCACCGTGGTTAAAGATCAAAACCGGGTGGCAGCTGGGGCAC
GCGTGCGAGCAAGAAGAAACGGCATACGCCGTGCTGATTCTGACCTACGCGTTTTATCTGGACGAGGTGAC
CGAGTCTCTGCGCCACGATATCAAAATTGCAATCGAGAATGGTTGCTCGTTCCTGAGCGAGCGCACCATGCAA
AGCAGCAGCGAGTGGCTGTGGGTCGAAAAGGTTACCTACAAGAGCGAAGTGCTGAGCGAAGCATACATCCT
GGCAGCTCTGAAACGTGCGGCAGACTTGCCGGATGAGAACGCTGAGGCAGCCCCAGTGATCAACGGTATCTC
TACCAATGGCTTTGAGCACACCGACCGCATTAATGGTAAACTCAAGGTCAATGGTACGAATGGCACCAACGGT
TCCCACGAAACGAACGGTATCAATGGCACCCATGAGATTGAGCAAATTAATGGTGTCAACGGCACGAATGGC
CATAGCGACGTGCCACATGACACGAATGGTTGGGTCGAGGAACCGACGCGATTAATGAAACGAACGGTCA
CTACGTTAACGGCACCAACCATGAGACTCCGCTGACCAATGGTATTAGCAATGGTGACTCCGTGAGCGTTCAC
ACCGACCATAGCGACAGCTACTATCAGCGTAGCGACTGGACCGCGGATGAAGAACAGATCCTGCTGGGTCCA
TTCGATTACCTGGAATCCCTGCCTGGTAAAAATATGCGCAGCCAGCTGATCCAGTCTTTCAATACGTGGCTGAA
GGTCCCGACCGAGAGCTTGGACGTGATTATTAAGGTCATTAGCATGCTGCACACTGCTAGCCTGCTGCTGAC
GATATTCAGGACCAAAGCATCCTGCGTCGTGGTCAGCCTGTGGCGCACTCGATCTTCGGCACCGCGCAAGCGA
TGAACTCTGGTAACTATGTTTACTTCCTGGCATTGCGTGAAGTTCAGAAATTGCAAAACCCGAAGGCTATCAGC
ATTTATGTGGACAGCTTGATCGATCTTCATCGCGGCCAGGGCATGGAACTGTTCTGGCGTGATTCTCTGATGT
GCCCGACTGAAGAACAGTATCTGGACATGGTGGCGAACAAGACCGGTGGCCTGTGTTTGTCTGGCGATTCAGC
TGATGCAGGCAGAAGCGACCATTCAGGTTGATTTTATTCCGCTGGTGCGTCTGCTGGGTATCATTTTCCAGATT
TGCGACGACTACCTGAACTTGAAAAGCACTGCGTATACCGACAACAAAGGTCTGTGAAGATCTTACCGAG
GGTAAATTCTCCTTCCCGATCATTCACAGCATCCGTAGCAATCCGGGCAATCGTCAGCTGATCAATATTCTGAA
GCAAAAACCGCGCGAAGATGACATCAAGCGTTACGCACTGTCCTATATGGAGAGCACGAATAGCTTCGAGTA
CACCCGTGGCGTCGTCCGTAAATTGAAAACCGAAGCAATTGACACGATTCAAGGTCTGGAGAAGCATGGCCT
GGAAGAAAACATTGGTATTCGTAAGATTCTGGCGCGTATGAGCCTGGAACTGTAA PvCPS, Multifunctional protein having prenyl-transferase and copalyl-diphosphate synthase,
amino acid sequence-SEQ ID NO: 60
MSPMDLQESAAALVRQLGERVEDRRGFGFMSPAIYDTAWVSMISKTIDDQKTWLFAECFQYILSHQLEDGGWA
MYASEIDAILNTSASLLSLKRHLSNPYQITSITQEDLSARINRAQNALQKLLNEWNVDSTLHVGFEILVPALLRYLEDE
GIAFAFSGRERLLEIEKQKLSKFKAQYLYLPIKVTALHSLEAFIGAIEFDKVSHHKVSGAFMASPSSTAAYMMHATQW
DDECEDYLRHVIAHASGKGSGGVPSAFPSTIFESVWPLSTLLKVGYDLNSAPFIEKIRSYLHDAYIAEKGILGFTPFVGA
DADDTATTILVLNLLNQPVSVDAMLKEFEEEHHFKTYSQERNPSFSANCNVLLALLYSQEPSLYSAQIEKAIRFLYKQF
TDSEMDVRDKWNLSPYYSWMLMTQAITRLTTLQKTSKLSTLRDDSISKGLISLLFRIASTVVKDQKPGGSWGTRAS
KEETAYAVLILTYAFYLDEVTESLRHDIKIAIENGCSFLSERTMQSDSEWLWVEKVTYKSEVLSEAYILAALKRAADLPD
```

ENAEAAPVINGISTNGFEHTDRINGKLKVNGTNGTNGSHETNGINGTHEIEQINGVNGTNGHSDVPHDTNGWVE
EPTAINETNGHYVNGTNHETPLTNGISNGDSVSVHTDHSDSYYQRSDWTADEEQILLGPFDYLESLPGKNMRSQLI
QSFNTWLKVPTESLDVIIKVISMLHTASLLIDDIQDQSILRRGQPVAHSIFGTAQAMNSGNYVYFLALREVQKLQNP
KAISIYVDSLIDLHRGQGMELFWRDSLMCPTEEQYLDMVANKTGGLFCLAIQLMQAEATIQVDFIPLVRLLGIIFQIC
DDYLNLKSTAYTDNKGLCEDLTEGKFSFPIIHSIRSNPGNRQLINILKQKPREDDIKRYALSYMESTNSFEYTRGVVRKL
KTEAIDTIQGLEKHGLEENIGIRKILARMSLEL

Ribosome binding site-SEQ ID NO: 61
AAGGAGGTAAAAAA

CrtE, GGPP synthase from *Pantoea agglomerans*, codon optimized for expression in *S. cerevisiae*-SEQ ID NO: 62
ATGGTTTCTGGTTCTAAGGCTGGTGTTTCTCCACACAGAGAAATCGAAGTTATGAGACAATCTATCGACGACC
ACTTGGCTGGTTTGTTGCCAGAAACTGACTCTCAAGACATCGTTTCTTTGGCTATGAGAGAAGGTGTTATGGCT
CCAGGTAAGAGAATCAGACCATTGTTGATGTTGTTGGCTGCTAGAGACTTGAGATACCAAGGTTCTATGCCAA
CTTTGTTGGACTTGGCTTGTGCTGTTGAATTGACTCACACTGCTTCTTTGATGTTGGACGACATGCCATGTATG
GACAACGCTGAATTGAGAGAGGTCAACCAACTACTCACAAGAAGTTCGGTGAATCTGTTGCTATCTTGGCTT
CTGTTGGTTTGTTGTCTAAGGCTTTCGGTTTGATCGCTGCTACTGGTGACTTGCCAGGTGAAAGAAGAGCTCA
AGCTGTTAACGAATTGTCTACTGCTGTTGGTGTTCAAGGTTTGGTTTTGGGTCAATTCAGAGACTTGAACGAC
GCTGCTTTGGACAGAACTCCAGACGCTATCTTGTCTACTAACCACTTGAAGACTGGTATCTTGTTCTCTGCTAT
GTTGCAAATCGTTGCTATCGCTTCTGCTTCTTCTCCATCTACTAGAGAAACTTTGCACGCTTTCGCTTTGGACTT
CGGTCAAGCTTTCCAATTGTTGGACGACTTGAGAGACGACCACCCAGAACATGGTAAGGACAGAAACAAGGA
CGCTGGTAAGTCTACTTTGGTTAACAGATTGGGTGCTGACGCTGCTAGACAAAAGTTGAGAGAACACATCGAC
TCTGCTGACAAGCACTTGACTTTCGCTTGTCCACAAGGTGGTGCTATCAGACAATTCATGCACTTGTGGTTCGG
TCACCACTTGGCTGACTGGTCTCCAGTTATGAAGATCGCTTAA SmCPS2, copalyl-pyrophosphate synthase from *Salvia miltiorrhiza*, codon optimized for expression in *S. cerevisiae*-SEQ ID NO: 63
ATGGCTACTGTTGACGCTCCACAAGTTCACGACCACGACGGTACTACTGTTCACCAAGGTCACGACGCTGTTA
AGAACATCGAAGACCCAATCGAATACATCAGAACTTTGTTGAGAACTACTGGTGACGGTAGAATCTCTGTTTC
TCCATACGACACTGCTTGGGTTGCTATGATCAAGGACGTTGAAGGTAGAGACGGTCCACAATTCCCATCTTCTT
TGGAATGGATCGTTCAAAACCAATTGGAAGACGGTTCTTGGGGTGACCAAAAGTTGTTCTGTGTTTACGACAG
ATTGGTTAACACTATCGCTTGTGTTGTTGCTTTGAGATCTTGGAACGTTCACGCTCACAAGGTTAAGAGAGGT
GTTACTTACATCAAGGAAAACGTTGACAAGTTGATGGAAGGTAACGAAGAACACATGTGTGGTTTCGAA
GTTGTTTTCCCAGCTTTGTTGCAAAAGGCTAAGTCTTTGGGTATCGAAGACTTGCCATACGACTCTCCAGCTGT
TCAAGAAGTTTACCACGTTAGAGAACAAAAGTTGAAGAGAATCCCATTGGAAATCATGCACAAGATCCCAACT
TCTTTGTTGTTCTCTTTGGAAGGTTTGGAAAACTTGGACTGGGACAAGTTGTTGAAGTTGCAATCTGCTGACG
GTTCTTTCTTGACTTCTCCATCTTCTACTGCTTTCGCTTTCATGCAAACTAAGGACGAAAAGTTGTTACCAATTCAT
CAAGAACACTATCGACACTTTCAACGGTGGTGCTCCACACACTTACCCAGTTGACGTTTTCGGTAGATTGTGGG
CTATCGACAGATTGCAAAGATTGGGTATCTCTAGATTCTTCGAACCAGAAATCGCTGACTGTTTGTCTCACATC
CACAAGTTCTGGACTGACAAGGGTGTTTTCTCTGGTAGAGAATCTGAATTCTGTGACATCGACGACACTTCTAT
GGGTATGAGATTGATGAGAATGCACGGTTACGACGTTGACCCAAACGTTTTGAGAAACTTCAAGCAAAAGGA
CGGTAAGTTCTCTTGTTACGGTGGTCAAATGATCGAATCTCCATCTCCAATCTACAACTTGTACAGAGCTTCTCA
ATTGAGATTCCCAGGTGAAGAAATCTTGGAAGACGCTAAGAGATTCGCTTACGACTTCTTGAAGGAAAAGTTG
GCTAACAACCAAATCTTGGACAAGTGGGTTATCTCTAAGCACTTGCCAGACGAAATCAAGTTGGGTTTGGAAA
TGCCATGGTTGGCTACTTTGCCAAGAGTTGAAGCTAAGTACTACATCCAATACTACGCTGGTTCTGGTGACGTT
TGGATCGGTAAGACTTTGTACAGAATGCCAGAAATCTCTAACGACACTTACCACGACTTGGCTAAGACTGACT
TCAAGAGATGTCAAGCTAAGCACCAATTCGAATGGTTGTACATGCAAGAATGGTACGAATCTTGTGGTATCGA
AGAATTCGGTATCTCTAGAAAGGACTTGTTGTTGTCTTACTTCTTGGCTACTGCTTCTATCTTCGAATTGGAAAG
AACTAACGAAAGAATCGCTTGGGCTAAGTCTCAAATCATCGCTAAGATGATCACTTCTTTCTTCAACAAGGAAA
CTACTTCTGAAGAAGACAAGAGAGCTTTGTTGAACGAATTGGGTAACATCAACGGTTTGAACGACACTAACG
GTGCTGGTAGAGAAGGTGGTGCTGGTTCTATCGCTTTGGCTACTTTGACTCAATTCTTGGAAGGTTTCGACAG
ATACACTAGACACCAATTGAAGAACGCTTGGTCTGTTTGGTTGACTCAATTGCAACACGGTGAAGCTGACGAC
GCTGAATTGTTGACTAACACTTTGAACATCTGTGCTGGTCACATCGCTTTCAGAGAAGAAATCTTGGCTCACAA
CGAATACAAGGCTTTGTCTAACTTGACTTCTAAGATCTGTAGACAATTGTCTTTCATCCAATCTGAAAAGGAAA
TGGGTGTTGAAGGTGAAATCGCTGCTAAGTCTTCTATCAAGAACAAGGAATTGGAAGAAGACATGCAAATGT
TGGTTAAGTTGGTTTTGGAAAAGTACGGTGGTATCGACAGAAACATCAAGAAGGCTTTCTTGGCTGTTGCTAA
GACTTACTACTACAGAGCTTACCACGCTGCTGACACTATCGACACTCACATGTTCAAGGTTTTGTTCGAACCAG
TTGCTTAA SmCPS2, copalyl-pyrophosphate synthase from *Salvia miltiorrhiza*, amino acid sequence-SEQ ID NO: 64
MATVDAPQVHDHDGTTVHQGHDAVKNIEDPIEYIRTLLRTTGDGRISVSPYDTAWVAMIKDVEGRDGPQFPSSLE
WIVQNQLEDGSWGDQKLFCVYDRLVNTIACVVALRSWNVHAHKVKRGVTYIKENVDKLMEGNEEHMTCGFEVV
FPALLQKAKSLGIEDLPYDSPAVQEVYHVREQKLKRIPLEIMHKIPTSLLFSLEGLENLDWDKLLKLQSADGSFLTSPSS
TAFAFMQTKDEKCYQFIKNTIDTFNGGAPHTYPVDVFGRLWAIDRLQRLGISRFFEPEIADCLSHIHKFWTDKGVFS
GRESEFCDIDDTSMGMRLMRMHGYDVDPNVLRNFKQKDGKFSCYGGQMIESPSPIYNLYRASQLRFPGEEILEDA
KRFAYDFLKEKLANNQILDKWVISKHLPDEIKLGLEMPWLATLPRVEAKYYIQYYAGSGDVWIGKTLYRMPEISNDT
YHDLAKTDFKRCQAKHQFEWLYMQEWYESCGIEEFGISRKDLLLSYFLATASIFELERTNERIAWAKSQIIAKMITSFF
NKETTSEEDKRALLNELGNINGLNDTNGAGREGGAGSIALATLTQFLEGFDRYTRHQLKNAWSVWLTQLQHGEA
DDAELLTNTLNICAGHIAFREEILAHNEYKALSNLTSKICRQLSFIQSEKEMGVEGEIAAKSSIKNKELEEDMQMLVKL
VLEKYGGIDRNIKKAFLAVAKTYYYRAYHAADTIDTHMFKVLFEPVA*

TalVeTPP, copalyl-pyrophosphate phosphatase, codon optimized for expression in *S. cerevisiae*-SEQ ID NO: 65
ATGTCTAACGACACTACTACTACTGCTTCTGCTGGTACTGCTACTTCTTCTAGATTCTTGTCTGTTGGTGGTGTT
GTTAACTTCAGAGAATTGGGTGGTTACCCATGTGACTCTGTTCCACCAGCTCCAGCTTCAACGGTTCTCCAGA
CAACGCTTCTGAAGCTACTTTGTGGGTTGGTCACTCTTCTATCAGACCAGGTTTCTTGTTCAGATCTGCTCAACC
ATCTCAAATCACTCCAGCTGGTATCGAAACTTTGATCAGACAATTGGGTATCCAAACTATCTTCGACTTCAGAT CTAGAACTGAAATCGAATTGGTTGCTACTAGATACCCAGACTCTTTGTTGGAAATCCCAGGTACTACTAGATAC
TCTGTTCCAGTTTTCTCTGAAGGTGACTACTCTCCAGCTTCTTTGGTTAAGAGATACGGTGTTTCTTCTGACACT
GCTACTGACTCTACTTCTTCTAAGTCTGCTAAGCCAACTGGTTTCGTTCACGCTTACGAAGCTATCGCTAGATCT
GCTGCTGAAAACGGTTCTTTCAGAAAGATCACTGACCACATCATCCAACACCCAGACAGACCAATCTTGTTCCA
CTGTACTTTGGGTAAGGACAGAACTGGTGTTTTCGCTGCTTTGTTGTTGTCTTTGTGGTGTTCCAGACGAAA
CTATCGTTGAAGACTACGCTATGACTACTGAAGGTTTCGGTGCTTGGAGAGAACACTTGATCCAAAGATTGTT
GCAAAGAAGGACGCTGCTACTAGAGAAGACGCTGAATCTATCATCGCTTCTCCACCAGAAACTATGAAGGCT
TTCTTGGAAGACGTTGTTGCTGCTAAGTTCGGTGGTGCTAGAAACTACTTCATCCAACACTGTGGTTTCACTGA
AGCTGAAGTTGACAAGTTGTCTCACACTTTGGCTATCACTAACTAA AzTolADH1, alcohol dehydrogenase from *Azoarcus toluclasticus*, codon optimized for expression
in *S. cerevisiae*-SEQ ID NO: 66
ATGGGTTCTATCCAAGACTCTTTGTTCATCAGAGCTAGAGCTGCTGTTTTGAGAACTGTTGGTGGTCCATTGGA
AATCGAAAACGTTAGAATCTCTCCACCAAAGGGTGACGAAGTTTTGGTTAGAATGGTTGGTGTTGGTGTTTGT
CACACTGACGTTGTTTGTAGAGACGGTTTCCCAGTTCCATTGCCAATCGTTTTGGGTCACGAAGGTTCTGGTAT
CGTTGAAGCTGTTGGTGAAAGAGTTACTAAGGTTAAGCCAGGTCAAAGAGTTGTTTTGTCTTTCAACTCTTGT
GGTCACTGTGCTTCTTGTTGTGAAGACCACCCAGCTACTTGTCACCAAATGTTGCCATTGAACTTCGGTGCTGC
TCAAAGAGTTGACGGTGGTACTGTTATCGACGCTTCTGGTGAAGCTGTTCAATCTTTGTTCTTCGGTCAATCTT
CTTTCGGTACTTACGCTTTGGCTAGAGAAGTTAACACTGTTCCAGTTCCAGACGCTGTTCCATTGGAAATCTTG
GGTCCATTGGGTTGTGGTATCCAAACTGGTGCTGGTGCTGCTATCAACTCTTTGGCTTTGAAGCCAGGTCAATC
TTTGGCTATCTTCGGTGGTGGTTCTGTTGGTTTGTCTGCTTTGTTGGGTGCTTTGGCTGTTGGTGCTGGTCCAG
TTGTTGTTATCGAACCAAACGAAAGAAGAAGAGCTTTGGCTTTGGACTTGGGTGCTTTCTCACGCTTTCTAACCCA
TTCAACACTGAAGACTTGGTTGCTTCTATCAAGGCTGCTACTGGTGGTGGTGTTACTCACTCTTTGGACTCTAC
TGGTTTGCCACCAGTTATCGCTAACGCTATCAACTGTACTTTGCCAGGTGGTACTGTTGGTTTGTTGGGTGTTC
CATCTCCAGAAGCTGCTGTTCCAGTTACTTTGTTGGACTTGTTGGTTAAGTCTGTTACTTTGAGACCAATCACTG
AAGGTGACGCTAACCCACAAGAATTCATCCCAAGAATGGTTCAATTGTACAGAGACGGTAAGTTCCCATTCGA
CAAGTTGATCACTACTTACAGATTCGACGACATCAACCAAGCTTTCAAGGCTACTGAAACTGGTGAAGCTATC
AAGCCAGTTTTGGTTTTCTAA PsAeroADH1, alcohol dehydrogenase from *Pseudomonas aeruginosa*, codon optimized for
expression in *S. cerevisiae*. -SEQ ID NO: 67
ATGAACTCTATCCAACCAACTCAAGCTAAGGCTGCTGTTTTGAGAGCTGTTGGTGGTCCATTCTCTATCGAACC
AATCAGAATCTCTCCACCAAAGGGTGACGAAGTTTTGGTTAGAATCGTTGGTGTTGGTGTTTGTCACACTGAC
GTTGTTTGTAGAGACTCTTTCCCAGTTCCATTGCCAATCATCTTGGGTCACGAAGGTTCTGGTGTTATCGAAGC
TGTTGGTGACCAAGTTACTGGTTTGAAGCCAGGTGACCACGTTGTTTTGTCTTTCAACTCTTGTGGTCACTGTT
ACAACTGTGGTCACGACGAACCAGCTTCTTGTTTGCAAATGTTGCCATTGAACTTCGGTGGTGCTGAAAGAGC
TGCTGACGGTACTATCGAAGACGACCAAGGTGCTGCTGTTAGAGGTTTGTTCTTCGGTCAATCTTCTTTCGGTT
CTTACGCTATCGCTAGAGCTGTTAACACTGTTAAGGTTGACGACGACTTGCCATTGGCTTTGTTGGGTCCATTG
GGTTGTGGTATCCAAACTGGTGCTGGTGCTGCTATGAACTCTTTGGGTTTGCAAGGTGGTCAATCTTTCATCGT
TTTCGGTGGTGGTGCTGTTGGTTTGTCTGCTGTTATGGCTGCTAAGGCTTTGGGTGTTTCTCCATTGATCGTTG
TTGAACCAAACGAAGCTAGAAGAGCTTTGGCTTTGGAATTGGGTGCTTCTCACGCTTTCGACCCATTCAACACT
GAAGACTTGGTTGCTTCTATCAGAGAAGTTGTTCCAGCTGGTGCTAACCACGCTTTGGACACTACTGGTTTGCC
AAAGGTTATCGCTAACGCTATCGACTGTATCATGTCTGGTGGTAAGTTGGGTTTTGTTGGGTATGGCTAACCCA
GAAGCTAACGTTCCAGCTACTTTCGTTGGACTTGTTGTCTAAGAACGTTACTTTGAAGCCAATCACTGAAGGTGA
CGCTAACCCACAAGAATTCATCCCAAGAATGTTGGCTTTGTACAGAGAAGGTAAGTTCCCATTCGACAAGTTG
ATCACTACTTTCCCATTCGAACACATCAACGAAGCTATGGAAGCTACTGAATCTGGTAAGGCTATCAAGCCAGT
TTTGACTTTGTAA SCH23-ADH1, alcohol dehydrogenase from *Hyphozyma roseonigra*, codon optimized for expression
in *S. cerevisiae*. -SEQ ID NO: 68
ATGCAATTCTCTATCGGTGACGTTTTGGCTATCGTTGACAAGACTATCTTGAACCCATTGGTTGTTTCTGCTGGT
TTGTTGTCTTTGCACTTCTTGACTAACGACAAGTACGCTATCACTGCTAACGACGGTTTGTTCCCATACCAAATC
TCTACTCCAGACTCTCACAGAAAGGCTTTGTTCGCTTTGGGTTTCGGTTTGTTGTTGAGAGCTAACAGATACAT
GTCTAGAAAGGCTTTGAACAACAACACTGCTGCTCAATTCGACTGGAACAGAGAAATCATCGTTGTTACTGGT
GGTTCTGGTGGTATCGGTGCTCAAGCTGCTCAAAAGTTGGCTGAAAGAGGTTCTAAGGTTATCGTTATCGACG
TTTTGCCATTGACTTTCGACAAGCCAAAGAACTTGTACCACTACAAGTGTGACTTGACTAACTACAAGGAATTG
CAAGAAGTTGCTGCTAAGATCGAAAGAGAAGTTGGTACTCCAACTTGTGTTGTTGCTAACGCTGGTATCTGTA
GAGGTAAGAACATCTTCGACGCTACTGAAAGAGACGTTCAATTGACTTTCGGTGTTAACAACTTGGGTTTGTT
GTGGACTGCTAAGACTTTCTTGCCATCTATGGCTAAGGCTAACGGTCACTTCTTGATCATCGCTTCTCAAACTG
GTCACTTGGCTACTGCTGGTGTTGTTGACTACGCTGCTACTAAGGCTGCTGCTATCGCTATCTACGAAGGT
TTGCAAACTGAAATGAAGCACTTCTACAAGGCTCCAGCTGTTAGAGTTTCTTGTATCTCTCCATCTGCTGTTAA
GACTAAGATGTTCGCTGGTATCAAGACTGGTGGTAACTTCTTCATGCCAATGTTGACTCCAGACGACTTGGGT
GACTTGATCGCTAAGACTTTGTGGGACGGTGTTGCTGTTAACATCTTGTCTCCAGCTGCTGCTTACATCTCTCC
ACCAACTAGAGCTTTGCCAGACTGGATGAGAGTTGGTATGCAAGACGCTGGTGCTGAAATCATGACTGAATT
GACTCCACACAAGCCATTGGAATAA SCH23-ADH1, alcohol dehydrogenase from *Hyphozyma roseonigra*, amino acid sequence-SEQ ID
NO: 69
MQFSIGDVLAIVDKTILNPLVVSAGLLSLHFLTNDKYAITANDGLFPYQISTPDSHRKALFALGFGLLLRANRYMSRKA
LNNNTAAQFDWNREIIVVTGGSGGIGAQAAQKLAERGSKVIVIDVLPLTFDKPKNLYHYKCDLTNYKELQEVAAKIE
REVGTPTCVVANAGICRGKNIFDATERDVQLTFGVNNLGLLWTAKTFLPSMAKANHGHFLIIASQTGHLATAGVV
DYAATKAAAIAIYEGLQTEMKHFYKAPAVRVSCISPSAVKTKMFAGIKTGGNFFMPMLTPDDLGDLIAKTLWDGV
AVNILSPAAAYISPPTRALPDWMRVGMQDAGAEIMTELTPHKPLE SCH24-ADH1a, alcohol dehydrogenase from *Cryptococcus albidus*, codon optimized for expression
in *S. cerevisiae*-SEQ ID NO: 70
ATGCCAACTCCAATCTTCGGTGCTAGAGAAGGTTTCACTATCGACTCTGTTTTGTCTATCTTGGACGCTACTGTT
TTGAACCCATGGTTCACTGGTGTTTGTTTGATCGCTGTTTGTGCTAGAGACAGAACTATCACTTACCCAGACTG
GCCAGCTGCTTTGGACCAAGTTTTGCCATTCTTGTCTCAAATGTGGAGAGAAACTGTTAGACCAACTTTCGGTG

```
ACAGAAACGTTTTGCACTTGTTGACTACTGTTTGTGTTGGTTTGGCTATCAGAACTAACAGAAGAATGTCTAGA
GGTGCTAGAAACAACTGGGTTTGGGACACTTCTTACGACTGGAAGAAGGAAATCGTTGTTGTTACTGGTGGT
GCTGCTGGTTTCGGTGCTGACATCGTTCAACAATTGGACACTAGAGGTATCCAAGTTGTTGTTTTGGACGTTG
GTTCTTTGACTTACAGACCATCTTCTAGAGTTCACTACTACAAGTGTGACGTTTCTAACCCACAAGACGTTGCTT
CTGTTGCTAAGGCTATCGTTTCTAACGTTGGTCACCCAACTATCTTGGTTAACAACGCTGGTGTTTTCAGAGGT
GCTACTATCTTGTCTACTACTCCAAGAGACTTGGACATGACTTACGACATCAACGTTAAGGCTCACTACCACTT
GACTAAGGCTTTCTTGCCAAACATGATCTCTAAGAACCACGGTCACATCGTTACTGTTTCTTCTGCTACTGCTTA
CGCTCAAGCTTGTTCTGGTGTTTCTTACTGTTCTTCTAAGGCTGCTATCTTGTCTTTCCACGAAGGTTTGTCTGA
AGAAATCTTGTGGATCTACAAGGCTCCAAAGGTTAGAACTTCTGTTATCTGTCCAGGTCACGTTAACACTGCTA
TGTTCACTGGTATCGGTGCTGCTGCTCCATCTTTCATGGCTCCAGCTTTGCACCCATCTACTGTTGCTGAAACTA
TCGTTGACGTTTTGTTGTCTTGTGAATCTCAACACGTTTTGATGCCAGCTGCTATGCACATGTCTGTTGCTGGTA
GAGCTTTGCCAACTTGGTTCTTCAGAGGTTTGTTGGCTTCTGGTAAGGACACTATGGGTTCTGTTGTTAGAAGA
TAA

SCH24-ADH1a, alcohol dehydrogenase from Cryptococcus albidus, amino acid sequence-SEQ ID
NO: 71
MPTPIFGAREGFTIDSVLSILDATVLNPWFTGVCLIAVCARDRTITYPDWPAALDQVLPFLSQMWRETVRPTFGDR
NVLHLLTTVCVGLAIRTNRRMSRGARNNWVWDTSYDWKKEIVVVTGGAAGFGADIVQQLDTRGIQVVVLDVGS
LTYRPSSRVHYYKCDVSNPQDVASVAKAIVSNVGHPTILVNNAGVFRGATILSTTPRDLDMTYDINVKAHYHLTKAF
LPNMISKNHGHIVTVSSATAYAQACSGVSYCSSKAAILSFHEGLSEEILWIYKAPKVRTSVICPGHVNTAMFTGIGAA
APSFMAPALHPSTVAETIVDVLLSCESQHVLMPAAMHMSVAGRALPTWFFRGLLASGKDTMGSVVRR*

Sequence for homologous recombination 1-SEQ ID NO: 72
GCACTTGCTACACTGTCAGGATAGCTTCCGTCACATGGTGGCGATCACCGTACATCTGAG Sequence for homologous recombination 2-SEQ ID NO: 73
AGGTGCAGTTCGCGTGCAATTATAACGTCGTGGCAACTGTTATCAGTCGTACCGCGCCAT Sequence for homologous recombination 3-SEQ ID NO: 74
TGGTCAGCAACAACGCCGAAGAATCACTCTCGTGTTGAGAATTGCACGCCTTGACCACGA Primer for LEU2 yeast marker 1-SEQ ID NO: 75
AGGTGCAGTTCGCGTGCAATTATAACGTCGTGGCAACTGTTATCAGTCGTACCGCGCCATTCGACTACGTCGT
AAGGCC Primer for LEU2 yeast marker 2-SEQ ID NO: 76
TCGTGGTCAAGGCGTGCAATTCTCAACACGAGAGTGATTCTTCGGCGTTGTTGCTGACCATCGACGGTCGAGG
AGAACTT Primer for AmpR bacterial marker 1-SEQ ID NO: 77
TGGTCAGCAACAACGCCGAAGAATCACTCTCGTGTTGAGAATTGCACGCCTTGACCACGACACGTTAAGGGAT
TTTGGTCATGAG Primer for AmpR bacterial marker 2-SEQ ID NO: 78
AACGCGTACCCTAAGTACGGCACCACAGTGACTATGCAGTCCGCACTTTGCCAATGCCAAAAATGTGCGCGGA
ACCCCTA Primer for yeast origin of replication 1-SEQ ID NO: 79
TTGGCATTGGCAAAGTGCGGACTGCATAGTCACTGTGGTGCCGTACTTAGGGTACGCGTTCCTGAACGAAGC
ATCTGTGCTTCA Primer for yeast origin of replication 2-SEQ ID NO: 80
CCGAGATGCCAAAGGATAGGTGCTATGTTGATGACTACGACACAGAACTGCGGGTGACATAATGATAGCATT
GAAGGATGAGACT Primer for E. coli origin of replication 1-SEQ ID NO: 81
ATGTCACCCGCAGTTCTGTGTCGTAGTCATCAACATAGCACCTATCCTTTGGCATCTCGGTGAGCAAAAGGCCA
GCAAAAGG Primer for E. coli origin of replication 2-SEQ ID NO: 82
CTCAGATGTACGGTGATCGCCACCATGTGACGGAAGCTATCCTGACAGTGTAGCAAGTGCTGAGCGTCAGAC
CCCGTAGAA Sequence for homologous recombination 4-SEQ ID NO: 83
ATTCCTAGTGACGGCCTTGGGAACTCGATACACGATGTTCAGTAGACCGCTCACACATGG
```

The invention claimed is:

1. A biocatalytic method of producing a terpene alcohol compound, of the general formula 1

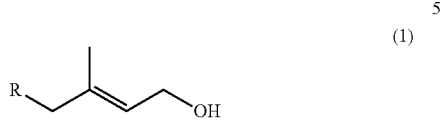
(1)

wherein
R represents H or a cyclic or non-cyclic, linear or branched, saturated or unsaturated, optionally substituted hydrocarbyl residue,
the method comprising the steps of:
(1) contacting the corresponding terpenyl diphosphate precursor of said terpene compound of formula (1) with a polypeptide having terpenyl-diphosphate phosphatase activity to form said terpene alcohol; and
(2) optionally isolating the terpene alcohol of step (1)
wherein said polypeptide having terpenyl-diphosphate phosphatase activity is selected from a diphosphate removing enzyme member of the protein tyrosine phosphatase family.

2. A biocatalytic method of producing a bicyclic diterpene alcohol compound,
the method comprising the steps of:
a) contacting the corresponding bicyclic diterpenyl diphosphate precursor of said bicyclic diterpene compound with a polypeptide having terpenyl-diphosphate phosphatase activity to form said bicyclic diterpene alcohol; and
b) optionally isolating the bicyclic diterpene alcohol of step (a).

3. The method of claim 2, wherein said polypeptide having terpenyl-diphosphate phosphatase activity is selected from a diphosphate removing enzyme member of the protein tyrosine phosphatase family.

4. The method of claim 1, wherein said polypeptide having terpenyl-diphosphate phosphatase activity is selected form a class of diphosphate removing enzymes characterized by an amino acid sequence having the following active site signature motif:

```
HCxxGxxR          (SEQ ID NO: 57)
``` wherein
each x independently of each other represents any natural amino acid residue.

5. The method of claim 4, wherein said active site signature motif is:

```
HC(T/S)xGKDRTG    (SEQ ID NO: 58)
``` wherein
x represents any natural amino acid residue.

6. The method of claim 1, wherein said polypeptide having terpenyl-diphosphate phosphatase activity is selected from the group consisting of the polypeptides:
a) TalVeTPP comprising an amino acid sequence according to SEQ ID NO: 2,
b) AspWeTPP comprising an amino acid sequence according to SEQ ID NO: 6,
c) HelGriTPP comprising an amino acid sequence according to SEQ ID NO: 10,
d) UmbPiTPP1, comprising an amino acid sequence according to SEQ ID NO: 13,
e) TalVeTPP2, comprising an amino acid sequence according to SEQ ID NO: 16,
f) HydPiTPP1, comprising an amino acid sequence according to SEQ ID NO: 19,
g) TalCeTPP1, comprising an amino acid sequence according to SEQ ID NO: 22,
h) TalMaTPP1, comprising an amino acid sequence according to SEQ ID NO: 25,
i) TalAstroTPP1 comprising an amino acid sequence according to SEQ ID NO: 28, and
j) PeSubTPP1 comprising an amino acid sequence according to SEQ ID NO: 31, and
k) a polypeptide having terpenyl-diphosphate phosphatase activity and comprising an amino acid sequence showing an degree of sequence identity of at least 60% to at least one of said amino acid sequence according to a) to j).

7. The method of claim 1, wherein a terpene alcohol compound of the general formula (1) is prepared, wherein R represents H or a non-cyclic, linear or branched, saturated or unsaturated, hydrocarbyl residue.

8. The method of claim 7 wherein the terpene alcohol of formula 1 is selected from farnesol and geranylgeraniol.

9. The method of claim 2, wherein step (1) also comprises contacting a noncyclic terpenyl diphosphate precursor with a polypeptide having bicyclic diterpenyl diphosphate synthase activity to form said bicyclic diterpenyl diphosphate precursor.

10. The method of claim 9, wherein said bicyclic diterpenyl diphosphate synthase is selected from
l) SmCPS2 comprising an amino acid sequence according to SEQ ID NO: 34,
m) TaTps1-del59 comprising an amino acid sequence according to SEQ ID NO: 40,
n) SsLPS comprising an amino acid sequence according to SEQ ID NO: 38, and
o) a polypeptide having bicyclic diterpenyl diphosphate synthase activity and comprising an amino acid sequence showing an degree of sequence identity of at least 60% to at least one of said amino acid sequences according to a), b) and c).

11. The method of claim 2, wherein said biocatalytically produced bicyclic diterpene alcohol is selected from copalol and labdendiol each either in essentially pure stereoisomeric form or in the form of a mixture of at least two stereoisomers.

12. The method of claim 1, further comprising as step (3) the processing of the terpene alcohol of step (1) or of step (2) to an alcohol derivative using chemical or biocatalytic synthesis or a combination of both.

13. The method of claim 12, wherein the derivative is a hydrocarbon, alcohol, diol, triol, acetal, ketal, aldehyde, acid, ether, amide, ketone, lactone, epoxide, acetate, glycoside and/or an ester.

14. The method of claim 12, wherein said terpene alcohol is biocatalytically oxidized.

15. The method of claim 14, wherein said terpene alcohol is converted by contacting with an alcohol dehydrogenase (ADH).

16. The method of claim 15, wherein said ADH is selected from
p) CymB comprising an amino acid sequence according to SEQ ID NO:42;
q) AspWeADH1 comprising an amino acid sequence according to SEQ ID NO: 44;

r) PsAeroADH1 comprising an amino acid sequence according to SEQ ID NO: 46;
s) AzTolADH1 comprising an amino acid sequence according to SEQ ID NO: 48;
t) AroAroADH1 comprising an amino acid sequence according to SEQ ID NO: 50;
u) ThTerpADH1 comprising an amino acid sequence according to SEQ ID NO: 52;
v) CdGeoA comprising an amino acid sequence according to SEQ ID NO: 54;
w) VoADH1 comprising an amino acid sequence according to SEQ ID NO: 56;
x) SCH23-ADH1 comprising an amino acid sequence according to SEQ ID NO: 68
y) SCH24-ADH1a comprising an amino acid sequence according to SEQ ID NO: 70; and
z) a polypeptide having ADH activity and comprising an amino acid sequence showing an degree of sequence identity of at least 60% to at least one of said amino acid sequence according to a) to j).

17. A method of preparing an ambrox-like compound of the general formula,

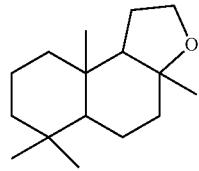

which method comprises
(1) providing a labdendiol or copalol compound by performing a biocatalytic process as defined in claim 1, optionally isolating said labdendiol or copalol compound; and
(2) converting said labdendiol or copalol compound of step (1) using chemical synthesis and/or biochemical synthesis to ambrox-like compound.

* * * * *

SEQUENCE LISTING

<160> NUMBER OF SEQ ID NOS: 83

<210> SEQ ID NO 1
<211> LENGTH: 936
<212> TYPE: DNA
<213> ORGANISM: Talaromyces verruculosus
<220> FEATURE:

<221> NAME/KEY: CDS
<222> LOCATION: (1)..(936)

<400> SEQUENCE: 1

| | | | | | | | | | | | | | | | | |
|---|---|---|---|---|---|---|---|---|---|---|---|---|---|---|---|---|
| atg | agc | aat | gac | acg | acg | acc | acc | gcg | agc | gcc | ggt | act | gca | act | tct | 48 |
| Met | Ser | Asn | Asp | Thr | Thr | Thr | Thr | Ala | Ser | Ala | Gly | Thr | Ala | Thr | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agc | cgt | ttt | ctg | agc | gtc | ggc | ggc | gtt | gtg | aat | ttt | cgc | gag | ctg | ggt | 96 |
| Ser | Arg | Phe | Leu | Ser | Val | Gly | Gly | Val | Val | Asn | Phe | Arg | Glu | Leu | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| ggc | tat | cca | tgc | gac | agc | gtg | ccg | ccg | gct | ccg | gca | agc | aac | ggt | tcg | 144 |
| Gly | Tyr | Pro | Cys | Asp | Ser | Val | Pro | Pro | Ala | Pro | Ala | Ser | Asn | Gly | Ser | |
| | | | 35 | | | | | 40 | | | | | 45 | | | |

| | | | | | | | | | | | | | | | | |
|---|---|---|---|---|---|---|---|---|---|---|---|---|---|---|---|---|
| cct | gat | aat | gcg | tcc | gag | gca | acg | ctg | tgg | gtt | ggt | cac | tcc | agc | att | 192 |
| Pro | Asp | Asn | Ala | Ser | Glu | Ala | Thr | Leu | Trp | Val | Gly | His | Ser | Ser | Ile | |
| | 50 | | | | | 55 | | | | | 60 | | | | | |

| | | | | | | | | | | | | | | | | |
|---|---|---|---|---|---|---|---|---|---|---|---|---|---|---|---|---|
| cgt | ccg | ggt | ttc | ctg | ttc | cgc | agc | gcg | cag | ccg | agc | cag | att | acg | ccg | 240 |
| Arg | Pro | Gly | Phe | Leu | Phe | Arg | Ser | Ala | Gln | Pro | Ser | Gln | Ile | Thr | Pro | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gcg | ggt | atc | gaa | acg | ctg | atc | cgc | caa | ctg | ggc | atc | cag | acc | att | ttt | 288 |
| Ala | Gly | Ile | Glu | Thr | Leu | Ile | Arg | Gln | Leu | Gly | Ile | Gln | Thr | Ile | Phe | |
| | | | | 85 | | | | | 90 | | | | | 95 | | |

| | | | | | | | | | | | | | | | | |
|---|---|---|---|---|---|---|---|---|---|---|---|---|---|---|---|---|
| gat | ttc | cgt | agc | cgt | acc | gag | atc | gaa | ctg | gtg | gcg | acc | cgt | tac | ccg | 336 |
| Asp | Phe | Arg | Ser | Arg | Thr | Glu | Ile | Glu | Leu | Val | Ala | Thr | Arg | Tyr | Pro | |
| | | | | 100 | | | | | 105 | | | | | 110 | | |

| | | | | | | | | | | | | | | | | |
|---|---|---|---|---|---|---|---|---|---|---|---|---|---|---|---|---|
| gac | tct | ctg | ttg | gaa | att | ccg | ggc | acc | acg | cgc | tat | tcc | gtc | ccg | gtt | 384 |
| Asp | Ser | Leu | Leu | Glu | Ile | Pro | Gly | Thr | Thr | Arg | Tyr | Ser | Val | Pro | Val | |
| | | | 115 | | | | | 120 | | | | | 125 | | | |

| | | | | | | | | | | | | | | | | |
|---|---|---|---|---|---|---|---|---|---|---|---|---|---|---|---|---|
| ttc | tcc | gag | ggt | gac | tat | tct | ccg | gcg | agc | ctg | gtg | aag | cgc | tat | ggt | 432 |
| Phe | Ser | Glu | Gly | Asp | Tyr | Ser | Pro | Ala | Ser | Leu | Val | Lys | Arg | Tyr | Gly | |
| | | 130 | | | | | 135 | | | | | 140 | | | | |

| | | | | | | | | | | | | | | | | |
|---|---|---|---|---|---|---|---|---|---|---|---|---|---|---|---|---|
| gtt | agc | agc | gat | acc | gcc | acg | gac | agc | acc | tct | agc | aag | agc | gcg | aag | 480 |
| Val | Ser | Ser | Asp | Thr | Ala | Thr | Asp | Ser | Thr | Ser | Ser | Lys | Ser | Ala | Lys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ccg | acc | ggc | ttc | gtt | cat | gca | tac | gaa | gcc | att | gcg | cgc | agc | gcc | gct | 528 |
| Pro | Thr | Gly | Phe | Val | His | Ala | Tyr | Glu | Ala | Ile | Ala | Arg | Ser | Ala | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| gag | aac | ggt | agc | ttc | cgt | aaa | att | acc | gac | cac | atc | atc | cag | cat | cct | 576 |
| Glu | Asn | Gly | Ser | Phe | Arg | Lys | Ile | Thr | Asp | His | Ile | Ile | Gln | His | Pro | |
| | | | 180 | | | | | 185 | | | | | 190 | | | |

| | | | | | | | | | | | | | | | | |
|---|---|---|---|---|---|---|---|---|---|---|---|---|---|---|---|---|
| gat | cgt | cca | att | ttg | ttc | cac | tgt | acc | ctg | ggt | aaa | gac | cgt | acg | ggt | 624 |
| Asp | Arg | Pro | Ile | Leu | Phe | His | Cys | Thr | Leu | Gly | Lys | Asp | Arg | Thr | Gly | |
| | | | 195 | | | | | 200 | | | | | 205 | | | |

| | | | | | | | | | | | | | | | | |
|---|---|---|---|---|---|---|---|---|---|---|---|---|---|---|---|---|
| gtc | ttt | gcg | gcg | ctg | ttg | ctg | agc | ctg | tgt | ggt | gtg | ccg | gac | gaa | acc | 672 |
| Val | Phe | Ala | Ala | Leu | Leu | Leu | Ser | Leu | Cys | Gly | Val | Pro | Asp | Glu | Thr | |
| | 210 | | | | | 215 | | | | | 220 | | | | | |

| | | | | | | | | | | | | | | | | |
|---|---|---|---|---|---|---|---|---|---|---|---|---|---|---|---|---|
| atc | gtc | gaa | gat | tac | gcg | atg | acc | acc | gaa | ggc | ttt | ggt | gca | tgg | cgt | 720 |
| Ile | Val | Glu | Asp | Tyr | Ala | Met | Thr | Thr | Glu | Gly | Phe | Gly | Ala | Trp | Arg | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gag | cac | ctg | atc | caa | cgt | ctg | ctg | caa | cgt | aaa | gac | gct | gca | acc | cgt | 768 |
| Glu | His | Leu | Ile | Gln | Arg | Leu | Leu | Gln | Arg | Lys | Asp | Ala | Ala | Thr | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| gaa | gat | gcc | gag | agc | atc | att | gcg | tcg | ccg | ccg | gag | act | atg | aaa | gca | 816 |
| Glu | Asp | Ala | Glu | Ser | Ile | Ile | Ala | Ser | Pro | Pro | Glu | Thr | Met | Lys | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| ttt | ctg | gaa | gat | gtt | gtg | gca | gcg | aaa | ttt | ggt | ggc | gcg | cgt | aac | tac | 864 |
| Phe | Leu | Glu | Asp | Val | Val | Ala | Ala | Lys | Phe | Gly | Gly | Ala | Arg | Asn | Tyr | |
| | | 275 | | | | | 280 | | | | | 285 | | | | |

| | | | | | | | | | | | | | | | | |
|---|---|---|---|---|---|---|---|---|---|---|---|---|---|---|---|---|
| ttc | att | caa | cat | tgc | ggc | ttc | act | gaa | gct | gaa | gtc | gat | aag | ctg | agc | 912 |
| Phe | Ile | Gln | His | Cys | Gly | Phe | Thr | Glu | Ala | Glu | Val | Asp | Lys | Leu | Ser | |

```
                      290                 295                 300
cac acc ctg gcg atc acg aac taa                                            936
His Thr Leu Ala Ile Thr Asn
305                 310
```

<210> SEQ ID NO 2
<211> LENGTH: 311
<212> TYPE: PRT
<213> ORGANISM: Talaromyces verruculosus

<400> SEQUENCE: 2

```
Met Ser Asn Asp Thr Thr Thr Ala Ser Ala Gly Thr Ala Thr Ser
1               5                   10                  15

Ser Arg Phe Leu Ser Val Gly Val Val Asn Phe Arg Glu Leu Gly
                20                  25                  30

Gly Tyr Pro Cys Asp Ser Val Pro Ala Pro Ala Ser Asn Gly Ser
                35                  40                  45

Pro Asp Asn Ala Ser Glu Ala Thr Leu Trp Val Gly His Ser Ile
    50                  55                  60

Arg Pro Gly Phe Leu Phe Arg Ser Ala Gln Pro Ser Gln Ile Thr Pro
65                  70                  75                  80

Ala Gly Ile Glu Thr Leu Ile Arg Gln Leu Gly Ile Gln Thr Ile Phe
                85                  90                  95

Asp Phe Arg Ser Arg Thr Glu Ile Glu Leu Val Ala Thr Arg Tyr Pro
                100                 105                 110

Asp Ser Leu Leu Glu Ile Pro Gly Thr Thr Arg Tyr Ser Val Pro Val
                115                 120                 125

Phe Ser Glu Gly Asp Tyr Ser Pro Ala Ser Leu Val Lys Arg Tyr Gly
                130                 135                 140

Val Ser Ser Asp Thr Ala Thr Asp Ser Thr Ser Ser Lys Ser Ala Lys
145                 150                 155                 160

Pro Thr Gly Phe Val His Ala Tyr Glu Ala Ile Ala Arg Ser Ala Ala
                165                 170                 175

Glu Asn Gly Ser Phe Arg Lys Ile Thr Asp His Ile Ile Gln His Pro
                180                 185                 190

Asp Arg Pro Ile Leu Phe His Cys Thr Leu Gly Lys Asp Arg Thr Gly
                195                 200                 205

Val Phe Ala Ala Leu Leu Leu Ser Leu Cys Gly Val Pro Asp Glu Thr
                210                 215                 220

Ile Val Glu Asp Tyr Ala Met Thr Thr Glu Gly Phe Gly Ala Trp Arg
225                 230                 235                 240

Glu His Leu Ile Gln Arg Leu Leu Gln Arg Lys Asp Ala Ala Thr Arg
                245                 250                 255

Glu Asp Ala Glu Ser Ile Ile Ala Ser Pro Pro Glu Thr Met Lys Ala
                260                 265                 270

Phe Leu Glu Asp Val Val Ala Ala Lys Phe Gly Gly Ala Arg Asn Tyr
                275                 280                 285

Phe Ile Gln His Cys Gly Phe Thr Glu Ala Glu Val Asp Lys Leu Ser
                290                 295                 300

His Thr Leu Ala Ile Thr Asn
305                 310
```

<210> SEQ ID NO 3
<211> LENGTH: 936
<212> TYPE: DNA
<213> ORGANISM: Talaromyces verruculosus

<400> SEQUENCE: 3

```
atgtctaatg acaccactac cacggcttct gccggaacag caacttcttc gcggtttctt      60
tccgtggggg gagttgtgaa cttccgtgaa ctgggcggtt acccatgtga ttctgtccct     120
cctgctcctg cctcaaacgg ctcaccggac aatgcatctg aagcgaccct tgggttggc     180
cactcgtcca ttcggcctgg atttctgttt cgatcggcac agccgtctca gattaccccg     240
gccggtattg agacattgat ccgccagctt ggcatccaga caattttga ctttcgttca      300
aggacggaaa ttgagcttgt tgccactcgc tatcctgatt cgctacttga datacctggc     360
acgactcgct attccgtgcc cgtcttctcg gaaggcgact attccccagc gtcattagtc     420
aagaggtacg gagtgtcctc cgatactgca accgattcca cttcctccaa agtgctaag      480
cctacaggat tcgtccacgc atatgaggct atcgcacgca gtgcagcaga aaacggcagt     540
tttcgtaaga taacggacca cataatacaa catccggacc ggcctattct gtttcactgt     600
acactgggga aagaccgaac cggtgtgttt gcagcattgt tattgagtct ttgcggggta     660
ccagacgaga cgatagttga agactatgct atgactaccg agggatttgg agcctggcgg     720
gaacatctaa ttcaacgctt gctacaaagg aaggatgcag ctacgcgcga ggatgcagaa     780
tccattattg ccagccccc ggagactatg aaggctttc tagaagatgt ggtagcagcc       840
aagttcgggg gtgctcgaaa ttactttatc cagcactgtg gatttacgga agctgaggtt     900
gataagttaa gccatacact ggccattacg aattga                                936
```

<210> SEQ ID NO 4
<211> LENGTH: 961
<212> TYPE: DNA
<213> ORGANISM: Talaromyces verruculosus

<400> SEQUENCE: 4

```
ggtaccaagg aggtaaaaaa tgagcaatga cacgacgacc accgcgagcg ccggtactgc      60
aacttctagc cgttttctga gcgtcggcgg cgttgtgaat tttcgcgagc tgggtggcta    120
tccatgcgac agcgtgccgc cggctccggc aagcaacggt tcgcctgata atgcgtccga    180
ggcaacgctg tgggttggtc actccagcat tcgtccgggt ttcctgttcc gcagcgcgca    240
gccgagccag attacgccgg cgggtatcga aacgctgatc cgccaactgg catccagac     300
catttttgat ttccgtagcc gtaccgagat cgaactggtg cgacccgtt acccggactc      360
tctgttggaa attccgggca ccacgcgcta ttccgtcccg gttttctccg agggtgacta    420
ttctccggcg agcctggtga agcgctatgg tgttagcagc gataccgcca cggacagcac    480
ctctagcaag agcgcgaagc cgaccggctt cgttcatgca tacgaagcca ttgcgcgcag    540
cgccgctgag aacggtagct tccgtaaaat taccgaccac atcatccagc atcctgatcg    600
tccaattttg ttccactgta ccctgggtaa agaccgtacg ggtgtctttg cggcgctgtt    660
gctgagcctg tgtggtgtgc cggacgaaac catcgtcgaa gattacgcga tgaccaccga    720
aggctttggt gcatggcgtg agcacctgat ccaacgtctg ctgcaacgta agacgctgc      780
aacccgtgaa gatgccgaga gcatcattgc gtcgccgccg gagactatga aagcatttct    840
ggaagatgtt gtggcagcga aatttggtgg cgcgcgtaac tacttcattc aacattgcgg    900
cttcactgaa gctgaagtcg ataagctgag ccacaccctg gcgatcacga actaactcga    960
g                                                                      961
```

<210> SEQ ID NO 5

```
<211> LENGTH: 852
<212> TYPE: DNA
<213> ORGANISM: Aspergillus wentii
<220> FEATURE:
<221> NAME/KEY: CDS
<222> LOCATION: (1)..(852)

<400> SEQUENCE: 5 atg gcg tct gtc cct gct cca ccg ttt gtt cat gtt gaa ggt atg tct      48
Met Ala Ser Val Pro Ala Pro Pro Phe Val His Val Glu Gly Met Ser
1               5                   10                  15 aat ttt cgt agc atc ggt ggc tac ccg ctg gag act gcc tcc acg aat      96
Asn Phe Arg Ser Ile Gly Gly Tyr Pro Leu Glu Thr Ala Ser Thr Asn
            20                  25                  30 aac cat cgc tcg acc cgt caa ggc ttc gcg ttt cgt agc gcg gac ccg     144
Asn His Arg Ser Thr Arg Gln Gly Phe Ala Phe Arg Ser Ala Asp Pro
        35                  40                  45 acg tat gtg acg cag aaa ggc ctg gaa acc att ctg tcc ctg gat att     192
Thr Tyr Val Thr Gln Lys Gly Leu Glu Thr Ile Leu Ser Leu Asp Ile
    50                  55                  60 acc cgc gca ttt gac ttg cgt agc ttg gaa gaa gca aag gca caa cgt     240
Thr Arg Ala Phe Asp Leu Arg Ser Leu Glu Glu Ala Lys Ala Gln Arg
65                  70                  75                  80 gcg aag ttg cag gcc gcg agc ggt tgt ctg gat tgc agc att agc caa     288
Ala Lys Leu Gln Ala Ala Ser Gly Cys Leu Asp Cys Ser Ile Ser Gln
                85                  90                  95 cac atg atc cac caa ccg acc ccg ctg ttc ccg gat ggt gac tgg tcc     336
His Met Ile His Gln Pro Thr Pro Leu Phe Pro Asp Gly Asp Trp Ser
            100                 105                 110 ccg gaa gcg gcg ggt gag cgc tac ttg cag tac gca caa gct gag ggt     384
Pro Glu Ala Ala Gly Glu Arg Tyr Leu Gln Tyr Ala Gln Ala Glu Gly
        115                 120                 125 gat ggt atc agc ggt tat gtc gaa gtt tat ggt aat atg ctg gaa gag     432
Asp Gly Ile Ser Gly Tyr Val Glu Val Tyr Gly Asn Met Leu Glu Glu
    130                 135                 140 ggc tgg atg gcg atc cgt gag att ctg ctg cac gtc cgt gac cgc ccg     480
Gly Trp Met Ala Ile Arg Glu Ile Leu Leu His Val Arg Asp Arg Pro
145                 150                 155                 160 acc gaa gca ttc ctg tgc cac tgt tcc gcc ggt aaa gat cgt acg ggt     528
Thr Glu Ala Phe Leu Cys His Cys Ser Ala Gly Lys Asp Arg Thr Gly
                165                 170                 175 atc gtg att gct gtt ctg ctc aaa gtc gcg ggt tgc agc gac gac ctg     576
Ile Val Ile Ala Val Leu Leu Lys Val Ala Gly Cys Ser Asp Asp Leu
            180                 185                 190 gtg tgt cgt gag tac gaa ctg acc gag att ggc ctg gcg cgc cgt aga     624
Val Cys Arg Glu Tyr Glu Leu Thr Glu Ile Gly Leu Ala Arg Arg Arg
        195                 200                 205 gag ttc atc gtt cag cat ctg ctg aag aaa ccg gaa atg aac ggc agc     672
Glu Phe Ile Val Gln His Leu Leu Lys Lys Pro Glu Met Asn Gly Ser
    210                 215                 220 cgt gag ctg gcg gag cgc gtc gca ggc gcc cgt tac gag aac atg aaa     720
Arg Glu Leu Ala Glu Arg Val Ala Gly Ala Arg Tyr Glu Asn Met Lys
225                 230                 235                 240 gaa acc ctg gaa atg gtg cag acc cgt tac cgc ggc atg cgc ggc tat     768
Glu Thr Leu Glu Met Val Gln Thr Arg Tyr Arg Gly Met Arg Gly Tyr
                245                 250                 255 tgc aaa gaa atc tgc ggt ctg acc gac gaa gat ctg agc att atc cag     816
Cys Lys Glu Ile Cys Gly Leu Thr Asp Glu Asp Leu Ser Ile Ile Gln
            260                 265                 270 ggt aac ctg acg agc ccg gag agc ccg att ttc taa                     852
Gly Asn Leu Thr Ser Pro Glu Ser Pro Ile Phe
```

<210> SEQ ID NO 6
<211> LENGTH: 283
<212> TYPE: PRT
<213> ORGANISM: Aspergillus wentii

<400> SEQUENCE: 6

```
Met Ala Ser Val Pro Ala Pro Phe Val His Val Glu Gly Met Ser
1               5                   10                  15

Asn Phe Arg Ser Ile Gly Gly Tyr Pro Leu Glu Thr Ala Ser Thr Asn
            20                  25                  30

Asn His Arg Ser Thr Arg Gln Gly Phe Ala Phe Arg Ser Ala Asp Pro
        35                  40                  45

Thr Tyr Val Thr Gln Lys Gly Leu Glu Thr Ile Leu Ser Leu Asp Ile
    50                  55                  60

Thr Arg Ala Phe Asp Leu Arg Ser Leu Glu Glu Ala Lys Ala Gln Arg
65                  70                  75                  80

Ala Lys Leu Gln Ala Ala Ser Gly Cys Leu Asp Cys Ser Ile Ser Gln
                85                  90                  95

His Met Ile His Gln Pro Thr Pro Leu Phe Pro Asp Gly Asp Trp Ser
            100                 105                 110

Pro Glu Ala Ala Gly Glu Arg Tyr Leu Gln Tyr Ala Gln Ala Glu Gly
        115                 120                 125

Asp Gly Ile Ser Gly Tyr Val Glu Val Tyr Gly Asn Met Leu Glu Glu
    130                 135                 140

Gly Trp Met Ala Ile Arg Glu Ile Leu Leu His Val Arg Asp Arg Pro
145                 150                 155                 160

Thr Glu Ala Phe Leu Cys His Cys Ser Ala Gly Lys Asp Arg Thr Gly
                165                 170                 175

Ile Val Ile Ala Val Leu Leu Lys Val Ala Gly Cys Ser Asp Asp Leu
            180                 185                 190

Val Cys Arg Glu Tyr Glu Leu Thr Glu Ile Gly Leu Ala Arg Arg Arg
        195                 200                 205

Glu Phe Ile Val Gln His Leu Leu Lys Lys Pro Glu Met Asn Gly Ser
    210                 215                 220

Arg Glu Leu Ala Glu Arg Val Ala Gly Ala Arg Tyr Glu Asn Met Lys
225                 230                 235                 240

Glu Thr Leu Glu Met Val Gln Thr Arg Tyr Arg Gly Met Arg Gly Tyr
                245                 250                 255

Cys Lys Glu Ile Cys Gly Leu Thr Asp Glu Asp Leu Ser Ile Ile Gln
            260                 265                 270

Gly Asn Leu Thr Ser Pro Glu Ser Pro Ile Phe
        275                 280
```

<210> SEQ ID NO 7
<211> LENGTH: 852
<212> TYPE: DNA
<213> ORGANISM: Aspergillus wentii

<400> SEQUENCE: 7

```
atggcatctg taccagctcc cccatttgtc cacgtcgaag gaatgagcaa tttccgatcg      60
ataggaggat atccccttga gacagcatcg acaaacaatc accgctccac gaggcaagga     120
ttcgcatttc gcagtgccga tccaacctac gtcacccaga aaggcctgga accatccttt     180
tcgctcgaca tcactcgagc ctttgacctc cgctcactgg aagaagcaaa ggcacagcgc     240
```

-continued

```
gcaaaactcc aggccgcctc aggatgtctc gactgcagca tcagccagca catgatccac    300
cagcccacac ccctatttcc agatggggac tggagtccag aggccgcagg ggagcggtat    360
ctgcagtacg cccaggctga gggagatggg atatcgggct acgtggaggt ctacggaaac    420
atgctcgagg aaggttggat ggcgattcgc gagattctgc ttcatgtccg ggaccggcct    480
acagaggcgt ttctatgcca ttgtagtgca gggaaagatc gtacggggat tgtcattgcg    540
gttttgttga aggttgcagg gtgctcggat gatcttgtgt gcagagagta tgagttgacc    600
gagatcgggt tggctcgacg gagggagttt atcgtgcagc atctgcttaa gaagccggaa    660
atgaatggat cgagggaact ggccgaaaga gtggcggggg ccaggtatga aatatgaag     720 gaaacgctgg agatggtgca aactagatat agagggatga ggggctattg caaggagatt    780
tgcggcttga ccgacgaaga tctatctatt atccagggga acttgactag tccggagagt    840
cctatcttct aa                                                        852

<210> SEQ ID NO 8
<211> LENGTH: 877
<212> TYPE: DNA
<213> ORGANISM: Aspergillus wentii

<400> SEQUENCE: 8
ggtaccaagg aggtaaaaaa tggcgtctgt ccctgctcca ccgtttgttc atgttgaagg     60
tatgtctaat tttcgtagca tcggtggcta cccgctggag actgcctcca cgaataacca    120
tcgctcgacc cgtcaaggct tcgcgtttcg tagcgcggac ccgacgtatg tgacgcagaa    180
aggcctggaa accattctgt ccctggatat tacccgcgca tttgacttgc gtagcttgga    240
agaagcaaag gcacaacgtg cgaagttgca ggccgcgagc ggttgtctgg attgcagcat    300
tagccaacac atgatccacc aaccgacccc gctgttcccg gatggtgact ggtccccgga    360
agcggcgggt gagcgctact tgcagtacgc acaagctgag ggtgatggta tcagcggtta    420
tgtcgaagtt tatggtaata tgctggaaga gggctggatg gcgatccgtg agattctgct    480
gcacgtccgt gaccgcccga ccgaagcatt cctgtgccac tgttccgccg gtaaagatcg    540
tacgggtatc gtgattgctg ttctgctcaa agtcgcgggt tgcagcgacg acctggtgtg    600
tcgtgagtac gaactgaccg agattggcct ggcgcgccgt agagagttca tcgttcagca    660
tctgctgaag aaaccggaaa tgaacggcag ccgtgagctg gcggagcgcg tcgcaggcgc    720
ccgttacgag aacatgaaag aaaccctgga atggtgcag acccgttacc gcggcatgcg     780
cggctattgc aaagaaatct gcggtctgac cgacgaagat ctgagcatta tccagggtaa    840
cctgacgagc ccggagagcc cgattttcta actcgag                             877

<210> SEQ ID NO 9
<211> LENGTH: 828
<212> TYPE: DNA
<213> ORGANISM: Helicocarpus griseus
<220> FEATURE:
<221> NAME/KEY: CDS
<222> LOCATION: (1)..(828)

<400> SEQUENCE: 9 atg gca tcc cca cca ggt cat ccg ttc gtt caa gtt gaa ggc gtt aat     48
Met Ala Ser Pro Pro Gly His Pro Phe Val Gln Val Glu Gly Val Asn
1               5                   10                  15 aat ttt cgc tct gtg ggt ggc tat ccg att acg cct agc agc gat gcg     96
Asn Phe Arg Ser Val Gly Gly Tyr Pro Ile Thr Pro Ser Ser Asp Ala
            20                  25                  30
```

| | | |
|---|---|---|
| cgc ttc acg cgt gac aac ttt atc tac cgt agc gct gat ccg tgt tac<br>Arg Phe Thr Arg Asp Asn Phe Ile Tyr Arg Ser Ala Asp Pro Cys Tyr<br>35 40 45 | | 144 |
| att act ccg gaa ggc cgt agc aag att cgc agc ctg ggt atc acc acc<br>Ile Thr Pro Glu Gly Arg Ser Lys Ile Arg Ser Leu Gly Ile Thr Thr<br>50 55 60 | | 192 |
| gtg ttc gat ctg cgt agc cag ccg gag gtt gac aag caa ctg gcg aaa<br>Val Phe Asp Leu Arg Ser Gln Pro Glu Val Asp Lys Gln Leu Ala Lys<br>65 70 75 80 | | 240 |
| gac ccg agc agc ggt gtg ccg att gcg gat ggt gtc att cgt cgc ttc<br>Asp Pro Ser Ser Gly Val Pro Ile Ala Asp Gly Val Ile Arg Arg Phe<br>85 90 95 | | 288 |
| acc ccg gtt ttt agc cgc gag gat tgg ggt ccg gaa gca tcc gcg gtt<br>Thr Pro Val Phe Ser Arg Glu Asp Trp Gly Pro Glu Ala Ser Ala Val<br>100 105 110 | | 336 |
| cgt cac aac ctg tat gca gac gcg tcc ggt gct agc ggt tac gtc gat<br>Arg His Asn Leu Tyr Ala Asp Ala Ser Gly Ala Ser Gly Tyr Val Asp<br>115 120 125 | | 384 |
| gtg tac gcg gat atc ctg gaa aac ggt ggc gca gcg ttc cgt gag atc<br>Val Tyr Ala Asp Ile Leu Glu Asn Gly Gly Ala Ala Phe Arg Glu Ile<br>130 135 140 | | 432 |
| ctg ctg cac gtg cgt gac cgt ccg ggt gac gct ctg ttg tgc cac tgc<br>Leu Leu His Val Arg Asp Arg Pro Gly Asp Ala Leu Leu Cys His Cys<br>145 150 155 160 | | 480 |
| tcc gca ggc aaa gac cgt acc ggc gtt gcg att gcg atc ctg ctc aaa<br>Ser Ala Gly Lys Asp Arg Thr Gly Val Ala Ile Ala Ile Leu Leu Lys<br>165 170 175 | | 528 |
| ctg gcc ggt tgc gaa gat gag tgc att tcg aaa gag tat gaa ctg acc<br>Leu Ala Gly Cys Glu Asp Glu Cys Ile Ser Lys Glu Tyr Glu Leu Thr<br>180 185 190 | | 576 |
| gag gtc ggt ctg gcc agc cgt aaa gaa ttt att atc gag tac ctg att<br>Glu Val Gly Leu Ala Ser Arg Lys Glu Phe Ile Ile Glu Tyr Leu Ile<br>195 200 205 | | 624 |
| aag caa cct gag ctg gaa ggc gac cgt gcg aaa gcc gag aaa att gct<br>Lys Gln Pro Glu Leu Glu Gly Asp Arg Ala Lys Ala Glu Lys Ile Ala<br>210 215 220 | | 672 |
| ggc gcg aaa tac gaa aac atg ttg ggt acg ctg cag atg atg gaa cag<br>Gly Ala Lys Tyr Glu Asn Met Leu Gly Thr Leu Gln Met Met Glu Gln<br>225 230 235 240 | | 720 |
| aaa tat ggt ggc gtt gag ggc tac gtg aag gcc tac tgt aag ttg acg<br>Lys Tyr Gly Gly Val Glu Gly Tyr Val Lys Ala Tyr Cys Lys Leu Thr<br>245 250 255 | | 768 |
| gat aaa gac atc gca acc atc cgt cgc aat ctg gtc agc ggt gac aag<br>Asp Lys Asp Ile Ala Thr Ile Arg Arg Asn Leu Val Ser Gly Asp Lys<br>260 265 270 | | 816 |
| atg att gcg taa<br>Met Ile Ala<br>275 | | 828 |

<210> SEQ ID NO 10
<211> LENGTH: 275
<212> TYPE: PRT
<213> ORGANISM: Helicocarpus griseus

<400> SEQUENCE: 10

Met Ala Ser Pro Pro Gly His Pro Phe Val Gln Val Glu Gly Val Asn
1               5                   10                  15

Asn Phe Arg Ser Val Gly Gly Tyr Pro Ile Thr Pro Ser Ser Asp Ala
            20                  25                  30

```
Arg Phe Thr Arg Asp Asn Phe Ile Tyr Arg Ser Ala Asp Pro Cys Tyr
             35                  40                  45

Ile Thr Pro Glu Gly Arg Ser Lys Ile Arg Ser Leu Gly Ile Thr Thr
 50                  55                  60

Val Phe Asp Leu Arg Ser Gln Pro Glu Val Asp Lys Gln Leu Ala Lys
 65                  70                  75                  80

Asp Pro Ser Ser Gly Val Pro Ile Ala Asp Gly Val Ile Arg Arg Phe
                 85                  90                  95

Thr Pro Val Phe Ser Arg Glu Asp Trp Gly Pro Glu Ala Ser Ala Val
            100                 105                 110

Arg His Asn Leu Tyr Ala Asp Ala Ser Gly Ala Ser Gly Tyr Val Asp
            115                 120                 125

Val Tyr Ala Asp Ile Leu Glu Asn Gly Gly Ala Ala Phe Arg Glu Ile
130                 135                 140

Leu Leu His Val Arg Asp Arg Pro Gly Asp Ala Leu Leu Cys His Cys
145                 150                 155                 160

Ser Ala Gly Lys Asp Arg Thr Gly Val Ala Ile Ala Ile Leu Leu Lys
                165                 170                 175

Leu Ala Gly Cys Glu Asp Glu Cys Ile Ser Lys Glu Tyr Glu Leu Thr
            180                 185                 190

Glu Val Gly Leu Ala Ser Arg Lys Glu Phe Ile Ile Glu Tyr Leu Ile
            195                 200                 205

Lys Gln Pro Glu Leu Glu Gly Asp Arg Ala Lys Ala Glu Lys Ile Ala
            210                 215                 220

Gly Ala Lys Tyr Glu Asn Met Leu Gly Thr Leu Gln Met Met Glu Gln
225                 230                 235                 240

Lys Tyr Gly Gly Val Glu Gly Tyr Val Lys Ala Tyr Cys Lys Leu Thr
                245                 250                 255

Asp Lys Asp Ile Ala Thr Ile Arg Arg Asn Leu Val Ser Gly Asp Lys
            260                 265                 270

Met Ile Ala
        275

<210> SEQ ID NO 11
<211> LENGTH: 828
<212> TYPE: DNA
<213> ORGANISM: Helicocarpus griseus

<400> SEQUENCE: 11
atggcatcac ccccagggca ccctttcgtg caagttgaag cgtcaacaa cttccgctct      60 gtaggaggat atcccatcac cccatcctcc gacgcacgct tcacacgaga taacttcatc    120
tatcgcagcg ccgacccgtg ttacatcacg cccgaaggac gctccaaaat ccgctcactc    180
ggaatcacga ctgtttttga tctgcgctcc cagccagagg ttgacaagca gcttgccaaa    240
gacccttcct caggggttcc aatcgccgac ggcgtcatta acgtttttac gccggtatttt   300 tcccgagagg attgggtcc ggaagcttcc gccgtccgcc ataatctgta tgctgatgcc     360
tctgggcttt ctgggtacgt cgatgtgtat gccgacattc tggagaatgg aggggcggca    420
ttccgcgaga tcttgttgca cgtaagagac cggcctggtg atgcgctgct atgtcattgt    480
agtgccggaa aagatcgtac cggcgtggcg atagcgatac tgctcaagct tgcggggtgc    540
gaggatgaat gtatctcaaa ggagtacgag ctgaccgagg ttggtctagc ctcaagaaag    600
gagttcatta tagagtacct catcaagcag ccggaactag aggggggatag agcaaaagct   660 gaaaaaattg cgggagccaa atatgagaac atgttaggga ccttgcaaat gatggaacag    720
```

-continued

```
aaatacgggg gtgttgaggg gtacgtgaaa gcgtattgca agttgacgga taaagatatt    780
gctacgatac gcaggaatct cgtctcaggt gacaaaatga ttgcctag                828
```

<210> SEQ ID NO 12
<211> LENGTH: 807
<212> TYPE: DNA
<213> ORGANISM: Umbilicaria pustulata
<220> FEATURE:
<221> NAME/KEY: CDS
<222> LOCATION: (1)..(807)

<400> SEQUENCE: 12

```
atg tcc ctg ctg cct agc cca ccg ttt gtt cca gtt gaa ggt att cac      48
Met Ser Leu Leu Pro Ser Pro Pro Phe Val Pro Val Glu Gly Ile His
1               5                   10                  15 aat ttt cgc gat ctg ggc ggc tat ccg gtt agc acc agc ccg agc aag      96
Asn Phe Arg Asp Leu Gly Gly Tyr Pro Val Ser Thr Ser Pro Ser Lys
            20                  25                  30 acc att cgt cgc aat atc atc ttt cgt tgt gcc gaa ccg tcg aaa atc     144
Thr Ile Arg Arg Asn Ile Ile Phe Arg Cys Ala Glu Pro Ser Lys Ile
        35                  40                  45 acc ccg aac ggc att caa acg ctg cag agc ctg ggt gtg gcg acg ttc     192
Thr Pro Asn Gly Ile Gln Thr Leu Gln Ser Leu Gly Val Ala Thr Phe
    50                  55                  60 ttt gac ctc cgt agc ggt ccg gaa atc gag aaa atg aaa gcg cat gca     240
Phe Asp Leu Arg Ser Gly Pro Glu Ile Glu Lys Met Lys Ala His Ala
65                  70                  75                  80 ccg gtc gtt gag atc aag ggt att gag cgt gtt ttc gtg ccg gtg ttc     288
Pro Val Val Glu Ile Lys Gly Ile Glu Arg Val Phe Val Pro Val Phe
                85                  90                  95 gcg gat ggt gat tat agc ccg gaa caa att gcg ctg cgt tac aaa gac     336
Ala Asp Gly Asp Tyr Ser Pro Glu Gln Ile Ala Leu Arg Tyr Lys Asp
            100                 105                 110 tat gcg tcc tct ggc act ggt ggc ttc acc cgt gcg tac cac gac att     384
Tyr Ala Ser Ser Gly Thr Gly Gly Phe Thr Arg Ala Tyr His Asp Ile
        115                 120                 125 ctg cgt tct gcc cct ccg agc tat cgt cgt atc ctg ctg cac ctg gca     432
Leu Arg Ser Ala Pro Pro Ser Tyr Arg Arg Ile Leu Leu His Leu Ala
    130                 135                 140 gag aag ccg aac cag ccg tgc gtg atc cac tgt acc gct ggc aaa gac     480
Glu Lys Pro Asn Gln Pro Cys Val Ile His Cys Thr Ala Gly Lys Asp
145                 150                 155                 160 cgc acg ggt gtt ctg gca gcg ctg att ctg gaa ctg gcg ggt gtc gat     528
Arg Thr Gly Val Leu Ala Ala Leu Ile Leu Glu Leu Ala Gly Val Asp
                165                 170                 175 caa gac acc atc gcg cat gag tac gcc ctg acc gag ctg ggc ctg aag     576
Gln Asp Thr Ile Ala His Glu Tyr Ala Leu Thr Glu Leu Gly Leu Lys
            180                 185                 190 gca tgg cgt ccg acg gtt gtc gag cac tta ctg cag aat ccg gcg ctg     624
Ala Trp Arg Pro Thr Val Val Glu His Leu Leu Gln Asn Pro Ala Leu
        195                 200                 205 gaa ggc aat cgc gag ggt gca ttg aat atg gtc agc gct cgt gcg gag     672
Glu Gly Asn Arg Glu Gly Ala Leu Asn Met Val Ser Ala Arg Ala Glu
    210                 215                 220 aac atg ctg gcc gcc ttg gaa atg att cgc gag atc tac ggt ggt gct     720
Asn Met Leu Ala Ala Leu Glu Met Ile Arg Glu Ile Tyr Gly Gly Ala
225                 230                 235                 240 gag gcg tac gtg aaa gaa aag tgc ggt ctg agc gac gaa gat att gca     768
Glu Ala Tyr Val Lys Glu Lys Cys Gly Leu Ser Asp Glu Asp Ile Ala
                245                 250                 255
```

```
cgc att cgc cag aac att ttg cat acg ccg agc ccg taa              807
Arg Ile Arg Gln Asn Ile Leu His Thr Pro Ser Pro
        260                 265
```

<210> SEQ ID NO 13
<211> LENGTH: 268
<212> TYPE: PRT
<213> ORGANISM: Umbilicaria pustulata

<400> SEQUENCE: 13

```
Met Ser Leu Leu Pro Ser Pro Phe Val Pro Val Glu Gly Ile His
1               5                   10                  15

Asn Phe Arg Asp Leu Gly Gly Tyr Pro Val Ser Thr Ser Pro Ser Lys
                20                  25                  30

Thr Ile Arg Arg Asn Ile Ile Phe Arg Cys Ala Glu Pro Ser Lys Ile
            35                  40                  45

Thr Pro Asn Gly Ile Gln Thr Leu Gln Ser Leu Gly Val Ala Thr Phe
        50                  55                  60

Phe Asp Leu Arg Ser Gly Pro Glu Ile Glu Lys Met Lys Ala His Ala
65                  70                  75                  80

Pro Val Val Glu Ile Lys Gly Ile Glu Arg Val Phe Pro Val Phe
                85                  90                  95

Ala Asp Gly Asp Tyr Ser Pro Glu Gln Ile Ala Leu Arg Tyr Lys Asp
            100                 105                 110

Tyr Ala Ser Ser Gly Thr Gly Gly Phe Thr Arg Ala Tyr His Asp Ile
        115                 120                 125

Leu Arg Ser Ala Pro Pro Ser Tyr Arg Arg Ile Leu Leu His Leu Ala
    130                 135                 140

Glu Lys Pro Asn Gln Pro Cys Val Ile His Cys Thr Ala Gly Lys Asp
145                 150                 155                 160

Arg Thr Gly Val Leu Ala Ala Leu Ile Leu Glu Leu Ala Gly Val Asp
                165                 170                 175

Gln Asp Thr Ile Ala His Glu Tyr Ala Leu Thr Glu Leu Gly Leu Lys
            180                 185                 190

Ala Trp Arg Pro Thr Val Val Glu His Leu Leu Gln Asn Pro Ala Leu
        195                 200                 205

Glu Gly Asn Arg Glu Gly Ala Leu Asn Met Val Ser Ala Arg Ala Glu
    210                 215                 220

Asn Met Leu Ala Ala Leu Glu Met Ile Arg Glu Ile Tyr Gly Gly Ala
225                 230                 235                 240

Glu Ala Tyr Val Lys Glu Lys Cys Gly Leu Ser Asp Glu Asp Ile Ala
                245                 250                 255

Arg Ile Arg Gln Asn Ile Leu His Thr Pro Ser Pro
            260                 265
```

<210> SEQ ID NO 14
<211> LENGTH: 807
<212> TYPE: DNA
<213> ORGANISM: Umbilicaria pustulata

<400> SEQUENCE: 14

```
atgtctctgc taccgtcacc tcccttcgta cccgttgagg gtatccacaa cttccgggac    60
ctaggcggct accccgtctc gacttcccct tccaagacca tacgtcgcaa catcatcttt   120
cgctgcgccg aaccctcgaa aatcactccc aatggcatcc agacgctcca atctttgggc   180
gtcgctacgt tcttcgacct ccgctccggc ccggaaatcg agaagatgaa agcacatgca   240
```

```
cctgtcgtcg agattaaggg catcgagcgt gtgttcgttc ccgtcttcgc cgacggggat      300
tactcgcccg aacaaatcgc tctgcgatac aaagactacg cttccagcgg aacgggggt       360 tttaccaggg cgtaccatga tatcctccga agtgcccctc cgagctatcg gcgcatacta     420
ttacatctgg cggagaagcc caaccagcca tgcgtcattc attgcacggc cgggaaagat    480
aggacgggcg tattggcggc gttgatactc gagttggccg gggttgatca ggatacaatt    540
gcgcacgagt acgcattgac ggaactgggg ttgaaggcct gcgtcccac tgtggtggag     600 cacctcttgc agaatccagc gttggaggga atcgggaag gggcattgaa catggtcagc     660
gcgagggcag agaacatgct ggcagccttg gagatgatcc gggagatcta tggcggcgcc    720
gaagcatatg tgaaggagaa gtgtggcctc agcgacgaag acattgcgcg gatacggcag    780
aatattctac acacgccatc tccgtga                                         807
```

<210> SEQ ID NO 15
<211> LENGTH: 858
<212> TYPE: DNA
<213> ORGANISM: Talaromyces verruculosus
<220> FEATURE:
<221> NAME/KEY: CDS
<222> LOCATION: (1)..(858)

<400> SEQUENCE: 15

```
atg tct gtc acc gaa cat gtt gtc gaa gct agc acc ccg tcc act ctg       48
Met Ser Val Thr Glu His Val Val Glu Ala Ser Thr Pro Ser Thr Leu
1               5                   10                  15 ccg cca ccg ttc att cac gtg gac ggt gtt ccg aac ttc cgt gac att       96
Pro Pro Pro Phe Ile His Val Asp Gly Val Pro Asn Phe Arg Asp Ile
                20                  25                  30 ggt ggc tat ccg att acc gat ctg ctg agc acc cgt cgc aat ttc gtt      144
Gly Gly Tyr Pro Ile Thr Asp Leu Leu Ser Thr Arg Arg Asn Phe Val
            35                  40                  45 tat cgc tcc gca gtt cct acc cgc atc acc cca acg ggc ctg cag acg      192
Tyr Arg Ser Ala Val Pro Thr Arg Ile Thr Pro Thr Gly Leu Gln Thr
50                  55                  60 ctg acc caa gat ctg cag att acg acg gtc tac gac tta cgt tcg aat      240
Leu Thr Gln Asp Leu Gln Ile Thr Thr Val Tyr Asp Leu Arg Ser Asn
65                  70                  75                  80 gct gag ctg cgt aaa gat cct atc gcg agc agc ccg ttg gac acc cac      288
Ala Glu Leu Arg Lys Asp Pro Ile Ala Ser Ser Pro Leu Asp Thr His
                85                  90                  95 gac agc gtg act gtc ctg cat acc ccg gtt ttc ccg gag cgc gat tct      336
Asp Ser Val Thr Val Leu His Thr Pro Val Phe Pro Glu Arg Asp Ser
            100                 105                 110 agc ccg gaa cag ctg gca aag cgt ttt gcc aac tat atg agc gcg aac      384
Ser Pro Glu Gln Leu Ala Lys Arg Phe Ala Asn Tyr Met Ser Ala Asn
        115                 120                 125 ggt tcc gag ggt ttc gtt gcg gcg tac gca gag att ctg cgt gat ggt      432
Gly Ser Glu Gly Phe Val Ala Ala Tyr Ala Glu Ile Leu Arg Asp Gly
    130                 135                 140 gtg gat gcc tac cgc aag gtt ttt gaa cac gtg cgt gac cgt ccg cgt      480
Val Asp Ala Tyr Arg Lys Val Phe Glu His Val Arg Asp Arg Pro Arg
145                 150                 155                 160 gat gcg ttt ctg gtg cac tgc acc ggt ggc aaa gac cgt acg ggt gtg      528
Asp Ala Phe Leu Val His Cys Thr Gly Gly Lys Asp Arg Thr Gly Val
                165                 170                 175 ttg gtt gcg ctg atg ctg ttg gtg gca ggc gtc aaa gac cgt gac gtt      576
Leu Val Ala Leu Met Leu Leu Val Ala Gly Val Lys Asp Arg Asp Val
            180                 185                 190
```

```
att gcc gat gag tac agc ctg acg gaa aag ggt ttt gcg gct gtc atc      624
Ile Ala Asp Glu Tyr Ser Leu Thr Glu Lys Gly Phe Ala Ala Val Ile
            195                 200                 205 aaa gcc gat gct gcg gaa aag atc atc aaa gac atg ggt gtt gac ggt      672
Lys Ala Asp Ala Ala Glu Lys Ile Ile Lys Asp Met Gly Val Asp Gly
210                 215                 220 gcc aat cgt gcg ggc atc gag cgt ctg ttg agc gca cgc aaa gaa aac      720
Ala Asn Arg Ala Gly Ile Glu Arg Leu Leu Ser Ala Arg Lys Glu Asn
225                 230                 235                 240 atg agc gcg acc ctg gag tac att gag aag caa ttt ggt ggc gca gag      768
Met Ser Ala Thr Leu Glu Tyr Ile Glu Lys Gln Phe Gly Gly Ala Glu
            245                 250                 255 ggc tat ctg cgc gac caa ctg ggt ttc ggc gac gaa gat gtg gaa cag      816
Gly Tyr Leu Arg Asp Gln Leu Gly Phe Gly Asp Glu Asp Val Glu Gln
            260                 265                 270 atc cgt aag agc ctg gtc gtt gag gat aaa ggc ctg ttc taa              858
Ile Arg Lys Ser Leu Val Val Glu Asp Lys Gly Leu Phe
            275                 280                 285

<210> SEQ ID NO 16
<211> LENGTH: 285
<212> TYPE: PRT
<213> ORGANISM: Talaromyces verruculosus

<400> SEQUENCE: 16

Met Ser Val Thr Glu His Val Val Glu Ala Ser Thr Pro Ser Thr Leu
1               5                   10                  15

Pro Pro Pro Phe Ile His Val Asp Gly Val Pro Asn Phe Arg Asp Ile
            20                  25                  30

Gly Gly Tyr Pro Ile Thr Asp Leu Leu Ser Thr Arg Arg Asn Phe Val
        35                  40                  45

Tyr Arg Ser Ala Val Pro Thr Arg Ile Thr Pro Thr Gly Leu Gln Thr
    50                  55                  60

Leu Thr Gln Asp Leu Gln Ile Thr Thr Val Tyr Asp Leu Arg Ser Asn
65                  70                  75                  80

Ala Glu Leu Arg Lys Asp Pro Ile Ala Ser Ser Pro Leu Asp Thr His
                85                  90                  95

Asp Ser Val Thr Val Leu His Thr Pro Val Phe Pro Glu Arg Asp Ser
            100                 105                 110

Ser Pro Glu Gln Leu Ala Lys Arg Phe Ala Asn Tyr Met Ser Ala Asn
        115                 120                 125

Gly Ser Glu Gly Phe Val Ala Ala Tyr Ala Glu Ile Leu Arg Asp Gly
    130                 135                 140

Val Asp Ala Tyr Arg Lys Val Phe Glu His Val Arg Asp Arg Pro Arg
145                 150                 155                 160

Asp Ala Phe Leu Val His Cys Thr Gly Gly Lys Asp Arg Thr Gly Val
                165                 170                 175

Leu Val Ala Leu Met Leu Leu Val Ala Gly Val Lys Asp Arg Asp Val
            180                 185                 190

Ile Ala Asp Glu Tyr Ser Leu Thr Glu Lys Gly Phe Ala Ala Val Ile
        195                 200                 205

Lys Ala Asp Ala Ala Glu Lys Ile Ile Lys Asp Met Gly Val Asp Gly
    210                 215                 220

Ala Asn Arg Ala Gly Ile Glu Arg Leu Leu Ser Ala Arg Lys Glu Asn
225                 230                 235                 240

Met Ser Ala Thr Leu Glu Tyr Ile Glu Lys Gln Phe Gly Gly Ala Glu
```

```
                  245                 250                 255
Gly Tyr Leu Arg Asp Gln Leu Gly Phe Gly Asp Glu Asp Val Glu Gln
            260                 265                 270

Ile Arg Lys Ser Leu Val Val Glu Asp Lys Gly Leu Phe
        275                 280                 285

<210> SEQ ID NO 17
<211> LENGTH: 858
<212> TYPE: DNA
<213> ORGANISM: Talaromyces verruculosus

<400> SEQUENCE: 17
atgagcgtca cagaacatgt agtcgaagcc tcgacaccat caaccettcc accaccettc      60 atccatgtcg acggcgtccc caacttccgc gacatcggcg gctacccat cacagactta     120 ctgtcaacac gacgaaactt cgtgtatcgc tccgcagtcc caacacgcat cactcccaca     180
ggtctacaga cactcaccca agacctccaa atcacaacag tctacgacct acgctccaac     240
gctgaactgc gcaaggatcc cattgcctcc agccctctag acacccatga ctctgtaacg     300
gtgctacaca cccccgtctt tcccgaacgg gactcaagtc ccgaacaact cgcaaagagg     360
tttgcgaatt acatgtccgc caacggctcg aagggtttg tagccgccta cgccgagatt      420
ttgcgtgatg gcgttgatgc ataccgcaag gtgtttgagc atgtccgtga tcggccccgg     480
gatgcgtttt tggtgcattg tactggtggg aaggatagaa cgggtgtcct tgtagcgctc     540
atgttacttg ttgcgggtgt caaggataga gatgtgattg ccgacgagta ctcgttgacg     600
gagaaggggt tgctgctgt tattaaggcg gatgcggcgg agaagattat aaaggatatg      660
ggagtggatg gggcgaatag ggcgggcatt gagagattgc tgtcggcgag gaggagaat      720 atgagtgcta cgttggagta tatcgagaaa cagtttggtg gggcggaggg ttatttgagg     780
gatcagttag ggtttggtga tgaggatgtt gagcagatta ggaagagtct tgtcgtggag     840
gataagggtt tattttag                                                   858

<210> SEQ ID NO 18
<211> LENGTH: 852
<212> TYPE: DNA
<213> ORGANISM: Hydnomerulius pinastri
<220> FEATURE:
<221> NAME/KEY: CDS
<222> LOCATION: (1)..(852)

<400> SEQUENCE: 18 atg act gca acc gac aat ggc tta gaa ccg ctg gac cct gca tac gtt      48
Met Thr Ala Thr Asp Asn Gly Leu Glu Pro Leu Asp Pro Ala Tyr Val
 1               5                  10                  15 gct gat gtg ttg agc cgt ccg ccg ttt gtc cag atc tcc ggc gtg tgt      96
Ala Asp Val Leu Ser Arg Pro Pro Phe Val Gln Ile Ser Gly Val Cys
             20                  25                  30 aac gtc aga gat ctg ggc agc tat ccg acc gct acc ccg aat gtg att     144
Asn Val Arg Asp Leu Gly Ser Tyr Pro Thr Ala Thr Pro Asn Val Ile
         35                  40                  45 acc aag cct ggt tat gca tac cgt ggt gcc gaa gtt tcc aat atc acc     192
Thr Lys Pro Gly Tyr Ala Tyr Arg Gly Ala Glu Val Ser Asn Ile Thr
     50                  55                  60 gaa gag ggc agc caa caa atg aaa gca ctg ggt att acc acg atc ttt     240
Glu Glu Gly Ser Gln Gln Met Lys Ala Leu Gly Ile Thr Thr Ile Phe
 65                  70                  75                  80 gat ctg cgt tct gac cca gag atg cag aag tac agc acg ccg att ccg     288
Asp Leu Arg Ser Asp Pro Glu Met Gln Lys Tyr Ser Thr Pro Ile Pro
```

| | | |
|---|---|---|
| cat atc gag ggt gtc ctg att ctg cgt acc ccg gtg ttc gcc acc gag<br>His Ile Glu Gly Val Leu Ile Leu Arg Thr Pro Val Phe Ala Thr Glu<br>100 105 110 | | 336 |
| gac tat agc ccg gag tcg atg gcg aag cgt ttt gag ctg tac gcg tct<br>Asp Tyr Ser Pro Glu Ser Met Ala Lys Arg Phe Glu Leu Tyr Ala Ser<br>115 120 125 | | 384 |
| ggt acg acc gaa gca ttc atg aag ctg tat agc cag att ctg gac cac<br>Gly Thr Thr Glu Ala Phe Met Lys Leu Tyr Ser Gln Ile Leu Asp His<br>130 135 140 | | 432 |
| ggc ggc aaa gcg ttc ggt act att ctg cgt cat gtt cgt gac cgc ccg<br>Gly Gly Lys Ala Phe Gly Thr Ile Leu Arg His Val Arg Asp Arg Pro<br>145 150 155 160 | | 480 |
| aac agc gtt ttt ctg ttt cac tgc acg gcc ggt aaa gat cgc acg ggc<br>Asn Ser Val Phe Leu Phe His Cys Thr Ala Gly Lys Asp Arg Thr Gly<br>165 170 175 | | 528 |
| att att gcg gcc atc ctg ttc aaa ttg gcg ggt gtg gat gat cac ttg<br>Ile Ile Ala Ala Ile Leu Phe Lys Leu Ala Gly Val Asp Asp His Leu<br>180 185 190 | | 576 |
| atc tgt cag gac tac agc ctg acg cgc atc ggt cgt gag cca gac cgt<br>Ile Cys Gln Asp Tyr Ser Leu Thr Arg Ile Gly Arg Glu Pro Asp Arg<br>195 200 205 | | 624 |
| gaa aaa gtt ctg cgc cgt ctg ctg aat gaa ccg ctg ttc gcg gcg aat<br>Glu Lys Val Leu Arg Arg Leu Leu Asn Glu Pro Leu Phe Ala Ala Asn<br>210 215 220 | | 672 |
| acc gag ctt gcg ctg cgc atg ttg acg agc cgc tac gaa acc atg caa<br>Thr Glu Leu Ala Leu Arg Met Leu Thr Ser Arg Tyr Glu Thr Met Gln<br>225 230 235 240 | | 720 |
| gcg acc ctg ggt ctg ttg agc gac aaa tat ggc ggt gtg gaa gca tac<br>Ala Thr Leu Gly Leu Leu Ser Asp Lys Tyr Gly Gly Val Glu Ala Tyr<br>245 250 255 | | 768 |
| gtc aag aac ttc tgc ggt ctg acc gat aac gac atc agc gtt atc cgt<br>Val Lys Asn Phe Cys Gly Leu Thr Asp Asn Asp Ile Ser Val Ile Arg<br>260 265 270 | | 816 |
| acc aac ctg gtt gtg ccg acg aaa gcg cgt atg taa<br>Thr Asn Leu Val Val Pro Thr Lys Ala Arg Met<br>275 280 | | 852 |

<210> SEQ ID NO 19
<211> LENGTH: 283
<212> TYPE: PRT
<213> ORGANISM: Hydnomerulius pinastri

<400> SEQUENCE: 19

Met Thr Ala Thr Asp Asn Gly Leu Glu Pro Leu Asp Pro Ala Tyr Val
1               5                   10                  15

Ala Asp Val Leu Ser Arg Pro Pro Phe Val Gln Ile Ser Gly Val Cys
                20                  25                  30

Asn Val Arg Asp Leu Gly Ser Tyr Pro Thr Ala Thr Pro Asn Val Ile
            35                  40                  45

Thr Lys Pro Gly Tyr Ala Tyr Arg Gly Ala Glu Val Ser Asn Ile Thr
        50                  55                  60

Glu Glu Gly Ser Gln Gln Met Lys Ala Leu Gly Ile Thr Thr Ile Phe
65                  70                  75                  80

Asp Leu Arg Ser Asp Pro Glu Met Gln Lys Tyr Ser Thr Pro Ile Pro
                85                  90                  95

His Ile Glu Gly Val Leu Ile Leu Arg Thr Pro Val Phe Ala Thr Glu
            100                 105                 110

```
Asp Tyr Ser Pro Glu Ser Met Ala Lys Arg Phe Glu Leu Tyr Ala Ser
            115                 120                 125

Gly Thr Thr Glu Ala Phe Met Lys Leu Tyr Ser Gln Ile Leu Asp His
        130                 135                 140

Gly Gly Lys Ala Phe Gly Thr Ile Leu Arg His Val Arg Asp Arg Pro
145                 150                 155                 160

Asn Ser Val Phe Leu Phe His Cys Thr Ala Gly Lys Asp Arg Thr Gly
                165                 170                 175

Ile Ile Ala Ala Ile Leu Phe Lys Leu Ala Gly Val Asp His Leu
                180                 185                 190

Ile Cys Gln Asp Tyr Ser Leu Thr Arg Ile Gly Arg Glu Pro Asp Arg
        195                 200                 205

Glu Lys Val Leu Arg Arg Leu Leu Asn Glu Pro Leu Phe Ala Ala Asn
    210                 215                 220

Thr Glu Leu Ala Leu Arg Met Leu Thr Ser Arg Tyr Glu Thr Met Gln
225                 230                 235                 240

Ala Thr Leu Gly Leu Leu Ser Asp Lys Tyr Gly Gly Val Glu Ala Tyr
                245                 250                 255

Val Lys Asn Phe Cys Gly Leu Thr Asp Asn Asp Ile Ser Val Ile Arg
                260                 265                 270

Thr Asn Leu Val Val Pro Thr Lys Ala Arg Met
            275                 280
```

<210> SEQ ID NO 20
<211> LENGTH: 852
<212> TYPE: DNA
<213> ORGANISM: Hydnomerulius pinastri

<400> SEQUENCE: 20

```
atgaccgcaa cagacaacgg actagaaccc ttagaccctg catatgtcgc agatgtgctc      60
tcaagaccac cattcgtaca aatatctggt gtttgcaacg tccgtgatct aggatcctac     120
cctaccgcca ctcccaatgt cataacaaag ccgggatatg cataccgggg cgcagaggtc     180
tctaacatta ccgaagaagg tagccagcaa atgaaggcgc taggcataac gactatattt     240
gatcttagat cggatccaga gatgcagaaa tacagcactc aatacccca cattgaaggc      300
gtactgatat tgcgcacgcc tgtcttcgcg accgaggatt atagtccgga agtatggcc      360
aagagatttg agctatacgc aagtggtact actgaagcat ttatgaaact atactctcaa     420
atactagacc atggaggcaa agccttcgga acaattctcc ggcacgttcg ggacaggcca     480
aattctgtct ttcttttcca ttgcactgcg gggaaagacc ggaccggcat cattgctgca     540
attctgttca agctcgccgg cgtagacgac catctcatat gtcaagatta ctccctcaca     600
cgaataggtc gcgagcctga tcgtgaaaag gtcctccggc gactcttgaa tgaacctcta     660
tttgccgcca acacggaact tgcactacga atgctcacgt ctcgatatga aactatgcaa     720
gcaacgttgg ggcttcttag cgataagtat ggcggggtgg aggcgtatgt gaagaatttc     780
tgtgggctca cggataatga tatatcggtc atacgaacaa atctcgttgt acctacaaag     840
gcgcggatgt ag                                                        852
```

<210> SEQ ID NO 21
<211> LENGTH: 936
<212> TYPE: DNA
<213> ORGANISM: Talaromyces cellulolyticus
<220> FEATURE:
<221> NAME/KEY: CDS
<222> LOCATION: (1)..(936)

<400> SEQUENCE: 21

```
atg agc aac gac acg acc agc acc gca tcc gca ggc acc gca act tct      48
Met Ser Asn Asp Thr Thr Ser Thr Ala Ser Ala Gly Thr Ala Thr Ser
1               5                   10                  15 tcg cgc ttt ctg agc gtc ggt ggc gtg gtt aac ttc cgt gag ttg ggt      96
Ser Arg Phe Leu Ser Val Gly Gly Val Val Asn Phe Arg Glu Leu Gly
            20                  25                  30 ggc tac ccg tgc gac agc gtt cct cct gca cca gca agc aat ggt agc     144
Gly Tyr Pro Cys Asp Ser Val Pro Pro Ala Pro Ala Ser Asn Gly Ser
        35                  40                  45 ccg gac aat gcg agc gaa gcg att ctg tgg gtt ggt cac agc agc att     192
Pro Asp Asn Ala Ser Glu Ala Ile Leu Trp Val Gly His Ser Ser Ile
    50                  55                  60 cgt ccg cgc ttc ttg ttt cgt agc gca cag ccg tcc cag atc acc ccg     240
Arg Pro Arg Phe Leu Phe Arg Ser Ala Gln Pro Ser Gln Ile Thr Pro
65                  70                  75                  80 gcc ggt att gaa acg ctg att cgc caa ctc ggt att caa gcg atc ttt     288
Ala Gly Ile Glu Thr Leu Ile Arg Gln Leu Gly Ile Gln Ala Ile Phe
                85                  90                  95 gac ttt cgt tcc cgt acc gag atc caa ctg gtg gca acc cgc tac cca     336
Asp Phe Arg Ser Arg Thr Glu Ile Gln Leu Val Ala Thr Arg Tyr Pro
            100                 105                 110 gat agc ctg ctg gaa att ccg ggc acg act cgt tac tct gtt ccg gtc     384
Asp Ser Leu Leu Glu Ile Pro Gly Thr Thr Arg Tyr Ser Val Pro Val
        115                 120                 125 ttt acc gag ggc gac tac agc ccg gct tct ctg gtt aag cgt tat ggt     432
Phe Thr Glu Gly Asp Tyr Ser Pro Ala Ser Leu Val Lys Arg Tyr Gly
    130                 135                 140 gtc tct agc gac acg gca acg gat agc acc agc tca aag tgc gcg aaa     480
Val Ser Ser Asp Thr Ala Thr Asp Ser Thr Ser Ser Lys Cys Ala Lys
145                 150                 155                 160 ccg acc ggc ttt gtg cat gct tat gaa gcg att gct cgt tct gcc gcg     528
Pro Thr Gly Phe Val His Ala Tyr Glu Ala Ile Ala Arg Ser Ala Ala
                165                 170                 175 gag aac ggt agc ttc cgc aag atc acc gac cac att atc caa cat ccg     576
Glu Asn Gly Ser Phe Arg Lys Ile Thr Asp His Ile Ile Gln His Pro
            180                 185                 190 gat cgc ccg atc ctg ttt cac tgc acg ctg ggc aaa gac cgt acc ggt     624
Asp Arg Pro Ile Leu Phe His Cys Thr Leu Gly Lys Asp Arg Thr Gly
        195                 200                 205 gtt ttc gca gcg ctg ctg ctg agc ttg tgt ggt gtc ccg aat gac acc     672
Val Phe Ala Ala Leu Leu Leu Ser Leu Cys Gly Val Pro Asn Asp Thr
    210                 215                 220 atc gtg gaa gat tat gcg atg acg acc gaa ggc ttc ggt gtg tgg cgt     720
Ile Val Glu Asp Tyr Ala Met Thr Thr Glu Gly Phe Gly Val Trp Arg
225                 230                 235                 240 gag cac ttg att cag cgt ctg ctg cag cgc aaa gat gcg gct acg cgt     768
Glu His Leu Ile Gln Arg Leu Leu Gln Arg Lys Asp Ala Ala Thr Arg
                245                 250                 255 gaa gat gcc gag ttc att atc gcg agc cat ccg gag agc atg aaa gcg     816
Glu Asp Ala Glu Phe Ile Ile Ala Ser His Pro Glu Ser Met Lys Ala
            260                 265                 270 ttc ctg gaa gat gtc gtt gcg acc aaa ttc ggt gac gcc cgc aac tac     864
Phe Leu Glu Asp Val Val Ala Thr Lys Phe Gly Asp Ala Arg Asn Tyr
        275                 280                 285 ttt atc cag cac tgt ggt ctg acc gaa gcc gaa gtg gat aag ctg atc     912
Phe Ile Gln His Cys Gly Leu Thr Glu Ala Glu Val Asp Lys Leu Ile
    290                 295                 300
```

-continued

```
cgt acg ctg gtg atc gcg aat taa                                        936
Arg Thr Leu Val Ile Ala Asn
305                 310
```

<210> SEQ ID NO 22
<211> LENGTH: 311
<212> TYPE: PRT
<213> ORGANISM: Talaromyces cellulolyticus

<400> SEQUENCE: 22

```
Met Ser Asn Asp Thr Thr Ser Thr Ala Ser Ala Gly Thr Ala Thr Ser
1               5                   10                  15

Ser Arg Phe Leu Ser Val Gly Val Val Asn Phe Arg Glu Leu Gly
            20                  25                  30

Gly Tyr Pro Cys Asp Ser Val Pro Ala Pro Ala Ser Asn Gly Ser
        35                  40                  45

Pro Asp Asn Ala Ser Glu Ala Ile Leu Trp Val Gly His Ser Ser Ile
50                  55                  60

Arg Pro Arg Phe Leu Phe Arg Ser Ala Gln Pro Ser Gln Ile Thr Pro
65                  70                  75                  80

Ala Gly Ile Glu Thr Leu Ile Arg Gln Leu Gly Ile Gln Ala Ile Phe
                85                  90                  95

Asp Phe Arg Ser Arg Thr Glu Ile Gln Leu Val Ala Thr Arg Tyr Pro
            100                 105                 110

Asp Ser Leu Leu Glu Ile Pro Gly Thr Thr Arg Tyr Ser Val Pro Val
        115                 120                 125

Phe Thr Glu Gly Asp Tyr Ser Pro Ala Ser Leu Val Lys Arg Tyr Gly
130                 135                 140

Val Ser Ser Asp Thr Ala Thr Asp Ser Thr Ser Ser Lys Cys Ala Lys
145                 150                 155                 160

Pro Thr Gly Phe Val His Ala Tyr Glu Ala Ile Ala Arg Ser Ala Ala
                165                 170                 175

Glu Asn Gly Ser Phe Arg Lys Ile Thr Asp His Ile Ile Gln His Pro
            180                 185                 190

Asp Arg Pro Ile Leu Phe His Cys Thr Leu Gly Lys Asp Arg Thr Gly
        195                 200                 205

Val Phe Ala Ala Leu Leu Leu Ser Leu Cys Gly Val Pro Asn Asp Thr
210                 215                 220

Ile Val Glu Asp Tyr Ala Met Thr Thr Glu Gly Phe Gly Val Trp Arg
225                 230                 235                 240

Glu His Leu Ile Gln Arg Leu Leu Gln Arg Lys Asp Ala Ala Thr Arg
                245                 250                 255

Glu Asp Ala Glu Phe Ile Ile Ala Ser His Pro Glu Ser Met Lys Ala
            260                 265                 270

Phe Leu Glu Asp Val Val Ala Thr Lys Phe Gly Asp Ala Arg Asn Tyr
        275                 280                 285

Phe Ile Gln His Cys Gly Leu Thr Glu Ala Glu Val Asp Lys Leu Ile
290                 295                 300

Arg Thr Leu Val Ile Ala Asn
305                 310
```

<210> SEQ ID NO 23
<211> LENGTH: 936
<212> TYPE: DNA
<213> ORGANISM: Talaromyces cellulolyticus

<400> SEQUENCE: 23

-continued

```
atgtctaatg acaccactag cacggcttct gccggaacag caacttcttc gcggtttctt      60
tctgtgggcg gagttgtgaa tttccgtgaa ctgggcggtt atccatgtga ttctgtccct     120
cctgctcctg cctcaaacgg ctcaccggac aacgcatctg aagcgatcct ttgggttggc     180
cactcgtcca ttcggcctag gtttctcttt cgatcggcac agccgtctca gattaccccg     240
gccggtattg agacattgat ccgccagctt ggcatccagg caattttga ctttcgttca      300
cggacggaaa ttcagcttgt cgccactcgc tatcctgatt cgctactcga gatacctggt     360
acgactcgct attccgtgcc cgtcttcacg gagggcgact attccccggc gtcattagtc     420
aagaggtacg gagtgtcctc cgatactgca actgattcca cttcctccaa atgtgccaag     480
cctacaggat tcgtccacgc atatgaggct atcgcacgca gcgcagcaga aaacggcagt     540
tttcgtaaaa taacggacca cataatacaa catcccgacc ggcctatcct gtttcactgt     600
acattgggaa aagaccgaac cggtgtattt gcagcattgt tattgagtct ttgcggggta     660
ccaaacgaca cgatagttga agactatgct atgactaccg agggatttgg ggtctggcga     720
gaacatctaa ttcaacgcct gttacaaaga aaggatgcag ctacgcgtga ggatgcagaa     780
ttcattattg ccagccaccc ggagagtatg aaggcttttc tagaagatgt ggtagcaacc     840
aagttcgggg atgctcgaaa ttactttatc cagcactgtg gattgacgga agcggaggtt     900
gataagctaa ttcggacact ggtcattgcg aattga                               936
```

```
<210> SEQ ID NO 24
<211> LENGTH: 990
<212> TYPE: DNA
<213> ORGANISM: Talaromyces marneffei
<220> FEATURE:
<221> NAME/KEY: CDS
<222> LOCATION: (1)..(990)

<400> SEQUENCE: 24
```

```
atg tgg aat ttg cac tat tat att ccg ggc tct gca cca gtt aat ttg        48
Met Trp Asn Leu His Tyr Tyr Ile Pro Gly Ser Ala Pro Val Asn Leu
1               5                   10                  15 aac gac atg ccg aac gat acg gcg acg acg gct tcc gca ggc act agc        96
Asn Asp Met Pro Asn Asp Thr Ala Thr Thr Ala Ser Ala Gly Thr Ser
            20                  25                  30 gcc acg agc cgc ttc ctc tgt gtc agc ggt gtt gcg aac ttc cgt gaa       144
Ala Thr Ser Arg Phe Leu Cys Val Ser Gly Val Ala Asn Phe Arg Glu
        35                  40                  45 ctg ggt ggc tat ccg tgc gac acc gtt cct cca gca ccg gcg agc aat       192
Leu Gly Gly Tyr Pro Cys Asp Thr Val Pro Pro Ala Pro Ala Ser Asn
    50                  55                  60 ggt agc ccg cat aat gca tcc gag gcc acg ctg caa ggt tcc cac tct       240
Gly Ser Pro His Asn Ala Ser Glu Ala Thr Leu Gln Gly Ser His Ser
65                  70                  75                  80 agc att cgt ccg ggc ttc atc ttc cgt agc gcg caa ccg agc cag atc       288
Ser Ile Arg Pro Gly Phe Ile Phe Arg Ser Ala Gln Pro Ser Gln Ile
                85                  90                  95 aat ccg gca ggc atc gcg acg ctg gcg cat gaa ctg tct att caa gtc       336
Asn Pro Ala Gly Ile Ala Thr Leu Ala His Glu Leu Ser Ile Gln Val
            100                 105                 110 atc ttc gac ttc cgt tcg cag acc gag atc cag ctg gtc acc acc cac       384
Ile Phe Asp Phe Arg Ser Gln Thr Glu Ile Gln Leu Val Thr Thr His
        115                 120                 125 tac ccg gat agc ctg ttg gag atc ccg tgt acc acc cgt tac agc gtg       432
Tyr Pro Asp Ser Leu Leu Glu Ile Pro Cys Thr Thr Arg Tyr Ser Val
    130                 135                 140
```

```
ccg gtg ttt aac gag ggt gac tat agc ccg gct tcg ctg gtc aag aaa      480
Pro Val Phe Asn Glu Gly Asp Tyr Ser Pro Ala Ser Leu Val Lys Lys
145                 150                 155                 160 tac ggt gtg agc ccg gac cca gtg acg cat tcc gct agc agc acc agc      528
Tyr Gly Val Ser Pro Asp Pro Val Thr His Ser Ala Ser Ser Thr Ser
                165                 170                 175 gcg aat cct gcc ggc ttt gtg ccg gcc tac gaa gca atc gct cgt agc      576
Ala Asn Pro Ala Gly Phe Val Pro Ala Tyr Glu Ala Ile Ala Arg Ser
            180                 185                 190 gca gcc gaa aac ggt agc ttt cgc aaa atc acc gag cac att att cag      624
Ala Ala Glu Asn Gly Ser Phe Arg Lys Ile Thr Glu His Ile Ile Gln
        195                 200                 205 cac ccg gat cag ccg att ttg ttt cat tgc acc ctg ggt aaa gat cgc      672
His Pro Asp Gln Pro Ile Leu Phe His Cys Thr Leu Gly Lys Asp Arg
    210                 215                 220 acg ggt gtg ttt gcg gcc ctg ctg ctg agc ctg tgc ggt gtt tcc acc      720
Thr Gly Val Phe Ala Ala Leu Leu Leu Ser Leu Cys Gly Val Ser Thr
225                 230                 235                 240 gaa aag atc gtg gaa gat tac gcg atg acc acc gag ggt ttc ggt gct      768
Glu Lys Ile Val Glu Asp Tyr Ala Met Thr Thr Glu Gly Phe Gly Ala
                245                 250                 255 tgg cgt gag cac ctg att aag cgc ctg ctg cag cgt aaa gat gcg gca      816
Trp Arg Glu His Leu Ile Lys Arg Leu Leu Gln Arg Lys Asp Ala Ala
            260                 265                 270 acc cgc caa gac gct gag ttc atc att gcc agc cac ccg gaa acc atg      864
Thr Arg Gln Asp Ala Glu Phe Ile Ile Ala Ser His Pro Glu Thr Met
        275                 280                 285 aaa tct ttt ctg gac gac gtt gtt cgt gcg aag ttt ggc tcc gcg cgt      912
Lys Ser Phe Leu Asp Asp Val Val Arg Ala Lys Phe Gly Ser Ala Arg
    290                 295                 300 aac tat ttc gtg caa cag tgc ggt ctg act gag tac gaa gtt gat aag      960
Asn Tyr Phe Val Gln Gln Cys Gly Leu Thr Glu Tyr Glu Val Asp Lys
305                 310                 315                 320 ctg att cat acg ctg gtc att atc aag taa                              990
Leu Ile His Thr Leu Val Ile Ile Lys
                325
```

<210> SEQ ID NO 25
<211> LENGTH: 329
<212> TYPE: PRT
<213> ORGANISM: Talaromyces marneffei

<400> SEQUENCE: 25

```
Met Trp Asn Leu His Tyr Tyr Ile Pro Gly Ser Ala Pro Val Asn Leu
1               5                   10                  15

Asn Asp Met Pro Asn Asp Thr Ala Thr Thr Ala Ser Ala Gly Thr Ser
                20                  25                  30

Ala Thr Ser Arg Phe Leu Cys Val Ser Gly Val Ala Asn Phe Arg Glu
            35                  40                  45

Leu Gly Gly Tyr Pro Cys Asp Thr Val Pro Pro Ala Pro Ala Ser Asn
        50                  55                  60

Gly Ser Pro His Asn Ala Ser Glu Ala Thr Leu Gln Gly Ser His Ser
65                  70                  75                  80

Ser Ile Arg Pro Gly Phe Ile Phe Arg Ser Ala Gln Pro Ser Gln Ile
                85                  90                  95

Asn Pro Ala Gly Ile Ala Thr Leu Ala His Glu Leu Ser Ile Gln Val
            100                 105                 110

Ile Phe Asp Phe Arg Ser Gln Thr Glu Ile Gln Leu Val Thr Thr His
```

```
                115                 120                 125
Tyr Pro Asp Ser Leu Leu Glu Ile Pro Cys Thr Thr Arg Tyr Ser Val
            130                 135                 140

Pro Val Phe Asn Glu Gly Asp Tyr Ser Pro Ala Ser Leu Val Lys Lys
145                 150                 155                 160

Tyr Gly Val Ser Pro Asp Pro Val Thr His Ser Ala Ser Ser Thr Ser
                165                 170                 175

Ala Asn Pro Ala Gly Phe Val Pro Ala Tyr Glu Ala Ile Ala Arg Ser
            180                 185                 190

Ala Ala Glu Asn Gly Ser Phe Arg Lys Ile Thr Glu His Ile Ile Gln
            195                 200                 205

His Pro Asp Gln Pro Ile Leu Phe His Cys Thr Leu Gly Lys Asp Arg
    210                 215                 220

Thr Gly Val Phe Ala Ala Leu Leu Leu Ser Leu Cys Gly Val Ser Thr
225                 230                 235                 240

Glu Lys Ile Val Glu Asp Tyr Ala Met Thr Thr Glu Gly Phe Gly Ala
                245                 250                 255

Trp Arg Glu His Leu Ile Lys Arg Leu Leu Gln Arg Lys Asp Ala Ala
            260                 265                 270

Thr Arg Gln Asp Ala Glu Phe Ile Ile Ala Ser His Pro Glu Thr Met
            275                 280                 285

Lys Ser Phe Leu Asp Asp Val Val Arg Ala Lys Phe Gly Ser Ala Arg
290                 295                 300

Asn Tyr Phe Val Gln Gln Cys Gly Leu Thr Glu Tyr Glu Val Asp Lys
305                 310                 315                 320

Leu Ile His Thr Leu Val Ile Ile Lys
                325

<210> SEQ ID NO 26
<211> LENGTH: 990
<212> TYPE: DNA
<213> ORGANISM: Talaromyces marneffei

<400> SEQUENCE: 26
atgtggaacc tacactacta tattcctgga tcagcaccag tcaacttgaa cgacatgcct    60
aatgacaccg ctaccacggc ttctgccgga acatcagcaa cttcacggtt tctttgcgtg   120
agcggagtgg cgaatttccg tgaactgggc ggttacccat gcgatactgt ccctcctgct   180
cctgcgtcaa acggttcacc gcacaatgca tctgaagcga ccctccaggg tagtcattcg   240
tctattcggc ctggatttat ctttcgatcg gctcagccgt cgcagattaa cccggctggt   300
attgccacat tagcacacga gcttagcatc caggtgattt ttgactttcg ttcgcaaacc   360
gaaattcagc ttgtcactac tcattatcct gattcgctac ttgagatacc ttgcacgact   420
cgctattccg tgccggtctt caatgagggc gactattccc agcgtcgtt agtcaagaag    480 tacggggtat cccccgatcc tgtaacacat tccgcttcct ccacgagtgc aatcctgca    540 ggatttgtcc ccgcgtatga agccatcgca cgaagcgcag cagaaaacgg cagtttccgt   600
aaaataacag agcacataat acagcatccg gaccagccga tcctgtttca ttgtactctg   660
ggaaaggacc ggaccggagt ttttgcagca ttgctattga gcctttgcgg tgtttcgact   720
gagaagatag ttgaagacta tgctatgact accgagggtt tcggagcctg cgggaacat    780 ctaattaaac gcctgctgca aaggaaagat gcagcaacac gccaggatgc ggaattcatt   840
atcgccagcc acccggagac tatgaagtct ttcctagacg atgtcgtgcg agctaagttc   900
```

```
ggaagtgctc gaaattactt tgtccagcag tgtggattga cagaatatga ggttgataag      960
ttaatccata cactcgtgat tataaaatga                                       990

<210> SEQ ID NO 27
<211> LENGTH: 906
<212> TYPE: DNA
<213> ORGANISM: Talaromyces atroroseus
<220> FEATURE:
<221> NAME/KEY: CDS
<222> LOCATION: (1)..(906)

<400> SEQUENCE: 27 atg tcc acc aat gca gat ccg acc acg ttt tcc gat aag tcc ccg ttc        48
Met Ser Thr Asn Ala Asp Pro Thr Thr Phe Ser Asp Lys Ser Pro Phe
1               5                   10                  15 atc aat gtc agc ggc gtg gtg aat ttt cgt gac ctg ggc ggc tac agc        96
Ile Asn Val Ser Gly Val Val Asn Phe Arg Asp Leu Gly Gly Tyr Ser
            20                  25                  30 tgc ttg acc ccg ttg acg cca gtc agc aac ggc agc ccg gta att gcg       144
Cys Leu Thr Pro Leu Thr Pro Val Ser Asn Gly Ser Pro Val Ile Ala
        35                  40                  45 tcg aag ggt agc cct tct agc tat atc cgt cca ggt ttc ctg ttt cgc       192
Ser Lys Gly Ser Pro Ser Ser Tyr Ile Arg Pro Gly Phe Leu Phe Arg
    50                  55                  60 tct gct cag ccg agc cag att acc gaa acc ggt atc gag gtc ctg acc       240
Ser Ala Gln Pro Ser Gln Ile Thr Glu Thr Gly Ile Glu Val Leu Thr
65                  70                  75                  80 cac aag ctg aat atc ggt gcg att ttt gac ttc cgt tcc caa acc gag       288
His Lys Leu Asn Ile Gly Ala Ile Phe Asp Phe Arg Ser Gln Thr Glu
                85                  90                  95 atc caa ctg gtt gcg acg cgt tac ccg gac agc ctg ctg gaa att ccg       336
Ile Gln Leu Val Ala Thr Arg Tyr Pro Asp Ser Leu Leu Glu Ile Pro
            100                 105                 110 ttt acc tct cgt tat gca gtc ccg gtt ttc gag cat tgt gat ttc agc       384
Phe Thr Ser Arg Tyr Ala Val Pro Val Phe Glu His Cys Asp Phe Ser
        115                 120                 125 ccg gtt agc ttg agc aag aaa tat ggt gcg ccg agc aac gca ccg cct       432
Pro Val Ser Leu Ser Lys Lys Tyr Gly Ala Pro Ser Asn Ala Pro Pro
    130                 135                 140 acc gaa gcg gag cac ggt agc ttt gtg cag gcg tac gaa gat att gcc       480
Thr Glu Ala Glu His Gly Ser Phe Val Gln Ala Tyr Glu Asp Ile Ala
145                 150                 155                 160 cgt agc gca gca gag aac ggc agc ttc cgc agc atc acg gac cac att       528
Arg Ser Ala Ala Glu Asn Gly Ser Phe Arg Ser Ile Thr Asp His Ile
                165                 170                 175 ttg cgc tac ccg gat atg ccg atc ctg ttc cac tgc acc gtg ggc aaa       576
Leu Arg Tyr Pro Asp Met Pro Ile Leu Phe His Cys Thr Val Gly Lys
            180                 185                 190 gac cgc acc ggc gtt ttt gcg gcg ctg ctg ctg aaa ctg tgt ggt gtg       624
Asp Arg Thr Gly Val Phe Ala Ala Leu Leu Leu Lys Leu Cys Gly Val
        195                 200                 205 agc gac gaa gtt gtg att cag gac tat gcc ctg act acg caa ggt ctg       672
Ser Asp Glu Val Val Ile Gln Asp Tyr Ala Leu Thr Thr Gln Gly Leu
    210                 215                 220 ggt gcc tgg aga gag cat ctg atc caa cgc ctg ctg cag cgt aat gac       720
Gly Ala Trp Arg Glu His Leu Ile Gln Arg Leu Leu Gln Arg Asn Asp
225                 230                 235                 240 gtc gcg acg cgt gaa gat gca gag ttt atc ctg gct agc cgt ccg gag       768
Val Ala Thr Arg Glu Asp Ala Glu Phe Ile Leu Ala Ser Arg Pro Glu
                245                 250                 255
```

```
act atg aaa tcg ttc ctg gcc gat gtt gtg gaa acc aag ttc ggt ggc    816
Thr Met Lys Ser Phe Leu Ala Asp Val Val Glu Thr Lys Phe Gly Gly
        260                 265                 270 gct cgc aac tac ttc acg ctg ctg tgc ggt ctg acc gaa gat gat gtt    864
Ala Arg Asn Tyr Phe Thr Leu Leu Cys Gly Leu Thr Glu Asp Asp Val
    275                 280                 285 aac aac ctg att agc ctg gtt gtc att cat aac acg aat taa            906
Asn Asn Leu Ile Ser Leu Val Val Ile His Asn Thr Asn
290                 295                 300
```

<210> SEQ ID NO 28
<211> LENGTH: 301
<212> TYPE: PRT
<213> ORGANISM: Talaromyces atroroseus

<400> SEQUENCE: 28

```
Met Ser Thr Asn Ala Asp Pro Thr Thr Phe Ser Asp Lys Ser Pro Phe
1               5                   10                  15

Ile Asn Val Ser Gly Val Val Asn Phe Arg Asp Leu Gly Gly Tyr Ser
            20                  25                  30

Cys Leu Thr Pro Leu Thr Pro Val Ser Asn Gly Ser Pro Val Ile Ala
        35                  40                  45

Ser Lys Gly Ser Pro Ser Ser Tyr Ile Arg Pro Gly Phe Leu Phe Arg
    50                  55                  60

Ser Ala Gln Pro Ser Gln Ile Thr Glu Thr Gly Ile Glu Val Leu Thr
65                  70                  75                  80

His Lys Leu Asn Ile Gly Ala Ile Phe Asp Phe Arg Ser Gln Thr Glu
                85                  90                  95

Ile Gln Leu Val Ala Thr Arg Tyr Pro Asp Ser Leu Leu Glu Ile Pro
            100                 105                 110

Phe Thr Ser Arg Tyr Ala Val Pro Val Phe Glu His Cys Asp Phe Ser
        115                 120                 125

Pro Val Ser Leu Ser Lys Lys Tyr Gly Ala Pro Ser Asn Ala Pro Pro
    130                 135                 140

Thr Glu Ala Glu His Gly Ser Phe Val Gln Ala Tyr Glu Asp Ile Ala
145                 150                 155                 160

Arg Ser Ala Ala Glu Asn Gly Ser Phe Arg Ser Ile Thr Asp His Ile
                165                 170                 175

Leu Arg Tyr Pro Asp Met Pro Ile Leu Phe His Cys Thr Val Gly Lys
            180                 185                 190

Asp Arg Thr Gly Val Phe Ala Ala Leu Leu Leu Lys Leu Cys Gly Val
        195                 200                 205

Ser Asp Glu Val Val Ile Gln Asp Tyr Ala Leu Thr Thr Gln Gly Leu
    210                 215                 220

Gly Ala Trp Arg Glu His Leu Ile Gln Arg Leu Leu Gln Arg Asn Asp
225                 230                 235                 240

Val Ala Thr Arg Glu Asp Ala Glu Phe Ile Leu Ala Ser Arg Pro Glu
                245                 250                 255

Thr Met Lys Ser Phe Leu Ala Asp Val Val Glu Thr Lys Phe Gly Gly
            260                 265                 270

Ala Arg Asn Tyr Phe Thr Leu Leu Cys Gly Leu Thr Glu Asp Asp Val
        275                 280                 285

Asn Asn Leu Ile Ser Leu Val Val Ile His Asn Thr Asn
    290                 295                 300
```

<210> SEQ ID NO 29

<210> SEQ ID NO 29
<211> LENGTH: 906
<212> TYPE: DNA
<213> ORGANISM: Talaromyces atroroseus

<400> SEQUENCE: 29

```
atgtctacca acgctgaccc tactactttt tccgataaat caccgtttat taacgtaagc      60
ggcgttgtca attttcgtga tctgggcggt tactcatgtc tcactcctct cacccctgtc     120
tcaaatggtt caccggtgat agcgtcaaag ggatccccct catcatacat tcgcccggc      180
ttcttgttcc gttcagcaca gccttcacaa attaccgaga ctggtatcga agttctgacg     240
cacaagctta atatcggagc tatatttgac tttcggtcac agacagaaat ccagcttgtt     300
gcgactcgat atccagattc cctgctcgaa ataccattta ctagccgata cgctgttcca     360
gtgttcgaac attgcgactt ttctccggtc tcgctgtcta agaagtatgg ggctccgtca     420
aacgctcctc ctacagaagc cgagcacggt agcttcgtcc aggcttatga agatatcgcc     480
cgcagtgcag cggaaaatgg aagttttcgc agcataacag atcatattct gcgatatccc     540
gacatgccaa ttcttttttca ttgtacggtt ggcaaagaca gaactggtgt gtttgcagca     600
ttgttgttga gctgtgtgg agtgtctgat gaagtagtta ttcaagacta cgcactcact     660
actcaaggcc taggtcatg gcgcgaacac ctgattcagc gcctgctgca aaggaatgat     720
gttgctaccc gtgaggatgc cgagttcata ctcgctagcc gaccagagac tatgaagtca     780
ttcttggcag atgtggtgga aaccaaattt ggaggagctc gcaactatt tactctgctg     840
tgcggattga ccgaggacga tgtcaataac ttgatctccc ttgtagttat tcataataca     900
aattag                                                                906
```

<210> SEQ ID NO 30
<211> LENGTH: 873
<212> TYPE: DNA
<213> ORGANISM: Penicillium subrubescens
<220> FEATURE:
<221> NAME/KEY: CDS
<222> LOCATION: (1)..(873)

<400> SEQUENCE: 30

```
atg caa cct ttt att agc gtc gat ggt gtg gtg aat ttt cgt gat att       48
Met Gln Pro Phe Ile Ser Val Asp Gly Val Val Asn Phe Arg Asp Ile
1               5                   10                  15 ggt ggt tat gtt tgc cgt aat ccg gcc ggt ttg tcg agc ctg ccg agc       96
Gly Gly Tyr Val Cys Arg Asn Pro Ala Gly Leu Ser Ser Leu Pro Ser
                20                  25                  30 aac gtt gac gaa acc ccg gaa aag caa tgg tgt atc cgc cca ggc ttc      144
Asn Val Asp Glu Thr Pro Glu Lys Gln Trp Cys Ile Arg Pro Gly Phe
            35                  40                  45 gtt ttc cgt gca gcg caa ccg tcc caa att acg ccg gct ggt atc gag      192
Val Phe Arg Ala Ala Gln Pro Ser Gln Ile Thr Pro Ala Gly Ile Glu
        50                  55                  60 att ctt aag aaa acg ctg gcg atc caa gcg att ttc gat ttt cgt agc      240
Ile Leu Lys Lys Thr Leu Ala Ile Gln Ala Ile Phe Asp Phe Arg Ser
65                  70                  75                  80 gag tcc gag atc caa ctg gtg agc aag cgt tac ccg gac agc ctg ctg      288
Glu Ser Glu Ile Gln Leu Val Ser Lys Arg Tyr Pro Asp Ser Leu Leu
                85                  90                  95 gac atc ccg ggc act acg cgt cat gct gtt ccg gtg ttt cag gag ggt      336
Asp Ile Pro Gly Thr Thr Arg His Ala Val Pro Val Phe Gln Glu Gly
                100                 105                 110 gat tac agc ccg atc tcg ttg gcc aaa cgt tac ggt gtg acc gcg gac      384
Asp Tyr Ser Pro Ile Ser Leu Ala Lys Arg Tyr Gly Val Thr Ala Asp
```

-continued

```
                    115                 120                 125
gag agc acc aac gat cag tcc ttc cgt ccg ggt ttt gtc aaa gcg tat      432
Glu Ser Thr Asn Asp Gln Ser Phe Arg Pro Gly Phe Val Lys Ala Tyr
    130                 135                 140 gaa gcc atc gca cgc aac gca gca cag gct ggt agc ttc cgc gcc att      480
Glu Ala Ile Ala Arg Asn Ala Ala Gln Ala Gly Ser Phe Arg Ala Ile
145                 150                 155                 160 atc cag cat atc ctg cag gac tcc gct ggc cca gtt ttg ttt cac tgc      528
Ile Gln His Ile Leu Gln Asp Ser Ala Gly Pro Val Leu Phe His Cys
            165                 170                 175 acc gta ggc aaa gat cgc acg ggt gtt ttc tct gca ctg att ctg aag      576
Thr Val Gly Lys Asp Arg Thr Gly Val Phe Ser Ala Leu Ile Leu Lys
        180                 185                 190 ctg tgc ggt gtg gcc gac gaa gat att gtg gca gac tat gcg ctg acc      624
Leu Cys Gly Val Ala Asp Glu Asp Ile Val Ala Asp Tyr Ala Leu Thr
    195                 200                 205 act cag ggc ctg ggt gtc tgg cgt gag cac ctg atc cag cgc ctg ttg      672
Thr Gln Gly Leu Gly Val Trp Arg Glu His Leu Ile Gln Arg Leu Leu
210                 215                 220 cag cgt ggt gaa gcg acc acc aaa gaa caa gcg gaa gcg atc atc tct      720
Gln Arg Gly Glu Ala Thr Thr Lys Glu Gln Ala Glu Ala Ile Ile Ser
225                 230                 235                 240 agc gac ccg cgc gac atg aaa gcg ttc ctg agc aac gtc gtt gag ggc      768
Ser Asp Pro Arg Asp Met Lys Ala Phe Leu Ser Asn Val Val Glu Gly
            245                 250                 255 gag ttt ggt ggc gca cgc aac tac ttc gtg aat ctg tgt ggc ctg cct      816
Glu Phe Gly Gly Ala Arg Asn Tyr Phe Val Asn Leu Cys Gly Leu Pro
        260                 265                 270 gaa ggc gag gtt gac cgt gtc att acc aaa ctg gtc gtc ccg aaa acc      864
Glu Gly Glu Val Asp Arg Val Ile Thr Lys Leu Val Val Pro Lys Thr
    275                 280                 285 acc aag taa                                                          873
Thr Lys
    290
```

<210> SEQ ID NO 31
<211> LENGTH: 290
<212> TYPE: PRT
<213> ORGANISM: Penicillium subrubescens

<400> SEQUENCE: 31

```
Met Gln Pro Phe Ile Ser Val Asp Gly Val Val Asn Phe Arg Asp Ile
1               5                   10                  15

Gly Gly Tyr Val Cys Arg Asn Pro Ala Gly Leu Ser Ser Leu Pro Ser
            20                  25                  30

Asn Val Asp Glu Thr Pro Glu Lys Gln Trp Cys Ile Arg Pro Gly Phe
        35                  40                  45

Val Phe Arg Ala Ala Gln Pro Ser Gln Ile Thr Pro Ala Gly Ile Glu
    50                  55                  60

Ile Leu Lys Lys Thr Leu Ala Ile Gln Ala Ile Phe Asp Phe Arg Ser
65                  70                  75                  80

Glu Ser Glu Ile Gln Leu Val Ser Lys Arg Tyr Pro Asp Ser Leu Leu
                85                  90                  95

Asp Ile Pro Gly Thr Thr Arg His Ala Val Pro Val Phe Gln Glu Gly
            100                 105                 110

Asp Tyr Ser Pro Ile Ser Leu Ala Lys Arg Tyr Gly Val Thr Ala Asp
        115                 120                 125

Glu Ser Thr Asn Asp Gln Ser Phe Arg Pro Gly Phe Val Lys Ala Tyr
```

```
                      130                 135                 140
Glu Ala Ile Ala Arg Asn Ala Ala Gln Ala Gly Ser Phe Arg Ala Ile
145                 150                 155                 160

Ile Gln His Ile Leu Gln Asp Ser Ala Gly Pro Val Leu Phe His Cys
                165                 170                 175

Thr Val Gly Lys Asp Arg Thr Gly Val Phe Ser Ala Leu Ile Leu Lys
            180                 185                 190

Leu Cys Gly Val Ala Asp Glu Asp Ile Val Ala Asp Tyr Ala Leu Thr
        195                 200                 205

Thr Gln Gly Leu Gly Val Trp Arg Glu His Leu Ile Gln Arg Leu Leu
    210                 215                 220

Gln Arg Gly Glu Ala Thr Thr Lys Glu Gln Ala Glu Ala Ile Ile Ser
225                 230                 235                 240

Ser Asp Pro Arg Asp Met Lys Ala Phe Leu Ser Asn Val Val Glu Gly
                245                 250                 255

Glu Phe Gly Gly Ala Arg Asn Tyr Phe Val Asn Leu Cys Gly Leu Pro
            260                 265                 270

Glu Gly Glu Val Asp Arg Val Ile Thr Lys Leu Val Val Pro Lys Thr
        275                 280                 285

Thr Lys
    290

<210> SEQ ID NO 32
<211> LENGTH: 873
<212> TYPE: DNA
<213> ORGANISM: Penicillium subrubescens

<400> SEQUENCE: 32
atgcagccat tcatctcggt ggatggagtc gtcaacttcc gcgatatcgg aggctatgta      60
tgccggaatc ccgctggttt atcctccttg ccctcgaatg tcgacgaaac cccagagaaa     120
cagtggtgca ttcggccagg attcgtcttc cgcgcggcac agccatccca aatcacccct     180
gcagggattg agatcctgaa aaagacccct gctatccaag ccatctttga ctttcggtca     240
gagagtgaga ttcagcttgt gtctaagcgc tatccagact ccctcctcga tattcccggg     300
acaactcgcc atgcagtacc ggtcttccaa gaaggtgatt actctcccat ctcactggca     360
aaacggtatg gagtcaccgc ggacgaatcc acgaatgatc agtcctttag accgggattc     420
gtcaaggcct acgaggccat tgcgcgcaac gcggctcaag cgggcagctt ccgtgcaatc     480
atacagcaca ttctgcagga ttcggccggc ccggtacttt tccactgcac ggtgggcaag     540
gaccggacag gggtcttttc ggctttgatc ctcaagctgt gcggggtggc cgatgaggac     600
attgtcgctg attatgcact caccacgcaa ggcttaggtg tgtggcggga gcatttgatt     660
caacggctct tgcagagagg ggaggccaca accaaggaac aagccgaagc cataatcagc     720
agtgacccga gagacatgaa ggcgttttg agcaatgtag tggaagggga atttggaggt      780
gctcggaact acttcgtcaa cctctgcgga ctaccggaag cgaagtcga tcgggttatc      840 accaagcttg tggtaccaaa gactactaaa tag                                  873

<210> SEQ ID NO 33
<211> LENGTH: 2211
<212> TYPE: DNA
<213> ORGANISM: Salvia miltiorrhiza
<220> FEATURE:
<221> NAME/KEY: CDS
<222> LOCATION: (1)..(2211)
```

```
<400> SEQUENCE: 33 atg gca act gtt gat gca cca caa gtt cac gat cat gac ggc acc act    48
Met Ala Thr Val Asp Ala Pro Gln Val His Asp His Asp Gly Thr Thr
1               5                  10                  15 gtt cac caa ggc cac gat gca gtc aag aat atc gag gac ccg atc gag    96
Val His Gln Gly His Asp Ala Val Lys Asn Ile Glu Asp Pro Ile Glu
            20                  25                  30 tac att cgc acg ctg ttg cgc acc acg ggc gac ggt cgt att tcc gtg   144
Tyr Ile Arg Thr Leu Leu Arg Thr Thr Gly Asp Gly Arg Ile Ser Val
        35                  40                  45 agc ccg tat gat acc gca tgg gtc gcg atg atc aaa gac gtt gag ggc   192
Ser Pro Tyr Asp Thr Ala Trp Val Ala Met Ile Lys Asp Val Glu Gly
    50                  55                  60 cgt gat ggt ccg cag ttt ccg tct agc ttg gaa tgg atc gtg caa aat   240
Arg Asp Gly Pro Gln Phe Pro Ser Ser Leu Glu Trp Ile Val Gln Asn
65                  70                  75                  80 cag ttg gaa gat ggt tcg tgg ggt gac cag aaa ctg ttt tgt gtg tat   288
Gln Leu Glu Asp Gly Ser Trp Gly Asp Gln Lys Leu Phe Cys Val Tyr
                85                  90                  95 gat cgc ttg gtt aat acg atc gcg tgt gtg gtt gct ttg cgt tct tgg   336
Asp Arg Leu Val Asn Thr Ile Ala Cys Val Val Ala Leu Arg Ser Trp
            100                 105                 110 aac gtg cac gcg cac aaa gtg aag cgt ggt gtg acc tat att aag gaa   384
Asn Val His Ala His Lys Val Lys Arg Gly Val Thr Tyr Ile Lys Glu
        115                 120                 125 aac gtt gat aag ctg atg gag ggt aac gag gag cac atg act tgc ggc   432
Asn Val Asp Lys Leu Met Glu Gly Asn Glu Glu His Met Thr Cys Gly
    130                 135                 140 ttc gaa gtc gtt ttc ccg gca ctg ctg cag aaa gcc aaa agc ctg ggt   480
Phe Glu Val Val Phe Pro Ala Leu Leu Gln Lys Ala Lys Ser Leu Gly
145                 150                 155                 160 att gag gat ttg cct tac gat tcg ccg gcg gtc caa gaa gtg tat cac   528
Ile Glu Asp Leu Pro Tyr Asp Ser Pro Ala Val Gln Glu Val Tyr His
                165                 170                 175 gtc cgc gaa caa aag ctg aag cgc atc ccg ttg gaa att atg cac aaa   576
Val Arg Glu Gln Lys Leu Lys Arg Ile Pro Leu Glu Ile Met His Lys
            180                 185                 190 att ccg acc agc ctg ctg ttt agc ctg gaa ggt ctg gag aat ctc gac   624
Ile Pro Thr Ser Leu Leu Phe Ser Leu Glu Gly Leu Glu Asn Leu Asp
        195                 200                 205 tgg gac aaa ctg ctg aaa ctc cag agc gct gac ggc tct ttt ctg acg   672
Trp Asp Lys Leu Leu Lys Leu Gln Ser Ala Asp Gly Ser Phe Leu Thr
    210                 215                 220 agc ccg agc agc acg gcg ttc gca ttt atg cag acg aaa gac gaa aaa   720
Ser Pro Ser Ser Thr Ala Phe Ala Phe Met Gln Thr Lys Asp Glu Lys
225                 230                 235                 240 tgc tat caa ttt att aag aat acg att gac acc ttc aat ggt ggc gcg   768
Cys Tyr Gln Phe Ile Lys Asn Thr Ile Asp Thr Phe Asn Gly Gly Ala
                245                 250                 255 ccg cat acc tat ccg gtg gat gtt ttt ggt cgt tta tgg gcg att gat   816
Pro His Thr Tyr Pro Val Asp Val Phe Gly Arg Leu Trp Ala Ile Asp
            260                 265                 270 cgt ctg cag aga ctg ggt att agc cgt ttc ttt gag ccg gaa att gcc   864
Arg Leu Gln Arg Leu Gly Ile Ser Arg Phe Phe Glu Pro Glu Ile Ala
        275                 280                 285 gat tgc ctg tct cat att cac aaa ttt tgg acc gac aag ggt gtt ttc   912
Asp Cys Leu Ser His Ile His Lys Phe Trp Thr Asp Lys Gly Val Phe
    290                 295                 300 tct ggt cgc gag agc gaa ttt tgc gac atc gac gac acc agc atg ggc   960
Ser Gly Arg Glu Ser Glu Phe Cys Asp Ile Asp Asp Thr Ser Met Gly
```

```
                Ser Gly Arg Glu Ser Glu Phe Cys Asp Ile Asp Thr Ser Met Gly
                305             310                 315                 320 atg cgc ctg atg cgc atg cac ggt tat gac gtc gat cca aat gtc ctg         1008
Met Arg Leu Met Arg Met His Gly Tyr Asp Val Asp Pro Asn Val Leu
            325                 330                 335 cgc aat ttc aaa caa aag gac ggc aag ttc agc tgc tac ggc ggc cag         1056
Arg Asn Phe Lys Gln Lys Asp Gly Lys Phe Ser Cys Tyr Gly Gly Gln
                340                 345                 350 atg atc gag tct ccg agc ccg atc tat aat ctg tat cgt gcg agc cag         1104
Met Ile Glu Ser Pro Ser Pro Ile Tyr Asn Leu Tyr Arg Ala Ser Gln
            355                 360                 365 ttg cgc ttc ccg ggt gaa gaa atc ctg gaa gat gcc aaa cgc ttt gct         1152
Leu Arg Phe Pro Gly Glu Glu Ile Leu Glu Asp Ala Lys Arg Phe Ala
370                 375                 380 tac gac ttc ttg aaa gag aaa ctg gcg aac aac cag att ctg gac aag         1200
Tyr Asp Phe Leu Lys Glu Lys Leu Ala Asn Asn Gln Ile Leu Asp Lys
385                 390                 395                 400 tgg gtt att tcg aaa cac ttg ccg gac gag atc aaa ctg ggc tta gaa         1248
Trp Val Ile Ser Lys His Leu Pro Asp Glu Ile Lys Leu Gly Leu Glu
                405                 410                 415 atg ccg tgg ttg gca acc ctg ccg cgc gtg gag gcg aag tac tac atc         1296
Met Pro Trp Leu Ala Thr Leu Pro Arg Val Glu Ala Lys Tyr Tyr Ile
            420                 425                 430 cag tac tac gcg ggc agc ggt gat gtt tgg atc ggc aaa acg ttg tac         1344
Gln Tyr Tyr Ala Gly Ser Gly Asp Val Trp Ile Gly Lys Thr Leu Tyr
            435                 440                 445 cgc atg cct gag atc tcg aac gac acc tat cac gac ctg gct aag acc         1392
Arg Met Pro Glu Ile Ser Asn Asp Thr Tyr His Asp Leu Ala Lys Thr
450                 455                 460 gat ttt aaa cgt tgt cag gcc aaa cac caa ttc gag tgg ctg tac atg         1440
Asp Phe Lys Arg Cys Gln Ala Lys His Gln Phe Glu Trp Leu Tyr Met
465                 470                 475                 480 caa gag tgg tat gaa agc tgc ggc atc gaa gag ttt ggt atc agc cgt         1488
Gln Glu Trp Tyr Glu Ser Cys Gly Ile Glu Glu Phe Gly Ile Ser Arg
                485                 490                 495 aaa gac ctc ctg ctg agc tat ttt ctg gcg acg gcg agc atc ttc gag         1536
Lys Asp Leu Leu Leu Ser Tyr Phe Leu Ala Thr Ala Ser Ile Phe Glu
            500                 505                 510 ttg gag cgc acc aac gaa cgt att gcg tgg gca aaa tct cag att atc         1584
Leu Glu Arg Thr Asn Glu Arg Ile Ala Trp Ala Lys Ser Gln Ile Ile
            515                 520                 525 gca aaa atg atc acg agc ttc ttt aac aaa gaa acc acg agc gag gaa         1632
Ala Lys Met Ile Thr Ser Phe Phe Asn Lys Glu Thr Thr Ser Glu Glu
530                 535                 540 gat aag cgc gcc ctg ctg aat gag ctg ggc aac atc aat ggt ctg aat         1680
Asp Lys Arg Ala Leu Leu Asn Glu Leu Gly Asn Ile Asn Gly Leu Asn
545                 550                 555                 560 gat acg aac ggt gca ggc cgc gag ggt ggt gct ggt agc atc gcg ctg         1728
Asp Thr Asn Gly Ala Gly Arg Glu Gly Gly Ala Gly Ser Ile Ala Leu
                565                 570                 575 gcg acc ctg acc caa ttt ctg gaa ggt ttc gac cgt tat acc cgc cat         1776
Ala Thr Leu Thr Gln Phe Leu Glu Gly Phe Asp Arg Tyr Thr Arg His
            580                 585                 590 caa ctc aaa aac gcc tgg agc gtg tgg ctg act cag tta cag cat ggc         1824
Gln Leu Lys Asn Ala Trp Ser Val Trp Leu Thr Gln Leu Gln His Gly
            595                 600                 605 gag gca gat gat gct gag ctg ctg acc aat acg ctc aac atc tgc gcg         1872
Glu Ala Asp Asp Ala Glu Leu Leu Thr Asn Thr Leu Asn Ile Cys Ala
610                 615                 620
```

```
ggc cat atc gcg ttc cgt gag gaa att ctg gcc cat aac gag tac aag    1920
Gly His Ile Ala Phe Arg Glu Glu Ile Leu Ala His Asn Glu Tyr Lys
625             630                 635                 640 gcc ttg agc aac ctg acc agc aaa atc tgc cgc caa ctg agc ttt att    1968
Ala Leu Ser Asn Leu Thr Ser Lys Ile Cys Arg Gln Leu Ser Phe Ile
        645                 650                 655 caa agc gaa aag gaa atg ggc gtc gag ggc gag att gcg gca aag agc    2016
Gln Ser Glu Lys Glu Met Gly Val Glu Gly Glu Ile Ala Ala Lys Ser
            660                 665                 670 agc atc aag aat aaa gaa ctg gaa gaa gat atg cag atg ctg gtc aaa    2064
Ser Ile Lys Asn Lys Glu Leu Glu Glu Asp Met Gln Met Leu Val Lys
675                 680                 685 ctg gtc ctg gaa aag tac ggt ggt atc gac cgt aac atc aaa aaa gcg    2112
Leu Val Leu Glu Lys Tyr Gly Gly Ile Asp Arg Asn Ile Lys Lys Ala
        690                 695                 700 ttt ctg gct gtc gcg aaa acc tat tac tat cgt gca tat cat gct gcg    2160
Phe Leu Ala Val Ala Lys Thr Tyr Tyr Tyr Arg Ala Tyr His Ala Ala
705                 710                 715                 720 gac acc atc gac acc cac atg ttt aag gtt ctg ttt gag ccg gtt gca    2208
Asp Thr Ile Asp Thr His Met Phe Lys Val Leu Phe Glu Pro Val Ala
            725                 730                 735 taa                                                                2211

<210> SEQ ID NO 34
<211> LENGTH: 736
<212> TYPE: PRT
<213> ORGANISM: Salvia miltiorrhiza

<400> SEQUENCE: 34

Met Ala Thr Val Asp Ala Pro Gln Val His Asp His Asp Gly Thr Thr
1               5                   10                  15

Val His Gln Gly His Asp Ala Val Lys Asn Ile Glu Asp Pro Ile Glu
            20                  25                  30

Tyr Ile Arg Thr Leu Leu Arg Thr Thr Gly Asp Gly Arg Ile Ser Val
        35                  40                  45

Ser Pro Tyr Asp Thr Ala Trp Val Ala Met Ile Lys Asp Val Glu Gly
50                  55                  60

Arg Asp Gly Pro Gln Phe Pro Ser Ser Leu Glu Trp Ile Val Gln Asn
65                  70                  75                  80

Gln Leu Glu Asp Gly Ser Trp Gly Asp Gln Lys Leu Phe Cys Val Tyr
            85                  90                  95

Asp Arg Leu Val Asn Thr Ile Ala Cys Val Val Ala Leu Arg Ser Trp
        100                 105                 110

Asn Val His Ala His Lys Val Lys Arg Gly Val Thr Tyr Ile Lys Glu
    115                 120                 125

Asn Val Asp Lys Leu Met Glu Gly Asn Glu Glu Met Thr Cys Gly
    130                 135                 140

Phe Glu Val Val Phe Pro Ala Leu Leu Gln Lys Ala Lys Ser Leu Gly
145                 150                 155                 160

Ile Glu Asp Leu Pro Tyr Asp Ser Pro Ala Val Gln Glu Val Tyr His
                165                 170                 175

Val Arg Glu Gln Lys Leu Lys Arg Ile Pro Leu Glu Ile Met His Lys
            180                 185                 190

Ile Pro Thr Ser Leu Leu Phe Ser Leu Glu Gly Leu Glu Asn Leu Asp
        195                 200                 205

Trp Asp Lys Leu Leu Lys Leu Gln Ser Ala Asp Gly Ser Phe Leu Thr
    210                 215                 220
```

```
Ser Pro Ser Ser Thr Ala Phe Ala Phe Met Gln Thr Lys Asp Glu Lys
225                 230                 235                 240

Cys Tyr Gln Phe Ile Lys Asn Thr Ile Asp Thr Phe Asn Gly Gly Ala
            245                 250                 255

Pro His Thr Tyr Pro Val Asp Val Phe Gly Arg Leu Trp Ala Ile Asp
        260                 265                 270

Arg Leu Gln Arg Leu Gly Ile Ser Arg Phe Phe Glu Pro Glu Ile Ala
    275                 280                 285

Asp Cys Leu Ser His Ile His Lys Phe Trp Thr Asp Lys Gly Val Phe
        290                 295                 300

Ser Gly Arg Glu Ser Glu Phe Cys Asp Ile Asp Asp Thr Ser Met Gly
305                 310                 315                 320

Met Arg Leu Met Arg Met His Gly Tyr Asp Val Asp Pro Asn Val Leu
                325                 330                 335

Arg Asn Phe Lys Gln Lys Asp Gly Lys Phe Ser Cys Tyr Gly Gly Gln
            340                 345                 350

Met Ile Glu Ser Pro Ser Pro Ile Tyr Asn Leu Tyr Arg Ala Ser Gln
        355                 360                 365

Leu Arg Phe Pro Gly Glu Glu Ile Leu Glu Asp Ala Lys Arg Phe Ala
    370                 375                 380

Tyr Asp Phe Leu Lys Glu Lys Leu Ala Asn Asn Gln Ile Leu Asp Lys
385                 390                 395                 400

Trp Val Ile Ser Lys His Leu Pro Asp Glu Ile Lys Leu Gly Leu Glu
                405                 410                 415

Met Pro Trp Leu Ala Thr Leu Pro Arg Val Glu Ala Lys Tyr Tyr Ile
            420                 425                 430

Gln Tyr Tyr Ala Gly Ser Gly Asp Val Trp Ile Gly Lys Thr Leu Tyr
        435                 440                 445

Arg Met Pro Glu Ile Ser Asn Asp Thr Tyr His Asp Leu Ala Lys Thr
    450                 455                 460

Asp Phe Lys Arg Cys Gln Ala Lys His Gln Phe Glu Trp Leu Tyr Met
465                 470                 475                 480

Gln Glu Trp Tyr Glu Ser Cys Gly Ile Glu Glu Phe Gly Ile Ser Arg
                485                 490                 495

Lys Asp Leu Leu Leu Ser Tyr Phe Leu Ala Thr Ala Ser Ile Phe Glu
            500                 505                 510

Leu Glu Arg Thr Asn Glu Arg Ile Ala Trp Ala Lys Ser Gln Ile Ile
        515                 520                 525

Ala Lys Met Ile Thr Ser Phe Asn Lys Glu Thr Thr Ser Glu Glu
    530                 535                 540

Asp Lys Arg Ala Leu Leu Asn Glu Leu Gly Asn Ile Asn Gly Leu Asn
545                 550                 555                 560

Asp Thr Asn Gly Ala Gly Arg Glu Gly Gly Ala Gly Ser Ile Ala Leu
                565                 570                 575

Ala Thr Leu Thr Gln Phe Leu Glu Gly Phe Asp Arg Tyr Thr Arg His
            580                 585                 590

Gln Leu Lys Asn Ala Trp Ser Val Trp Leu Thr Gln Leu Gln His Gly
        595                 600                 605

Glu Ala Asp Asp Ala Glu Leu Leu Thr Asn Thr Leu Asn Ile Cys Ala
    610                 615                 620

Gly His Ile Ala Phe Arg Glu Glu Ile Leu Ala His Asn Glu Tyr Lys
625                 630                 635                 640
```

-continued

```
Ala Leu Ser Asn Leu Thr Ser Lys Ile Cys Arg Gln Leu Ser Phe Ile
            645                 650                 655

Gln Ser Glu Lys Glu Met Gly Val Glu Gly Glu Ile Ala Ala Lys Ser
        660                 665                 670

Ser Ile Lys Asn Lys Glu Leu Glu Glu Asp Met Gln Met Leu Val Lys
            675                 680                 685

Leu Val Leu Glu Lys Tyr Gly Gly Ile Asp Arg Asn Ile Lys Lys Ala
    690                 695                 700

Phe Leu Ala Val Ala Lys Thr Tyr Tyr Tyr Arg Ala Tyr His Ala Ala
705                 710                 715                 720

Asp Thr Ile Asp Thr His Met Phe Lys Val Leu Phe Glu Pro Val Ala
                725                 730                 735

<210> SEQ ID NO 35
<211> LENGTH: 924
<212> TYPE: DNA
<213> ORGANISM: Pantoea agglomerans
<220> FEATURE:
<221> NAME/KEY: CDS
<222> LOCATION: (1)..(924)

<400> SEQUENCE: 35 atg gtt tct ggt tcg aaa gca gga gta tca cct cat agg gaa atc gaa      48
Met Val Ser Gly Ser Lys Ala Gly Val Ser Pro His Arg Glu Ile Glu
1               5                   10                  15 gtc atg aga cag tcc att gat gac cac tta gca gga ttg ttg cca gaa      96
Val Met Arg Gln Ser Ile Asp Asp His Leu Ala Gly Leu Leu Pro Glu
            20                  25                  30 aca gat tcc cag gat atc gtt agc ctt gct atg aga gaa ggt gtt atg     144
Thr Asp Ser Gln Asp Ile Val Ser Leu Ala Met Arg Glu Gly Val Met
        35                  40                  45 gca cct ggt aaa cgt atc aga cct ttg ctg atg tta ctt gct gca aga     192
Ala Pro Gly Lys Arg Ile Arg Pro Leu Leu Met Leu Leu Ala Ala Arg
    50                  55                  60 gac ctg aga tat cag ggt tct atg cct aca cta ctg gat cta gct tgt     240
Asp Leu Arg Tyr Gln Gly Ser Met Pro Thr Leu Leu Asp Leu Ala Cys
65                  70                  75                  80 gct gtt gaa ctg aca cat act gct tcc ttg atg ctg gat gac atg cct     288
Ala Val Glu Leu Thr His Thr Ala Ser Leu Met Leu Asp Asp Met Pro
                85                  90                  95 tgt atg gac aat gcg gaa ctt aga aga ggt caa cca aca acc cac aag     336
Cys Met Asp Asn Ala Glu Leu Arg Arg Gly Gln Pro Thr Thr His Lys
            100                 105                 110 aaa ttc gga gaa tct gtt gcc att ttg gct tct gta ggt ctg ttg tcg     384
Lys Phe Gly Glu Ser Val Ala Ile Leu Ala Ser Val Gly Leu Leu Ser
        115                 120                 125 aaa gca ttt ggc ttg att gct gca act ggt gat ctt cca ggt gaa agg     432
Lys Ala Phe Gly Leu Ile Ala Ala Thr Gly Asp Leu Pro Gly Glu Arg
    130                 135                 140 aga gca caa gct gta aac gag cta tct act gca gtt ggt gtt caa ggt     480
Arg Ala Gln Ala Val Asn Glu Leu Ser Thr Ala Val Gly Val Gln Gly
145                 150                 155                 160 cta gtc tta gga cag ttc aga gat ttg aat gac gca gct ttg gac aga     528
Leu Val Leu Gly Gln Phe Arg Asp Leu Asn Asp Ala Ala Leu Asp Arg
                165                 170                 175 act cct gat gct atc ctg tct acg aac cat ctg aag act ggc atc ttg     576
Thr Pro Asp Ala Ile Leu Ser Thr Asn His Leu Lys Thr Gly Ile Leu
            180                 185                 190 ttc tca gct atg ttg caa atc gta gcc att gct tct gct tct tca cca     624
Phe Ser Ala Met Leu Gln Ile Val Ala Ile Ala Ser Ala Ser Ser Pro
```

```
            195                 200                 205
tct act agg gaa acg tta cac gca ttc gca ttg gac ttt ggt caa gcc      672
Ser Thr Arg Glu Thr Leu His Ala Phe Ala Leu Asp Phe Gly Gln Ala
210                 215                 220 ttt caa ctg cta gac gat ttg agg gat gat cat cca gag aca ggt aaa      720
Phe Gln Leu Leu Asp Asp Leu Arg Asp Asp His Pro Glu Thr Gly Lys
225                 230                 235                 240 gac cgt aac aaa gac gct ggt aaa agc act cta gtc aac aga ttg ggt      768
Asp Arg Asn Lys Asp Ala Gly Lys Ser Thr Leu Val Asn Arg Leu Gly
                245                 250                 255 gct gat gca gct aga cag aaa ctg aga gag cac att gac tct gct gac      816
Ala Asp Ala Ala Arg Gln Lys Leu Arg Glu His Ile Asp Ser Ala Asp
            260                 265                 270 aaa cac ctg aca ttt gca tgt cca caa gga ggt gct ata agg cag ttt      864
Lys His Leu Thr Phe Ala Cys Pro Gln Gly Gly Ala Ile Arg Gln Phe
275                 280                 285 atg cac cta tgg ttt gga cac cat ctt gct gat tgg tct cca gtg atg      912
Met His Leu Trp Phe Gly His His Leu Ala Asp Trp Ser Pro Val Met
290                 295                 300 aag atc gcc taa                                                      924
Lys Ile Ala
305

<210> SEQ ID NO 36
<211> LENGTH: 307
<212> TYPE: PRT
<213> ORGANISM: Pantoea agglomerans

<400> SEQUENCE: 36

Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
                20                  25                  30

Thr Asp Ser Gln Asp Ile Val Ser Leu Ala Met Arg Glu Gly Val Met
            35                  40                  45

Ala Pro Gly Lys Arg Ile Arg Pro Leu Leu Met Leu Leu Ala Ala Arg
        50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
            100                 105                 110

Lys Phe Gly Glu Ser Val Ala Ile Leu Ala Ser Val Gly Leu Leu Ser
        115                 120                 125

Lys Ala Phe Gly Leu Ile Ala Thr Gly Asp Leu Pro Gly Glu Arg
    130                 135                 140

Arg Ala Gln Ala Val Asn Glu Leu Ser Thr Ala Val Gly Val Gln Gly
145                 150                 155                 160

Leu Val Leu Gly Gln Phe Arg Asp Leu Asn Asp Ala Ala Leu Asp Arg
                165                 170                 175

Thr Pro Asp Ala Ile Leu Ser Thr Asn His Leu Lys Thr Gly Ile Leu
            180                 185                 190

Phe Ser Ala Met Leu Gln Ile Val Ala Ile Ala Ser Ala Ser Ser Pro
        195                 200                 205

Ser Thr Arg Glu Thr Leu His Ala Phe Ala Leu Asp Phe Gly Gln Ala
    210                 215                 220
```

```
Phe Gln Leu Leu Asp Asp Leu Arg Asp Asp His Pro Glu Thr Gly Lys
225                 230                 235                 240

Asp Arg Asn Lys Asp Ala Gly Lys Ser Thr Leu Val Asn Arg Leu Gly
            245                 250                 255

Ala Asp Ala Ala Arg Gln Lys Leu Arg Glu His Ile Asp Ser Ala Asp
        260                 265                 270

Lys His Leu Thr Phe Ala Cys Pro Gln Gly Gly Ala Ile Arg Gln Phe
    275                 280                 285

Met His Leu Trp Phe Gly His His Leu Ala Asp Trp Ser Pro Val Met
290                 295                 300

Lys Ile Ala
305

<210> SEQ ID NO 37
<211> LENGTH: 2172
<212> TYPE: DNA
<213> ORGANISM: Salvia sclarea
<220> FEATURE:
<221> NAME/KEY: CDS
<222> LOCATION: (1)..(2172)

<400> SEQUENCE: 37 atg gca tcc caa gcg tcc gag aaa gat att agc ctg gtt caa acc ccg      48
Met Ala Ser Gln Ala Ser Glu Lys Asp Ile Ser Leu Val Gln Thr Pro
1               5                   10                  15 cat aag gtc gag gtc aac gaa aag atc gaa gag agc atc gag tac gtc      96
His Lys Val Glu Val Asn Glu Lys Ile Glu Glu Ser Ile Glu Tyr Val
                20                  25                  30 caa aat ctg ctg atg acg agc ggt gac ggt cgt atc tcc gtg tct ccg     144
Gln Asn Leu Leu Met Thr Ser Gly Asp Gly Arg Ile Ser Val Ser Pro
            35                  40                  45 tac gat acc gcg gtc atc gct ctg att aaa gat ctg aag ggt cgc gac     192
Tyr Asp Thr Ala Val Ile Ala Leu Ile Lys Asp Leu Lys Gly Arg Asp
        50                  55                  60 gca ccg cag ttc ccg agc tgt ctg gag tgg att gcg cac cac cag tta     240
Ala Pro Gln Phe Pro Ser Cys Leu Glu Trp Ile Ala His His Gln Leu
65                  70                  75                  80 gcg gat ggt agc tgg ggc gac gag ttc ttt tgt atc tat gac cgc att     288
Ala Asp Gly Ser Trp Gly Asp Glu Phe Phe Cys Ile Tyr Asp Arg Ile
                85                  90                  95 ttg aat acc ctg gcg tgc gtc gtc gca ctg aaa tct tgg aat ctg cac     336
Leu Asn Thr Leu Ala Cys Val Val Ala Leu Lys Ser Trp Asn Leu His
            100                 105                 110 agc gac att att gaa aaa ggc gtg acc tac att aag gaa aac gtc cat     384
Ser Asp Ile Ile Glu Lys Gly Val Thr Tyr Ile Lys Glu Asn Val His
        115                 120                 125 aag ctg aaa ggc gcg aat gtt gag cat aga acc gcc ggt ttt gag ctg     432
Lys Leu Lys Gly Ala Asn Val Glu His Arg Thr Ala Gly Phe Glu Leu
    130                 135                 140 gtt gtt ccg acc ttc atg cag atg gcg act gac ctg ggt att cag gat     480
Val Val Pro Thr Phe Met Gln Met Ala Thr Asp Leu Gly Ile Gln Asp
145                 150                 155                 160 ctg ccg tac gat cat cct ctt atc aaa gaa atc gct gat acg aag caa     528
Leu Pro Tyr Asp His Pro Leu Ile Lys Glu Ile Ala Asp Thr Lys Gln
                165                 170                 175 cag cgc ctg aaa gaa att ccg aaa gat ttg gtt tat cag atg ccg acc     576
Gln Arg Leu Lys Glu Ile Pro Lys Asp Leu Val Tyr Gln Met Pro Thr
            180                 185                 190 aat ctg ctg tat agc ctg gaa ggc ctg ggc gat tta gag tgg gag cgt     624
```

```
Asn Leu Leu Tyr Ser Leu Glu Gly Leu Gly Asp Leu Glu Trp Glu Arg
            195                 200                 205 ttg ctg aag ctg cag tct ggt aat ggt agc ttc ctg acg agc cca agc     672
Leu Leu Lys Leu Gln Ser Gly Asn Gly Ser Phe Leu Thr Ser Pro Ser
210                 215                 220 agc acg gcg gca gtt ctg atg cat acc aaa gac gag aag tgt ttg aaa     720
Ser Thr Ala Ala Val Leu Met His Thr Lys Asp Glu Lys Cys Leu Lys
225                 230                 235                 240 tac att gag aat gcg ctg aag aac tgc gac ggt ggc gct cct cat acg     768
Tyr Ile Glu Asn Ala Leu Lys Asn Cys Asp Gly Gly Ala Pro His Thr
            245                 250                 255 tat ccg gtt gac atc ttt agc cgc ttg tgg gcg atc gac cgt ttg caa     816
Tyr Pro Val Asp Ile Phe Ser Arg Leu Trp Ala Ile Asp Arg Leu Gln
        260                 265                 270 cgt ctg ggc att agc cgt ttc ttc caa cac gag atc aaa tac ttt ctg     864
Arg Leu Gly Ile Ser Arg Phe Phe Gln His Glu Ile Lys Tyr Phe Leu
    275                 280                 285 gac cac atc gag tca gtc tgg gaa gaa acc ggc gtg ttt agc ggt cgt     912
Asp His Ile Glu Ser Val Trp Glu Glu Thr Gly Val Phe Ser Gly Arg
290                 295                 300 tac acg aag ttt agc gac atc gat gac acg agc atg ggt gtc cgc ctg     960
Tyr Thr Lys Phe Ser Asp Ile Asp Asp Thr Ser Met Gly Val Arg Leu
305                 310                 315                 320 ctg aaa atg cac ggt tac gac gta gac cca aac gtg ttg aaa cac ttt    1008
Leu Lys Met His Gly Tyr Asp Val Asp Pro Asn Val Leu Lys His Phe
            325                 330                 335 aag cag caa gac ggc aaa ttc agc tgc tac atc ggc cag agc gtc gag    1056
Lys Gln Gln Asp Gly Lys Phe Ser Cys Tyr Ile Gly Gln Ser Val Glu
        340                 345                 350 agc gcg agc ccg atg tat aat ctg tac cgt gcc gcc cag ctg cgt ttc    1104
Ser Ala Ser Pro Met Tyr Asn Leu Tyr Arg Ala Ala Gln Leu Arg Phe
    355                 360                 365 ccg ggt gaa gaa gtg ctt gaa gaa gca act aaa ttc gcg ttt aac ttc    1152
Pro Gly Glu Glu Val Leu Glu Glu Ala Thr Lys Phe Ala Phe Asn Phe
370                 375                 380 ctg caa gag atg ctg gtg aag gat cgc ttg caa gag cgt tgg gtt att    1200
Leu Gln Glu Met Leu Val Lys Asp Arg Leu Gln Glu Arg Trp Val Ile
385                 390                 395                 400 agc gat cac ctg ttt gac gag att aag ctc ggt ctg aag atg ccg tgg    1248
Ser Asp His Leu Phe Asp Glu Ile Lys Leu Gly Leu Lys Met Pro Trp
            405                 410                 415 tat gct acc ctg ccg cgt gtt gag gcc gct tat tac ctg gat cac tat    1296
Tyr Ala Thr Leu Pro Arg Val Glu Ala Ala Tyr Tyr Leu Asp His Tyr
        420                 425                 430 gcg ggt agc ggt gat gtg tgg att ggt aag tct ttt tac cgc atg ccg    1344
Ala Gly Ser Gly Asp Val Trp Ile Gly Lys Ser Phe Tyr Arg Met Pro
    435                 440                 445 gag att agc aat gac acc tac aaa gaa ttg gcc atc ctg gac ttt aac    1392
Glu Ile Ser Asn Asp Thr Tyr Lys Glu Leu Ala Ile Leu Asp Phe Asn
450                 455                 460 cgt tgt cag act cag cat cag ctg gag tgg att cac atg caa gag tgg    1440
Arg Cys Gln Thr Gln His Gln Leu Glu Trp Ile His Met Gln Glu Trp
465                 470                 475                 480 tat gac cgc tgc tct ctg tcc gag ttt ggt att agc aag cgt gag ctg    1488
Tyr Asp Arg Cys Ser Leu Ser Glu Phe Gly Ile Ser Lys Arg Glu Leu
            485                 490                 495 ctg cgt agc tac ttc ctg gct gcc gca acc att ttc gaa ccg gaa cgc    1536
Leu Arg Ser Tyr Phe Leu Ala Ala Ala Thr Ile Phe Glu Pro Glu Arg
        500                 505                 510
```

| | | | | | | | | | | | | | | | | |
|---|---|---|---|---|---|---|---|---|---|---|---|---|---|---|---|---|
| acc | caa | gag | cgt | ctg | ctc | tgg | gca | aag | acc | cgc | atc | ctg | agc | aag | atg | 1584 |
| Thr | Gln | Glu | Arg | Leu | Leu | Trp | Ala | Lys | Thr | Arg | Ile | Leu | Ser | Lys | Met | |
| | | 515 | | | | 520 | | | | | 525 | | | | | |
| att | acc | agc | ttc | gtc | aac | atc | tcc | ggt | acg | acc | ctg | agc | ctg | gat | tac | 1632 |
| Ile | Thr | Ser | Phe | Val | Asn | Ile | Ser | Gly | Thr | Thr | Leu | Ser | Leu | Asp | Tyr | |
| 530 | | | | | 535 | | | | | 540 | | | | | | |
| aac | ttc | aac | ggt | ttg | gat | gag | atc | att | tcc | agc | gcg | aat | gaa | gat | cag | 1680 |
| Asn | Phe | Asn | Gly | Leu | Asp | Glu | Ile | Ile | Ser | Ser | Ala | Asn | Glu | Asp | Gln | |
| 545 | | | | 550 | | | | | 555 | | | | | 560 | | |
| ggt | ctg | gcg | ggt | acg | ctg | ttg | gcc | acg | ttc | cat | caa | ctg | ctg | gat | ggt | 1728 |
| Gly | Leu | Ala | Gly | Thr | Leu | Leu | Ala | Thr | Phe | His | Gln | Leu | Leu | Asp | Gly | |
| | | | 565 | | | | | 570 | | | | | 575 | | | |
| ttc | gac | att | tac | acc | ctg | cac | caa | ctg | aaa | cac | gtc | tgg | tcg | caa | tgg | 1776 |
| Phe | Asp | Ile | Tyr | Thr | Leu | His | Gln | Leu | Lys | His | Val | Trp | Ser | Gln | Trp | |
| | | | 580 | | | | | 585 | | | | | 590 | | | |
| ttt | atg | aaa | gtt | cag | caa | ggc | gag | ggc | tcc | ggc | ggc | gaa | gat | gcg | gtc | 1824 |
| Phe | Met | Lys | Val | Gln | Gln | Gly | Glu | Gly | Ser | Gly | Gly | Glu | Asp | Ala | Val | |
| | | | 595 | | | | | 600 | | | | | 605 | | | |
| ctg | ctg | gca | aat | act | ctg | aat | atc | tgc | gcg | ggt | ctg | aat | gaa | gat | gtg | 1872 |
| Leu | Leu | Ala | Asn | Thr | Leu | Asn | Ile | Cys | Ala | Gly | Leu | Asn | Glu | Asp | Val | |
| | 610 | | | | | 615 | | | | | 620 | | | | | |
| ctg | tcg | aac | aac | gag | tat | acc | gcg | ctg | agc | acg | ctg | acg | aac | aag | atc | 1920 |
| Leu | Ser | Asn | Asn | Glu | Tyr | Thr | Ala | Leu | Ser | Thr | Leu | Thr | Asn | Lys | Ile | |
| 625 | | | | | 630 | | | | | 635 | | | | | 640 | |
| tgc | aac | cgt | ctg | gcc | cag | atc | cag | gac | aac | aag | att | ctg | caa | gtg | gtg | 1968 |
| Cys | Asn | Arg | Leu | Ala | Gln | Ile | Gln | Asp | Asn | Lys | Ile | Leu | Gln | Val | Val | |
| | | | | 645 | | | | | 650 | | | | | 655 | | |
| gac | ggc | agc | atc | aaa | gac | aaa | gaa | ctg | gaa | cag | gat | atg | cag | gca | ttg | 2016 |
| Asp | Gly | Ser | Ile | Lys | Asp | Lys | Glu | Leu | Glu | Gln | Asp | Met | Gln | Ala | Leu | |
| | | | 660 | | | | | 665 | | | | | 670 | | | |
| gtt | aaa | ctg | gtg | ctg | cag | gaa | aac | ggt | ggc | gca | gtg | gac | cgt | aac | atc | 2064 |
| Val | Lys | Leu | Val | Leu | Gln | Glu | Asn | Gly | Gly | Ala | Val | Asp | Arg | Asn | Ile | |
| | | 675 | | | | | 680 | | | | | 685 | | | | |
| cgt | cac | acg | ttt | ctg | agc | gtt | agc | aag | acc | ttc | tac | tat | gac | gcg | tat | 2112 |
| Arg | His | Thr | Phe | Leu | Ser | Val | Ser | Lys | Thr | Phe | Tyr | Tyr | Asp | Ala | Tyr | |
| | 690 | | | | | 695 | | | | | 700 | | | | | |
| cac | gac | gat | gaa | acc | acc | gat | ctg | cat | atc | ttt | aaa | gtc | ctg | ttc | cgt | 2160 |
| His | Asp | Asp | Glu | Thr | Thr | Asp | Leu | His | Ile | Phe | Lys | Val | Leu | Phe | Arg | |
| 705 | | | | | 710 | | | | | 715 | | | | | 720 | |
| ccg | gtt | gtt | taa | | | | | | | | | | | | | 2172 |
| Pro | Val | Val | | | | | | | | | | | | | | |

<210> SEQ ID NO 38
<211> LENGTH: 723
<212> TYPE: PRT
<213> ORGANISM: Salvia sclarea

<400> SEQUENCE: 38

Met Ala Ser Gln Ala Ser Glu Lys Asp Ile Ser Leu Val Gln Thr Pro
1               5                   10                  15

His Lys Val Glu Val Asn Glu Lys Ile Glu Glu Ser Ile Glu Tyr Val
            20                  25                  30

Gln Asn Leu Leu Met Thr Ser Gly Asp Gly Arg Ile Ser Val Ser Pro
        35                  40                  45

Tyr Asp Thr Ala Val Ile Ala Leu Ile Lys Asp Leu Lys Gly Arg Asp
    50                  55                  60

Ala Pro Gln Phe Pro Ser Cys Leu Glu Trp Ile Ala His Gln Leu
65                  70                  75                  80

Ala Asp Gly Ser Trp Gly Asp Glu Phe Phe Cys Ile Tyr Asp Arg Ile

```
                    85                  90                  95
Leu Asn Thr Leu Ala Cys Val Val Ala Leu Lys Ser Trp Asn Leu His
                100                 105                 110

Ser Asp Ile Ile Glu Lys Gly Val Thr Tyr Ile Lys Glu Asn Val His
                115                 120                 125

Lys Leu Lys Gly Ala Asn Val Glu His Arg Thr Ala Gly Phe Glu Leu
            130                 135                 140

Val Val Pro Thr Phe Met Gln Met Ala Thr Asp Leu Gly Ile Gln Asp
145                 150                 155                 160

Leu Pro Tyr Asp His Pro Leu Ile Lys Glu Ile Ala Asp Thr Lys Gln
                165                 170                 175

Gln Arg Leu Lys Glu Ile Pro Lys Asp Leu Val Tyr Gln Met Pro Thr
            180                 185                 190

Asn Leu Leu Tyr Ser Leu Glu Gly Leu Gly Asp Leu Glu Trp Glu Arg
            195                 200                 205

Leu Leu Lys Leu Gln Ser Gly Asn Gly Ser Phe Leu Thr Ser Pro Ser
        210                 215                 220

Ser Thr Ala Ala Val Leu Met His Thr Lys Asp Glu Lys Cys Leu Lys
225                 230                 235                 240

Tyr Ile Glu Asn Ala Leu Lys Asn Cys Asp Gly Gly Ala Pro His Thr
                245                 250                 255

Tyr Pro Val Asp Ile Phe Ser Arg Leu Trp Ala Ile Asp Arg Leu Gln
            260                 265                 270

Arg Leu Gly Ile Ser Arg Phe Phe Gln His Glu Ile Lys Tyr Phe Leu
        275                 280                 285

Asp His Ile Glu Ser Val Trp Glu Glu Thr Gly Val Phe Ser Gly Arg
        290                 295                 300

Tyr Thr Lys Phe Ser Asp Ile Asp Asp Thr Ser Met Gly Val Arg Leu
305                 310                 315                 320

Leu Lys Met His Gly Tyr Asp Val Asp Pro Asn Val Leu Lys His Phe
                325                 330                 335

Lys Gln Gln Asp Gly Lys Phe Ser Cys Tyr Ile Gly Gln Ser Val Glu
            340                 345                 350

Ser Ala Ser Pro Met Tyr Asn Leu Tyr Arg Ala Ala Gln Leu Arg Phe
        355                 360                 365

Pro Gly Glu Glu Val Leu Glu Glu Ala Thr Lys Phe Ala Phe Asn Phe
370                 375                 380

Leu Gln Glu Met Leu Val Lys Asp Arg Leu Gln Glu Arg Trp Val Ile
                385                 390                 395                 400

Ser Asp His Leu Phe Asp Glu Ile Lys Leu Gly Leu Lys Met Pro Trp
            405                 410                 415

Tyr Ala Thr Leu Pro Arg Val Glu Ala Ala Tyr Tyr Leu Asp His Tyr
        420                 425                 430

Ala Gly Ser Gly Asp Val Trp Ile Gly Lys Ser Phe Tyr Arg Met Pro
        435                 440                 445

Glu Ile Ser Asn Asp Thr Tyr Lys Glu Leu Ala Ile Leu Asp Phe Asn
450                 455                 460

Arg Cys Gln Thr Gln His Gln Leu Glu Trp Ile His Met Gln Glu Trp
465                 470                 475                 480

Tyr Asp Arg Cys Ser Leu Ser Glu Phe Gly Ile Ser Lys Arg Glu Leu
            485                 490                 495

Leu Arg Ser Tyr Phe Leu Ala Ala Ala Thr Ile Phe Glu Pro Glu Arg
            500                 505                 510
```

-continued

```
Thr Gln Glu Arg Leu Leu Trp Ala Lys Thr Arg Ile Leu Ser Lys Met
            515                 520                 525

Ile Thr Ser Phe Val Asn Ile Ser Gly Thr Thr Leu Ser Leu Asp Tyr
        530                 535                 540

Asn Phe Asn Gly Leu Asp Glu Ile Ile Ser Ser Ala Asn Glu Asp Gln
545                 550                 555                 560

Gly Leu Ala Gly Thr Leu Leu Ala Thr Phe His Gln Leu Leu Asp Gly
                565                 570                 575

Phe Asp Ile Tyr Thr Leu His Gln Leu Lys His Val Trp Ser Gln Trp
            580                 585                 590

Phe Met Lys Val Gln Gln Gly Glu Gly Ser Gly Gly Glu Asp Ala Val
        595                 600                 605

Leu Leu Ala Asn Thr Leu Asn Ile Cys Ala Gly Leu Asn Glu Asp Val
    610                 615                 620

Leu Ser Asn Asn Glu Tyr Thr Ala Leu Ser Thr Leu Thr Asn Lys Ile
625                 630                 635                 640

Cys Asn Arg Leu Ala Gln Ile Gln Asp Asn Lys Ile Leu Gln Val Val
                645                 650                 655

Asp Gly Ser Ile Lys Asp Lys Glu Leu Glu Gln Asp Met Gln Ala Leu
            660                 665                 670

Val Lys Leu Val Leu Gln Glu Asn Gly Gly Ala Val Asp Arg Asn Ile
        675                 680                 685

Arg His Thr Phe Leu Ser Val Ser Lys Thr Phe Tyr Tyr Asp Ala Tyr
    690                 695                 700

His Asp Asp Glu Thr Thr Asp Leu His Ile Phe Lys Val Leu Phe Arg
705                 710                 715                 720

Pro Val Val
```

<210> SEQ ID NO 39
<211> LENGTH: 2100
<212> TYPE: DNA
<213> ORGANISM: Triticum aestivum
<220> FEATURE:
<221> NAME/KEY: CDS
<222> LOCATION: (1)..(2100)

<400> SEQUENCE: 39

```
atg tat cgc caa aga act gat gag cca agc gaa acc cgc cag atg atc      48
Met Tyr Arg Gln Arg Thr Asp Glu Pro Ser Glu Thr Arg Gln Met Ile
1               5                   10                  15 gat gat att cgc acc gct ttg gct agc ctg ggt gac gat gaa acc agc      96
Asp Asp Ile Arg Thr Ala Leu Ala Ser Leu Gly Asp Asp Glu Thr Ser
            20                  25                  30 atg agc gtg agc gca tac gac acc gcc ctg gtt gcc ctg gtg aag aac    144
Met Ser Val Ser Ala Tyr Asp Thr Ala Leu Val Ala Leu Val Lys Asn
        35                  40                  45 ctg gac ggt ggc gat ggc ccg cag ttc ccg agc tgc att gac tgg att    192
Leu Asp Gly Gly Asp Gly Pro Gln Phe Pro Ser Cys Ile Asp Trp Ile
    50                  55                  60 gtt cag aac cag ctg ccg gac ggt agc tgg ggc gac ccg gct ttc ttt    240
Val Gln Asn Gln Leu Pro Asp Gly Ser Trp Gly Asp Pro Ala Phe Phe
65                  70                  75                  80 atg gtt cag gac cgt atg atc agc acc ctg gcc tgt gtc gtg gcc gtg    288
Met Val Gln Asp Arg Met Ile Ser Thr Leu Ala Cys Val Val Ala Val
                85                  90                  95 aaa tcc tgg aat atc gat cgt gac aac ttg tgc gat cgt ggt gtc ctg    336
Lys Ser Trp Asn Ile Asp Arg Asp Asn Leu Cys Asp Arg Gly Val Leu
```

```
                100                 105                 110
ttt atc aaa gaa aac atg tcg cgt ctg gtt gaa gaa gaa caa gat tgg      384
Phe Ile Lys Glu Asn Met Ser Arg Leu Val Glu Glu Glu Gln Asp Trp
        115                 120                 125 atg cca tgt ggc ttc gag att aac ttt cct gca ctg ttg gag aaa gct      432
Met Pro Cys Gly Phe Glu Ile Asn Phe Pro Ala Leu Leu Glu Lys Ala
130                 135                 140 aaa gac ctg gac ttg gac att ccg tac gat cat cct gtg ctg gaa gag      480
Lys Asp Leu Asp Leu Asp Ile Pro Tyr Asp His Pro Val Leu Glu Glu
145                 150                 155                 160 att tac gcg aag cgt aat ctg aaa ctg ctg aag att ccg tta gat gtc      528
Ile Tyr Ala Lys Arg Asn Leu Lys Leu Leu Lys Ile Pro Leu Asp Val
                165                 170                 175 ctc cat gcg atc ccg acg acg ctg ttg ttt tcc gtt gag ggt atg gtc      576
Leu His Ala Ile Pro Thr Thr Leu Leu Phe Ser Val Glu Gly Met Val
                180                 185                 190 gat ctg ccg ctg gat tgg gag aaa ctg ctg cgt ctg cgt tgc ccg gac      624
Asp Leu Pro Leu Asp Trp Glu Lys Leu Leu Arg Leu Arg Cys Pro Asp
                195                 200                 205 ggt tct ttt cat tct agc ccg gcg gcg acg gca gcg gcg ctg agc cac      672
Gly Ser Phe His Ser Ser Pro Ala Ala Thr Ala Ala Ala Leu Ser His
        210                 215                 220 acg ggt gac aaa gag tgt cac gcc ttc ctg gac cgc ctg att caa aag      720
Thr Gly Asp Lys Glu Cys His Ala Phe Leu Asp Arg Leu Ile Gln Lys
225                 230                 235                 240 ttc gag ggt ggc gtc ccg tgc tcc cac agc atg gac acc ttc gag caa      768
Phe Glu Gly Gly Val Pro Cys Ser His Ser Met Asp Thr Phe Glu Gln
                245                 250                 255 ctg tgg gtt gtt gac cgt ttg atg cgt ctg ggt atc agc cgt cat ttt      816
Leu Trp Val Val Asp Arg Leu Met Arg Leu Gly Ile Ser Arg His Phe
                260                 265                 270 acg agc gag atc cag cag tgc ttg gag ttc atc tat cgt cgt tgg acc      864
Thr Ser Glu Ile Gln Gln Cys Leu Glu Phe Ile Tyr Arg Arg Trp Thr
                275                 280                 285 cag aaa ggt ctg gcg cac aat atg cac tgc ccg atc ccg gac att gat      912
Gln Lys Gly Leu Ala His Asn Met His Cys Pro Ile Pro Asp Ile Asp
        290                 295                 300 gac act gcg atg ggt ttt cgt ctg ttg aga cag cac ggt tac gac gtg      960
Asp Thr Ala Met Gly Phe Arg Leu Leu Arg Gln His Gly Tyr Asp Val
305                 310                 315                 320 acc ccg tcg gtt ttc aag cat ttc gag aaa gac ggc aag ttc gta tgc     1008
Thr Pro Ser Val Phe Lys His Phe Glu Lys Asp Gly Lys Phe Val Cys
                325                 330                 335 ttc ccg atg gaa acc aac cat gcg agc gtg acg ccg atg cac aat acc     1056
Phe Pro Met Glu Thr Asn His Ala Ser Val Thr Pro Met His Asn Thr
                340                 345                 350 tac cgt gcg agc cag ttc atg ttc ccg ggt gat gac gac gtg ctg gcc     1104
Tyr Arg Ala Ser Gln Phe Met Phe Pro Gly Asp Asp Asp Val Leu Ala
                355                 360                 365 cgt gcc ggc cgc tac tgt cgc gca ttc ttg caa gag cgt cag agc tct     1152
Arg Ala Gly Arg Tyr Cys Arg Ala Phe Leu Gln Glu Arg Gln Ser Ser
        370                 375                 380 aac aag ttg tac gat aag tgg att atc acg aaa gat ctg ccg ggt gag     1200
Asn Lys Leu Tyr Asp Lys Trp Ile Ile Thr Lys Asp Leu Pro Gly Glu
385                 390                 395                 400 gtt ggc tac acg ctg aac ttt ccg tgg aaa agc tcc ctg ccg cgt att     1248
Val Gly Tyr Thr Leu Asn Phe Pro Trp Lys Ser Ser Leu Pro Arg Ile
                405                 410                 415 gaa act cgt atg tat ctg gat cag tac ggt ggc aat aac gat gtc tgg     1296
Glu Thr Arg Met Tyr Leu Asp Gln Tyr Gly Gly Asn Asn Asp Val Trp
```

|     |     |     |     |     |     |     |     |     |     |     |     |     |     |      |
|-----|-----|-----|-----|-----|-----|-----|-----|-----|-----|-----|-----|-----|-----|------|
| Glu | Thr | Arg | Met | Tyr | Leu | Asp | Gln | Tyr | Gly | Gly | Asn | Asn | Asp | Val | Trp |
|     |     |     | 420 |     |     |     |     | 425 |     |     |     |     | 430 |     |     |

```
att gca aag gtc ctg tat cgc atg aac ctg gtt agc aat gac ctg tac      1344
Ile Ala Lys Val Leu Tyr Arg Met Asn Leu Val Ser Asn Asp Leu Tyr
            435                 440                 445 ctg aaa atg gcg aaa gcc gac ttt acc gag tat caa cgt ctg tct cgc      1392
Leu Lys Met Ala Lys Ala Asp Phe Thr Glu Tyr Gln Arg Leu Ser Arg
450                 455                 460 att gag tgg aac ggc ctg cgc aaa tgg tat ttt cgc aat cat ctg cag      1440
Ile Glu Trp Asn Gly Leu Arg Lys Trp Tyr Phe Arg Asn His Leu Gln
465                 470                 475                 480 cgt tac ggt gcg acc ccg aag tcc gcg ctg aaa gcg tat ttc ctg gcg      1488
Arg Tyr Gly Ala Thr Pro Lys Ser Ala Leu Lys Ala Tyr Phe Leu Ala
            485                 490                 495 tcg gca aac atc ttt gag cct ggc cgc gca gcc gag cgc ctg gca tgg      1536
Ser Ala Asn Ile Phe Glu Pro Gly Arg Ala Ala Glu Arg Leu Ala Trp
            500                 505                 510 gca cgt atg gcc gtg ctg gct gaa gct gta acg act cat ttc cgt cac      1584
Ala Arg Met Ala Val Leu Ala Glu Ala Val Thr Thr His Phe Arg His
            515                 520                 525 att ggc ggc ccg tgc tac agc acc gag aat ctg gaa gaa ctg atc gac      1632
Ile Gly Gly Pro Cys Tyr Ser Thr Glu Asn Leu Glu Glu Leu Ile Asp
530                 535                 540 ctt gtt agc ttc gac gac gtg agc ggc ggc ttg cgt gag gcg tgg aag      1680
Leu Val Ser Phe Asp Asp Val Ser Gly Gly Leu Arg Glu Ala Trp Lys
545                 550                 555                 560 caa tgg ctg atg gcg tgg acc gca aaa gaa tca cac ggc agc gtg gac      1728
Gln Trp Leu Met Ala Trp Thr Ala Lys Glu Ser His Gly Ser Val Asp
            565                 570                 575 ggt gac acg gca ctg ctg ttt gtc cgc acg att gag att tgc agc ggc      1776
Gly Asp Thr Ala Leu Leu Phe Val Arg Thr Ile Glu Ile Cys Ser Gly
            580                 585                 590 cgc atc gtt tcc agc gag cag aaa ctg aat ctg tgg gat tac agc cag      1824
Arg Ile Val Ser Ser Glu Gln Lys Leu Asn Leu Trp Asp Tyr Ser Gln
            595                 600                 605 tta gag caa ttg acc agc agc atc tgt cat aaa ctg gcc acc atc ggt      1872
Leu Glu Gln Leu Thr Ser Ser Ile Cys His Lys Leu Ala Thr Ile Gly
610                 615                 620 ctg agc cag aac gaa gct agc atg gaa aat acc gaa gat ctg cac caa      1920
Leu Ser Gln Asn Glu Ala Ser Met Glu Asn Thr Glu Asp Leu His Gln
625                 630                 635                 640 caa gtc gat ttg gaa atg caa gaa ctg tca tgg cgt gtt cac cag ggt      1968
Gln Val Asp Leu Glu Met Gln Glu Leu Ser Trp Arg Val His Gln Gly
            645                 650                 655 tgt cac ggt att aat cgc gaa acc cgt caa acc ttc ctg aat gtt gtt      2016
Cys His Gly Ile Asn Arg Glu Thr Arg Gln Thr Phe Leu Asn Val Val
            660                 665                 670 aag tct ttt tat tac tcc gca cac tgc agc ccg gaa acc gtg gac agc      2064
Lys Ser Phe Tyr Tyr Ser Ala His Cys Ser Pro Glu Thr Val Asp Ser
            675                 680                 685 cat att gca aaa gtg atc ttt caa gac gtt atc tga                      2100
His Ile Ala Lys Val Ile Phe Gln Asp Val Ile
            690                 695
```

<210> SEQ ID NO 40
<211> LENGTH: 699
<212> TYPE: PRT
<213> ORGANISM: Triticum aestivum

<400> SEQUENCE: 40

```
Met Tyr Arg Gln Arg Thr Asp Glu Pro Ser Glu Thr Arg Gln Met Ile
1               5                   10                  15

Asp Asp Ile Arg Thr Ala Leu Ala Ser Leu Gly Asp Asp Glu Thr Ser
            20                  25                  30

Met Ser Val Ser Ala Tyr Asp Thr Ala Leu Val Ala Leu Val Lys Asn
        35                  40                  45

Leu Asp Gly Gly Pro Gln Phe Pro Ser Cys Ile Asp Trp Ile
    50              55                  60

Val Gln Asn Gln Leu Pro Asp Gly Ser Trp Gly Asp Pro Ala Phe Phe
65              70                  75                  80

Met Val Gln Asp Arg Met Ile Ser Thr Leu Ala Cys Val Val Ala Val
                85                  90                  95

Lys Ser Trp Asn Ile Asp Arg Asp Asn Leu Cys Asp Arg Gly Val Leu
            100                 105                 110

Phe Ile Lys Glu Asn Met Ser Arg Leu Val Glu Glu Gln Asp Trp
        115                 120                 125

Met Pro Cys Gly Phe Glu Ile Asn Phe Pro Ala Leu Leu Glu Lys Ala
    130                 135                 140

Lys Asp Leu Asp Leu Asp Ile Pro Tyr Asp His Pro Val Leu Glu Glu
145             150                 155                 160

Ile Tyr Ala Lys Arg Asn Leu Lys Leu Leu Lys Ile Pro Leu Asp Val
            165                 170                 175

Leu His Ala Ile Pro Thr Thr Leu Leu Phe Ser Val Glu Gly Met Val
            180                 185                 190

Asp Leu Pro Leu Asp Trp Glu Lys Leu Leu Arg Leu Arg Cys Pro Asp
        195                 200                 205

Gly Ser Phe His Ser Ser Pro Ala Ala Thr Ala Ala Ala Leu Ser His
        210                 215                 220

Thr Gly Asp Lys Glu Cys His Ala Phe Leu Asp Arg Leu Ile Gln Lys
225                 230                 235                 240

Phe Glu Gly Gly Val Pro Cys Ser His Ser Met Asp Thr Phe Glu Gln
                245                 250                 255

Leu Trp Val Val Asp Arg Leu Met Arg Leu Gly Ile Ser Arg His Phe
            260                 265                 270

Thr Ser Glu Ile Gln Gln Cys Leu Glu Phe Ile Tyr Arg Arg Trp Thr
        275                 280                 285

Gln Lys Gly Leu Ala His Asn Met His Cys Pro Ile Pro Asp Ile Asp
        290                 295                 300

Asp Thr Ala Met Gly Phe Arg Leu Leu Arg Gln His Gly Tyr Asp Val
305                 310                 315                 320

Thr Pro Ser Val Phe Lys His Phe Glu Lys Asp Gly Lys Phe Val Cys
                325                 330                 335

Phe Pro Met Glu Thr Asn His Ala Ser Val Thr Pro Met His Asn Thr
            340                 345                 350

Tyr Arg Ala Ser Gln Phe Met Phe Pro Gly Asp Asp Val Leu Ala
            355                 360                 365

Arg Ala Gly Arg Tyr Cys Arg Ala Phe Leu Gln Glu Arg Gln Ser Ser
    370                 375                 380

Asn Lys Leu Tyr Asp Lys Trp Ile Ile Thr Lys Asp Leu Pro Gly Glu
385                 390                 395                 400

Val Gly Tyr Thr Leu Asn Phe Pro Trp Lys Ser Ser Leu Pro Arg Ile
            405                 410                 415

Glu Thr Arg Met Tyr Leu Asp Gln Tyr Gly Gly Asn Asn Asp Val Trp
```

```
            420              425              430
Ile Ala Lys Val Leu Tyr Arg Met Asn Leu Val Ser Asn Asp Leu Tyr
            435              440              445

Leu Lys Met Ala Lys Ala Asp Phe Thr Glu Tyr Gln Arg Leu Ser Arg
    450              455              460

Ile Glu Trp Asn Gly Leu Arg Lys Trp Tyr Phe Arg Asn His Leu Gln
465              470              475              480

Arg Tyr Gly Ala Thr Pro Lys Ser Ala Leu Lys Ala Tyr Phe Leu Ala
            485              490              495

Ser Ala Asn Ile Phe Glu Pro Gly Arg Ala Ala Glu Arg Leu Ala Trp
                500              505              510

Ala Arg Met Ala Val Leu Ala Glu Ala Val Thr Thr His Phe Arg His
            515              520              525

Ile Gly Gly Pro Cys Tyr Ser Thr Glu Asn Leu Glu Glu Leu Ile Asp
            530              535              540

Leu Val Ser Phe Asp Asp Val Ser Gly Gly Leu Arg Glu Ala Trp Lys
545              550              555              560

Gln Trp Leu Met Ala Trp Thr Ala Lys Glu Ser His Gly Ser Val Asp
                565              570              575

Gly Asp Thr Ala Leu Leu Phe Val Arg Thr Ile Glu Ile Cys Ser Gly
            580              585              590

Arg Ile Val Ser Ser Glu Gln Lys Leu Asn Leu Trp Asp Tyr Ser Gln
            595              600              605

Leu Glu Gln Leu Thr Ser Ser Ile Cys His Lys Leu Ala Thr Ile Gly
    610              615              620

Leu Ser Gln Asn Glu Ala Ser Met Glu Asn Thr Glu Asp Leu His Gln
625              630              635              640

Gln Val Asp Leu Glu Met Gln Glu Leu Ser Trp Arg Val His Gln Gly
                645              650              655

Cys His Gly Ile Asn Arg Glu Thr Arg Gln Thr Phe Leu Asn Val Val
            660              665              670

Lys Ser Phe Tyr Tyr Ser Ala His Cys Ser Pro Glu Thr Val Asp Ser
            675              680              685

His Ile Ala Lys Val Ile Phe Gln Asp Val Ile
    690              695
```

<210> SEQ ID NO 41
<211> LENGTH: 1125
<212> TYPE: DNA
<213> ORGANISM: Pseudomonas sp. 19-rlim
<220> FEATURE:
<221> NAME/KEY: CDS
<222> LOCATION: (1)..(1125)

<400> SEQUENCE: 41

```
atg act atc aat tct att caa ccg att caa gca aaa gcc gct gtg ctg      48
Met Thr Ile Asn Ser Ile Gln Pro Ile Gln Ala Lys Ala Ala Val Leu
1               5                  10                  15 cgt gcc gta ggc tcc ccg ttt aac att gag ccg att cgt atc agc ccg      96
Arg Ala Val Gly Ser Pro Phe Asn Ile Glu Pro Ile Arg Ile Ser Pro
                20                  25                  30 ccg aag ggt gat gaa gtt ctg gtc cgt att gtg ggt gtg ggt gtc tgc     144
Pro Lys Gly Asp Glu Val Leu Val Arg Ile Val Gly Val Gly Val Cys
            35                  40                  45 cat acc gac gtc gtt tgc cgt gac agc ttc ccg gtt ccg ctg cca atc     192
His Thr Asp Val Val Cys Arg Asp Ser Phe Pro Val Pro Leu Pro Ile
        50                  55                  60
```

| | |
|---|---|
| atc ctg ggt cac gaa ggc tcg ggt gtg att gaa gcg atc ggt gat caa<br>Ile Leu Gly His Glu Gly Ser Gly Val Ile Glu Ala Ile Gly Asp Gln<br>65                                70                        75                      80 | 240 |
| gtt acg agc ctg aag cca ggt gac cac gtc gtt ctg agc ttc aat agc<br>Val Thr Ser Leu Lys Pro Gly Asp His Val Val Leu Ser Phe Asn Ser<br>                          85                        90                        95 | 288 |
| tgc ggc cac tgt tat aac tgc ggt cat gcg gag ccg gca agc tgc ctg<br>Cys Gly His Cys Tyr Asn Cys Gly His Ala Glu Pro Ala Ser Cys Leu<br>                        100                     105                    110 | 336 |
| cag atg tta ccg ttg aac ttt ggt ggc gcg gag cgt gcg gcg gac ggc<br>Gln Met Leu Pro Leu Asn Phe Gly Gly Ala Glu Arg Ala Ala Asp Gly<br>           115                    120                    125 | 384 |
| acc atc caa gac gac aag ggt gaa gcc gtc cgc ggt atg ttc ttt ggc<br>Thr Ile Gln Asp Asp Lys Gly Glu Ala Val Arg Gly Met Phe Phe Gly<br>130                              135                    140 | 432 |
| cag tcc agc ttt ggc acg tac gca atc gca cgt gcg gtg aat gct gtc<br>Gln Ser Ser Phe Gly Thr Tyr Ala Ile Ala Arg Ala Val Asn Ala Val<br>145                              150                    155                    160 | 480 |
| aaa gtt gac gac gat ctg ccg ctg cct ctg ttg ggc ccg ctg ggc tgt<br>Lys Val Asp Asp Asp Leu Pro Leu Pro Leu Leu Gly Pro Leu Gly Cys<br>                        165                     170                    175 | 528 |
| ggt atc cag acc ggt gcg ggt gca gcg atg aac agc ctg tct ctg cag<br>Gly Ile Gln Thr Gly Ala Gly Ala Ala Met Asn Ser Leu Ser Leu Gln<br>                   180                    185                    190 | 576 |
| agc ggt cag agc ttc atc gtt ttc ggt ggc ggc gcg gtc ggt ctg agc<br>Ser Gly Gln Ser Phe Ile Val Phe Gly Gly Gly Ala Val Gly Leu Ser<br>           195                    200                    205 | 624 |
| gct gtt atg gca gct aaa gcg ctg ggc gtg agc ccg ctg atc gtt gtg<br>Ala Val Met Ala Ala Lys Ala Leu Gly Val Ser Pro Leu Ile Val Val<br>210                              215                    220 | 672 |
| gag ccg aac gaa agc cgc cgc gcc ctg gcc ctg gaa ctg ggt gca tcc<br>Glu Pro Asn Glu Ser Arg Arg Ala Leu Ala Leu Glu Leu Gly Ala Ser<br>225                              230                    235                    240 | 720 |
| cac gtg ttt gat ccg ttc aac acc gaa gat ctg gtt gcc agc att cgc<br>His Val Phe Asp Pro Phe Asn Thr Glu Asp Leu Val Ala Ser Ile Arg<br>                        245                     250                    255 | 768 |
| gaa gtc gtg cct gcg ggt gcg aac cat gca ctg gac acg acc ggt ctg<br>Glu Val Val Pro Ala Gly Ala Asn His Ala Leu Asp Thr Thr Gly Leu<br>           260                    265                    270 | 816 |
| ccg aaa gtg atc gcg agc gcg att gat tgt att atg agc ggt ggc aaa<br>Pro Lys Val Ile Ala Ser Ala Ile Asp Cys Ile Met Ser Gly Gly Lys<br>           275                    280                    285 | 864 |
| ctg ggt ttg ctg ggt atg gcg agc ccg gaa gcg aat gtg ccg gct acc<br>Leu Gly Leu Leu Gly Met Ala Ser Pro Glu Ala Asn Val Pro Ala Thr<br>290                              295                    300 | 912 |
| ctg ttg gat ttg ctg agc aaa aat gtc acg ctg aag ccg atc acc gag<br>Leu Leu Asp Leu Leu Ser Lys Asn Val Thr Leu Lys Pro Ile Thr Glu<br>305                              310                    315                    320 | 960 |
| ggc gat gcg aac cca caa gag ttc atc ccg cgt atg ctg gca ctc tac<br>Gly Asp Ala Asn Pro Gln Glu Phe Ile Pro Arg Met Leu Ala Leu Tyr<br>                        325                     330                    335 | 1008 |
| cgt gag ggt aag ttc ccg ttt gag aaa ctg atc acg acc ttt ccg ttt<br>Arg Glu Gly Lys Phe Pro Phe Glu Lys Leu Ile Thr Thr Phe Pro Phe<br>           340                    345                    350 | 1056 |
| gag cac att aat gaa gca atg gaa gcc act gag tcc ggt aag gcc att<br>Glu His Ile Asn Glu Ala Met Glu Ala Thr Glu Ser Gly Lys Ala Ile<br>           355                    360                    365 | 1104 |
| aaa ccg gtt ctg acg ctg taa<br>Lys Pro Val Leu Thr Leu | 1125 |

<210> SEQ ID NO 42
<211> LENGTH: 374
<212> TYPE: PRT
<213> ORGANISM: Pseudomonas sp. 19-rlim

<400> SEQUENCE: 42

Met Thr Ile Asn Ser Ile Gln Pro Ile Gln Ala Lys Ala Ala Val Leu
1               5                   10                  15

Arg Ala Val Gly Ser Pro Phe Asn Ile Glu Pro Ile Arg Ile Ser Pro
                20                  25                  30

Pro Lys Gly Asp Glu Val Leu Val Arg Ile Val Gly Val Gly Val Cys
            35                  40                  45

His Thr Asp Val Val Cys Arg Asp Ser Phe Pro Val Pro Leu Pro Ile
        50                  55                  60

Ile Leu Gly His Glu Gly Ser Gly Val Ile Glu Ala Ile Gly Asp Gln
65                  70                  75                  80

Val Thr Ser Leu Lys Pro Gly Asp His Val Val Leu Ser Phe Asn Ser
                85                  90                  95

Cys Gly His Cys Tyr Asn Cys Gly His Ala Glu Pro Ala Ser Cys Leu
                100                 105                 110

Gln Met Leu Pro Leu Asn Phe Gly Gly Ala Glu Arg Ala Ala Asp Gly
            115                 120                 125

Thr Ile Gln Asp Asp Lys Gly Glu Ala Val Arg Gly Met Phe Phe Gly
        130                 135                 140

Gln Ser Ser Phe Gly Thr Tyr Ala Ile Ala Arg Ala Val Asn Ala Val
145                 150                 155                 160

Lys Val Asp Asp Asp Leu Pro Leu Pro Leu Leu Gly Pro Leu Gly Cys
                165                 170                 175

Gly Ile Gln Thr Gly Ala Gly Ala Ala Met Asn Ser Leu Ser Leu Gln
            180                 185                 190

Ser Gly Gln Ser Phe Ile Val Phe Gly Gly Gly Ala Val Gly Leu Ser
        195                 200                 205

Ala Val Met Ala Ala Lys Ala Leu Gly Val Ser Pro Leu Ile Val Val
210                 215                 220

Glu Pro Asn Glu Ser Arg Arg Ala Leu Ala Leu Glu Leu Gly Ala Ser
225                 230                 235                 240

His Val Phe Asp Pro Phe Asn Thr Glu Asp Leu Val Ala Ser Ile Arg
                245                 250                 255

Glu Val Val Pro Ala Gly Ala Asn His Ala Leu Asp Thr Thr Gly Leu
            260                 265                 270

Pro Lys Val Ile Ala Ser Ala Ile Asp Cys Ile Met Ser Gly Gly Lys
        275                 280                 285

Leu Gly Leu Leu Gly Met Ala Ser Pro Glu Ala Asn Val Pro Ala Thr
        290                 295                 300

Leu Leu Asp Leu Leu Ser Lys Asn Val Thr Leu Lys Pro Ile Thr Glu
305                 310                 315                 320

Gly Asp Ala Asn Pro Gln Glu Phe Ile Pro Arg Met Leu Ala Leu Tyr
                325                 330                 335

Arg Glu Gly Lys Phe Pro Phe Glu Lys Leu Ile Thr Thr Phe Pro Phe
            340                 345                 350

Glu His Ile Asn Glu Ala Met Glu Ala Thr Glu Ser Gly Lys Ala Ile
        355                 360                 365

```
Lys Pro Val Leu Thr Leu
    370

<210> SEQ ID NO 43
<211> LENGTH: 1017
<212> TYPE: DNA
<213> ORGANISM: Aspergillus wentii DTO 134E9
<220> FEATURE:
<221> NAME/KEY: CDS
<222> LOCATION: (1)..(1017)

<400> SEQUENCE: 43 atg ggt agc att act gaa gat atc cca acc atg cgc gct gct act gtt      48
Met Gly Ser Ile Thr Glu Asp Ile Pro Thr Met Arg Ala Ala Thr Val
1               5                   10                  15 gtt gag tac aat aag ccg ctt caa atc ctg aat atc cct att ccg acc      96
Val Glu Tyr Asn Lys Pro Leu Gln Ile Leu Asn Ile Pro Ile Pro Thr
            20                  25                  30 ccg tcc cag gat cag att ctg gtc aag gtc acc gca tgc agc ctg tgc     144
Pro Ser Gln Asp Gln Ile Leu Val Lys Val Thr Ala Cys Ser Leu Cys
        35                  40                  45 aac agc gac ctg gcg ggc tgg ctg ggt gtt gtt ggt gcg gtt gcg ccg     192
Asn Ser Asp Leu Ala Gly Trp Leu Gly Val Val Gly Ala Val Ala Pro
    50                  55                  60 tat tgt ccg ggc cat gaa ccg gtg ggt gta att gag agc gtc ggt agc     240
Tyr Cys Pro Gly His Glu Pro Val Gly Val Ile Glu Ser Val Gly Ser
65                  70                  75                  80 gcc gtt cgc ggt ttc aag aaa ggc gac cgt gcc ggt ttc atg ccg agc     288
Ala Val Arg Gly Phe Lys Lys Gly Asp Arg Ala Gly Phe Met Pro Ser
                85                  90                  95 tcc ttt acg tgt aaa gac tgc aat gaa tgt caa acc ggt aat cat cgt     336
Ser Phe Thr Cys Lys Asp Cys Asn Glu Cys Gln Thr Gly Asn His Arg
            100                 105                 110 ttt tgt aat aag aaa acc agc gtg ggt ttc cag ggt ccg tat ggc ggc     384
Phe Cys Asn Lys Lys Thr Ser Val Gly Phe Gln Gly Pro Tyr Gly Gly
        115                 120                 125 ttc agc caa tat gcc gtt gct gac ccg ttg agc acg gtt aag atc ccg     432
Phe Ser Gln Tyr Ala Val Ala Asp Pro Leu Ser Thr Val Lys Ile Pro
    130                 135                 140 gac gcg ctg tct gat gaa gtc acg gcg ccg ctg ttg tgc gcg ggt gtg     480
Asp Ala Leu Ser Asp Glu Val Thr Ala Pro Leu Leu Cys Ala Gly Val
145                 150                 155                 160 acg gcg tat ggc gca ctg cgc aag gtc ccg cca ggc gtg cag agc gtg     528
Thr Ala Tyr Gly Ala Leu Arg Lys Val Pro Pro Gly Val Gln Ser Val
                165                 170                 175 aac gtt atc ggt tgc ggt ggc gtt ggc cac ctg gtg atc caa tat gcg     576
Asn Val Ile Gly Cys Gly Gly Val Gly His Leu Val Ile Gln Tyr Ala
            180                 185                 190 aag gct ctg ggt tac tac gtg cgt ggc ttt gac gtt aac gac aag aaa     624
Lys Ala Leu Gly Tyr Tyr Val Arg Gly Phe Asp Val Asn Asp Lys Lys
        195                 200                 205 ctg ggc ctg gca gcg cgt agc ggt gcg gat gaa acc ttt tac agc acc     672
Leu Gly Leu Ala Ala Arg Ser Gly Ala Asp Glu Thr Phe Tyr Ser Thr
    210                 215                 220 gat gcc acc cat gcg gac cag gca tct gca acg atc gtc gcg acc ggc     720
Asp Ala Thr His Ala Asp Gln Ala Ser Ala Thr Ile Val Ala Thr Gly
225                 230                 235                 240 gcg gtt gca gcg tac aaa gcc gca ttc gca gtc acc gcc aac cac ggt     768
Ala Val Ala Ala Tyr Lys Ala Ala Phe Ala Val Thr Ala Asn His Gly
                245                 250                 255 cgt atc att gcg atc ggt gtc ccg aag ggt gag att ccg gtg tcg ctg     816
Arg Ile Ile Ala Ile Gly Val Pro Lys Gly Glu Ile Pro Val Ser Leu
```

```
                    Arg Ile Ile Ala Ile Gly Val Pro Lys Gly Glu Ile Pro Val Ser Leu
                                    260                 265                 270 ctg gac atg gtc aaa cgt gat ctg agc tta gtg gcg acg aac caa ggc           864
Leu Asp Met Val Lys Arg Asp Leu Ser Leu Val Ala Thr Asn Gln Gly
            275                 280                 285 tcc aaa gaa gaa ttg gaa gag gct ctg gaa att gca gtg caa cac cag           912
Ser Lys Glu Glu Leu Glu Glu Ala Leu Glu Ile Ala Val Gln His Gln
        290                 295                 300 atc gca ccg gag tac gaa att cgc cag ctg gac cag ctg aac gat ggc           960
Ile Ala Pro Glu Tyr Glu Ile Arg Gln Leu Asp Gln Leu Asn Asp Gly
305                 310                 315                 320 ttt caa gag atg atg aaa ggt gag agc cac ggt cgt ctg gtg tac cgt          1008
Phe Gln Glu Met Met Lys Gly Glu Ser His Gly Arg Leu Val Tyr Arg
                325                 330                 335 ctg tgg taa                                                              1017
Leu Trp <210> SEQ ID NO 44
<211> LENGTH: 338
<212> TYPE: PRT
<213> ORGANISM: Aspergillus wentii DTO 134E9

<400> SEQUENCE: 44

Met Gly Ser Ile Thr Glu Asp Ile Pro Thr Met Arg Ala Ala Thr Val
1               5                   10                  15

Val Glu Tyr Asn Lys Pro Leu Gln Ile Leu Asn Ile Pro Ile Pro Thr
            20                  25                  30

Pro Ser Gln Asp Gln Ile Leu Val Lys Val Thr Ala Cys Ser Leu Cys
        35                  40                  45

Asn Ser Asp Leu Ala Gly Trp Leu Gly Val Val Gly Ala Val Ala Pro
    50                  55                  60

Tyr Cys Pro Gly His Glu Pro Val Gly Val Ile Glu Ser Val Gly Ser
65                  70                  75                  80

Ala Val Arg Gly Phe Lys Lys Gly Asp Arg Ala Gly Phe Met Pro Ser
                85                  90                  95

Ser Phe Thr Cys Lys Asp Cys Asn Glu Cys Gln Thr Gly Asn His Arg
            100                 105                 110

Phe Cys Asn Lys Lys Thr Ser Val Gly Phe Gln Gly Pro Tyr Gly Gly
        115                 120                 125

Phe Ser Gln Tyr Ala Val Ala Asp Pro Leu Ser Thr Val Lys Ile Pro
    130                 135                 140

Asp Ala Leu Ser Asp Glu Val Thr Ala Pro Leu Leu Cys Ala Gly Val
145                 150                 155                 160

Thr Ala Tyr Gly Ala Leu Arg Lys Val Pro Pro Gly Val Gln Ser Val
                165                 170                 175

Asn Val Ile Gly Cys Gly Gly Val Gly His Leu Val Ile Gln Tyr Ala
            180                 185                 190

Lys Ala Leu Gly Tyr Tyr Val Arg Gly Phe Asp Val Asn Asp Lys Lys
        195                 200                 205

Leu Gly Leu Ala Ala Arg Ser Gly Ala Asp Glu Thr Phe Tyr Ser Thr
    210                 215                 220

Asp Ala Thr His Ala Asp Gln Ala Ser Ala Thr Ile Val Ala Thr Gly
225                 230                 235                 240

Ala Val Ala Ala Tyr Lys Ala Ala Phe Ala Val Thr Ala Asn His Gly
                245                 250                 255

Arg Ile Ile Ala Ile Gly Val Pro Lys Gly Glu Ile Pro Val Ser Leu
```

```
                260                 265                 270
Leu Asp Met Val Lys Arg Asp Leu Ser Leu Val Ala Thr Asn Gln Gly
            275                 280                 285

Ser Lys Glu Leu Glu Glu Ala Leu Glu Ile Ala Val Gln His Gln
        290                 295                 300

Ile Ala Pro Glu Tyr Glu Ile Arg Gln Leu Asp Gln Leu Asn Asp Gly
305                 310                 315                 320

Phe Gln Glu Met Met Lys Gly Glu Ser His Gly Arg Leu Val Tyr Arg
                325                 330                 335

Leu Trp

<210> SEQ ID NO 45
<211> LENGTH: 1119
<212> TYPE: DNA
<213> ORGANISM: Pseudomonas aeruginosa
<220> FEATURE:
<221> NAME/KEY: CDS
<222> LOCATION: (1)..(1119)

<400> SEQUENCE: 45
```

| | | | | | | | | | | | | | | | | |
|---|---|---|---|---|---|---|---|---|---|---|---|---|---|---|---|---|
| atg | aac | tcg | atc | caa | cct | act | caa | gca | aaa | gca | gca | gtc | ttg | cgc | gca | 48 |
| Met | Asn | Ser | Ile | Gln | Pro | Thr | Gln | Ala | Lys | Ala | Ala | Val | Leu | Arg | Ala | |
| 1 | | | | 5 | | | | | 10 | | | | | 15 | | |

| gtc | ggc | ggc | ccg | ttc | tct | att | gag | ccg | atc | cgc | atc | agc | cca | ccg | aag | 96 |
|---|---|---|---|---|---|---|---|---|---|---|---|---|---|---|---|---|
| Val | Gly | Gly | Pro | Phe | Ser | Ile | Glu | Pro | Ile | Arg | Ile | Ser | Pro | Pro | Lys | |
| | | 20 | | | | | 25 | | | | | 30 | | | | |

| ggt | gac | gaa | gtg | ctg | gtt | cgt | atc | gtt | ggt | gtg | ggt | gtc | tgc | cac | acc | 144 |
|---|---|---|---|---|---|---|---|---|---|---|---|---|---|---|---|---|
| Gly | Asp | Glu | Val | Leu | Val | Arg | Ile | Val | Gly | Val | Gly | Val | Cys | His | Thr | |
| | 35 | | | | | 40 | | | | | 45 | | | | | |

| gac | gtc | gtc | tgt | cgt | gat | agc | ttt | ccg | gtg | ccg | ttg | ccg | atc | att | ctg | 192 |
|---|---|---|---|---|---|---|---|---|---|---|---|---|---|---|---|---|
| Asp | Val | Val | Cys | Arg | Asp | Ser | Phe | Pro | Val | Pro | Leu | Pro | Ile | Ile | Leu | |
| 50 | | | | | 55 | | | | | 60 | | | | | | |

| ggt | cac | gag | ggc | tcc | ggt | gtg | att | gaa | gct | gtg | ggt | gac | caa | gtg | acc | 240 |
|---|---|---|---|---|---|---|---|---|---|---|---|---|---|---|---|---|
| Gly | His | Glu | Gly | Ser | Gly | Val | Ile | Glu | Ala | Val | Gly | Asp | Gln | Val | Thr | |
| 65 | | | | 70 | | | | | 75 | | | | | 80 | | |

| ggt | ctg | aaa | ccg | ggt | gac | cac | gtt | gtg | ctg | tcc | ttc | aat | agc | tgc | ggc | 288 |
|---|---|---|---|---|---|---|---|---|---|---|---|---|---|---|---|---|
| Gly | Leu | Lys | Pro | Gly | Asp | His | Val | Val | Leu | Ser | Phe | Asn | Ser | Cys | Gly | |
| | | | 85 | | | | | 90 | | | | | 95 | | | |

| cat | tgc | tac | aac | tgt | ggt | cat | gac | gag | cct | gcg | tct | tgt | ctg | cag | atg | 336 |
|---|---|---|---|---|---|---|---|---|---|---|---|---|---|---|---|---|
| His | Cys | Tyr | Asn | Cys | Gly | His | Asp | Glu | Pro | Ala | Ser | Cys | Leu | Gln | Met | |
| | | | 100 | | | | | 105 | | | | | 110 | | | |

| ctg | ccg | ttg | aat | ttc | ggt | ggc | gcg | gag | cgt | gcg | gcg | gac | ggc | acc | atc | 384 |
|---|---|---|---|---|---|---|---|---|---|---|---|---|---|---|---|---|
| Leu | Pro | Leu | Asn | Phe | Gly | Gly | Ala | Glu | Arg | Ala | Ala | Asp | Gly | Thr | Ile | |
| | | 115 | | | | | 120 | | | | | 125 | | | | |

| gaa | gat | gac | cag | ggc | gca | gct | gtt | cgt | ggc | ctg | ttc | ttc | ggc | caa | agc | 432 |
|---|---|---|---|---|---|---|---|---|---|---|---|---|---|---|---|---|
| Glu | Asp | Asp | Gln | Gly | Ala | Ala | Val | Arg | Gly | Leu | Phe | Phe | Gly | Gln | Ser | |
| | 130 | | | | | 135 | | | | | 140 | | | | | |

| tcc | ttt | ggt | agc | tac | gcg | att | gca | cgt | gcg | gtt | aac | act | gtc | aaa | gtt | 480 |
|---|---|---|---|---|---|---|---|---|---|---|---|---|---|---|---|---|
| Ser | Phe | Gly | Ser | Tyr | Ala | Ile | Ala | Arg | Ala | Val | Asn | Thr | Val | Lys | Val | |
| 145 | | | | | 150 | | | | | 155 | | | | | 160 | |

| gat | gac | gat | ctg | ccg | ttg | gcg | ctg | ctg | ggt | ccg | ctg | ggt | tgc | ggt | att | 528 |
|---|---|---|---|---|---|---|---|---|---|---|---|---|---|---|---|---|
| Asp | Asp | Asp | Leu | Pro | Leu | Ala | Leu | Leu | Gly | Pro | Leu | Gly | Cys | Gly | Ile | |
| | | | | 165 | | | | | 170 | | | | | 175 | | |

| cag | acc | ggc | gcg | ggt | gca | gcc | atg | aat | agc | ctg | ggt | tta | cag | ggt | ggc | 576 |
|---|---|---|---|---|---|---|---|---|---|---|---|---|---|---|---|---|
| Gln | Thr | Gly | Ala | Gly | Ala | Ala | Met | Asn | Ser | Leu | Gly | Leu | Gln | Gly | Gly | |
| | | | 180 | | | | | 185 | | | | | 190 | | | |

| cag | agc | ttc | att | gtg | ttt | ggc | ggc | gcc | gtc | ggt | ctg | agc | gcg | gtc | | 624 |
|---|---|---|---|---|---|---|---|---|---|---|---|---|---|---|---|---|
| Gln | Ser | Phe | Ile | Val | Phe | Gly | Gly | Ala | Val | Gly | Leu | Ser | Ala | Val | | |
| | | | 195 | | | | | 200 | | | | | 205 | | | |

```
atg gcc gcc aag gcc ctg ggt gtt agc ccg ctg att gtt gtg gag ccg    672
Met Ala Ala Lys Ala Leu Gly Val Ser Pro Leu Ile Val Val Glu Pro
210             215                 220 aac gaa gct cgc cgt gcg ctg gca ctg gaa ttg ggt gcg agc cac gcg    720
Asn Glu Ala Arg Arg Ala Leu Ala Leu Glu Leu Gly Ala Ser His Ala
225             230                 235                 240 ttt gac cca ttt aac acc gaa gat ctg gtc gcg agc att cgc gaa gtc    768
Phe Asp Pro Phe Asn Thr Glu Asp Leu Val Ala Ser Ile Arg Glu Val
                245                 250                 255 gtt ccg gct ggc gca aac cac gcg ctg gac acg acg ggt ctg ccg aaa    816
Val Pro Ala Gly Ala Asn His Ala Leu Asp Thr Thr Gly Leu Pro Lys
            260                 265                 270 gtt att gcc aac gcg atc gat tgc atc atg agc ggc ggc aaa ctg ggt    864
Val Ile Ala Asn Ala Ile Asp Cys Ile Met Ser Gly Gly Lys Leu Gly
                275                 280                 285 ctg ctc ggt atg gcg aat ccg gaa gcg aat gtg ccg gcg acc ctg ctg    912
Leu Leu Gly Met Ala Asn Pro Glu Ala Asn Val Pro Ala Thr Leu Leu
290             295                 300 gat ctg ctg agc aaa aat gtg acg ctg aag ccg atc acc gag ggt gac    960
Asp Leu Leu Ser Lys Asn Val Thr Leu Lys Pro Ile Thr Glu Gly Asp
305             310                 315                 320 gca aac cca caa gaa ttt att ccg cgt atg ctg gct ctg tat cgt gag   1008
Ala Asn Pro Gln Glu Phe Ile Pro Arg Met Leu Ala Leu Tyr Arg Glu
                325                 330                 335 ggt aag ttt ccg ttc gat aag ctg atc acc acg ttc ccg ttc gag cat   1056
Gly Lys Phe Pro Phe Asp Lys Leu Ile Thr Thr Phe Pro Phe Glu His
                340                 345                 350 atc aac gaa gca atg gaa gct acc gag agc ggt aag gcc att aaa ccg   1104
Ile Asn Glu Ala Met Glu Ala Thr Glu Ser Gly Lys Ala Ile Lys Pro
355                 360                 365 gtt ctg acc ctg taa                                                1119
Val Leu Thr Leu
    370
```

<210> SEQ ID NO 46
<211> LENGTH: 372
<212> TYPE: PRT
<213> ORGANISM: Pseudomonas aeruginosa

<400> SEQUENCE: 46

```
Met Asn Ser Ile Gln Pro Thr Gln Ala Lys Ala Val Leu Arg Ala
1               5                   10                  15

Val Gly Gly Pro Phe Ser Ile Glu Pro Ile Arg Ile Ser Pro Pro Lys
                20                  25                  30

Gly Asp Glu Val Leu Val Arg Ile Val Gly Val Gly Val Cys His Thr
            35                  40                  45

Asp Val Val Cys Arg Asp Ser Phe Pro Val Pro Leu Pro Ile Ile Leu
        50                  55                  60

Gly His Glu Gly Ser Gly Val Ile Glu Ala Val Gly Asp Gln Val Thr
65                  70                  75                  80

Gly Leu Lys Pro Gly Asp His Val Val Leu Ser Phe Asn Ser Cys Gly
                85                  90                  95

His Cys Tyr Asn Cys Gly His Asp Glu Pro Ala Ser Cys Leu Gln Met
            100                 105                 110

Leu Pro Leu Asn Phe Gly Gly Ala Glu Arg Ala Ala Asp Gly Thr Ile
        115                 120                 125

Glu Asp Asp Gln Gly Ala Ala Val Arg Gly Leu Phe Phe Gly Gln Ser
    130                 135                 140
```

```
Ser Phe Gly Ser Tyr Ala Ile Ala Arg Ala Val Asn Thr Val Lys Val
145                 150                 155                 160

Asp Asp Asp Leu Pro Leu Ala Leu Leu Gly Pro Leu Gly Cys Gly Ile
            165                 170                 175

Gln Thr Gly Ala Gly Ala Ala Met Asn Ser Leu Gly Leu Gln Gly Gly
            180                 185                 190

Gln Ser Phe Ile Val Phe Gly Gly Ala Val Gly Leu Ser Ala Val
            195                 200                 205

Met Ala Ala Lys Ala Leu Gly Val Ser Pro Leu Ile Val Val Glu Pro
210                 215                 220

Asn Glu Ala Arg Arg Ala Leu Ala Leu Glu Leu Gly Ala Ser His Ala
225                 230                 235                 240

Phe Asp Pro Phe Asn Thr Glu Asp Leu Val Ala Ser Ile Arg Glu Val
                245                 250                 255

Val Pro Ala Gly Ala Asn His Ala Leu Asp Thr Thr Gly Leu Pro Lys
                260                 265                 270

Val Ile Ala Asn Ala Ile Asp Cys Ile Met Ser Gly Gly Lys Leu Gly
            275                 280                 285

Leu Leu Gly Met Ala Asn Pro Glu Ala Asn Val Pro Ala Thr Leu Leu
290                 295                 300

Asp Leu Leu Ser Lys Asn Val Thr Leu Lys Pro Ile Thr Glu Gly Asp
305                 310                 315                 320

Ala Asn Pro Gln Glu Phe Ile Pro Arg Met Leu Ala Leu Tyr Arg Glu
                325                 330                 335

Gly Lys Phe Pro Phe Asp Lys Leu Ile Thr Thr Phe Pro Phe Glu His
            340                 345                 350

Ile Asn Glu Ala Met Glu Ala Thr Glu Ser Gly Lys Ala Ile Lys Pro
            355                 360                 365

Val Leu Thr Leu
370

<210> SEQ ID NO 47
<211> LENGTH: 1128
<212> TYPE: DNA
<213> ORGANISM: Azoarcus toluclasticus
<220> FEATURE:
<221> NAME/KEY: CDS
<222> LOCATION: (1)..(1128)

<400> SEQUENCE: 47 atg ggt tct att caa gat tct ctg ttc atc cgt gca cgc gcc gct gtt    48
Met Gly Ser Ile Gln Asp Ser Leu Phe Ile Arg Ala Arg Ala Ala Val
1               5                   10                  15 ctg cgt act gtc ggt ggc ccg ctg gaa att gaa aac gtc cgc att agc    96
Leu Arg Thr Val Gly Gly Pro Leu Glu Ile Glu Asn Val Arg Ile Ser
            20                  25                  30 cct ccg aag ggt gac gaa gtg ctc gtg cgt atg gtt ggt gtt ggt gtg   144
Pro Pro Lys Gly Asp Glu Val Leu Val Arg Met Val Gly Val Gly Val
        35                  40                  45 tgc cat acc gac gtt gtg tgt cgc gat ggc ttc ccg gtt ccg ctg ccg   192
Cys His Thr Asp Val Val Cys Arg Asp Gly Phe Pro Val Pro Leu Pro
    50                  55                  60 att gtg ctg ggt cac gag ggc agc ggt att gtc gag gca gtg ggc gag   240
Ile Val Leu Gly His Glu Gly Ser Gly Ile Val Glu Ala Val Gly Glu
65                  70                  75                  80 cgt gtg acc aag gtt aaa ccg ggt cag cgt gtc gtt tta tcc ttc aat   288
Arg Val Thr Lys Val Lys Pro Gly Gln Arg Val Val Leu Ser Phe Asn
                85                  90                  95
```

```
agc tgt ggt cat tgc gcg tcc tgc tgc gag gac cac ccg gcc acc tgt      336
Ser Cys Gly His Cys Ala Ser Cys Cys Glu Asp His Pro Ala Thr Cys
            100                 105                 110 cac cag atg ctg cca ctg aac ttt ggt gcg gcg cag cgc gtg gat ggt      384
His Gln Met Leu Pro Leu Asn Phe Gly Ala Ala Gln Arg Val Asp Gly
            115                 120                 125 ggc acc gtt atc gac gcg agc ggc gag gca gtg cag agc ctg ttt ttt      432
Gly Thr Val Ile Asp Ala Ser Gly Glu Ala Val Gln Ser Leu Phe Phe
130                 135                 140 ggt caa agc tct ttc ggt acg tat gca ttg gcg cgt gaa gtc aat acc      480
Gly Gln Ser Ser Phe Gly Thr Tyr Ala Leu Ala Arg Glu Val Asn Thr
145                 150                 155                 160 gta ccg gtg ccg gat gca gtt ccg ttg gaa atc ctg ggc ccg ttg ggt      528
Val Pro Val Pro Asp Ala Val Pro Leu Glu Ile Leu Gly Pro Leu Gly
                165                 170                 175 tgc ggc atc cag acg ggt gcg ggt gcg gct atc aac agc ctg gcg ctg      576
Cys Gly Ile Gln Thr Gly Ala Gly Ala Ala Ile Asn Ser Leu Ala Leu
            180                 185                 190 aaa cct ggt caa tcg ctg gca atc ttc ggt ggc ggc agc gtc ggt ctg      624
Lys Pro Gly Gln Ser Leu Ala Ile Phe Gly Gly Gly Ser Val Gly Leu
            195                 200                 205 tcc gcc ctg ctg ggc gcg ctg gcc gtg ggc gcg ggc ccg gtc gtt gtc      672
Ser Ala Leu Leu Gly Ala Leu Ala Val Gly Ala Gly Pro Val Val Val
210                 215                 220 att gag ccg aac gaa cgt cgt cgt gcg ttg gcg ctg gac ctg ggt gcg      720
Ile Glu Pro Asn Glu Arg Arg Arg Ala Leu Ala Leu Asp Leu Gly Ala
225                 230                 235                 240 agc cat gca ttt gat ccg ttc aac act gaa gat ttg gtt gcg agc atc      768
Ser His Ala Phe Asp Pro Phe Asn Thr Glu Asp Leu Val Ala Ser Ile
                245                 250                 255 aaa gcc gct acg ggt ggc ggc gtt acc cac agc ctg gac agc acg ggt      816
Lys Ala Ala Thr Gly Gly Gly Val Thr His Ser Leu Asp Ser Thr Gly
            260                 265                 270 ctg ccg ccg gtc atc gcg aat gca atc aac tgt acc ttg ccg ggc ggc      864
Leu Pro Pro Val Ile Ala Asn Ala Ile Asn Cys Thr Leu Pro Gly Gly
            275                 280                 285 acg gtc ggt ctg ctg ggc gtc ccg agc cca gag gct gcc gtt ccg gtg      912
Thr Val Gly Leu Leu Gly Val Pro Ser Pro Glu Ala Ala Val Pro Val
290                 295                 300 acg ctg ctg gat ctg ctg gtt aaa tca gtt acc ctg cgt ccg att acc      960
Thr Leu Leu Asp Leu Leu Val Lys Ser Val Thr Leu Arg Pro Ile Thr
305                 310                 315                 320 gag ggt gac gcc aat ccg caa gaa ttt att ccg cgt atg gtc cag ctg     1008
Glu Gly Asp Ala Asn Pro Gln Glu Phe Ile Pro Arg Met Val Gln Leu
                325                 330                 335 tac cgc gac ggt aaa ttt ccg ttt gat aag ctg att acg acc tac cgc     1056
Tyr Arg Asp Gly Lys Phe Pro Phe Asp Lys Leu Ile Thr Thr Tyr Arg
            340                 345                 350 ttc gac gac atc aat caa gcg ttc aag gca acc gaa acc ggt gaa gcg     1104
Phe Asp Asp Ile Asn Gln Ala Phe Lys Ala Thr Glu Thr Gly Glu Ala
            355                 360                 365 att aag cca gtg ctg gtg ttt taa                                      1128
Ile Lys Pro Val Leu Val Phe
    370                 375
```

<210> SEQ ID NO 48
<211> LENGTH: 375
<212> TYPE: PRT
<213> ORGANISM: Azoarcus toluclasticus

<400> SEQUENCE: 48

```
Met Gly Ser Ile Gln Asp Ser Leu Phe Ile Arg Ala Arg Ala Ala Val
1               5                   10                  15

Leu Arg Thr Val Gly Gly Pro Leu Glu Ile Glu Asn Val Arg Ile Ser
            20                  25                  30

Pro Pro Lys Gly Asp Glu Val Leu Val Arg Met Val Gly Val Gly Val
        35                  40                  45

Cys His Thr Asp Val Val Cys Arg Asp Gly Phe Pro Val Pro Leu Pro
    50                  55                  60

Ile Val Leu Gly His Glu Gly Ser Gly Ile Val Glu Ala Val Gly Glu
65                  70                  75                  80

Arg Val Thr Lys Val Lys Pro Gly Gln Arg Val Val Leu Ser Phe Asn
                85                  90                  95

Ser Cys Gly His Cys Ala Ser Cys Cys Glu Asp His Pro Ala Thr Cys
            100                 105                 110

His Gln Met Leu Pro Leu Asn Phe Gly Ala Ala Gln Arg Val Asp Gly
        115                 120                 125

Gly Thr Val Ile Asp Ala Ser Gly Glu Ala Val Gln Ser Leu Phe Phe
    130                 135                 140

Gly Gln Ser Ser Phe Gly Thr Tyr Ala Leu Ala Arg Glu Val Asn Thr
145                 150                 155                 160

Val Pro Val Pro Asp Ala Val Pro Leu Glu Ile Leu Gly Pro Leu Gly
                165                 170                 175

Cys Gly Ile Gln Thr Gly Ala Gly Ala Ala Ile Asn Ser Leu Ala Leu
            180                 185                 190

Lys Pro Gly Gln Ser Leu Ala Ile Phe Gly Gly Ser Val Gly Leu
        195                 200                 205

Ser Ala Leu Leu Gly Ala Leu Ala Val Gly Ala Gly Pro Val Val Val
210                 215                 220

Ile Glu Pro Asn Glu Arg Arg Arg Ala Leu Ala Leu Asp Leu Gly Ala
225                 230                 235                 240

Ser His Ala Phe Asp Pro Phe Asn Thr Glu Asp Leu Val Ala Ser Ile
                245                 250                 255

Lys Ala Ala Thr Gly Gly Gly Val Thr His Ser Leu Asp Ser Thr Gly
            260                 265                 270

Leu Pro Pro Val Ile Ala Asn Ala Ile Asn Cys Thr Leu Pro Gly Gly
        275                 280                 285

Thr Val Gly Leu Leu Gly Val Pro Ser Pro Glu Ala Ala Val Pro Val
    290                 295                 300

Thr Leu Leu Asp Leu Leu Val Lys Ser Val Thr Leu Arg Pro Ile Thr
305                 310                 315                 320

Glu Gly Asp Ala Asn Pro Gln Glu Phe Ile Pro Arg Met Val Gln Leu
                325                 330                 335

Tyr Arg Asp Gly Lys Phe Pro Phe Asp Lys Leu Ile Thr Thr Tyr Arg
            340                 345                 350

Phe Asp Asp Ile Asn Gln Ala Phe Lys Ala Thr Glu Thr Gly Glu Ala
        355                 360                 365

Ile Lys Pro Val Leu Val Phe
    370                 375
```

<210> SEQ ID NO 49
<211> LENGTH: 1128
<212> TYPE: DNA
<213> ORGANISM: Aromatoleum aromaticum

```
<220> FEATURE:
<221> NAME/KEY: CDS
<222> LOCATION: (1)..(1128)

<400> SEQUENCE: 49 atg ggc tca att caa gat tct ctg ttc atc ccg gct aga gcg gca gtg      48
Met Gly Ser Ile Gln Asp Ser Leu Phe Ile Pro Ala Arg Ala Ala Val
1               5                   10                  15 ttg cgt gcg gtc ggt ggc cca ctg gaa atc gaa gat gtt cgt atc agc      96
Leu Arg Ala Val Gly Gly Pro Leu Glu Ile Glu Asp Val Arg Ile Ser
            20                  25                  30 ccg cct aag ggc gac gaa gtt ctg gtc cgt atg gtt ggc gtg ggc gtt     144
Pro Pro Lys Gly Asp Glu Val Leu Val Arg Met Val Gly Val Gly Val
        35                  40                  45 tgc cac acc gac gtt gtg tgc cgc gat ggt ttc ccg gtc ccg ctg ccg     192
Cys His Thr Asp Val Val Cys Arg Asp Gly Phe Pro Val Pro Leu Pro
    50                  55                  60 att gtc ttg ggt cac gag ggt gcg ggt atc gtg gaa gct gtg ggt gag     240
Ile Val Leu Gly His Glu Gly Ala Gly Ile Val Glu Ala Val Gly Glu
65                  70                  75                  80 cgt gtg acc aag gtc aaa cct ggc cag cgt gtg gtg ctg agc ttc aac     288
Arg Val Thr Lys Val Lys Pro Gly Gln Arg Val Val Leu Ser Phe Asn
                85                  90                  95 agc tgc ggt cac tgc agc tcc tgt ggt gag gat cac ccg gcg acg tgt     336
Ser Cys Gly His Cys Ser Ser Cys Gly Glu Asp His Pro Ala Thr Cys
            100                 105                 110 cat cag atg ctg ccg ctg aat ttt ggt gca gcg caa cgt gtt gac ggt     384
His Gln Met Leu Pro Leu Asn Phe Gly Ala Ala Gln Arg Val Asp Gly
        115                 120                 125 ggc tgt gtc acc gat gcg agc ggt gaa gct gta cat agc ctg ttt ttc     432
Gly Cys Val Thr Asp Ala Ser Gly Glu Ala Val His Ser Leu Phe Phe
    130                 135                 140 ggt cag agc tct ttt tgc acc ttt gca ctg gcg cgc gaa gtg aac acc     480
Gly Gln Ser Ser Phe Cys Thr Phe Ala Leu Ala Arg Glu Val Asn Thr
145                 150                 155                 160 gtt cct gtc ggt gac ggc gtt ccg ctg gaa att ctg ggt ccg ctg ggt     528
Val Pro Val Gly Asp Gly Val Pro Leu Glu Ile Leu Gly Pro Leu Gly
                165                 170                 175 tgt ggt att caa acc ggt gca ggc gca gcg atc aac agc ctg gcc att     576
Cys Gly Ile Gln Thr Gly Ala Gly Ala Ala Ile Asn Ser Leu Ala Ile
            180                 185                 190 aaa ccg ggt cag agc ctg gcg att ttc ggt ggc ggc agc gtt ggt ctg     624
Lys Pro Gly Gln Ser Leu Ala Ile Phe Gly Gly Gly Ser Val Gly Leu
        195                 200                 205 tcc gcc ctg ctg ggc gca ctg gcc gtg ggc gcg ggt ccg gtt gtt gtg     672
Ser Ala Leu Leu Gly Ala Leu Ala Val Gly Ala Gly Pro Val Val Val
    210                 215                 220 gtg gag ccg aat gat cgt cgt cgt gca ctg gcc ctg gac ctg ggt gcg     720
Val Glu Pro Asn Asp Arg Arg Arg Ala Leu Ala Leu Asp Leu Gly Ala
225                 230                 235                 240 tcg cat gtg ttt gac ccg ttc aat acc gaa gat ctg gtt gcg agc att     768
Ser His Val Phe Asp Pro Phe Asn Thr Glu Asp Leu Val Ala Ser Ile
                245                 250                 255 aaa gcc gcg acg ggt ggc ggc gtt act cac agc ctg gac agc act ggc     816
Lys Ala Ala Thr Gly Gly Gly Val Thr His Ser Leu Asp Ser Thr Gly
            260                 265                 270 ttg ccg ccg gtg atc gca aag gcc att gat tgt acg ttg ccg ggt ggc     864
Leu Pro Pro Val Ile Ala Lys Ala Ile Asp Cys Thr Leu Pro Gly Gly
        275                 280                 285 acc gtc ggt tta ctg ggt gtt ccg gct ccg gac gcc gca gtg ccg gtc     912
```

```

Thr Val Gly Leu Leu Gly Val Pro Ala Pro Asp Ala Ala Val Pro Val
    290                 295                 300 acg ctg ctg gac ttg ctg gtg aag tcc gtt acc ctg cgc ccg atc acc        960
Thr Leu Leu Asp Leu Leu Val Lys Ser Val Thr Leu Arg Pro Ile Thr
305                 310                 315                 320 gag ggt gac gca aac ccg caa gaa ttt att cca cgc atg gtt cag ctc       1008
Glu Gly Asp Ala Asn Pro Gln Glu Phe Ile Pro Arg Met Val Gln Leu
                325                 330                 335 tac cgt gat ggt aag ttc cca ttt gat aaa ctg atc acc acg tat cgt       1056
Tyr Arg Asp Gly Lys Phe Pro Phe Asp Lys Leu Ile Thr Thr Tyr Arg
            340                 345                 350 ttt gag aac atc aat gac gcg ttc aaa gcg acg gaa acg ggt gaa gcg       1104
Phe Glu Asn Ile Asn Asp Ala Phe Lys Ala Thr Glu Thr Gly Glu Ala
        355                 360                 365 atc aaa ccg gtc ctg gtt ttc taa                                       1128
Ile Lys Pro Val Leu Val Phe
    370                 375

<210> SEQ ID NO 50
<211> LENGTH: 375
<212> TYPE: PRT
<213> ORGANISM: Aromatoleum aromaticum

<400> SEQUENCE: 50

Met Gly Ser Ile Gln Asp Ser Leu Phe Ile Pro Ala Arg Ala Val
1               5                   10                  15

Leu Arg Ala Val Gly Gly Pro Leu Glu Ile Glu Asp Val Arg Ile Ser
                20                  25                  30

Pro Pro Lys Gly Asp Glu Val Leu Val Arg Met Val Gly Val Gly Val
            35                  40                  45

Cys His Thr Asp Val Val Cys Arg Asp Gly Phe Pro Val Pro Leu Pro
        50                  55                  60

Ile Val Leu Gly His Glu Gly Ala Gly Ile Val Glu Ala Val Gly Glu
65                  70                  75                  80

Arg Val Thr Lys Val Lys Pro Gly Gln Arg Val Val Leu Ser Phe Asn
                85                  90                  95

Ser Cys Gly His Cys Ser Ser Cys Gly Glu Asp His Pro Ala Thr Cys
                100                 105                 110

His Gln Met Leu Pro Leu Asn Phe Gly Ala Ala Gln Arg Val Asp Gly
            115                 120                 125

Gly Cys Val Thr Asp Ala Ser Gly Glu Ala Val His Ser Leu Phe Phe
        130                 135                 140

Gly Gln Ser Ser Phe Cys Thr Phe Ala Leu Ala Arg Glu Val Asn Thr
145                 150                 155                 160

Val Pro Val Gly Asp Gly Val Pro Leu Glu Ile Leu Gly Pro Leu Gly
                165                 170                 175

Cys Gly Ile Gln Thr Gly Ala Gly Ala Ala Ile Asn Ser Leu Ala Ile
            180                 185                 190

Lys Pro Gly Gln Ser Leu Ala Ile Phe Gly Gly Ser Val Gly Leu
        195                 200                 205

Ser Ala Leu Leu Gly Ala Leu Ala Val Gly Ala Gly Pro Val Val Val
210                 215                 220

Val Glu Pro Asn Asp Arg Arg Arg Ala Leu Ala Leu Asp Leu Gly Ala
225                 230                 235                 240

Ser His Val Phe Asp Pro Phe Asn Thr Glu Asp Leu Val Ala Ser Ile
                245                 250                 255
```

```
Lys Ala Ala Thr Gly Gly Val Thr His Ser Leu Asp Ser Thr Gly
                260             265             270

Leu Pro Pro Val Ile Ala Lys Ala Ile Asp Cys Thr Leu Pro Gly Gly
        275                 280                 285

Thr Val Gly Leu Leu Gly Val Pro Ala Pro Asp Ala Ala Val Pro Val
    290                 295                 300

Thr Leu Leu Asp Leu Leu Val Lys Ser Val Thr Leu Arg Pro Ile Thr
305                 310                 315                 320

Glu Gly Asp Ala Asn Pro Gln Glu Phe Ile Pro Arg Met Val Gln Leu
                325                 330                 335

Tyr Arg Asp Gly Lys Phe Pro Phe Asp Lys Leu Ile Thr Thr Tyr Arg
            340                 345                 350

Phe Glu Asn Ile Asn Asp Ala Phe Lys Ala Thr Glu Thr Gly Glu Ala
                355                 360                 365

Ile Lys Pro Val Leu Val Phe
            370             375

<210> SEQ ID NO 51
<211> LENGTH: 1122
<212> TYPE: DNA
<213> ORGANISM: Thauera terpenica
<220> FEATURE:
<221> NAME/KEY: CDS
<222> LOCATION: (1)..(1122)

<400> SEQUENCE: 51 atg tgt agc aat cat gat ttc acc gca gcc cgt gca gca gtc tta cgt       48
Met Cys Ser Asn His Asp Phe Thr Ala Ala Arg Ala Ala Val Leu Arg
1               5                   10                  15 aaa gtt ggt ggc ccg ttg gaa atc gaa gat gtc cgt att tct gcc ccg       96
Lys Val Gly Gly Pro Leu Glu Ile Glu Asp Val Arg Ile Ser Ala Pro
            20                  25                  30 aaa ggc gac gaa gtc ctg gtg cgt atg gtt ggc gtg ggt gtg tgt cat      144
Lys Gly Asp Glu Val Leu Val Arg Met Val Gly Val Gly Val Cys His
        35                  40                  45 acc gac ctc gtc tgc cgt gat gcg ttc ccg gtg ccg ctg cct att gtt      192
Thr Asp Leu Val Cys Arg Asp Ala Phe Pro Val Pro Leu Pro Ile Val
    50                  55                  60 ctg ggt cac gag ggt gca ggc atc gtt gaa gcc gtg ggt gag ggc gtg      240
Leu Gly His Glu Gly Ala Gly Ile Val Glu Ala Val Gly Glu Gly Val
65                  70                  75                  80 cgc tcc ctg gag ccg ggt gac cgt gtt gtg ctg agc ttc aat agc tgc      288
Arg Ser Leu Glu Pro Gly Asp Arg Val Val Leu Ser Phe Asn Ser Cys
                85                  90                  95 ggc cgc tgt ggc aac tgc ggt agc ggt cac ccg agc aac tgc ctg caa      336
Gly Arg Cys Gly Asn Cys Gly Ser Gly His Pro Ser Asn Cys Leu Gln
            100                 105                 110 atg ctg ccg ctg aat ttt ggt ggc gcg caa cgc gtt gac ggt ggc cgc      384
Met Leu Pro Leu Asn Phe Gly Gly Ala Gln Arg Val Asp Gly Gly Arg
        115                 120                 125 atg ttg gac gcg gcg ggt aac gct gtc cag ggt ctg ttt ttt ggt caa      432
Met Leu Asp Ala Ala Gly Asn Ala Val Gln Gly Leu Phe Phe Gly Gln
    130                 135                 140 tct agc ttc ggc acg tat gcg atc gcg cgt gag att aac gcc gtg aaa      480
Ser Ser Phe Gly Thr Tyr Ala Ile Ala Arg Glu Ile Asn Ala Val Lys
145                 150                 155                 160 gtc gcc gaa gat ctg ccg ctg gaa atc ctg ggt ccg ctg ggt tgc ggt      528
Val Ala Glu Asp Leu Pro Leu Glu Ile Leu Gly Pro Leu Gly Cys Gly
                165                 170                 175
```

| | | |
|---|---|---|
| att cag acc ggt gcg ggt gcg gcg att aac agc ctg ggt att ggt ccg<br>Ile Gln Thr Gly Ala Gly Ala Ala Ile Asn Ser Leu Gly Ile Gly Pro<br>180                         185                   190 | | 576 |
| ggt cag tcc ttg gct gtg ttc ggt ggc ggc gtg ggt ctt agc gcg<br>Gly Gln Ser Leu Ala Val Phe Gly Gly Gly Val Gly Leu Ser Ala<br>    195                      200                   205 | | 624 |
| ttg ctg ggc gct cgt gct gtg ggt gcc gcc caa gtt gtt gtt gtt gag<br>Leu Leu Gly Ala Arg Ala Val Gly Ala Ala Gln Val Val Val Val Glu<br>210                       215                   220 | | 672 |
| ccg aac gcc gca cgt cgc gcg ctg gcg ctg gaa ctg ggt gcg agc cat<br>Pro Asn Ala Ala Arg Arg Ala Leu Ala Leu Glu Leu Gly Ala Ser His<br>225                    230                   235                   240 | | 720 |
| gca ttc gac ccg ttt gcg ggt gac gac ctg gtc gcg gcg atc cgc gca<br>Ala Phe Asp Pro Phe Ala Gly Asp Asp Leu Val Ala Ala Ile Arg Ala<br>              245                   250                   255 | | 768 |
| gcg acg ggt ggc ggc gca acc cac gcg ctg gat acg acc ggc ctg ccg<br>Ala Thr Gly Gly Gly Ala Thr His Ala Leu Asp Thr Thr Gly Leu Pro<br>        260                   265                   270 | | 816 |
| tcg gtg att ggc aat gca atc gat tgt act ttg ccg ggt ggc acg gtt<br>Ser Val Ile Gly Asn Ala Ile Asp Cys Thr Leu Pro Gly Gly Thr Val<br>275                       280                   285 | | 864 |
| ggt atg gtc ggc atg cca gcg cct gac gct gcg gtc ccg gcg acc ctg<br>Gly Met Val Gly Met Pro Ala Pro Asp Ala Ala Val Pro Ala Thr Leu<br>290                       295                   300 | | 912 |
| ctg gat ttg ctg act aag agc gtc acg ctg cgt ccg atc acc gag ggt<br>Leu Asp Leu Leu Thr Lys Ser Val Thr Leu Arg Pro Ile Thr Glu Gly<br>305                       310                   315                   320 | | 960 |
| gac gca gat ccg cag gcc ttc atc cca cag atg ctg cgc ttt tac cgt<br>Asp Ala Asp Pro Gln Ala Phe Ile Pro Gln Met Leu Arg Phe Tyr Arg<br>              325                   330                   335 | | 1008 |
| gag ggt aag ttc ccg ttt gac cgt ctg att acc cgt tac cgt ttt gat<br>Glu Gly Lys Phe Pro Phe Asp Arg Leu Ile Thr Arg Tyr Arg Phe Asp<br>        340                   345                   350 | | 1056 |
| cag atc aat gaa gct ctg cac gca acc gaa aag ggt ggc gcg att aaa<br>Gln Ile Asn Glu Ala Leu His Ala Thr Glu Lys Gly Gly Ala Ile Lys<br>355                       360                   365 | | 1104 |
| ccg gtt ctg gtg ttc taa<br>Pro Val Leu Val Phe<br>    370 | | 1122 |

```
<210> SEQ ID NO 52
<211> LENGTH: 373
<212> TYPE: PRT
<213> ORGANISM: Thauera terpenica

<400> SEQUENCE: 52
```

Met Cys Ser Asn His Asp Phe Thr Ala Ala Arg Ala Ala Val Leu Arg
1                  5                      10                     15

Lys Val Gly Gly Pro Leu Glu Ile Glu Asp Val Arg Ile Ser Ala Pro
                  20                      25                     30

Lys Gly Asp Glu Val Leu Val Arg Met Val Gly Val Gly Val Cys His
           35                      40                     45

Thr Asp Leu Val Cys Arg Asp Ala Phe Pro Val Pro Leu Pro Ile Val
 50                      55                      60

Leu Gly His Glu Gly Ala Gly Ile Val Glu Ala Val Gly Glu Gly Val
65                  70                      75                     80

Arg Ser Leu Glu Pro Gly Asp Arg Val Val Leu Ser Phe Asn Ser Cys
           85                      90                     95

Gly Arg Cys Gly Asn Cys Gly Ser Gly His Pro Ser Asn Cys Leu Gln

```
            100              105                 110
Met Leu Pro Leu Asn Phe Gly Gly Ala Gln Arg Val Asp Gly Gly Arg
        115                 120             125

Met Leu Asp Ala Ala Gly Asn Ala Val Gln Gly Leu Phe Phe Gly Gln
        130                 135             140

Ser Ser Phe Gly Thr Tyr Ala Ile Ala Arg Glu Ile Asn Ala Val Lys
145                 150                 155                 160

Val Ala Glu Asp Leu Pro Leu Glu Ile Leu Gly Pro Leu Gly Cys Gly
            165                 170                 175

Ile Gln Thr Gly Ala Gly Ala Ala Ile Asn Ser Leu Gly Ile Gly Pro
        180                 185                 190

Gly Gln Ser Leu Ala Val Phe Gly Gly Gly Val Gly Leu Ser Ala
        195                 200                 205

Leu Leu Gly Ala Arg Ala Val Gly Ala Ala Gln Val Val Val Val Glu
        210                 215                 220

Pro Asn Ala Ala Arg Arg Ala Leu Ala Leu Glu Leu Gly Ala Ser His
225                 230                 235                 240

Ala Phe Asp Pro Phe Ala Gly Asp Leu Val Ala Ala Ile Arg Ala
            245                 250                 255

Ala Thr Gly Gly Gly Ala Thr His Ala Leu Asp Thr Gly Leu Pro
            260                 265                 270

Ser Val Ile Gly Asn Ala Ile Asp Cys Thr Leu Pro Gly Gly Thr Val
            275                 280                 285

Gly Met Val Gly Met Pro Ala Pro Asp Ala Ala Val Pro Ala Thr Leu
        290                 295                 300

Leu Asp Leu Leu Thr Lys Ser Val Thr Leu Arg Pro Ile Thr Glu Gly
305                 310                 315                 320

Asp Ala Asp Pro Gln Ala Phe Ile Pro Gln Met Leu Arg Phe Tyr Arg
                325                 330                 335

Glu Gly Lys Phe Pro Phe Asp Arg Leu Ile Thr Arg Tyr Arg Phe Asp
            340                 345                 350

Gln Ile Asn Glu Ala Leu His Ala Thr Glu Lys Gly Gly Ala Ile Lys
        355                 360                 365

Pro Val Leu Val Phe
        370

<210> SEQ ID NO 53
<211> LENGTH: 1122
<212> TYPE: DNA
<213> ORGANISM: Castellaniella defragrans
<220> FEATURE:
<221> NAME/KEY: CDS
<222> LOCATION: (1)..(1122)

<400> SEQUENCE: 53 atg aac gat acg cag gat ttt att agc gcc caa gcc gca gtg tta cgt      48
Met Asn Asp Thr Gln Asp Phe Ile Ser Ala Gln Ala Ala Val Leu Arg
1               5                   10                  15 cag gtc ggt ggc ccg ctg gcc gtt gag cct gtt cgt atc agc atg ccg      96
Gln Val Gly Gly Pro Leu Ala Val Glu Pro Val Arg Ile Ser Met Pro
            20                  25                  30 aag ggt gac gaa gtc ctg att cgt atc gcg ggt gtt ggt gtg tgc cac     144
Lys Gly Asp Glu Val Leu Ile Arg Ile Ala Gly Val Gly Val Cys His
        35                  40                  45 acc gac ttg gtt tgc cgt gat ggc ttc ccg gtg ccg ctg cca att gtg     192
Thr Asp Leu Val Cys Arg Asp Gly Phe Pro Val Pro Leu Pro Ile Val
    50                  55                  60
```

```
ctg ggt cac gag ggt agc ggt act gtc gaa gcc gtc ggt gaa caa gtc       240
Leu Gly His Glu Gly Ser Gly Thr Val Glu Ala Val Gly Glu Gln Val
65                  70                  75                  80 cgt acc ctg aaa ccg ggc gat cgc gtc gtg ctg agc ttt aac agc tgc       288
Arg Thr Leu Lys Pro Gly Asp Arg Val Val Leu Ser Phe Asn Ser Cys
                85                  90                  95 ggt cat tgc ggt aac tgt cac gac ggt cac ccg agc aat tgc ctg cag       336
Gly His Cys Gly Asn Cys His Asp Gly His Pro Ser Asn Cys Leu Gln
            100                 105                 110 atg ctg ccg ctg aac ttc ggt ggc gcg caa cgc gtg gac ggt ggc caa       384
Met Leu Pro Leu Asn Phe Gly Gly Ala Gln Arg Val Asp Gly Gly Gln
        115                 120                 125 gtt ttg gac ggt gcg ggt cat ccg gtt cag tcc atg ttt ttc ggc cag       432
Val Leu Asp Gly Ala Gly His Pro Val Gln Ser Met Phe Phe Gly Gln
    130                 135                 140 tcc agc ttt ggc acc cac gca gta gcg cgc gag atc aac gca gtc aag       480
Ser Ser Phe Gly Thr His Ala Val Ala Arg Glu Ile Asn Ala Val Lys
145                 150                 155                 160 gtc ggc gat gat ctg cca ctg gaa ctg ctg ggt ccg ttg ggt tgt ggc       528
Val Gly Asp Asp Leu Pro Leu Glu Leu Leu Gly Pro Leu Gly Cys Gly
                165                 170                 175 att caa acc ggt gcg ggt gca gct atc aat tct ctg ggc att ggt ccg       576
Ile Gln Thr Gly Ala Gly Ala Ala Ile Asn Ser Leu Gly Ile Gly Pro
            180                 185                 190 ggt cag tct ctg gct atc ttc ggc ggc ggc ggc gtg ggt ctg agc gca       624
Gly Gln Ser Leu Ala Ile Phe Gly Gly Gly Gly Val Gly Leu Ser Ala
        195                 200                 205 ctg ctg ggc gcc cgt gcg gtg ggt gcc gac cgt gtt gtt gtc att gag       672
Leu Leu Gly Ala Arg Ala Val Gly Ala Asp Arg Val Val Val Ile Glu
    210                 215                 220 ccg aat gca gcg cgc cgt gcg ctg gca ttg gaa ctg ggt gcc agc cac       720
Pro Asn Ala Ala Arg Arg Ala Leu Ala Leu Glu Leu Gly Ala Ser His
225                 230                 235                 240 gca ctg gac ccg cat gcc gag ggc gac ctt gtt gcg gcg att aaa gct       768
Ala Leu Asp Pro His Ala Glu Gly Asp Leu Val Ala Ala Ile Lys Ala
                245                 250                 255 gcg acg ggt ggc ggc gct acg cat agc ttg gat acg acc ggc ctg ccg       816
Ala Thr Gly Gly Gly Ala Thr His Ser Leu Asp Thr Thr Gly Leu Pro
            260                 265                 270 cca gtc att ggc tcc gcg atc gcg tgt act ctg ccg ggt ggc acc gtt       864
Pro Val Ile Gly Ser Ala Ile Ala Cys Thr Leu Pro Gly Gly Thr Val
        275                 280                 285 ggt atg gtt ggt ctg ccg gcg ccg gac gca ccg gtc cct gcg acg ctg       912
Gly Met Val Gly Leu Pro Ala Pro Asp Ala Pro Val Pro Ala Thr Leu
    290                 295                 300 ttg gat ctg ctg agc aaa tcg gtt acc ctg cgt ccg att acc gag ggt       960
Leu Asp Leu Leu Ser Lys Ser Val Thr Leu Arg Pro Ile Thr Glu Gly
305                 310                 315                 320 gac gct gac ccg caa cgc ttc atc ccg cgt atg ctg gat ttc cat cgt      1008
Asp Ala Asp Pro Gln Arg Phe Ile Pro Arg Met Leu Asp Phe His Arg
                325                 330                 335 gcg ggc aag ttt ccg ttc gac cgc ctg atc acc cgt tac cgc ttt gat      1056
Ala Gly Lys Phe Pro Phe Asp Arg Leu Ile Thr Arg Tyr Arg Phe Asp
            340                 345                 350 cag atc aat gaa gcg ctg cac gcg acc gag aaa ggt gaa gca atc aaa      1104
Gln Ile Asn Glu Ala Leu His Ala Thr Glu Lys Gly Glu Ala Ile Lys
        355                 360                 365 ccg gtt ctg gtg ttt taa                                              1122
Pro Val Leu Val Phe
```

<210> SEQ ID NO 54
<211> LENGTH: 373
<212> TYPE: PRT
<213> ORGANISM: Castellaniella defragrans

<400> SEQUENCE: 54

Met Asn Asp Thr Gln Asp Phe Ile Ser Ala Gln Ala Val Leu Arg
1               5                   10                  15

Gln Val Gly Gly Pro Leu Ala Val Glu Pro Val Arg Ile Ser Met Pro
            20                  25                  30

Lys Gly Asp Glu Val Leu Ile Arg Ile Ala Gly Val Gly Val Cys His
        35                  40                  45

Thr Asp Leu Val Cys Arg Asp Gly Phe Pro Val Pro Leu Pro Ile Val
    50                  55                  60

Leu Gly His Glu Gly Ser Gly Thr Val Glu Ala Val Gly Glu Gln Val
65                  70                  75                  80

Arg Thr Leu Lys Pro Gly Asp Arg Val Val Leu Ser Phe Asn Ser Cys
                85                  90                  95

Gly His Cys Gly Asn Cys His Asp Gly His Pro Ser Asn Cys Leu Gln
            100                 105                 110

Met Leu Pro Leu Asn Phe Gly Gly Ala Gln Arg Val Asp Gly Gly Gln
        115                 120                 125

Val Leu Asp Gly Ala Gly His Pro Val Gln Ser Met Phe Phe Gly Gln
    130                 135                 140

Ser Ser Phe Gly Thr His Ala Val Ala Arg Glu Ile Asn Ala Val Lys
145                 150                 155                 160

Val Gly Asp Asp Leu Pro Leu Glu Leu Leu Gly Pro Leu Gly Cys Gly
                165                 170                 175

Ile Gln Thr Gly Ala Gly Ala Ala Ile Asn Ser Leu Gly Ile Gly Pro
            180                 185                 190

Gly Gln Ser Leu Ala Ile Phe Gly Gly Gly Val Gly Leu Ser Ala
        195                 200                 205

Leu Leu Gly Ala Arg Ala Val Gly Ala Asp Arg Val Val Val Ile Glu
    210                 215                 220

Pro Asn Ala Ala Arg Arg Ala Leu Ala Leu Glu Leu Gly Ala Ser His
225                 230                 235                 240

Ala Leu Asp Pro His Ala Glu Gly Asp Leu Val Ala Ala Ile Lys Ala
                245                 250                 255

Ala Thr Gly Gly Gly Ala Thr His Ser Leu Asp Thr Thr Gly Leu Pro
            260                 265                 270

Pro Val Ile Gly Ser Ala Ile Ala Cys Thr Leu Pro Gly Gly Thr Val
        275                 280                 285

Gly Met Val Gly Leu Pro Ala Pro Asp Ala Pro Val Pro Ala Thr Leu
    290                 295                 300

Leu Asp Leu Leu Ser Lys Ser Val Thr Leu Arg Pro Ile Thr Glu Gly
305                 310                 315                 320

Asp Ala Asp Pro Gln Arg Phe Ile Pro Arg Met Leu Asp Phe His Arg
                325                 330                 335

Ala Gly Lys Phe Pro Phe Asp Arg Leu Ile Thr Arg Tyr Arg Phe Asp
            340                 345                 350

Gln Ile Asn Glu Ala Leu His Ala Thr Glu Lys Gly Glu Ala Ile Lys
        355                 360                 365

```
Pro Val Leu Val Phe
    370

<210> SEQ ID NO 55
<211> LENGTH: 1146
<212> TYPE: DNA
<213> ORGANISM: Valeriana officinalis
<220> FEATURE:
<221> NAME/KEY: CDS
<222> LOCATION: (1)..(1146)

<400> SEQUENCE: 55 atg act aaa tcc agc ggt gaa gtg att tct tgt aag gca gca gtg atc       48
Met Thr Lys Ser Ser Gly Glu Val Ile Ser Cys Lys Ala Ala Val Ile
1               5                   10                  15 tat aag agc ggt gag cct gct aaa gtt gaa gaa att cgt gtt gat ccg       96
Tyr Lys Ser Gly Glu Pro Ala Lys Val Glu Glu Ile Arg Val Asp Pro
                20                  25                  30 cct aag agc agc gaa gtt cgt att aag atg ctg tac gcc tcc ttg tgt      144
Pro Lys Ser Ser Glu Val Arg Ile Lys Met Leu Tyr Ala Ser Leu Cys
            35                  40                  45 cac acg gac att ctg tgt tgc aac ggc ctg ccg gtg ccg ctg ttt ccg      192
His Thr Asp Ile Leu Cys Cys Asn Gly Leu Pro Val Pro Leu Phe Pro
        50                  55                  60 cgc att ccg ggt cac gag ggc gtg ggt gtt gtg gag agc gcg ggt gaa      240
Arg Ile Pro Gly His Glu Gly Val Gly Val Val Glu Ser Ala Gly Glu
65                  70                  75                  80 gat gtg aaa gat gtt aaa gag ggc gac atc gtt atg cca ctg tac ctg      288
Asp Val Lys Asp Val Lys Glu Gly Asp Ile Val Met Pro Leu Tyr Leu
                85                  90                  95 ggc gag tgt ggt gag tgc ctc aat tgc agc agc ggt aag acg aat ctg      336
Gly Glu Cys Gly Glu Cys Leu Asn Cys Ser Ser Gly Lys Thr Asn Leu
            100                 105                 110 tgc cac aag tac cca ctg gac ttc tct ggt gtg ctg ccg agc gac ggt      384
Cys His Lys Tyr Pro Leu Asp Phe Ser Gly Val Leu Pro Ser Asp Gly
        115                 120                 125 acg agc cgc atg tca gta gca aaa tcc ggt gag aaa att ttc cat cac      432
Thr Ser Arg Met Ser Val Ala Lys Ser Gly Glu Lys Ile Phe His His
    130                 135                 140 ttc agc tgt agc acc tgg tcc gaa tat gtt gtc atc gag agc tcg tat      480
Phe Ser Cys Ser Thr Trp Ser Glu Tyr Val Val Ile Glu Ser Ser Tyr
145                 150                 155                 160 gtc gtc aaa gtt gat agc cgt ctg ccg ctg ccg cat gcg tcc ttt ctg      528
Val Val Lys Val Asp Ser Arg Leu Pro Leu Pro His Ala Ser Phe Leu
                165                 170                 175 gca tgc ggc ttc acc acg ggt tac ggc gcg gcg tgg aaa gag gct gac      576
Ala Cys Gly Phe Thr Thr Gly Tyr Gly Ala Ala Trp Lys Glu Ala Asp
            180                 185                 190 att ccg aag ggc agc acc gtc gcg gtg ctg ggc ctg ggt gcg gtc ggt      624
Ile Pro Lys Gly Ser Thr Val Ala Val Leu Gly Leu Gly Ala Val Gly
        195                 200                 205 ctg ggt gtg gtt gct ggt gcg cgt tct cag ggt gcg agc cgc att att      672
Leu Gly Val Val Ala Gly Ala Arg Ser Gln Gly Ala Ser Arg Ile Ile
    210                 215                 220 ggc gtg gac atc aac gac aag aaa aaa gca aaa gcc gag atc ttt ggt      720
Gly Val Asp Ile Asn Asp Lys Lys Lys Ala Lys Ala Glu Ile Phe Gly
225                 230                 235                 240 gtt act gag ttt ctg aat ccg aag caa ctg ggt aaa agc gcg agc gaa      768
Val Thr Glu Phe Leu Asn Pro Lys Gln Leu Gly Lys Ser Ala Ser Glu
                245                 250                 255 agc atc aaa gac gtc acc ggc ggc ctg ggc gtt gac tac tgt ttc gag      816
```

```
Ser Ile Lys Asp Val Thr Gly Gly Leu Gly Val Asp Tyr Cys Phe Glu
                260                 265                 270 tgc acc ggt gtc ccg gcc ctg ttg aac gaa gcc gtg gat gcg agc aag       864
Cys Thr Gly Val Pro Ala Leu Leu Asn Glu Ala Val Asp Ala Ser Lys
            275                 280                 285 atc ggc ttg ggt acg atc gtc atg att ggt gcg ggt atg gaa acc agc       912
Ile Gly Leu Gly Thr Ile Val Met Ile Gly Ala Gly Met Glu Thr Ser
        290                 295                 300 ggt gtt att aac tat atc ccg ctg ctg tgc ggc cgt aaa ctg atc ggt       960
Gly Val Ile Asn Tyr Ile Pro Leu Leu Cys Gly Arg Lys Leu Ile Gly
305                 310                 315                 320 agc att tac ggt ggc gtt cgc atc cgt agc gac tta ccg ctg atc att      1008
Ser Ile Tyr Gly Gly Val Arg Ile Arg Ser Asp Leu Pro Leu Ile Ile
                325                 330                 335 gag aaa tgc atc aac aaa gaa att ccg ctg aac gaa ctg cag acc cac      1056
Glu Lys Cys Ile Asn Lys Glu Ile Pro Leu Asn Glu Leu Gln Thr His
            340                 345                 350 gaa gtg agc ttg gaa ggc att aat gat gca ttc ggc atg ctg aag caa      1104
Glu Val Ser Leu Glu Gly Ile Asn Asp Ala Phe Gly Met Leu Lys Gln
        355                 360                 365 ccg gac tgc gtt aag atc gtc atc aag ttc gag cag aaa taa              1146
Pro Asp Cys Val Lys Ile Val Ile Lys Phe Glu Gln Lys
370                 375                 380

<210> SEQ ID NO 56
<211> LENGTH: 381
<212> TYPE: PRT
<213> ORGANISM: Valeriana officinalis

<400> SEQUENCE: 56

Met Thr Lys Ser Ser Gly Glu Val Ile Ser Cys Lys Ala Val Ile
1               5                   10                  15

Tyr Lys Ser Gly Glu Pro Ala Lys Val Glu Ile Arg Val Asp Pro
                20                  25                  30

Pro Lys Ser Ser Glu Val Arg Ile Lys Met Leu Tyr Ala Ser Leu Cys
            35                  40                  45

His Thr Asp Ile Leu Cys Cys Asn Gly Leu Pro Val Pro Leu Phe Pro
        50                  55                  60

Arg Ile Pro Gly His Glu Gly Val Gly Val Val Glu Ser Ala Gly Glu
65                  70                  75                  80

Asp Val Lys Asp Val Lys Glu Gly Asp Ile Val Met Pro Leu Tyr Leu
                85                  90                  95

Gly Glu Cys Gly Glu Cys Leu Asn Cys Ser Ser Gly Lys Thr Asn Leu
            100                 105                 110

Cys His Lys Tyr Pro Leu Asp Phe Ser Gly Val Leu Pro Ser Asp Gly
        115                 120                 125

Thr Ser Arg Met Ser Val Ala Lys Ser Gly Glu Lys Ile Phe His His
130                 135                 140

Phe Ser Cys Ser Thr Trp Ser Glu Tyr Val Val Ile Glu Ser Ser Tyr
145                 150                 155                 160

Val Val Lys Val Asp Ser Arg Leu Pro Leu Pro His Ala Ser Phe Leu
                165                 170                 175

Ala Cys Gly Phe Thr Thr Gly Tyr Gly Ala Ala Trp Lys Glu Ala Asp
            180                 185                 190

Ile Pro Lys Gly Ser Thr Val Ala Val Leu Gly Leu Gly Ala Val Gly
        195                 200                 205

Leu Gly Val Val Ala Gly Ala Arg Ser Gln Gly Ala Ser Arg Ile Ile
```

```
                210                 215                 220
Gly Val Asp Ile Asn Asp Lys Lys Ala Lys Ala Glu Ile Phe Gly
225                 230                 235                 240

Val Thr Glu Phe Leu Asn Pro Lys Gln Leu Gly Lys Ser Ala Ser Glu
                245                 250                 255

Ser Ile Lys Asp Val Thr Gly Gly Leu Gly Val Asp Tyr Cys Phe Glu
                260                 265                 270

Cys Thr Gly Val Pro Ala Leu Leu Asn Glu Ala Val Asp Ala Ser Lys
                275                 280                 285

Ile Gly Leu Gly Thr Ile Val Met Ile Gly Ala Gly Met Glu Thr Ser
                290                 295                 300

Gly Val Ile Asn Tyr Ile Pro Leu Leu Cys Gly Arg Lys Leu Ile Gly
305                 310                 315                 320

Ser Ile Tyr Gly Gly Val Arg Ile Arg Ser Asp Leu Pro Leu Ile Ile
                325                 330                 335

Glu Lys Cys Ile Asn Lys Glu Ile Pro Leu Asn Glu Leu Gln Thr His
                340                 345                 350

Glu Val Ser Leu Glu Gly Ile Asn Asp Ala Phe Gly Met Leu Lys Gln
                355                 360                 365

Pro Asp Cys Val Lys Ile Val Ile Lys Phe Glu Gln Lys
                370                 375                 380

<210> SEQ ID NO 57
<211> LENGTH: 8
<212> TYPE: PRT
<213> ORGANISM: Artificial Sequence
<220> FEATURE:
<223> OTHER INFORMATION: active site signature motif
<220> FEATURE:
<221> NAME/KEY: MISC_FEATURE
<222> LOCATION: (3)..(4)
<223> OTHER INFORMATION: Xaa independently of each other represents any
      natural amino acid residue
<220> FEATURE:
<221> NAME/KEY: MISC_FEATURE
<222> LOCATION: (6)..(7)
<223> OTHER INFORMATION: Xaa independently of each other represents any
      natural amino acid residue

<400> SEQUENCE: 57

His Cys Xaa Xaa Gly Xaa Xaa Arg
1               5

<210> SEQ ID NO 58
<211> LENGTH: 10
<212> TYPE: PRT
<213> ORGANISM: Artificial Sequence
<220> FEATURE:
<223> OTHER INFORMATION: active site signature motif
<220> FEATURE:
<221> NAME/KEY: MISC_FEATURE
<222> LOCATION: (3)..(3)
<223> OTHER INFORMATION: Xaa represents T or S
<220> FEATURE:
<221> NAME/KEY: MISC_FEATURE
<222> LOCATION: (4)..(4)
<223> OTHER INFORMATION: Xaa represents any natural amino acid residue

<400> SEQUENCE: 58

His Cys Xaa Xaa Gly Lys Asp Arg Thr Gly
1               5                   10

<210> SEQ ID NO 59
<211> LENGTH: 2892
```

```
<212> TYPE: DNA
<213> ORGANISM: Talaromyces ferruculosus
<220> FEATURE:
<221> NAME/KEY: CDS
<222> LOCATION: (1)..(2892)

<400> SEQUENCE: 59 atg agc cct atg gat ttg caa gaa agc gcc gca gcc ctg gtc cgt caa        48
Met Ser Pro Met Asp Leu Gln Glu Ser Ala Ala Ala Leu Val Arg Gln
1               5                   10                  15 ttg ggt gaa cgc gtt gag gat cgc cgc ggt ttt ggt ttc atg agc ccg        96
Leu Gly Glu Arg Val Glu Asp Arg Arg Gly Phe Gly Phe Met Ser Pro
            20                  25                  30 gcc att tat gac acg gcc tgg gtt agc atg att agc aag acc atc gac       144
Ala Ile Tyr Asp Thr Ala Trp Val Ser Met Ile Ser Lys Thr Ile Asp
        35                  40                  45 gac caa aaa act tgg ctg ttt gcg gag tgc ttc cag tac att ctg tct       192
Asp Gln Lys Thr Trp Leu Phe Ala Glu Cys Phe Gln Tyr Ile Leu Ser
    50                  55                  60 cac caa ctg gaa gat ggt ggc tgg gcg atg tac gca tcc gaa atc gat       240
His Gln Leu Glu Asp Gly Gly Trp Ala Met Tyr Ala Ser Glu Ile Asp
65                  70                  75                  80 gcc atc ttg aat act tcc gcg tca ctg ctg tcc ctg aaa cgc cac ctg       288
Ala Ile Leu Asn Thr Ser Ala Ser Leu Leu Ser Leu Lys Arg His Leu
                85                  90                  95 tcc aac cct tac cag atc acc agc atc act cag gaa gat ctg agc gct       336
Ser Asn Pro Tyr Gln Ile Thr Ser Ile Thr Gln Glu Asp Leu Ser Ala
            100                 105                 110 cgc atc aac cgc gct caa aac gcc ctg cag aaa ttg ctg aac gag tgg       384
Arg Ile Asn Arg Ala Gln Asn Ala Leu Gln Lys Leu Leu Asn Glu Trp
        115                 120                 125 aac gtt gac tcc acg ctg cac gtc ggt ttc gag att ctg gtt ccg gcg       432
Asn Val Asp Ser Thr Leu His Val Gly Phe Glu Ile Leu Val Pro Ala
    130                 135                 140 ctg ctg cgc tat ctg gaa gat gaa ggc atc gcg ttt gcg ttc tcg ggt       480
Leu Leu Arg Tyr Leu Glu Asp Glu Gly Ile Ala Phe Ala Phe Ser Gly
145                 150                 155                 160 cgt gag cgt ttg tta gag att gag aaa caa aaa ctg tcc aag ttt aaa       528
Arg Glu Arg Leu Leu Glu Ile Glu Lys Gln Lys Leu Ser Lys Phe Lys
                165                 170                 175 gcg cag tat ttg tac tta ccg att aag gtc acc gca ctg cat agc ctg       576
Ala Gln Tyr Leu Tyr Leu Pro Ile Lys Val Thr Ala Leu His Ser Leu
            180                 185                 190 gaa gcc ttc atc ggc gct att gag ttc gac aaa gtc agc cat cac aaa       624
Glu Ala Phe Ile Gly Ala Ile Glu Phe Asp Lys Val Ser His His Lys
        195                 200                 205 gta tcc ggt gct ttc atg gcg tcg ccg tct agc acc gca gca tac atg       672
Val Ser Gly Ala Phe Met Ala Ser Pro Ser Ser Thr Ala Ala Tyr Met
    210                 215                 220 atg cat gcg acg caa tgg gat gac gaa tgt gag gat tac ttg cgt cac       720
Met His Ala Thr Gln Trp Asp Asp Glu Cys Glu Asp Tyr Leu Arg His
225                 230                 235                 240 gtg atc gcg cat gcg tca ggt aag ggt tct ggc ggc gtg ccg agc gcc       768
Val Ile Ala His Ala Ser Gly Lys Gly Ser Gly Gly Val Pro Ser Ala
                245                 250                 255 ttt ccg agc acc atc ttc gag agc gtt tgg ccg ctg tct act ctg ctg       816
Phe Pro Ser Thr Ile Phe Glu Ser Val Trp Pro Leu Ser Thr Leu Leu
            260                 265                 270 aaa gtt ggc tat gat ctg aat agc gct ccg ttc atc gag aaa att cgt       864
Lys Val Gly Tyr Asp Leu Asn Ser Ala Pro Phe Ile Glu Lys Ile Arg
        275                 280                 285
```

```
agc tac ttg cac gat gcc tat atc gca gag aaa ggt att ctc ggt ttc      912
Ser Tyr Leu His Asp Ala Tyr Ile Ala Glu Lys Gly Ile Leu Gly Phe
    290                 295                 300 acc ccg ttc gtt ggc gct gac gcg gac gac acc gct acc acg att ctg      960
Thr Pro Phe Val Gly Ala Asp Ala Asp Asp Thr Ala Thr Thr Ile Leu
305                 310                 315                 320 gtg ttg aat ctg ctg aac caa ccg gtg agc gtg gac gcg atg ttg aaa     1008
Val Leu Asn Leu Leu Asn Gln Pro Val Ser Val Asp Ala Met Leu Lys
                325                 330                 335 gaa ttt gaa gag gaa cat cac ttc aag acc tac agc caa gag cgt aat     1056
Glu Phe Glu Glu Glu His His Phe Lys Thr Tyr Ser Gln Glu Arg Asn
            340                 345                 350 ccg agc ttt tcc gca aac tgt aat gtt ctg ctg gcg ctg ctg tac agc     1104
Pro Ser Phe Ser Ala Asn Cys Asn Val Leu Leu Ala Leu Leu Tyr Ser
        355                 360                 365 cag gaa ccg agc ctg tac agc gcg caa atc gaa aaa gcg atc cgt ttt     1152
Gln Glu Pro Ser Leu Tyr Ser Ala Gln Ile Glu Lys Ala Ile Arg Phe
    370                 375                 380 ctg tat aag caa ttc acc gac tct gag atg gat gtg cgc gat aaa tgg     1200
Leu Tyr Lys Gln Phe Thr Asp Ser Glu Met Asp Val Arg Asp Lys Trp
385                 390                 395                 400 aac ctg tcc ccg tat tat agc tgg atg ctg atg acc cag gcc atc acc     1248
Asn Leu Ser Pro Tyr Tyr Ser Trp Met Leu Met Thr Gln Ala Ile Thr
                405                 410                 415 cgt ctg acg acc ctg caa aag acc agc aag ctg agc acg ctg cgt gat     1296
Arg Leu Thr Thr Leu Gln Lys Thr Ser Lys Leu Ser Thr Leu Arg Asp
            420                 425                 430 gac agc att agc aag ggc ctg att tct ctg ctg ttc cgc att gca tcc     1344
Asp Ser Ile Ser Lys Gly Leu Ile Ser Leu Leu Phe Arg Ile Ala Ser
        435                 440                 445 acc gtg gtt aaa gat caa aaa ccg ggt ggc agc tgg ggc acg cgt gcg     1392
Thr Val Val Lys Asp Gln Lys Pro Gly Gly Ser Trp Gly Thr Arg Ala
    450                 455                 460 agc aaa gaa gaa acg gca tac gcc gtg ctg att ctg acc tac gcg ttt     1440
Ser Lys Glu Glu Thr Ala Tyr Ala Val Leu Ile Leu Thr Tyr Ala Phe
465                 470                 475                 480 tat ctg gac gag gtg acc gag tct ctg cgc cac gat atc aaa att gca     1488
Tyr Leu Asp Glu Val Thr Glu Ser Leu Arg His Asp Ile Lys Ile Ala
                485                 490                 495 atc gag aat ggt tgc tcg ttc ctg agc gag cgc acc atg caa agc gac     1536
Ile Glu Asn Gly Cys Ser Phe Leu Ser Glu Arg Thr Met Gln Ser Asp
            500                 505                 510 agc gag tgg ctg tgg gtc gaa aag gtt acc tac aag agc gaa gtg ctg     1584
Ser Glu Trp Leu Trp Val Glu Lys Val Thr Tyr Lys Ser Glu Val Leu
        515                 520                 525 agc gaa gca tac atc ctg gca gct ctg aaa cgt gcg gca gac ttg ccg     1632
Ser Glu Ala Tyr Ile Leu Ala Ala Leu Lys Arg Ala Ala Asp Leu Pro
    530                 535                 540 gat gag aac gct gag gca gcc cca gtg atc aac ggt atc tct acc aat     1680
Asp Glu Asn Ala Glu Ala Ala Pro Val Ile Asn Gly Ile Ser Thr Asn
545                 550                 555                 560 ggc ttt gag cac acc gac cgc att aat ggt aaa ctc aag gtc aat ggt     1728
Gly Phe Glu His Thr Asp Arg Ile Asn Gly Lys Leu Lys Val Asn Gly
                565                 570                 575 acg aat ggc acc aac ggt tcc cac gaa acg aac ggt atc aat ggc acc     1776
Thr Asn Gly Thr Asn Gly Ser His Glu Thr Asn Gly Ile Asn Gly Thr
            580                 585                 590 cat gag att gag caa att aat ggt gtc aac ggc acg aat ggc cat agc     1824
His Glu Ile Glu Gln Ile Asn Gly Val Asn Gly Thr Asn Gly His Ser
```

-continued

```
              595                 600                 605
gac gtg cca cat gac acg aat ggt tgg gtc gag gaa ccg acg gcg att       1872
Asp Val Pro His Asp Thr Asn Gly Trp Val Glu Glu Pro Thr Ala Ile
        610                 615                 620 aat gaa acg aac ggt cac tac gtt aac ggc acc aac cat gag act ccg       1920
Asn Glu Thr Asn Gly His Tyr Val Asn Gly Thr Asn His Glu Thr Pro
625                 630                 635                 640 ctg acc aat ggt att agc aat ggt gac tcc gtg agc gtt cac acc gac       1968
Leu Thr Asn Gly Ile Ser Asn Gly Asp Ser Val Ser Val His Thr Asp
                645                 650                 655 cat agc gac agc tac tat cag cgt agc gac tgg acc gcg gat gaa gaa       2016
His Ser Asp Ser Tyr Tyr Gln Arg Ser Asp Trp Thr Ala Asp Glu Glu
            660                 665                 670 cag atc ctg ctg ggt cca ttc gat tac ctg gaa tcc ctg cct ggt aaa       2064
Gln Ile Leu Leu Gly Pro Phe Asp Tyr Leu Glu Ser Leu Pro Gly Lys
        675                 680                 685 aat atg cgc agc cag ctg atc cag tct ttc aat acg tgg ctg aag gtc       2112
Asn Met Arg Ser Gln Leu Ile Gln Ser Phe Asn Thr Trp Leu Lys Val
690                 695                 700 ccg acc gag agc ttg gac gtg att att aag gtc att agc atg ctg cac       2160
Pro Thr Glu Ser Leu Asp Val Ile Ile Lys Val Ile Ser Met Leu His
705                 710                 715                 720 act gct agc ctg ctg atc gac gat att cag gac caa agc atc ctg cgt       2208
Thr Ala Ser Leu Leu Ile Asp Asp Ile Gln Asp Gln Ser Ile Leu Arg
                725                 730                 735 cgt ggt cag cct gtg gcg cac tcg atc ttc ggc acc gcg caa gcg atg       2256
Arg Gly Gln Pro Val Ala His Ser Ile Phe Gly Thr Ala Gln Ala Met
            740                 745                 750 aac tct ggt aac tat gtt tac ttc ctg gca ttg cgt gaa gtt cag aaa       2304
Asn Ser Gly Asn Tyr Val Tyr Phe Leu Ala Leu Arg Glu Val Gln Lys
        755                 760                 765 ttg caa aac ccg aag gct atc agc att tat gtg gac agc ttg atc gat       2352
Leu Gln Asn Pro Lys Ala Ile Ser Ile Tyr Val Asp Ser Leu Ile Asp
770                 775                 780 ctt cat cgc ggc cag ggc atg gaa ctg ttc tgg cgt gat tct ctg atg       2400
Leu His Arg Gly Gln Gly Met Glu Leu Phe Trp Arg Asp Ser Leu Met
785                 790                 795                 800 tgc ccg act gaa gaa cag tat ctg gac atg gtg gcg aac aag acc ggt       2448
Cys Pro Thr Glu Glu Gln Tyr Leu Asp Met Val Ala Asn Lys Thr Gly
                805                 810                 815 ggc ctg ttt tgt ctg gcg att cag ctg atg cag gca gaa gcg acc att       2496
Gly Leu Phe Cys Leu Ala Ile Gln Leu Met Gln Ala Glu Ala Thr Ile
            820                 825                 830 cag gtt gat ttt att ccg ctg gtg cgt ctg ctg ggt atc att ttc cag       2544
Gln Val Asp Phe Ile Pro Leu Val Arg Leu Leu Gly Ile Ile Phe Gln
        835                 840                 845 att tgc gac gac tac ctg aac ttg aaa agc act gcg tat acc gac aac       2592
Ile Cys Asp Asp Tyr Leu Asn Leu Lys Ser Thr Ala Tyr Thr Asp Asn
850                 855                 860 aaa ggt ctg tgt gaa gat ctt acc gag ggt aaa ttc tcc ttc ccg atc       2640
Lys Gly Leu Cys Glu Asp Leu Thr Glu Gly Lys Phe Ser Phe Pro Ile
865                 870                 875                 880 att cac agc atc cgt agc aat ccg ggc aat cgt cag ctg atc aat att       2688
Ile His Ser Ile Arg Ser Asn Pro Gly Asn Arg Gln Leu Ile Asn Ile
                885                 890                 895 ctg aag caa aaa ccg cgc gaa gat gac atc aag cgt tac gca ctg tcc       2736
Leu Lys Gln Lys Pro Arg Glu Asp Asp Ile Lys Arg Tyr Ala Leu Ser
            900                 905                 910 tat atg gag agc acg aat agc ttc gag tac acc cgt ggc gtc gtc cgt       2784
Tyr Met Glu Ser Thr Asn Ser Phe Glu Tyr Thr Arg Gly Val Val Arg
```

```
Tyr Met Glu Ser Thr Asn Ser Phe Glu Tyr Thr Arg Gly Val Val Arg
        915                 920                 925 aaa ttg aaa acc gaa gca att gac acg att caa ggt ctg gag aag cat     2832
Lys Leu Lys Thr Glu Ala Ile Asp Thr Ile Gln Gly Leu Glu Lys His
        930                 935                 940 ggc ctg gaa gaa aac att ggt att cgt aag att ctg gcg cgt atg agc     2880
Gly Leu Glu Glu Asn Ile Gly Ile Arg Lys Ile Leu Ala Arg Met Ser
945                 950                 955                 960 ctg gaa ctg taa                                                     2892
Leu Glu Leu <210> SEQ ID NO 60
<211> LENGTH: 963
<212> TYPE: PRT
<213> ORGANISM: Talaromyces ferruculosus

<400> SEQUENCE: 60

Met Ser Pro Met Asp Leu Gln Glu Ser Ala Ala Leu Val Arg Gln
1               5                   10                  15

Leu Gly Glu Arg Val Glu Asp Arg Arg Gly Phe Gly Phe Met Ser Pro
                20                  25                  30

Ala Ile Tyr Asp Thr Ala Trp Val Ser Met Ile Ser Lys Thr Ile Asp
            35                  40                  45

Asp Gln Lys Thr Trp Leu Phe Ala Glu Cys Phe Gln Tyr Ile Leu Ser
        50                  55                  60

His Gln Leu Glu Asp Gly Gly Trp Ala Met Tyr Ala Ser Glu Ile Asp
65                  70                  75                  80

Ala Ile Leu Asn Thr Ser Ala Ser Leu Leu Ser Leu Lys Arg His Leu
                85                  90                  95

Ser Asn Pro Tyr Gln Ile Thr Ser Ile Thr Gln Glu Asp Leu Ser Ala
                100                 105                 110

Arg Ile Asn Arg Ala Gln Asn Ala Leu Gln Lys Leu Leu Asn Glu Trp
            115                 120                 125

Asn Val Asp Ser Thr Leu His Val Gly Phe Glu Ile Leu Val Pro Ala
        130                 135                 140

Leu Leu Arg Tyr Leu Glu Asp Glu Gly Ile Ala Phe Ala Phe Ser Gly
145                 150                 155                 160

Arg Glu Arg Leu Leu Glu Ile Glu Lys Gln Lys Leu Ser Lys Phe Lys
                165                 170                 175

Ala Gln Tyr Leu Tyr Leu Pro Ile Lys Val Thr Ala Leu His Ser Leu
            180                 185                 190

Glu Ala Phe Ile Gly Ala Ile Glu Phe Asp Lys Val Ser His His Lys
        195                 200                 205

Val Ser Gly Ala Phe Met Ala Ser Pro Ser Ser Thr Ala Ala Tyr Met
210                 215                 220

Met His Ala Thr Gln Trp Asp Asp Glu Cys Glu Asp Tyr Leu Arg His
225                 230                 235                 240

Val Ile Ala His Ala Ser Gly Lys Gly Ser Gly Val Pro Ser Ala
                245                 250                 255

Phe Pro Ser Thr Ile Phe Glu Ser Val Trp Pro Leu Ser Thr Leu Leu
            260                 265                 270

Lys Val Gly Tyr Asp Leu Asn Ser Ala Pro Phe Ile Glu Lys Ile Arg
        275                 280                 285

Ser Tyr Leu His Asp Ala Tyr Ile Ala Glu Lys Gly Ile Leu Gly Phe
        290                 295                 300
```

```
Thr Pro Phe Val Gly Ala Asp Ala Asp Asp Thr Ala Thr Thr Ile Leu
305                 310                 315                 320

Val Leu Asn Leu Leu Asn Gln Pro Val Ser Val Asp Ala Met Leu Lys
            325                 330                 335

Glu Phe Glu Glu Glu His His Phe Lys Thr Tyr Ser Gln Glu Arg Asn
            340                 345                 350

Pro Ser Phe Ser Ala Asn Cys Asn Val Leu Ala Leu Leu Tyr Ser
        355                 360                 365

Gln Glu Pro Ser Leu Tyr Ser Ala Gln Ile Glu Lys Ala Ile Arg Phe
            370                 375                 380

Leu Tyr Lys Gln Phe Thr Asp Ser Glu Met Asp Val Arg Asp Lys Trp
385                 390                 395                 400

Asn Leu Ser Pro Tyr Tyr Ser Trp Met Leu Met Thr Gln Ala Ile Thr
                405                 410                 415

Arg Leu Thr Thr Leu Gln Lys Thr Ser Lys Leu Ser Thr Leu Arg Asp
            420                 425                 430

Asp Ser Ile Ser Lys Gly Leu Ile Ser Leu Leu Phe Arg Ile Ala Ser
            435                 440                 445

Thr Val Val Lys Asp Gln Lys Pro Gly Gly Ser Trp Gly Thr Arg Ala
450                 455                 460

Ser Lys Glu Glu Thr Ala Tyr Ala Val Leu Ile Leu Thr Tyr Ala Phe
465                 470                 475                 480

Tyr Leu Asp Glu Val Thr Glu Ser Leu Arg His Asp Ile Lys Ile Ala
                485                 490                 495

Ile Glu Asn Gly Cys Ser Phe Leu Ser Glu Arg Thr Met Gln Ser Asp
            500                 505                 510

Ser Glu Trp Leu Trp Val Glu Lys Val Thr Tyr Lys Ser Glu Val Leu
            515                 520                 525

Ser Glu Ala Tyr Ile Leu Ala Ala Leu Lys Arg Ala Ala Asp Leu Pro
            530                 535                 540

Asp Glu Asn Ala Glu Ala Ala Pro Val Ile Asn Gly Ile Ser Thr Asn
545                 550                 555                 560

Gly Phe Glu His Thr Asp Arg Ile Asn Gly Lys Leu Lys Val Asn Gly
                565                 570                 575

Thr Asn Gly Thr Asn Gly Ser His Glu Thr Asn Gly Ile Asn Gly Thr
            580                 585                 590

His Glu Ile Glu Gln Ile Asn Gly Val Asn Gly Thr Asn Gly His Ser
            595                 600                 605

Asp Val Pro His Asp Thr Asn Gly Trp Val Glu Glu Pro Thr Ala Ile
            610                 615                 620

Asn Glu Thr Asn Gly His Tyr Val Asn Gly Thr Asn His Glu Thr Pro
625                 630                 635                 640

Leu Thr Asn Gly Ile Ser Asn Gly Asp Ser Val Ser Val His Thr Asp
                645                 650                 655

His Ser Asp Ser Tyr Tyr Gln Arg Ser Asp Trp Thr Ala Asp Glu Glu
            660                 665                 670

Gln Ile Leu Leu Gly Pro Phe Asp Tyr Leu Glu Ser Leu Pro Gly Lys
            675                 680                 685

Asn Met Arg Ser Gln Leu Ile Gln Ser Phe Asn Thr Trp Leu Lys Val
            690                 695                 700

Pro Thr Glu Ser Leu Asp Val Ile Ile Lys Val Ile Ser Met Leu His
705                 710                 715                 720

Thr Ala Ser Leu Leu Ile Asp Asp Ile Gln Asp Gln Ser Ile Leu Arg
```

```
                        725                 730                 735
Arg Gly Gln Pro Val Ala His Ser Ile Phe Gly Thr Ala Gln Ala Met
                    740                 745                 750
Asn Ser Gly Asn Tyr Val Tyr Phe Leu Ala Leu Arg Glu Val Gln Lys
                755                 760                 765
Leu Gln Asn Pro Lys Ala Ile Ser Ile Tyr Val Asp Ser Leu Ile Asp
            770                 775                 780
Leu His Arg Gly Gln Gly Met Glu Leu Phe Trp Arg Asp Ser Leu Met
785                 790                 795                 800
Cys Pro Thr Glu Glu Gln Tyr Leu Asp Met Val Ala Asn Lys Thr Gly
                805                 810                 815
Gly Leu Phe Cys Leu Ala Ile Gln Leu Met Gln Ala Glu Ala Thr Ile
                820                 825                 830
Gln Val Asp Phe Ile Pro Leu Val Arg Leu Leu Gly Ile Ile Phe Gln
                835                 840                 845
Ile Cys Asp Asp Tyr Leu Asn Leu Lys Ser Thr Ala Tyr Thr Asp Asn
850                 855                 860
Lys Gly Leu Cys Glu Asp Leu Thr Glu Gly Lys Phe Ser Phe Pro Ile
865                 870                 875                 880
Ile His Ser Ile Arg Ser Asn Pro Gly Asn Arg Gln Leu Ile Asn Ile
                885                 890                 895
Leu Lys Gln Lys Pro Arg Glu Asp Asp Ile Lys Arg Tyr Ala Leu Ser
                900                 905                 910
Tyr Met Glu Ser Thr Asn Ser Phe Glu Tyr Thr Arg Gly Val Val Arg
                915                 920                 925
Lys Leu Lys Thr Glu Ala Ile Asp Thr Ile Gln Gly Leu Glu Lys His
                930                 935                 940
Gly Leu Glu Glu Asn Ile Gly Ile Arg Lys Ile Leu Ala Arg Met Ser
945                 950                 955                 960
Leu Glu Leu

<210> SEQ ID NO 61
<211> LENGTH: 14
<212> TYPE: DNA
<213> ORGANISM: Artificial Sequence
<220> FEATURE:
<223> OTHER INFORMATION: Ribosome binding site

<400> SEQUENCE: 61
aaggaggtaa aaaa                                                      14

<210> SEQ ID NO 62
<211> LENGTH: 924
<212> TYPE: DNA
<213> ORGANISM: Pantoea agglomerans

<400> SEQUENCE: 62
atggtttctg gttctaaggc tggtgtttct ccacacagag aaatcgaagt tatgagacaa      60
tctatcgacg accacttggc tggtttgttg ccagaaactg actctcaaga catcgtttct     120
ttggctatga gaaaggtgt tatggctcca ggtaagagaa tcagaccatt gttgatgttg      180
ttggctgcta gagacttgag ataccaaggt tctatgccaa ctttgttgga cttggcttgt     240
gctgttgaat gactcacac tgcttctttg atgttggacg acatgccatg tatggacaac     300
gctgaattga agaggtca accaactact cacaagaagt cggtgaatc tgttgctatc      360 ttggcttctg ttggtttgtt gtctaaggct ttcggtttga tcgctgctac tggtgacttg     420
```

```
ccaggtgaaa gaagagctca agctgttaac gaattgtcta ctgctgttgg tgttcaaggt    480
ttggttttgg gtcaattcag agacttgaac gacgctgctt tggacagaac tccagacgct    540
atcttgtcta ctaaccactt gaagactggt atcttgttct ctgctatgtt gcaaatcgtt    600
gctatcgctt ctgcttcttc tccatctact agagaaactt gcacgctttt cgctttggac    660
ttcggtcaag ctttccaatt gttggacgac ttgagagacg accacccaga aactggtaag    720
gacagaaaca aggacgctgg taagtctact ttggttaaca gattgggtgc tgacgctgct    780
agacaaaagt tgagagaaca catcgactct gctgacaagc acttgacttt cgcttgtcca    840
caaggtggtg ctatcagaca attcatgcac ttgtggttcg gtcaccactt ggctgactgg    900
tctccagtta tgaagatcgc ttaa                                           924
```

<210> SEQ ID NO 63
<211> LENGTH: 2211
<212> TYPE: DNA
<213> ORGANISM: Salvia miltiorrhiza
<220> FEATURE:
<221> NAME/KEY: CDS
<222> LOCATION: (1)..(2211)

<400> SEQUENCE: 63

```
atg gct act gtt gac gct cca caa gtt cac gac cac gac ggt act act     48
Met Ala Thr Val Asp Ala Pro Gln Val His Asp His Asp Gly Thr Thr
1               5                   10                  15 gtt cac caa ggt cac gac gct gtt aag aac atc gaa gac cca atc gaa     96
Val His Gln Gly His Asp Ala Val Lys Asn Ile Glu Asp Pro Ile Glu
            20                  25                  30 tac atc aga act ttg ttg aga act act ggt gac ggt aga atc tct gtt    144
Tyr Ile Arg Thr Leu Leu Arg Thr Thr Gly Asp Gly Arg Ile Ser Val
        35                  40                  45 tct cca tac gac act gct tgg gtt gct atg atc aag gac gtt gaa ggt    192
Ser Pro Tyr Asp Thr Ala Trp Val Ala Met Ile Lys Asp Val Glu Gly
    50                  55                  60 aga gac ggt cca caa ttc cca tct tct ttg gaa tgg atc gtt caa aac    240
Arg Asp Gly Pro Gln Phe Pro Ser Ser Leu Glu Trp Ile Val Gln Asn
65                  70                  75                  80 caa ttg gaa gac ggt tct tgg ggt gac caa aag ttg ttc tgt gtt tac    288
Gln Leu Glu Asp Gly Ser Trp Gly Asp Gln Lys Leu Phe Cys Val Tyr
                85                  90                  95 gac aga ttg gtt aac act atc gct tgt gtt gtt gct ttg aga tct tgg    336
Asp Arg Leu Val Asn Thr Ile Ala Cys Val Val Ala Leu Arg Ser Trp
            100                 105                 110 aac gtt cac gct cac aag gtt aag aga ggt gtt act tac atc aag gaa    384
Asn Val His Ala His Lys Val Lys Arg Gly Val Thr Tyr Ile Lys Glu
        115                 120                 125 aac gtt gac aag ttg atg gaa ggt aac gaa gaa cac atg act tgt ggt    432
Asn Val Asp Lys Leu Met Glu Gly Asn Glu Glu His Met Thr Cys Gly
    130                 135                 140 ttc gaa gtt gtt ttc cca gct ttg ttg caa aag gct aag tct ttg ggt    480
Phe Glu Val Val Phe Pro Ala Leu Leu Gln Lys Ala Lys Ser Leu Gly
145                 150                 155                 160 atc gaa gac ttg cca tac gac tct cca gct gtt caa gaa gtt tac cac    528
Ile Glu Asp Leu Pro Tyr Asp Ser Pro Ala Val Gln Glu Val Tyr His
                165                 170                 175 gtt aga gaa caa aag ttg aag aga atc cca ttg gaa atc atg cac aag    576
Val Arg Glu Gln Lys Leu Lys Arg Ile Pro Leu Glu Ile Met His Lys
            180                 185                 190 atc cca act tct ttg ttg ttc tct ttg gaa ggt ttg gaa aac ttg gac    624
Ile Pro Thr Ser Leu Leu Phe Ser Leu Glu Gly Leu Glu Asn Leu Asp
```

```
Ile Pro Thr Ser Leu Leu Phe Ser Leu Glu Gly Leu Glu Asn Leu Asp
        195                 200                 205 tgg gac aag ttg ttg aag ttg caa tct gct gac ggt tct ttc ttg act      672
Trp Asp Lys Leu Leu Lys Leu Gln Ser Ala Asp Gly Ser Phe Leu Thr
        210                 215                 220 tct cca tct tct act gct ttc gct ttc atg caa act aag gac gaa aag      720
Ser Pro Ser Ser Thr Ala Phe Ala Phe Met Gln Thr Lys Asp Glu Lys
225                 230                 235                 240 tgt tac caa ttc atc aag aac act atc gac act ttc aac ggt ggt gct      768
Cys Tyr Gln Phe Ile Lys Asn Thr Ile Asp Thr Phe Asn Gly Gly Ala
                245                 250                 255 cca cac act tac cca gtt gac gtt ttc ggt aga ttg tgg gct atc gac      816
Pro His Thr Tyr Pro Val Asp Val Phe Gly Arg Leu Trp Ala Ile Asp
            260                 265                 270 aga ttg caa aga ttg ggt atc tct aga ttc ttc gaa cca gaa atc gct      864
Arg Leu Gln Arg Leu Gly Ile Ser Arg Phe Phe Glu Pro Glu Ile Ala
        275                 280                 285 gac tgt ttg tct cac atc cac aag ttc tgg act gac aag ggt gtt ttc      912
Asp Cys Leu Ser His Ile His Lys Phe Trp Thr Asp Lys Gly Val Phe
    290                 295                 300 tct ggt aga gaa tct gaa ttc tgt gac atc gac gac act tct atg ggt      960
Ser Gly Arg Glu Ser Glu Phe Cys Asp Ile Asp Asp Thr Ser Met Gly
305                 310                 315                 320 atg aga ttg atg aga atg cac ggt tac gac gtt gac cca aac gtt ttg     1008
Met Arg Leu Met Arg Met His Gly Tyr Asp Val Asp Pro Asn Val Leu
                325                 330                 335 aga aac ttc aag caa aag gac ggt aag ttc tct tgt tac ggt ggt caa     1056
Arg Asn Phe Lys Gln Lys Asp Gly Lys Phe Ser Cys Tyr Gly Gly Gln
            340                 345                 350 atg atc gaa tct cca tct cca atc tac aac ttg tac aga gct tct caa     1104
Met Ile Glu Ser Pro Ser Pro Ile Tyr Asn Leu Tyr Arg Ala Ser Gln
        355                 360                 365 ttg aga ttc cca ggt gaa gaa atc ttg gaa gac gct aag aga ttc gct     1152
Leu Arg Phe Pro Gly Glu Glu Ile Leu Glu Asp Ala Lys Arg Phe Ala
    370                 375                 380 tac gac ttc ttg aag gaa aag ttg gct aac aac caa atc ttg gac aag     1200
Tyr Asp Phe Leu Lys Glu Lys Leu Ala Asn Asn Gln Ile Leu Asp Lys
385                 390                 395                 400 tgg gtt atc tct aag cac ttg cca gac gaa atc aag ttg ggt ttg gaa     1248
Trp Val Ile Ser Lys His Leu Pro Asp Glu Ile Lys Leu Gly Leu Glu
                405                 410                 415 atg cca tgg ttg gct act ttg cca aga gtt gaa gct aag tac tac atc     1296
Met Pro Trp Leu Ala Thr Leu Pro Arg Val Glu Ala Lys Tyr Tyr Ile
            420                 425                 430 caa tac tac gct ggt tct ggt gac gtt tgg atc ggt aag act ttg tac     1344
Gln Tyr Tyr Ala Gly Ser Gly Asp Val Trp Ile Gly Lys Thr Leu Tyr
        435                 440                 445 aga atg cca gaa atc tct aac gac act tac cac gac ttg gct aag act     1392
Arg Met Pro Glu Ile Ser Asn Asp Thr Tyr His Asp Leu Ala Lys Thr
    450                 455                 460 gac ttc aag aga tgt caa gct aag cac caa ttc gaa tgg ttg tac atg     1440
Asp Phe Lys Arg Cys Gln Ala Lys His Gln Phe Glu Trp Leu Tyr Met
465                 470                 475                 480 caa gaa tgg tac gaa tct tgt ggt atc gaa gaa ttc ggt atc tct aga     1488
Gln Glu Trp Tyr Glu Ser Cys Gly Ile Glu Glu Phe Gly Ile Ser Arg
                485                 490                 495 aag gac ttg ttg ttg tct tac ttc ttg gct act gct tct atc ttc gaa     1536
Lys Asp Leu Leu Leu Ser Tyr Phe Leu Ala Thr Ala Ser Ile Phe Glu
            500                 505                 510
```

```
ttg gaa aga act aac gaa aga atc gct tgg gct aag tct caa atc atc    1584
Leu Glu Arg Thr Asn Glu Arg Ile Ala Trp Ala Lys Ser Gln Ile Ile
        515                 520                 525 gct aag atg atc act tct ttc ttc aac aag gaa act act tct gaa gaa    1632
Ala Lys Met Ile Thr Ser Phe Phe Asn Lys Glu Thr Thr Ser Glu Glu
530                 535                 540 gac aag aga gct ttg ttg aac gaa ttg ggt aac atc aac ggt ttg aac    1680
Asp Lys Arg Ala Leu Leu Asn Glu Leu Gly Asn Ile Asn Gly Leu Asn
545                 550                 555                 560 gac act aac ggt gct ggt aga gaa ggt ggt gct ggt tct atc gct ttg    1728
Asp Thr Asn Gly Ala Gly Arg Glu Gly Gly Ala Gly Ser Ile Ala Leu
                565                 570                 575 gct act ttg act caa ttc ttg gaa ggt ttc gac aga tac act aga cac    1776
Ala Thr Leu Thr Gln Phe Leu Glu Gly Phe Asp Arg Tyr Thr Arg His
            580                 585                 590 caa ttg aag aac gct tgg tct gtt tgg ttg act caa ttg caa cac ggt    1824
Gln Leu Lys Asn Ala Trp Ser Val Trp Leu Thr Gln Leu Gln His Gly
        595                 600                 605 gaa gct gac gac gct gaa ttg ttg act aac act ttg aac atc tgt gct    1872
Glu Ala Asp Asp Ala Glu Leu Leu Thr Asn Thr Leu Asn Ile Cys Ala
610                 615                 620 ggt cac atc gct ttc aga gaa gaa atc ttg gct cac aac gaa tac aag    1920
Gly His Ile Ala Phe Arg Glu Glu Ile Leu Ala His Asn Glu Tyr Lys
625                 630                 635                 640 gct ttg tct aac ttg act tct aag atc tgt aga caa ttg tct ttc atc    1968
Ala Leu Ser Asn Leu Thr Ser Lys Ile Cys Arg Gln Leu Ser Phe Ile
                645                 650                 655 caa tct gaa aag gaa atg ggt gtt gaa ggt gaa atc gct gct aag tct    2016
Gln Ser Glu Lys Glu Met Gly Val Glu Gly Glu Ile Ala Ala Lys Ser
            660                 665                 670 tct atc aag aac aag gaa ttg gaa gaa gac atg caa atg ttg gtt aag    2064
Ser Ile Lys Asn Lys Glu Leu Glu Glu Asp Met Gln Met Leu Val Lys
        675                 680                 685 ttg gtt ttg gaa aag tac ggt ggt atc gac aga aac atc aag aag gct    2112
Leu Val Leu Glu Lys Tyr Gly Gly Ile Asp Arg Asn Ile Lys Lys Ala
690                 695                 700 ttc ttg gct gtt gct aag act tac tac tac aga gct tac cac gct gct    2160
Phe Leu Ala Val Ala Lys Thr Tyr Tyr Tyr Arg Ala Tyr His Ala Ala
705                 710                 715                 720 gac act atc gac act cac atg ttc aag gtt ttg ttc gaa cca gtt gct    2208
Asp Thr Ile Asp Thr His Met Phe Lys Val Leu Phe Glu Pro Val Ala
                725                 730                 735 taa                                                                2211

<210> SEQ ID NO 64
<211> LENGTH: 736
<212> TYPE: PRT
<213> ORGANISM: Salvia miltiorrhiza

<400> SEQUENCE: 64

Met Ala Thr Val Asp Ala Pro Gln Val His Asp His Asp Gly Thr Thr
1               5                   10                  15

Val His Gln Gly His Asp Ala Val Lys Asn Ile Glu Asp Pro Ile Glu
            20                  25                  30

Tyr Ile Arg Thr Leu Leu Arg Thr Gly Asp Gly Ile Ser Val
        35                  40                  45

Ser Pro Tyr Asp Thr Ala Trp Val Ala Met Ile Lys Asp Val Glu Gly
    50                  55                  60

Arg Asp Gly Pro Gln Phe Pro Ser Ser Leu Glu Trp Ile Val Gln Asn
```

```
                65                  70                  75                  80
Gln Leu Glu Asp Gly Ser Trp Gly Asp Gln Lys Leu Phe Cys Val Tyr
                    85                  90                  95

Asp Arg Leu Val Asn Thr Ile Ala Cys Val Ala Leu Arg Ser Trp
            100                 105                 110

Asn Val His Ala His Lys Val Lys Arg Gly Val Thr Tyr Ile Lys Glu
            115                 120                 125

Asn Val Asp Lys Leu Met Glu Gly Asn Glu Glu His Met Thr Cys Gly
            130                 135                 140

Phe Glu Val Val Phe Pro Ala Leu Leu Gln Lys Ala Lys Ser Leu Gly
145                 150                 155                 160

Ile Glu Asp Leu Pro Tyr Asp Ser Pro Ala Val Gln Glu Val Tyr His
                165                 170                 175

Val Arg Glu Gln Lys Leu Lys Arg Ile Pro Leu Glu Ile Met His Lys
                180                 185                 190

Ile Pro Thr Ser Leu Leu Phe Ser Leu Glu Gly Leu Glu Asn Leu Asp
                195                 200                 205

Trp Asp Lys Leu Leu Lys Leu Gln Ser Ala Asp Gly Ser Phe Leu Thr
        210                 215                 220

Ser Pro Ser Ser Thr Ala Phe Ala Phe Met Gln Thr Lys Asp Glu Lys
225                 230                 235                 240

Cys Tyr Gln Phe Ile Lys Asn Thr Ile Asp Thr Phe Asn Gly Gly Ala
                245                 250                 255

Pro His Thr Tyr Pro Val Asp Val Phe Gly Arg Leu Trp Ala Ile Asp
                260                 265                 270

Arg Leu Gln Arg Leu Gly Ile Ser Arg Phe Phe Glu Pro Glu Ile Ala
        275                 280                 285

Asp Cys Leu Ser His Ile His Lys Phe Trp Thr Asp Lys Gly Val Phe
        290                 295                 300

Ser Gly Arg Glu Ser Glu Phe Cys Asp Ile Asp Asp Thr Ser Met Gly
305                 310                 315                 320

Met Arg Leu Met Arg Met His Gly Tyr Asp Val Asp Pro Asn Val Leu
                325                 330                 335

Arg Asn Phe Lys Gln Lys Asp Gly Lys Phe Ser Cys Tyr Gly Gly Gln
                340                 345                 350

Met Ile Glu Ser Pro Ser Pro Ile Tyr Asn Leu Tyr Arg Ala Ser Gln
            355                 360                 365

Leu Arg Phe Pro Gly Glu Glu Ile Leu Glu Asp Ala Lys Arg Phe Ala
    370                 375                 380

Tyr Asp Phe Leu Lys Glu Lys Leu Ala Asn Asn Gln Ile Leu Asp Lys
385                 390                 395                 400

Trp Val Ile Ser Lys His Leu Pro Asp Glu Ile Lys Leu Gly Leu Glu
                405                 410                 415

Met Pro Trp Leu Ala Thr Leu Pro Arg Val Glu Ala Lys Tyr Tyr Ile
            420                 425                 430

Gln Tyr Tyr Ala Gly Ser Gly Asp Val Trp Ile Gly Lys Thr Leu Tyr
            435                 440                 445

Arg Met Pro Glu Ile Ser Asn Asp Thr Tyr His Asp Leu Ala Lys Thr
    450                 455                 460

Asp Phe Lys Arg Cys Gln Ala Lys His Gln Phe Glu Trp Leu Tyr Met
465                 470                 475                 480

Gln Glu Trp Tyr Glu Ser Cys Gly Ile Glu Glu Phe Gly Ile Ser Arg
                485                 490                 495
```

Lys Asp Leu Leu Leu Ser Tyr Phe Leu Ala Thr Ala Ser Ile Phe Glu
             500                 505                 510

Leu Glu Arg Thr Asn Glu Arg Ile Ala Trp Ala Lys Ser Gln Ile Ile
             515                 520                 525

Ala Lys Met Ile Thr Ser Phe Phe Asn Lys Glu Thr Thr Ser Glu Glu
             530                 535                 540

Asp Lys Arg Ala Leu Leu Asn Glu Leu Gly Asn Ile Asn Gly Leu Asn
545                 550                 555                 560

Asp Thr Asn Gly Ala Gly Arg Glu Gly Gly Ala Gly Ser Ile Ala Leu
                 565                 570                 575

Ala Thr Leu Thr Gln Phe Leu Glu Gly Phe Asp Arg Tyr Thr Arg His
             580                 585                 590

Gln Leu Lys Asn Ala Trp Ser Val Trp Leu Thr Gln Leu Gln His Gly
             595                 600                 605

Glu Ala Asp Asp Ala Glu Leu Leu Thr Asn Thr Leu Asn Ile Cys Ala
             610                 615                 620

Gly His Ile Ala Phe Arg Glu Glu Ile Leu Ala His Asn Glu Tyr Lys
625                 630                 635                 640

Ala Leu Ser Asn Leu Thr Ser Lys Ile Cys Arg Gln Leu Ser Phe Ile
             645                 650                 655

Gln Ser Glu Lys Glu Met Gly Val Gly Glu Ile Ala Ala Lys Ser
             660                 665                 670

Ser Ile Lys Asn Lys Glu Leu Glu Glu Asp Met Gln Met Leu Val Lys
             675                 680                 685

Leu Val Leu Glu Lys Tyr Gly Gly Ile Asp Arg Asn Ile Lys Lys Ala
             690                 695                 700

Phe Leu Ala Val Ala Lys Thr Tyr Tyr Arg Ala Tyr His Ala Ala
705                 710                 715                 720

Asp Thr Ile Asp Thr His Met Phe Lys Val Leu Phe Glu Pro Val Ala
             725                 730                 735

<210> SEQ ID NO 65
<211> LENGTH: 936
<212> TYPE: DNA
<213> ORGANISM: Talaromyces verruculosus

<400> SEQUENCE: 65
atgtctaacg acactactac tactgcttct gctggtactg ctacttcttc tagattcttg      60
tctgttggtg gtgttgttaa cttcagagaa ttgggtggtt acccatgtga ctctgttcca     120
ccagctccag cttctaacgg ttctccagac aacgcttctg aagctacttt gtgggttggt     180
cactcttcta tcagaccagg tttcttgttc agatctgctc aaccatctca atcactcca      240
gctggtatcg aaactttgat cagacaattg ggtatccaaa ctatcttcga cttcagatct     300
agaactgaaa tcgaattggt tgctactaga tacccagact ctttgttgga atcccaggt      360
actactagat actctgttcc agtttttctct gaaggtgact actctccagc ttctttggtt    420
aagagatacg gtgtttcttc tgacactgct actgactcta cttcttctaa gtctgctaag     480
ccaactggtt tcgttcacgc ttacgaagct atcgctagat ctgctgctga aaacggttct     540
ttcagaaaga tcactgacca catcatccaa cacccagaca gaccaatctt gttccactgt     600
actttgggta aggacagaac tggtgttttc gctgctttgt tgttgtcttt gtgtggtgtt     660
ccagacgaaa ctatcgttga agactacgct atgactacta aggtttcgg tgcttggaga     720
gaacacttga tccaaagatt gttgcaaaga aaggacgctg ctactagaga agacgctgaa     780

| | | |
|---|---|---|
| tctatcatcg cttctccacc agaaactatg aaggctttct tggaagacgt tgttgctgct | | 840 |
| aagttcggtg gtgctagaaa ctacttcatc caacactgtg gtttcactga agctgaagtt | | 900 |
| gacaagttgt ctcacacttt ggctatcact aactaa | | 936 |

<210> SEQ ID NO 66
<211> LENGTH: 1128
<212> TYPE: DNA
<213> ORGANISM: Azoarcus toluclasticus

<400> SEQUENCE: 66

| | | |
|---|---|---|
| atgggttcta tccaagactc tttgttcatc agagctagag ctgctgtttt gagaactgtt | | 60 |
| ggtggtccat ggaaatcga aaacgttaga atctctccac caagggtga cgaagttttg | | 120 |
| gttagaatgg ttggtgttgg tgtttgtcac actgacgttg tttgtagaga cggtttccca | | 180 |
| gttccattgc caatcgtttt gggtcacgaa ggttctggta tcgttgaagc tgttggtgaa | | 240 |
| agagttacta aggttaagcc aggtcaaaga gttgttttgt ctttcaactc ttgtggtcac | | 300 |
| tgtgcttctt gttgtgaaga ccacccagct acttgtcacc aaatgttgcc attgaacttc | | 360 |
| ggtgctgctc aaagagttga cggtggtact gttatcgacg cttctggtga agctgttcaa | | 420 |
| tctttgttct ccggtcaatc ttctttcggt acttacgctt ggctagaga agttaacact | | 480 |
| gttccagttc cagacgctgt tccattggaa atcttgggtc cattgggttg tggtatccaa | | 540 |
| actggtgctg gtgctgctat caactctttg gctttgaagc caggtcaatc tttggctatc | | 600 |
| ttcggtggtg gttctgttgg tttgtctgct ttgttgggtg cttttggctgt tggtgctggt | | 660 |
| ccagttgttg ttatcgaacc aaacgaaaga agaagagctt tggctttgga cttgggtgct | | 720 |
| tctcacgctt tcgacccatt caacactgaa gacttggttg cttctatcaa ggctgctact | | 780 |
| ggtggtggtg ttactcactc tttggactct actggtttgc caccagttat cgctaacgct | | 840 |
| atcaactgta ctttgccagg tggtactgtt ggtttgttgg gtgttccatc tccagaagct | | 900 |
| gctgttccag ttactttgtt ggacttgttg gttaagtctg ttactttgag accaatcact | | 960 |
| gaaggtgacg ctaacccaca agaattcatc ccaagaatgg ttcaattgta cagagacggt | | 1020 |
| aagttcccat tcgacaagtt gatcactact tacagattcg acgacatcaa ccaagctttc | | 1080 |
| aaggctactg aaactggtga agctatcaag ccagttttgg ttttctaa | | 1128 |

<210> SEQ ID NO 67
<211> LENGTH: 1119
<212> TYPE: DNA
<213> ORGANISM: Pseudomonas aeruginosa

<400> SEQUENCE: 67

| | | |
|---|---|---|
| atgaactcta tccaaccaac tcaagctaag gctgctgttt tgagagctgt tggtggtcca | | 60 |
| ttctctatcg aaccaatcag aatctctcca ccaaagggtg acgaagtttt ggttagaatc | | 120 |
| gttggtgttg gtgtttgtca cactgacgtt gtttgtagag actcttccc agttccattg | | 180 |
| ccaatcatct gggtcacga aggttctggt gttatcgaag ctgttggtga ccaagttact | | 240 |
| ggtttgaagc aggtgacca cgttgttttg tctttcaact cttgtggtca ctgttacaac | | 300 |
| tgtggtcacg acgaaccagc ttcttgtttg caaatgttgc cattgaactt cggtggtgct | | 360 |
| gaaagagctg ctgacggtac tatcgaagac gaccaaggtg ctgctgttag aggtttgttc | | 420 |
| ttcggtcaat cttctttcgg ttcttacgct atcgctagag ctgttaacac tgttaaggtt | | 480 |
| gacgacgact tgccattggc tttgttgggt ccattgggtt gtggtatcca aactggtgct | | 540 |

-continued

```
ggtgctgcta tgaactcttt gggtttgcaa ggtggtcaat ctttcatcgt tttcggtggt      600
ggtgctgttg gtttgtctgc tgttatggct gctaaggctt tgggtgtttc tccattgatc      660
gttgttgaac caaacgaagc tagaagagct ttggctttgg aattgggtgc ttctcacgct      720
ttcgacccat caacactga agacttggtt gcttctatca gagaagttgt tccagctggt       780
gctaaccacg ctttggacac tactggtttg ccaaaggtta tcgctaacgc tatcgactgt      840
atcatgtctg gtggtaagtt gggtttgttg ggtatggcta acccagaagc taacgttcca      900
gctactttgt tggacttgtt gtctaagaac gttactttga agccaatcac tgaaggtgac      960
gctaacccac aagaattcat cccaagaatg ttggctttgt acagagaagg taagttccca     1020
ttcgacaagt tgatcactac tttcccattc gaacacatca cgaagctat ggaagctact      1080
gaatctggta aggctatcaa gccagttttg actttgtaa                             1119
```

<210> SEQ ID NO 68
<211> LENGTH: 1056
<212> TYPE: DNA
<213> ORGANISM: Hyphozyma roseonigra
<220> FEATURE:
<221> NAME/KEY: CDS
<222> LOCATION: (1)..(1056)

<400> SEQUENCE: 68

```
atg caa ttc tct atc ggt gac gtt ttg gct atc gtt gac aag act atc        48
Met Gln Phe Ser Ile Gly Asp Val Leu Ala Ile Val Asp Lys Thr Ile
1               5                   10                  15 ttg aac cca ttg gtt gtt tct gct ggt ttg ttg tct ttg cac ttc ttg        96
Leu Asn Pro Leu Val Val Ser Ala Gly Leu Leu Ser Leu His Phe Leu
            20                  25                  30 act aac gac aag tac gct atc act gct aac gac ggt ttg ttc cca tac       144
Thr Asn Asp Lys Tyr Ala Ile Thr Ala Asn Asp Gly Leu Phe Pro Tyr
        35                  40                  45 caa atc tct act cca gac tct cac aga aag gct ttg ttc gct ttg ggt       192
Gln Ile Ser Thr Pro Asp Ser His Arg Lys Ala Leu Phe Ala Leu Gly
    50                  55                  60 ttc ggt ttg ttg ttg aga gct aac aga tac atg tct aga aag gct ttg       240
Phe Gly Leu Leu Leu Arg Ala Asn Arg Tyr Met Ser Arg Lys Ala Leu
65                  70                  75                  80 aac aac aac act gct gct caa ttc gac tgg aac aga gaa atc atc gtt       288
Asn Asn Asn Thr Ala Ala Gln Phe Asp Trp Asn Arg Glu Ile Ile Val
                85                  90                  95 gtt act ggt ggt tct ggt ggt atc ggt gct caa gct gct caa aag ttg       336
Val Thr Gly Gly Ser Gly Gly Ile Gly Ala Gln Ala Ala Gln Lys Leu
            100                 105                 110 gct gaa aga ggt tct aag gtt atc gtt atc gac gtt ttg cca ttg act       384
Ala Glu Arg Gly Ser Lys Val Ile Val Ile Asp Val Leu Pro Leu Thr
        115                 120                 125 ttc gac aag cca aag aac ttg tac cac tac aag tgt gac ttg act aac       432
Phe Asp Lys Pro Lys Asn Leu Tyr His Tyr Lys Cys Asp Leu Thr Asn
    130                 135                 140 tac aag gaa ttg caa gaa gtt gct gct aag atc gaa aga gaa gtt ggt       480
Tyr Lys Glu Leu Gln Glu Val Ala Ala Lys Ile Glu Arg Glu Val Gly
145                 150                 155                 160 act cca act tgt gtt gtt gct aac gct ggt atc tgt aga ggt aag aac       528
Thr Pro Thr Cys Val Val Ala Asn Ala Gly Ile Cys Arg Gly Lys Asn
                165                 170                 175 atc ttc gac gct act gaa aga gac gtt caa ttg act ttc ggt gtt aac       576
Ile Phe Asp Ala Thr Glu Arg Asp Val Gln Leu Thr Phe Gly Val Asn
            180                 185                 190
```

| | | |
|---|---|---|
| aac ttg ggt ttg ttg tgg act gct aag act ttc ttg cca tct atg gct<br>Asn Leu Gly Leu Leu Trp Thr Ala Lys Thr Phe Leu Pro Ser Met Ala<br>        195                    200                  205 | | 624 |
| aag gct aac cac ggt cac ttc ttg atc atc gct tct caa act ggt cac<br>Lys Ala Asn His Gly His Phe Leu Ile Ile Ala Ser Gln Thr Gly His<br>210                    215                    220 | | 672 |
| ttg gct act gct ggt gtt gtt gac tac gct gct act aag gct gct gct<br>Leu Ala Thr Ala Gly Val Val Asp Tyr Ala Ala Thr Lys Ala Ala Ala<br>225                    230                    235                  240 | | 720 |
| atc gct atc tac gaa ggt ttg caa act gaa atg aag cac ttc tac aag<br>Ile Ala Ile Tyr Glu Gly Leu Gln Thr Glu Met Lys His Phe Tyr Lys<br>        245                    250                  255 | | 768 |
| gct cca gct gtt aga gtt tct tgt atc tct cca tct gct gtt aag act<br>Ala Pro Ala Val Arg Val Ser Cys Ile Ser Pro Ser Ala Val Lys Thr<br>260                    265                    270 | | 816 |
| aag atg ttc gct ggt atc aag act ggt ggt aac ttc ttc atg cca atg<br>Lys Met Phe Ala Gly Ile Lys Thr Gly Gly Asn Phe Phe Met Pro Met<br>        275                    280                  285 | | 864 |
| ttg act cca gac gac ttg ggt gac ttg atc gct aag act ttg tgg gac<br>Leu Thr Pro Asp Asp Leu Gly Asp Leu Ile Ala Lys Thr Leu Trp Asp<br>290                    295                    300 | | 912 |
| ggt gtt gct gtt aac atc ttg tct cca gct gct gct tac atc tct cca<br>Gly Val Ala Val Asn Ile Leu Ser Pro Ala Ala Ala Tyr Ile Ser Pro<br>305                    310                    315                  320 | | 960 |
| cca act aga gct ttg cca gac tgg atg aga gtt ggt atg caa gac gct<br>Pro Thr Arg Ala Leu Pro Asp Trp Met Arg Val Gly Met Gln Asp Ala<br>                325                    330                  335 | | 1008 |
| ggt gct gaa atc atg act gaa ttg act cca cac aag cca ttg gaa taa<br>Gly Ala Glu Ile Met Thr Glu Leu Thr Pro His Lys Pro Leu Glu<br>340                    345                    350 | | 1056 |

<210> SEQ ID NO 69
<211> LENGTH: 351
<212> TYPE: PRT
<213> ORGANISM: Hyphozyma roseonigra

<400> SEQUENCE: 69

Met Gln Phe Ser Ile Gly Asp Val Leu Ala Ile Val Asp Lys Thr Ile
1               5                   10                  15

Leu Asn Pro Leu Val Val Ser Ala Gly Leu Leu Ser Leu His Phe Leu
            20                  25                  30

Thr Asn Asp Lys Tyr Ala Ile Thr Ala Asn Asp Gly Leu Phe Pro Tyr
        35                  40                  45

Gln Ile Ser Thr Pro Asp Ser His Arg Lys Ala Leu Phe Ala Leu Gly
    50                  55                  60

Phe Gly Leu Leu Leu Arg Ala Asn Arg Tyr Met Ser Arg Lys Ala Leu
65                  70                  75                  80

Asn Asn Asn Thr Ala Ala Gln Phe Asp Trp Asn Arg Glu Ile Ile Val
                85                  90                  95

Val Thr Gly Gly Ser Gly Gly Ile Gly Ala Gln Ala Ala Gln Lys Leu
            100                 105                 110

Ala Glu Arg Gly Ser Lys Val Ile Val Ile Asp Val Leu Pro Leu Thr
        115                 120                 125

Phe Asp Lys Pro Lys Asn Leu Tyr His Tyr Lys Cys Asp Leu Thr Asn
    130                 135                 140

Tyr Lys Glu Leu Gln Glu Val Ala Ala Lys Ile Glu Arg Glu Val Gly
145                 150                 155                 160

Thr Pro Thr Cys Val Val Ala Asn Ala Gly Ile Cys Arg Gly Lys Asn

```
                    165                 170                 175
Ile Phe Asp Ala Thr Glu Arg Asp Val Gln Leu Thr Phe Gly Val Asn
            180                 185                 190

Asn Leu Gly Leu Leu Trp Thr Ala Lys Thr Phe Leu Pro Ser Met Ala
        195                 200                 205

Lys Ala Asn His Gly His Phe Leu Ile Ile Ala Ser Gln Thr Gly His
    210                 215                 220

Leu Ala Thr Ala Gly Val Val Asp Tyr Ala Ala Thr Lys Ala Ala Ala
225                 230                 235                 240

Ile Ala Ile Tyr Glu Gly Leu Gln Thr Glu Met Lys His Phe Tyr Lys
                245                 250                 255

Ala Pro Ala Val Arg Val Ser Cys Ile Ser Pro Ser Ala Val Lys Thr
            260                 265                 270

Lys Met Phe Ala Gly Ile Lys Thr Gly Gly Asn Phe Phe Met Pro Met
        275                 280                 285

Leu Thr Pro Asp Asp Leu Gly Asp Leu Ile Ala Lys Thr Leu Trp Asp
    290                 295                 300

Gly Val Ala Val Asn Ile Leu Ser Pro Ala Ala Tyr Ile Ser Pro
305                 310                 315                 320

Pro Thr Arg Ala Leu Pro Asp Trp Met Arg Val Gly Met Gln Asp Ala
                325                 330                 335

Gly Ala Glu Ile Met Thr Glu Leu Thr Pro His Lys Pro Leu Glu
            340                 345                 350

<210> SEQ ID NO 70
<211> LENGTH: 1116
<212> TYPE: DNA
<213> ORGANISM: Cryptococcus albidus
<220> FEATURE:
<221> NAME/KEY: CDS
<222> LOCATION: (1)..(1116)

<400> SEQUENCE: 70 atg cca act cca atc ttc ggt gct aga gaa ggt ttc act atc gac tct      48
Met Pro Thr Pro Ile Phe Gly Ala Arg Glu Gly Phe Thr Ile Asp Ser
1               5                   10                  15 gtt ttg tct atc ttg gac gct act gtt ttg aac cca tgg ttc act ggt      96
Val Leu Ser Ile Leu Asp Ala Thr Val Leu Asn Pro Trp Phe Thr Gly
                20                  25                  30 gtt tgt ttg atc gct gtt tgt gct aga gac aga act atc act tac cca     144
Val Cys Leu Ile Ala Val Cys Ala Arg Asp Arg Thr Ile Thr Tyr Pro
            35                  40                  45 gac tgg cca gct gct ttg gac caa gtt ttg cca ttc ttg tct caa atg     192
Asp Trp Pro Ala Ala Leu Asp Gln Val Leu Pro Phe Leu Ser Gln Met
        50                  55                  60 tgg aga gaa act gtt aga cca act ttc ggt gac aga aac gtt ttg cac     240
Trp Arg Glu Thr Val Arg Pro Thr Phe Gly Asp Arg Asn Val Leu His
65                  70                  75                  80 ttg ttg act act gtt tgt gtt ggt ttg gct atc aga act aac aga aga     288
Leu Leu Thr Thr Val Cys Val Gly Leu Ala Ile Arg Thr Asn Arg Arg
                85                  90                  95 atg tct aga ggt gct aga aac aac tgg gtt tgg gac act tct tac gac     336
Met Ser Arg Gly Ala Arg Asn Asn Trp Val Trp Asp Thr Ser Tyr Asp
            100                 105                 110 tgg aag aag gaa atc gtt gtt gtt act ggt ggt gct gct ggt ttc ggt     384
Trp Lys Lys Glu Ile Val Val Val Thr Gly Gly Ala Ala Gly Phe Gly
        115                 120                 125 gct gac atc gtt caa caa ttg gac act aga ggt atc caa gtt gtt gtt     432
```

```
Ala Asp Ile Val Gln Gln Leu Asp Thr Arg Gly Ile Gln Val Val
    130                 135                 140 ttg gac gtt ggt tct ttg act tac aga cca tct tct aga gtt cac tac        480
Leu Asp Val Gly Ser Leu Thr Tyr Arg Pro Ser Ser Arg Val His Tyr
145                 150                 155                 160 tac aag tgt gac gtt tct aac cca caa gac gtt gct tct gtt gct aag        528
Tyr Lys Cys Asp Val Ser Asn Pro Gln Asp Val Ala Ser Val Ala Lys
                165                 170                 175 gct atc gtt tct aac gtt ggt cac cca act atc ttg gtt aac aac gct        576
Ala Ile Val Ser Asn Val Gly His Pro Thr Ile Leu Val Asn Asn Ala
            180                 185                 190 ggt gtt ttc aga ggt gct act atc ttg tct act act cca aga gac ttg        624
Gly Val Phe Arg Gly Ala Thr Ile Leu Ser Thr Thr Pro Arg Asp Leu
        195                 200                 205 gac atg act tac gac atc aac gtt aag gct cac tac cac ttg act aag        672
Asp Met Thr Tyr Asp Ile Asn Val Lys Ala His Tyr His Leu Thr Lys
    210                 215                 220 gct ttc ttg cca aac atg atc tct aag aac cac ggt cac atc gtt act        720
Ala Phe Leu Pro Asn Met Ile Ser Lys Asn His Gly His Ile Val Thr
225                 230                 235                 240 gtt tct tct gct act gct tac gct caa gct tgt tct ggt gtt tct tac        768
Val Ser Ser Ala Thr Ala Tyr Ala Gln Ala Cys Ser Gly Val Ser Tyr
                245                 250                 255 tgt tct tct aag gct gct atc ttg tct ttc cac gaa ggt ttg tct gaa        816
Cys Ser Ser Lys Ala Ala Ile Leu Ser Phe His Glu Gly Leu Ser Glu
            260                 265                 270 gaa atc ttg tgg atc tac aag gct cca aag gtt aga act tct gtt atc        864
Glu Ile Leu Trp Ile Tyr Lys Ala Pro Lys Val Arg Thr Ser Val Ile
        275                 280                 285 tgt cca ggt cac gtt aac act gct atg ttc act ggt atc ggt gct gct        912
Cys Pro Gly His Val Asn Thr Ala Met Phe Thr Gly Ile Gly Ala Ala
    290                 295                 300 gct cca tct ttc atg gct cca gct ttg cac cca tct act gtt gct gaa        960
Ala Pro Ser Phe Met Ala Pro Ala Leu His Pro Ser Thr Val Ala Glu
305                 310                 315                 320 act atc gtt gac gtt ttg ttg tct tgt gaa tct caa cac gtt ttg atg       1008
Thr Ile Val Asp Val Leu Leu Ser Cys Glu Ser Gln His Val Leu Met
                325                 330                 335 cca gct gct atg cac atg tct gtt gct ggt aga gct ttg cca act tgg       1056
Pro Ala Ala Met His Met Ser Val Ala Gly Arg Ala Leu Pro Thr Trp
            340                 345                 350 ttc ttc aga ggt ttg ttg gct tct ggt aag gac act atg ggt tct gtt       1104
Phe Phe Arg Gly Leu Leu Ala Ser Gly Lys Asp Thr Met Gly Ser Val
        355                 360                 365 gtt aga aga taa                                                        1116
Val Arg Arg
    370

<210> SEQ ID NO 71
<211> LENGTH: 371
<212> TYPE: PRT
<213> ORGANISM: Cryptococcus albidus

<400> SEQUENCE: 71

Met Pro Thr Pro Ile Phe Gly Arg Glu Gly Phe Thr Ile Asp Ser
1               5                   10                  15

Val Leu Ser Ile Leu Asp Ala Thr Val Leu Asn Pro Trp Phe Thr Gly
                20                  25                  30

Val Cys Leu Ile Ala Val Cys Ala Arg Asp Arg Thr Ile Thr Tyr Pro
            35                  40                  45
```

Asp Trp Pro Ala Ala Leu Asp Gln Val Leu Pro Phe Leu Ser Gln Met
 50                  55                  60

Trp Arg Glu Thr Val Arg Pro Thr Phe Gly Asp Arg Asn Val Leu His
 65                  70                  75                  80

Leu Leu Thr Thr Val Cys Val Gly Leu Ala Ile Arg Thr Asn Arg Arg
                 85                  90                  95

Met Ser Arg Gly Ala Arg Asn Asn Trp Val Trp Asp Thr Ser Tyr Asp
            100                 105                 110

Trp Lys Lys Glu Ile Val Val Thr Gly Gly Ala Ala Gly Phe Gly
        115                 120                 125

Ala Asp Ile Val Gln Gln Leu Asp Thr Arg Gly Ile Gln Val Val Val
130                 135                 140

Leu Asp Val Gly Ser Leu Thr Tyr Arg Pro Ser Ser Arg Val His Tyr
145                 150                 155                 160

Tyr Lys Cys Asp Val Ser Asn Pro Gln Asp Val Ala Ser Val Ala Lys
                165                 170                 175

Ala Ile Val Ser Asn Val Gly His Pro Thr Ile Leu Val Asn Asn Ala
            180                 185                 190

Gly Val Phe Arg Gly Ala Thr Ile Leu Ser Thr Thr Pro Arg Asp Leu
        195                 200                 205

Asp Met Thr Tyr Asp Ile Asn Val Lys Ala His Tyr His Leu Thr Lys
210                 215                 220

Ala Phe Leu Pro Asn Met Ile Ser Lys Asn His Gly His Ile Val Thr
225                 230                 235                 240

Val Ser Ser Ala Thr Ala Tyr Ala Gln Ala Cys Ser Gly Val Ser Tyr
                245                 250                 255

Cys Ser Ser Lys Ala Ala Ile Leu Ser Phe His Glu Gly Leu Ser Glu
            260                 265                 270

Glu Ile Leu Trp Ile Tyr Lys Ala Pro Lys Val Arg Thr Ser Val Ile
        275                 280                 285

Cys Pro Gly His Val Asn Thr Ala Met Phe Thr Gly Ile Gly Ala Ala
290                 295                 300

Ala Pro Ser Phe Met Ala Pro Ala Leu His Pro Ser Thr Val Ala Glu
305                 310                 315                 320

Thr Ile Val Asp Val Leu Leu Ser Cys Glu Ser Gln His Val Leu Met
                325                 330                 335

Pro Ala Ala Met His Met Ser Val Ala Gly Arg Ala Leu Pro Thr Trp
            340                 345                 350

Phe Phe Arg Gly Leu Leu Ala Ser Gly Lys Asp Thr Met Gly Ser Val
        355                 360                 365

Val Arg Arg
    370

<210> SEQ ID NO 72
<211> LENGTH: 60
<212> TYPE: DNA
<213> ORGANISM: Artificial Sequence
<220> FEATURE:
<223> OTHER INFORMATION: Sequence for homologous recombination

<400> SEQUENCE: 72
gcacttgcta cactgtcagg atagcttccg tcacatggtg gcgatcaccg tacatctgag    60

<210> SEQ ID NO 73
<211> LENGTH: 60

```
<212> TYPE: DNA
<213> ORGANISM: Artificial Sequence
<220> FEATURE:
<223> OTHER INFORMATION: Sequence for homologous recombination

<400> SEQUENCE: 73
aggtgcagtt cgcgtgcaat tataacgtcg tggcaactgt tatcagtcgt accgcgccat     60

<210> SEQ ID NO 74
<211> LENGTH: 60
<212> TYPE: DNA
<213> ORGANISM: Artificial Sequence
<220> FEATURE:
<223> OTHER INFORMATION: Sequence for homologous recombination

<400> SEQUENCE: 74
tggtcagcaa caacgccgaa gaatcactct cgtgttgaga attgcacgcc ttgaccacga     60

<210> SEQ ID NO 75
<211> LENGTH: 79
<212> TYPE: DNA
<213> ORGANISM: Artificial Sequence
<220> FEATURE:
<223> OTHER INFORMATION: Primer for LEU2 yeast marker

<400> SEQUENCE: 75
aggtgcagtt cgcgtgcaat tataacgtcg tggcaactgt tatcagtcgt accgcgccat     60
tcgactacgt cgtaaggcc                                                  79

<210> SEQ ID NO 76
<211> LENGTH: 80
<212> TYPE: DNA
<213> ORGANISM: Artificial Sequence
<220> FEATURE:
<223> OTHER INFORMATION: Primer for LEU2 yeast marker

<400> SEQUENCE: 76
tcgtggtcaa ggcgtgcaat tctcaacacg agagtgattc ttcggcgttg ttgctgacca     60
tcgacggtcg aggagaactt                                                 80

<210> SEQ ID NO 77
<211> LENGTH: 85
<212> TYPE: DNA
<213> ORGANISM: Artificial Sequence
<220> FEATURE:
<223> OTHER INFORMATION: Primer for AmpR bacterial marker

<400> SEQUENCE: 77
tggtcagcaa caacgccgaa gaatcactct cgtgttgaga attgcacgcc ttgaccacga     60
cacgttaagg gattttggtc atgag                                           85

<210> SEQ ID NO 78
<211> LENGTH: 80
<212> TYPE: DNA
<213> ORGANISM: Artificial Sequence
<220> FEATURE:
<223> OTHER INFORMATION: Primer for AmpR bacterial marker

<400> SEQUENCE: 78
aacgcgtacc ctaagtacgg caccacagtg actatgcagt ccgcactttg ccaatgccaa     60
aaatgtgcgc ggaacccta                                                  80

<210> SEQ ID NO 79
```

```
<211> LENGTH: 84
<212> TYPE: DNA
<213> ORGANISM: Artificial Sequence
<220> FEATURE:
<223> OTHER INFORMATION: Primer for yeast origin of replication

<400> SEQUENCE: 79
ttggcattgg caaagtgcgg actgcatagt cactgtggtg ccgtacttag ggtacgcgtt    60
cctgaacgaa gcatctgtgc ttca                                          84

<210> SEQ ID NO 80
<211> LENGTH: 85
<212> TYPE: DNA
<213> ORGANISM: Artificial Sequence
<220> FEATURE:
<223> OTHER INFORMATION: Primer for yeast origin of replication

<400> SEQUENCE: 80
ccgagatgcc aaaggatagg tgctatgttg atgactacga cacagaactg cgggtgacat    60
aatgatagca ttgaaggatg agact                                         85

<210> SEQ ID NO 81
<211> LENGTH: 82
<212> TYPE: DNA
<213> ORGANISM: Artificial Sequence
<220> FEATURE:
<223> OTHER INFORMATION: Primer for E. coli origin of replication

<400> SEQUENCE: 81
atgtcacccg cagttctgtg tcgtagtcat caacatagca cctatccttt ggcatctcgg    60
tgagcaaaag gccagcaaaa gg                                            82

<210> SEQ ID NO 82
<211> LENGTH: 81
<212> TYPE: DNA
<213> ORGANISM: Artificial Sequence
<220> FEATURE:
<223> OTHER INFORMATION: Primer for E. coli origin of replication

<400> SEQUENCE: 82
ctcagatgta cggtgatcgc caccatgtga cggaagctat cctgacagtg tagcaagtgc    60
tgagcgtcag accccgtaga a                                             81

<210> SEQ ID NO 83
<211> LENGTH: 60
<212> TYPE: DNA
<213> ORGANISM: Artificial Sequence
<220> FEATURE:
<223> OTHER INFORMATION: Sequence for homologous recombination

<400> SEQUENCE: 83
attcctagtg acggccttgg gaactcgata cacgatgttc agtagaccgc tcacacatgg    60
```